(12) United States Patent
McAuley et al.

(10) Patent No.: US 12,042,603 B2
(45) Date of Patent: Jul. 23, 2024

(54) BREATHING ASSISTANCE APPARATUS

(71) Applicant: Fisher & Paykel Healthcare Limited, Auckland (NZ)

(72) Inventors: Alastair Edwin McAuley, Auckland (NZ); Craig Robert Prentice, Auckland (NZ); Rory Alexander Monro, Auckland (NZ); Isaac Tristram Tane Mason, Auckland (NZ); Nadjean Maurice Gabriel Geslain, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1436 days.

(21) Appl. No.: 16/444,664

(22) Filed: Jun. 18, 2019

(65) Prior Publication Data
US 2019/0298957 A1 Oct. 3, 2019

Related U.S. Application Data

(63) Continuation of application No. 14/726,278, filed on May 29, 2015, now Pat. No. 10,376,666, which is a
(Continued)

(51) Int. Cl.
*A61M 16/06* (2006.01)
*A61M 16/00* (2006.01)
(Continued)

(52) U.S. Cl.
CPC .... *A61M 16/0666* (2013.01); *A61M 16/0066* (2013.01); *A61M 16/06* (2013.01); *A61M 16/0616* (2014.02); *A61M 16/0622* (2014.02); *A61M 16/0683* (2013.01); *A61M 16/0816* (2013.01); *A61M 16/0875* (2013.01); *A61M 16/16* (2013.01); *A61M 16/0825* (2014.02); *A61M 2210/0618* (2013.01)

(58) Field of Classification Search
CPC .................. A61M 16/0666; A61M 16/0672
See application file for complete search history.

(56) References Cited

U.S. PATENT DOCUMENTS

| 4,367,735 A | 1/1983 | Dali |
| 4,660,555 A | 4/1987 | Payton |

(Continued)

FOREIGN PATENT DOCUMENTS

| EP | 2022528 A2 | 2/2009 |
| WO | WO 2005/016403 A2 | 2/2005 |

(Continued)

OTHER PUBLICATIONS

International Search Report; Sep. 24, 2009; 6 pages.
Written Opinion of the International Search Authority; Sep. 24, 2009; 14 pages.

*Primary Examiner* — LaToya M Louis
(74) *Attorney, Agent, or Firm* — Knobbe, Martens, Olson & Bear, LLP

(57) ABSTRACT

Breathing assistance apparatus for treating sleep apnoea can include nasal interfaces for the supply of respiratory gases, but most particularly positive pressure gases are described. The nasal interfaces may include various forms of nasal pillows or nasal plugs. Associated elements, such as manifolds or housings to hold or secure the pillows or plugs or headgear, can be included.

18 Claims, 82 Drawing Sheets

Related U.S. Application Data continuation of application No. 12/997,559, filed as application No. PCT/NZ2009/000105 on Jun. 12, 2009, now Pat. No. 9,072,855.

(60) Provisional application No. 61/060,855, filed on Jun. 12, 2008, provisional application No. 61/082,877, filed on Jul. 23, 2008, provisional application No. 61/148,476, filed on Jan. 30, 2009, provisional application No. 61/166,306, filed on Apr. 3, 2009, provisional application No. 61/173,855, filed on Apr. 29, 2009.

(51) Int. Cl.
*A61M 16/08* (2006.01)
*A61M 16/16* (2006.01)

(56) References Cited

U.S. PATENT DOCUMENTS

| | | |
|---|---|---|
| 5,533,506 A | 7/1996 | Wood |
| 7,195,018 B1 | 3/2007 | Goldstein |
| 2003/0168067 A1 | 9/2003 | Dougill et al. |
| 2003/0172938 A1 | 9/2003 | Falco |
| 2005/0166927 A1 | 8/2005 | McAuley et al. |
| 2006/0283461 A1 | 12/2006 | Lubke |
| 2007/0144525 A1 | 6/2007 | Davidson et al. |
| 2007/0163600 A1 | 7/2007 | Hoffman |
| 2009/0032026 A1 | 2/2009 | Price et al. |
| 2009/0044808 A1 | 2/2009 | Guney |
| 2009/0183739 A1 | 7/2009 | Wondka |
| 2009/0320851 A1 | 12/2009 | Selvarajan |
| 2016/0256653 A1 | 9/2016 | McAuley et al. |

FOREIGN PATENT DOCUMENTS

| | | |
|---|---|---|
| WO | WO 2006/130903 A1 | 12/2006 |
| WO | WO 2008/014543 A1 | 2/2008 |
| WO | WO2009/052560 | 4/2009 |

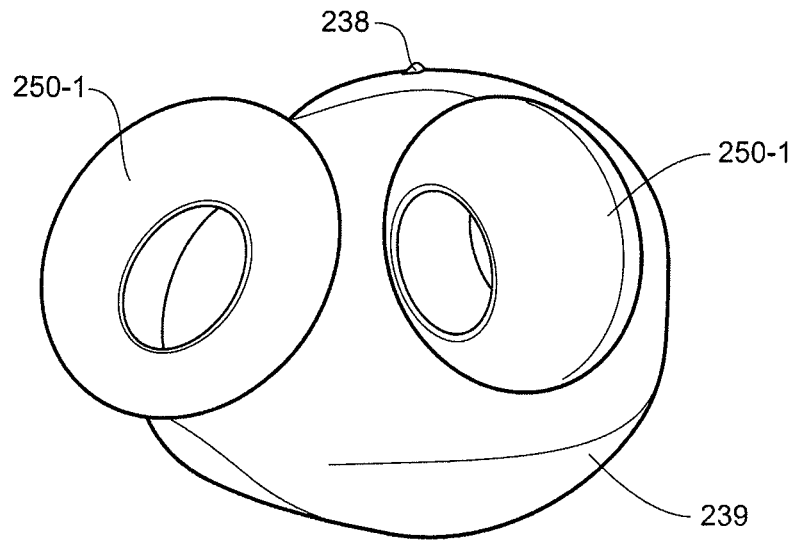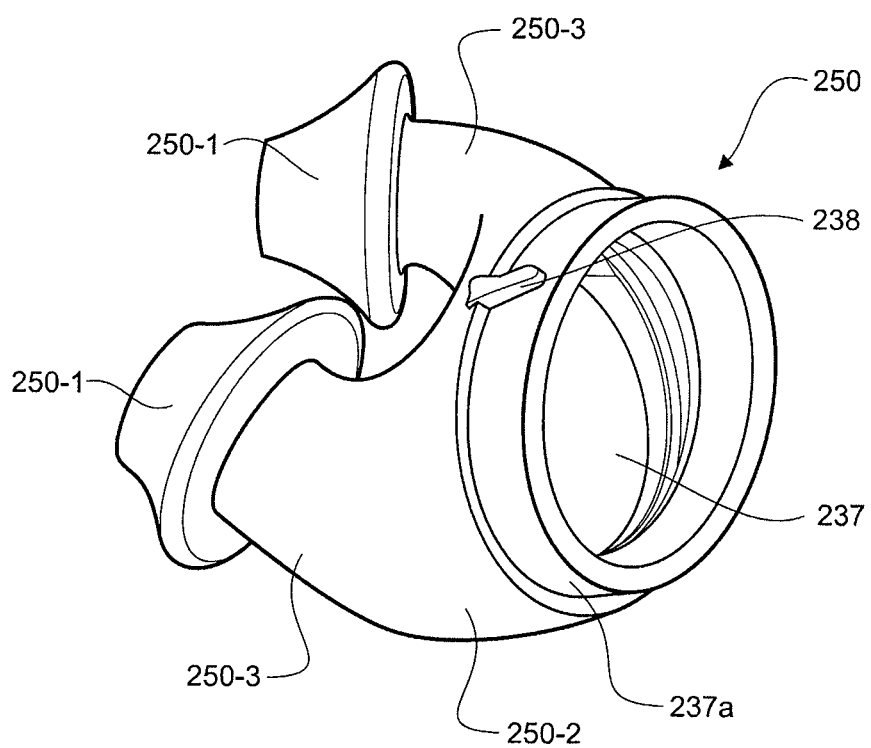
FIGURE 2d

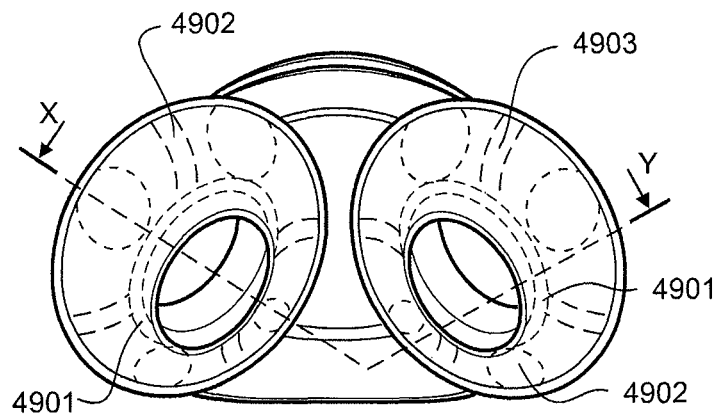
FIGURE 49a
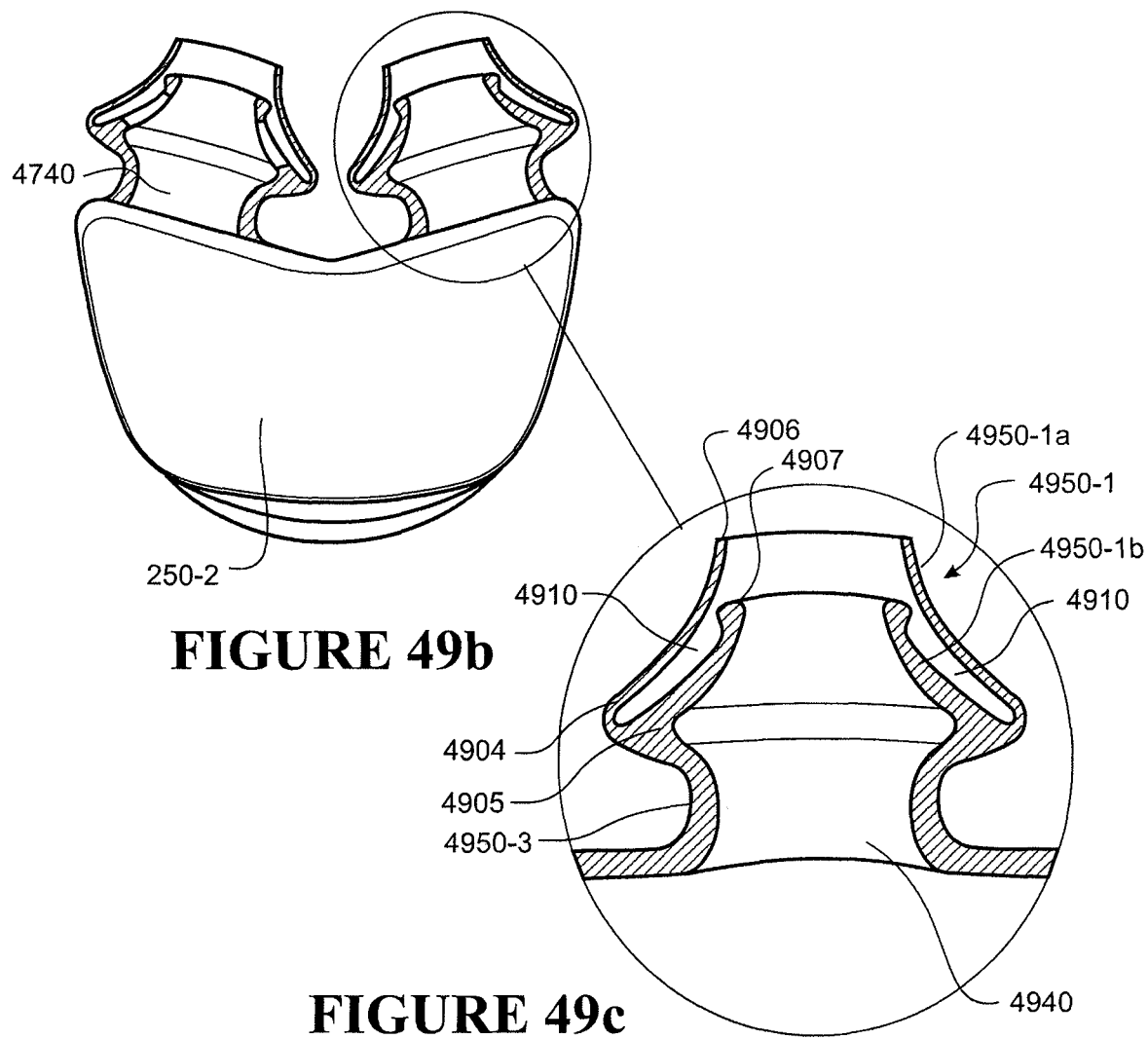
FIGURE 49b
FIGURE 49c

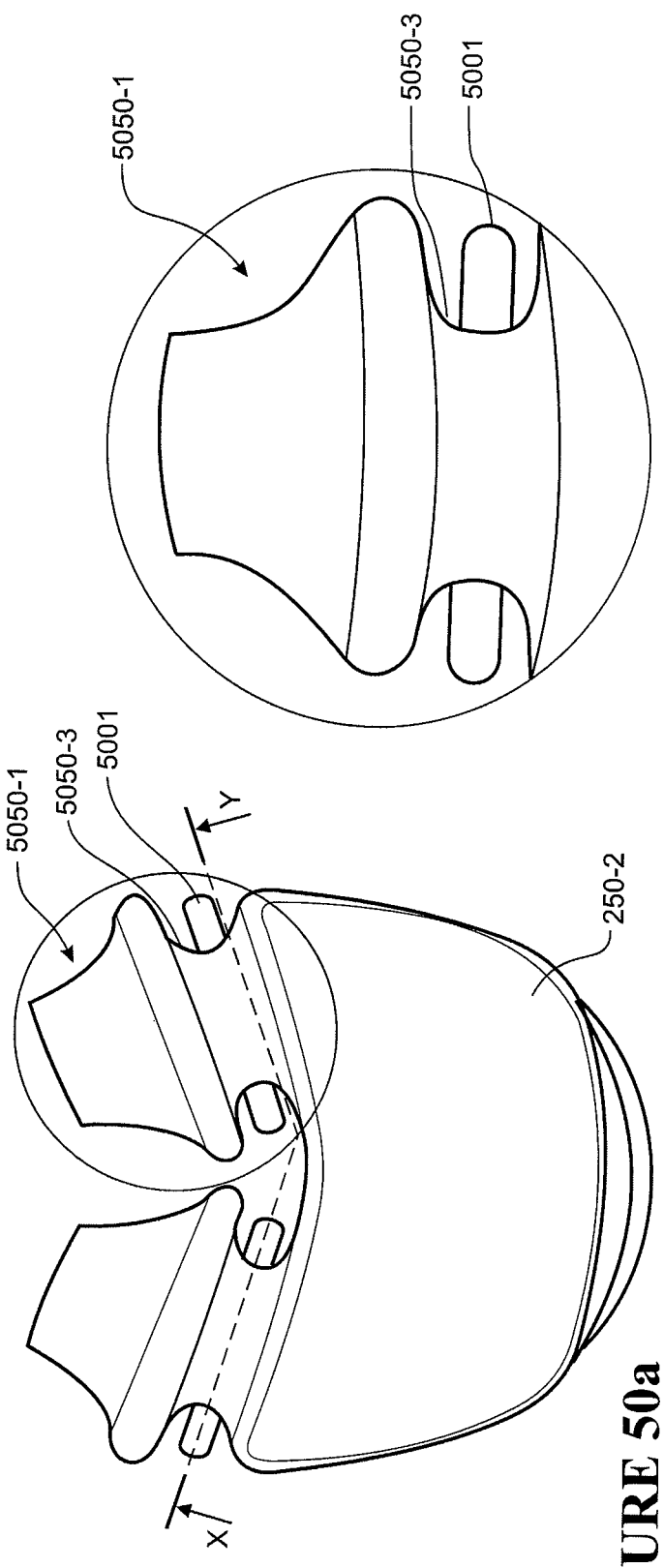
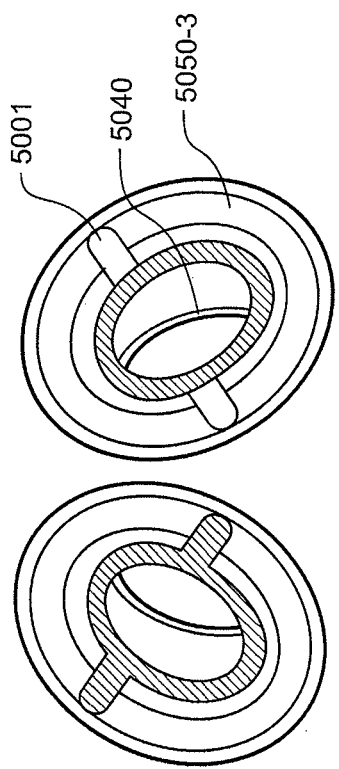
FIGURE 50a
FIGURE 50b
FIGURE 50c

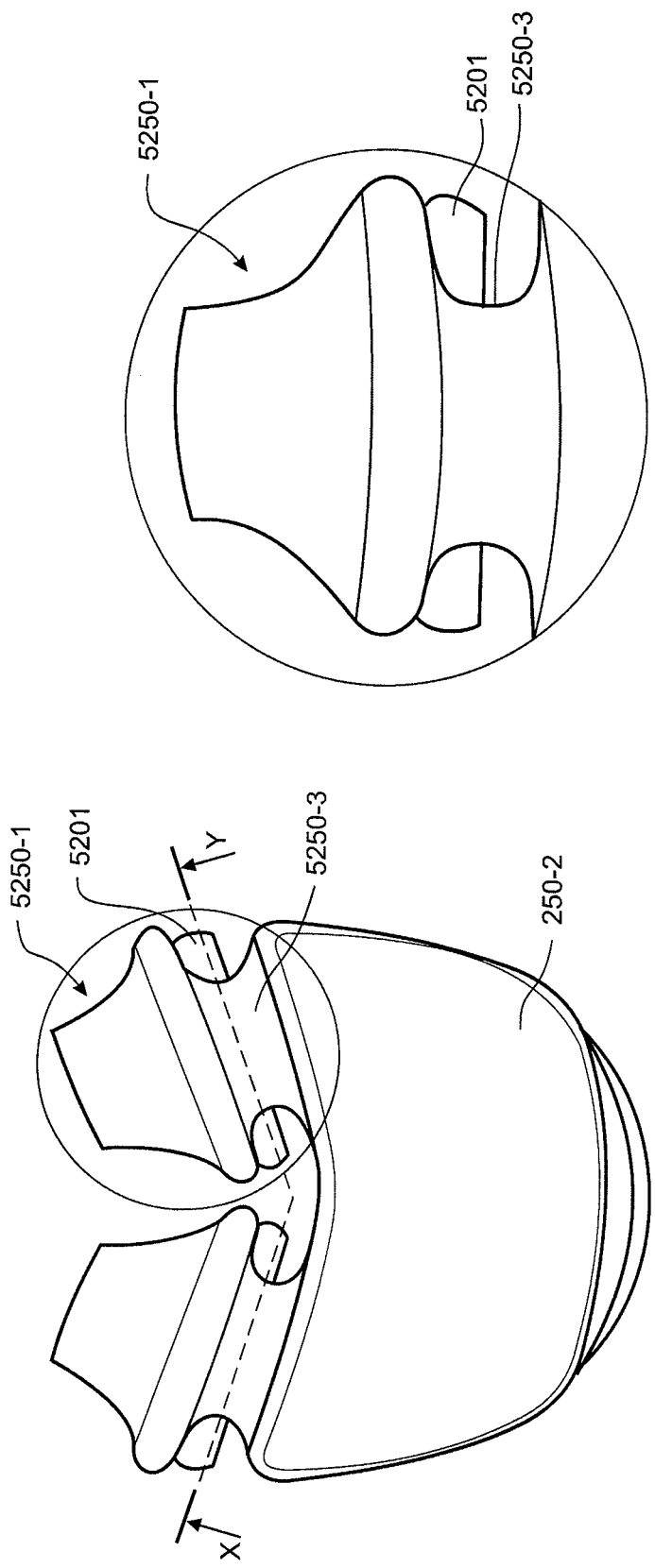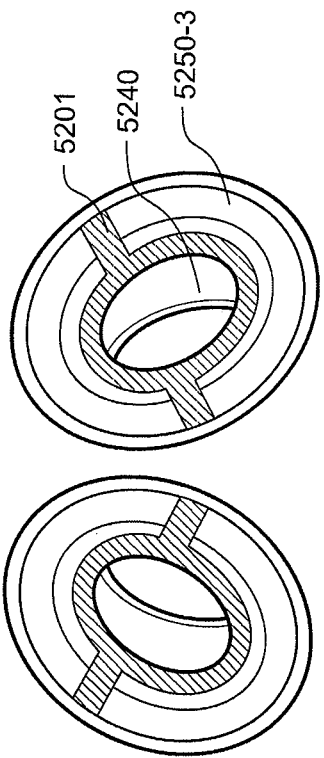
FIGURE 52c
FIGURE 52a
FIGURE 52b

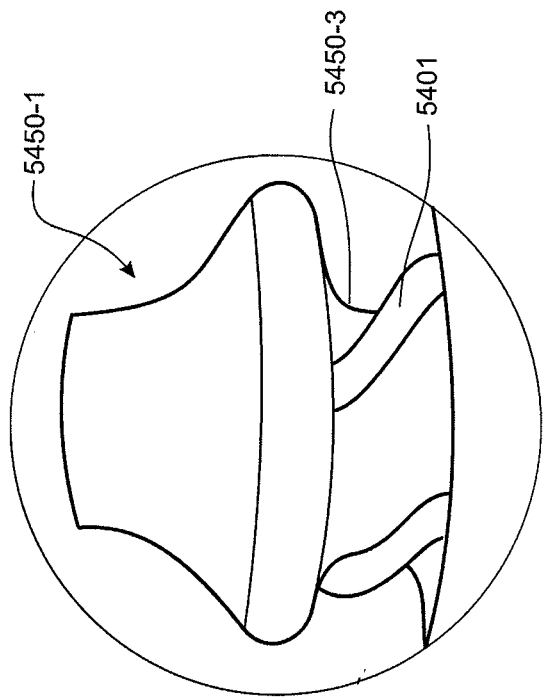
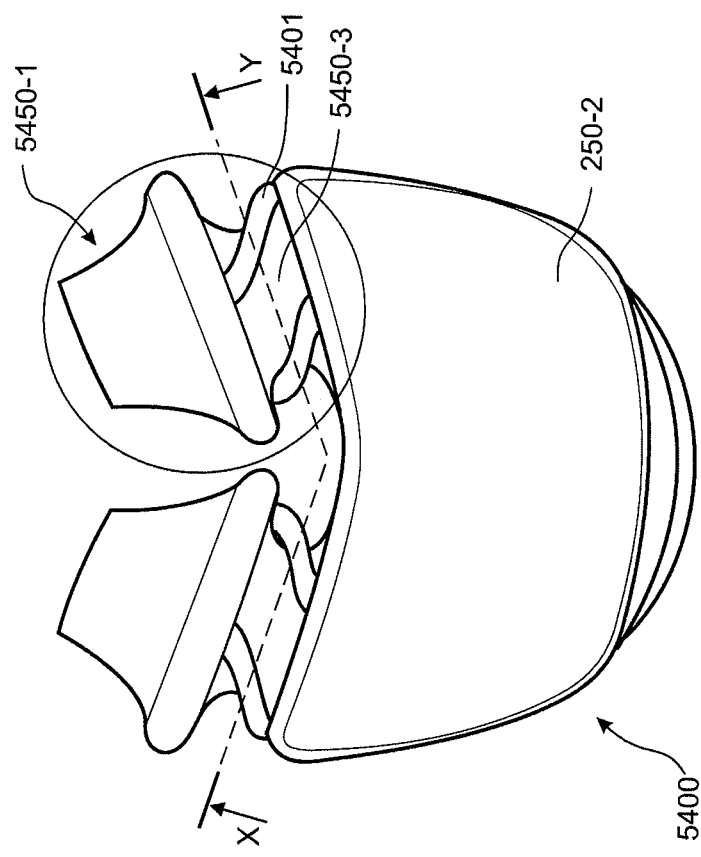
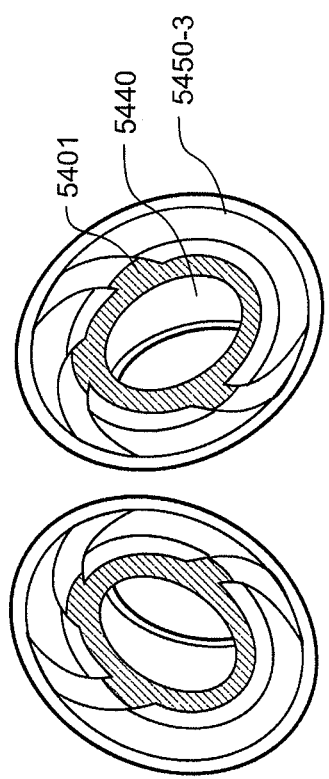
FIGURE 54c
FIGURE 54a
FIGURE 54b

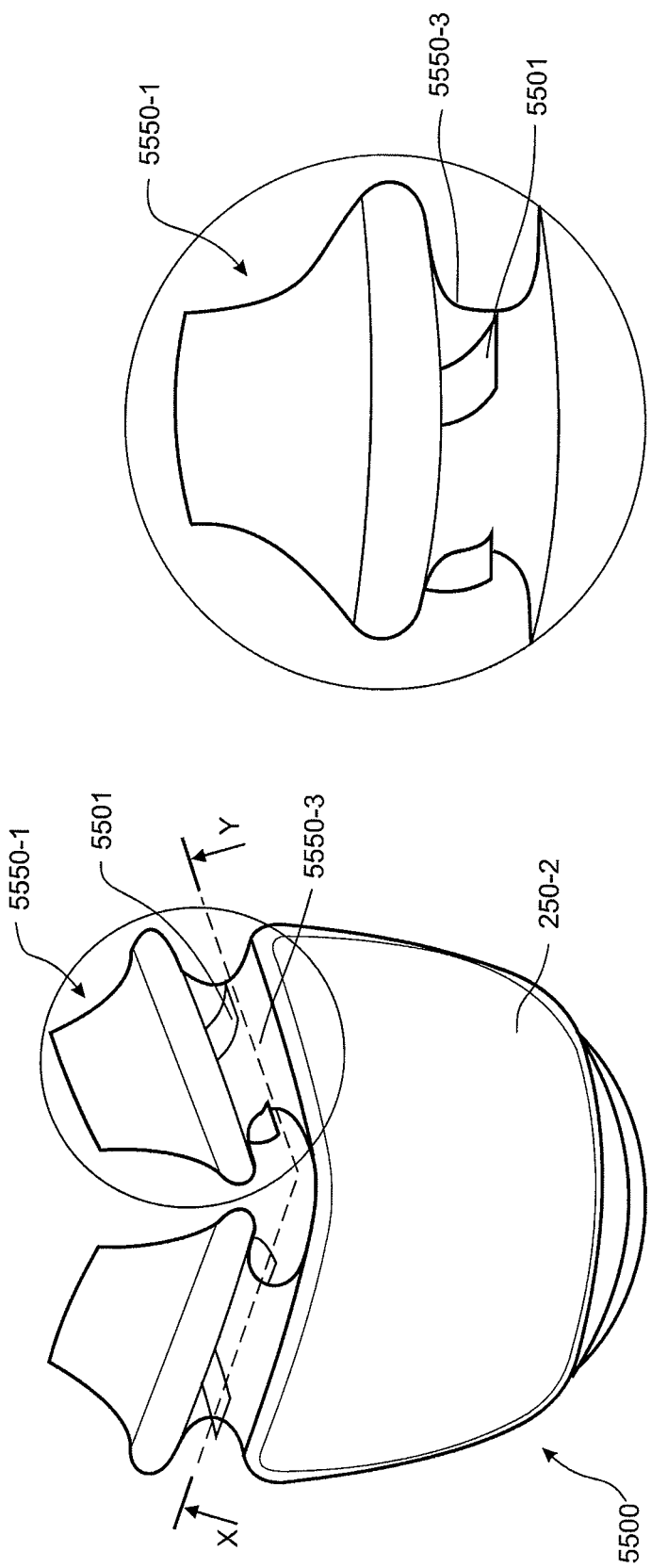
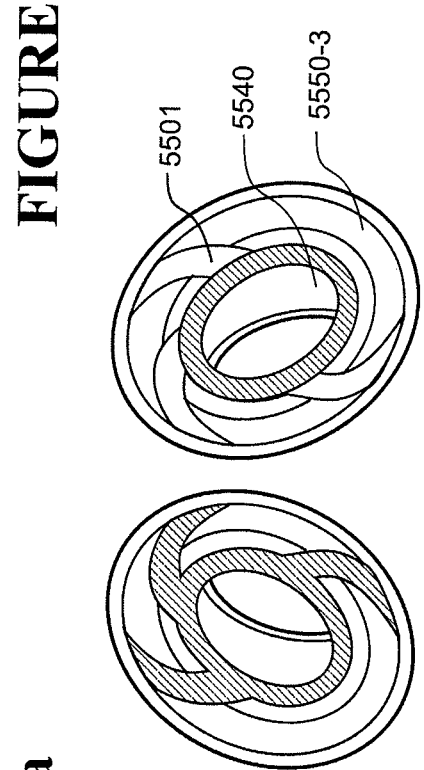
FIGURE 55a
FIGURE 55b
FIGURE 55c

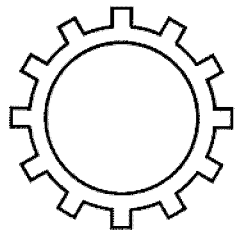
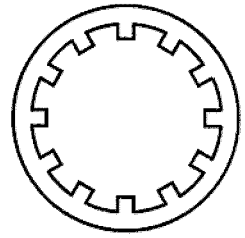
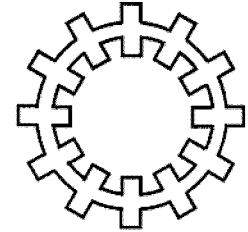
FIG. 75(a)    FIG. 75(b)    FIG. 75(c)
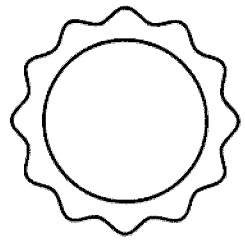
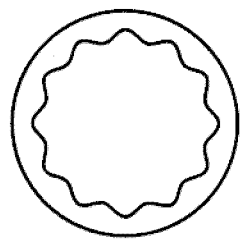
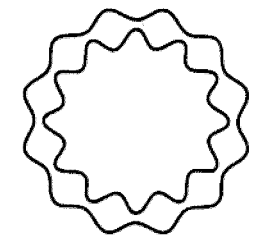
FIG. 75(d)    FIG. 75(e)    FIG. 75(f)
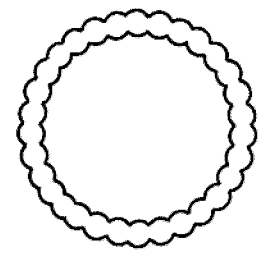
FIG. 75(g)

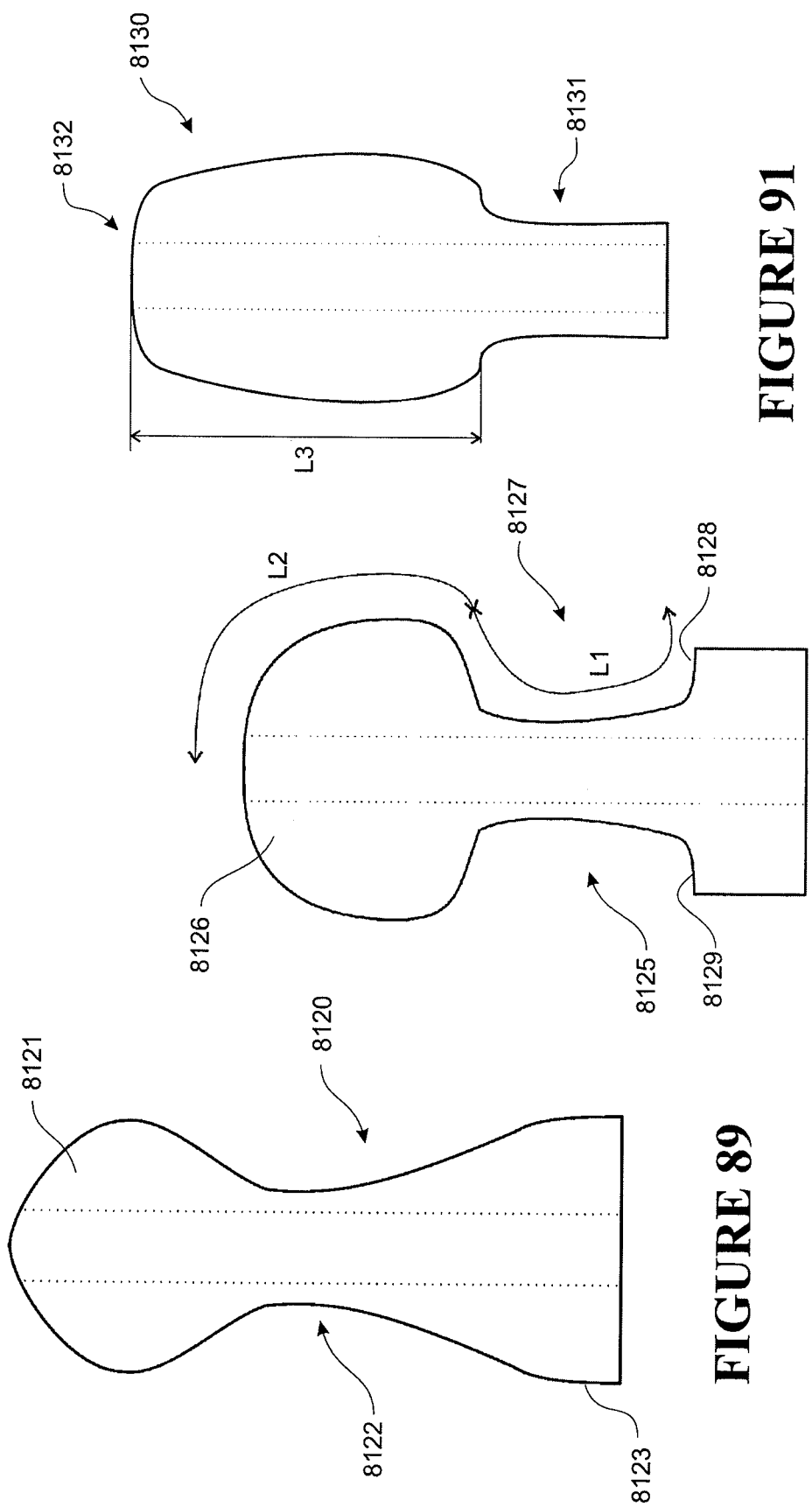

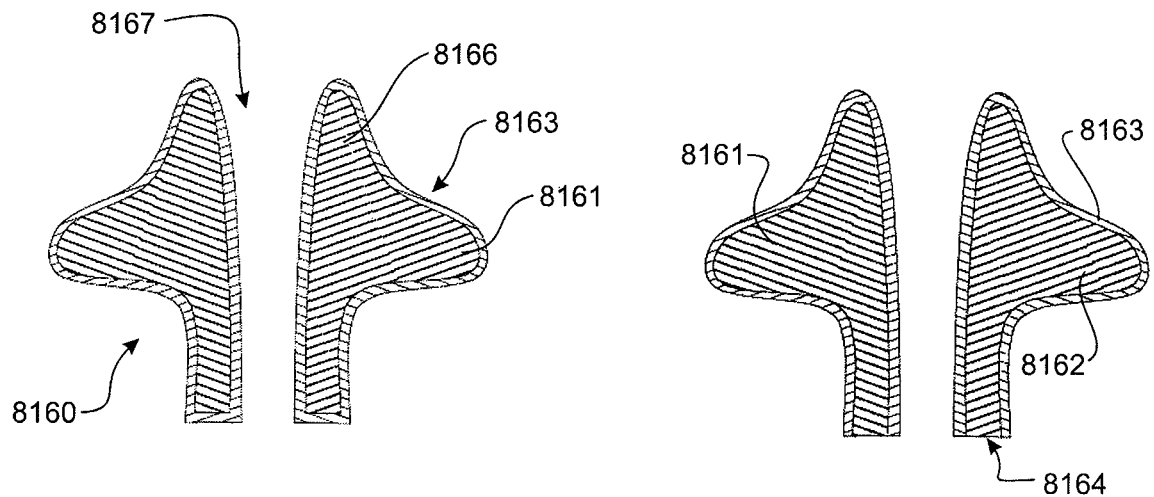
FIGURE 97  FIGURE 98
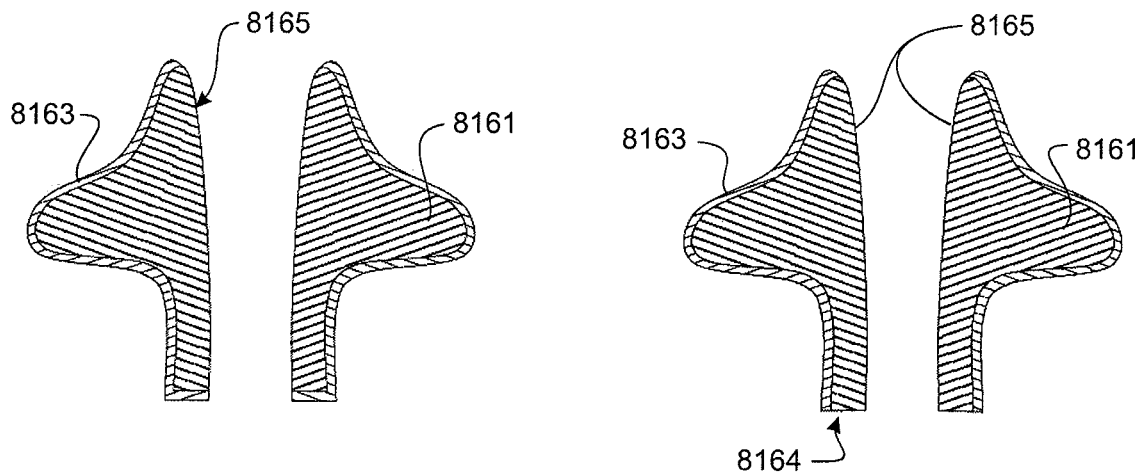
FIGURE 99  FIGURE 100
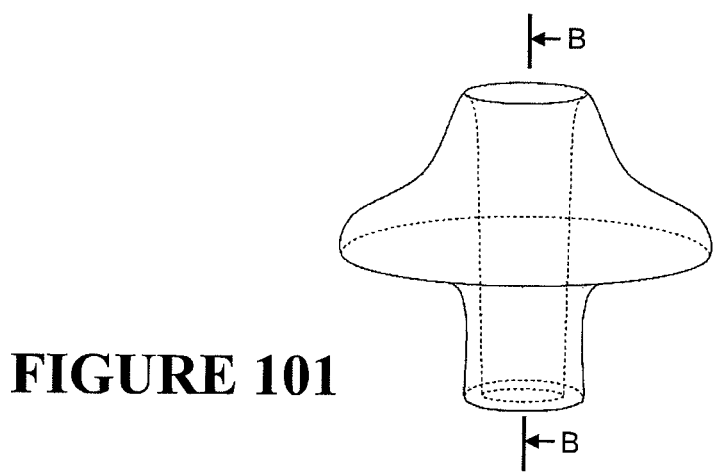
FIGURE 101

BREATHING ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND OF THE INVENTION

Field of the Invention

The present invention relates to a breathing assistance apparatus for treating sleep apnoea. More specifically, the present invention provides nasal interface for the supply of respiratory gases, but most particularly positive pressure gases.

The invention also relates to a patient interface which includes nasal pillows, or nasal plugs and which may also include associated elements such as headgear.

Description of the Related Art

Obstructive Sleep Apnoea (OSA) is a sleep disorder that affects up to at least 5% of the population in which muscles that normally hold the airway open relax and ultimately collapse, sealing the airway. The sleep pattern of an OSA sufferer is characterised by repeated sequences of snoring, breathing difficulty, lack of breathing, waking with a start and then returning to sleep. Often the sufferer is unaware of this pattern occurring. Sufferers of OSA usually experience daytime drowsiness and irritability due to a lack of good continuous sleep.

In an effort to treat OSA sufferers, a technique known as Continuous Positive Airway Pressure (CPAP) was devised. A CPAP device consists of a gases supply (or blower) with a conduit connected to supply pressurised gases to a patient, usually through a mask, nasal prongs, plugs or pillows. The pressurised air supplied to the patient effectively assists the muscles to keep the patient's airway open, eliminating the typical OSA sleep pattern.

The procedure for administering CPAP treatment has been well documented in both the technical and patent literature. Briefly stated, CPAP treatment acts as a pneumatic splint of the airway by the provision of a positive pressure, usually in the range 4 to 20 cm H2O. The air is supplied to the airway by a motor driven blower whose outlet passes via an air delivery hose to a nose (or nose and/or mouth) mask sealingly engaged to a patient's face by means of a harness or other headgear.

It is known to provide a flow of respiratory gases to a user via a nasal cannula to relieve a number of ailments, for example, sleep apnoea or snoring. One problem with supplying a flow of gases to a user via an interface such as a nasal interface, prongs or plugs ("nasal interface") is that it can be difficult to form a good seal between the nasal interface and the user's nostrils. The nasal interface is often held in place against the user's nose by headgear worn on the user's head. The head gear may be over tightened so that the nasal interface is pressed uncomfortably onto the user's nose. Alternatively the headgear may be applied to the user's head too loosely, preventing an effective seal being formed between the interface and user's nostrils. Also, the seal between the interface and the user's nostrils may be broken if the interface is knocked while the user sleeps, or if the user moves while sleeping.

There are a number of different mechanisms which are known in the art which are intended to offer a solution to this problem.

U.S. Pat. No. 4,782,832 describes a nasal puff assembly with a pair of bellows type corrugated nare elements designed to sit adjacent to and partially within the nose of the user. The assembly includes a hollow plenum to which the pair of nare elements are operationally connected. The plenum is configured to allow the nare elements to rotate and also shift laterally in order to custom fit the assembly to a wide variety of users.

US 2006/0107958 describes an adjustable ventilation interface including a nasal cannula body. The cannula body has a pair of nasal prongs that are adjustable with respect to each other. The nasal prongs are located on the top portion of the nasal cannula body to create a sealing interface with a user's nose. The cannula body has first and second bellows-like structures. The first bellows like structure provides adjustability in a centre-to-centre distance between the nasal prongs. The second bellows-like structure creates a sealing engagement with a bottom area of the user's nose. The nasal prongs have thin corrugated walls that are designed to inflate under pressure. In a compressed or folded state the prongs can be easily inserted into a user's nose. In an inflated state the prongs assume a barrel-shaped structure to provide a large, even sealing surface in the nares. The prongs are folded or corrugated when not in use, so that their outer perimeter or profile is smaller than when they are inflated. This allows them to be easily inserted into the user's nostrils. In use the prongs inflate and seal against the user's nostrils. Because the inner surface of the user's nostrils is smooth, in use when the gas is flowing through the prongs, the prongs will inflate and have a smooth outer surface.

U.S. Pat. No. 6,431,172 describes a nasal cannula with an inflatable plenum chamber mounted on a rigid support. A pair of nares elements are mounted on the inflatable plenum chamber for insertion into the nostrils of the user. The inflatable plenum chamber is flaccid when not pressurised and not effective in transmitting forces between nares elements and the rigid support. When inflated the inflatable plenum acts to absorb shocks and jolts without transmitting the shocks and jolts to the user. The inflatable plenum provides additional degrees of freedom for movement of the nares elements while at the same time increasing the range of movement in all directions to accommodate large physical differences between users. For example each nares element can move axially, laterally, rotate and tilt.

The prior art further includes a nasal pillows interface in which headgear retains a soft plenum in the vicinity of the user's nose. A pair of flexible protrusions engage against the nares of the recipient. Typically, the protrusions are able to axially compress and have a lateral freedom of movement relative to the supporting cushion. Examples are the ResMed Mirage Swift™ II, or the Fisher and Paykel Opus™ 360 interfaces or nasal masks. A variety of different pillow configurations which could be used with these interfaces are described and shown in WO 2008/014543 and US 2009/044808.

The prior art still further includes a nasal cannula interface. The nasal canal interface includes a plenum portion that rests against the upper lip of the user and a pair of prongs. Each prong extends into the nostril of the user. An example is the Nasal-Aire interface made by Innomed, where gases are provided to the interface and the prongs by conduits or hoses that extend from the users nose across their cheeks, over their ears and around the back of their head.

Interfaces such as those described above are frequently used for delivering pressurised gases to a person being treated for obstructive sleep apnea (OSA) or other sleep disorders. These users typically wear the interface in a home sleeping environment. Comfort and effective sealing even under conditions of patient movement are major considerations.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

SUMMARY OF THE INVENTION

It is an object of the present invention to attempt to provide an interface that goes some way to overcoming disadvantages in the prior art or which will at least provide the industry with a useful choice.

In a first aspect the present invention consists in a nasal interface for supplying a flow of respiratory gases to a user comprising: head gear, in use the head gear being fitted to the user's head, a manifold having a manifold inlet, in use the manifold being attached to the head gear so that the manifold locates adjacent the user's nose, the inlet adapted to in use receive a flow of gases from a gases supply, a pair of nasal pillows, each nasal pillow comprising a nasal puff and a tubular base, the nasal puff being connected to and in fluid communication with the tubular base, in use, each said tubular base being attached to and in fluid communication with the manifold, the tubular base and the nasal puff adapted to allow the flow of gases to enter the pillow through the tubular base and exit the pillow through the nasal puff, the pair of nasal puffs sealingly engaging with the user's nostrils, each said tubular base having a ribbed section which extends at least part way around the circumferential perimeter of the tubular base, the ribbed section formed by a plurality of thick walled portions spaced apart, each thick walled portion being separated from adjacent thick walled portions by intervening thin walled portions.

In a second aspect the present invention consists in a nasal pillow for use with a nasal interface for supplying a flow of respiratory gases to a user, the nasal pillow comprising:
  a nasal puff and a tubular base, the nasal puff being connected to and in fluid communication with the tubular base,
  the tubular base and the nasal puff adapted to allow the flow of gases to enter the pillow through the tubular base and exit the pillow through the nasal puff, in use the nasal puff sealingly engaging with the user's nostril,
  the tubular base having a ribbed section which extends at least part way around the circumferential perimeter of the tubular base,
  the ribbed section formed by a plurality of thick walled portions spaced apart, each thick walled portion being separated from adjacent thick walled portions by intervening thin walled portions.

In a third aspect the present invention consists in a nasal cannula assembly for use with a nasal interface for supplying a flow of respiratory gases to a user, the nasal cannula assembly comprising:
  a manifold having a manifold inlet, in use the manifold being located adjacent the user's nose, in use the inlet receiving a flow of gases from a gases supply,
  a pair of nasal pillows, each nasal pillow comprising a nasal puff and a tubular base, the nasal puff being connected to and in fluid communication with the tubular base,
  in use, each said tubular base being attached to and in fluid communication with the manifold, the tubular base and the nasal puff adapted to allow the flow of gases to enter the pillow through the tubular base and exit the pillow through the nasal puff, the pair of nasal puffs sealingly engaging with the user's nostrils,
  each said tubular base having a ribbed section which extends at least part way around the circumferential perimeter of the tubular base,
  the ribbed section formed by a plurality of thick walled portions spaced apart, each thick walled portion being separated from adjacent thick walled portions by intervening thin walled portions.

In a fourth aspect the present invention consists in a system for supplying a flow of respiratory gases to a user comprising:
  a blower for supplying the flow of respiratory gases through the system,
  a humidifier unit, the blower supplying the flow of respiratory gases to the humidifier unit, the humidifier unit humidifying the flow of respiratory gases to a humidification level,
  a conduit for transporting the flow of gases from the humidification unit to a nasal interface, in use the nasal interface supplying the flow of respiratory gases to a user, the nasal interface comprising:
  head gear, in use the head gear being fitted to the user's head,
  a manifold having a manifold inlet, in use the manifold being attached to the head gear so that the manifold locates adjacent the user's nose, the inlet adapted to in use receive a flow of gases from a gases supply,
  a pair of nasal pillows, each nasal pillow comprising a nasal puff and a tubular base, the nasal puff being connected to and in fluid communication with the tubular base,
  in use, each said tubular base being attached to and in fluid communication with the manifold, the tubular base and the nasal puff adapted to allow the flow of gases to enter the pillow through the tubular base and exit the pillow through the nasal puff, the pair of nasal puffs sealingly engaging with the user's nostrils,
  each said tubular base having a ribbed section which extends at least part way around the circumferential perimeter of the tubular base,
  the ribbed section formed by a plurality of thick walled portions spaced apart, each thick walled portion being separated from adjacent thick walled portions by intervening thin walled portions.

In a fifth aspect the invention consists in an interface for use as part of an apparatus for providing a stream of gases to a user, comprising:

a manifold, including a gases supply aperture adapted for connection to a flexible and lightweight gases supply conduit or tube in use to receive a stream of gases therefrom, a pair of supple nasal pillows fluidically connected to said manifold so that in use said stream of gases passes through said nasal pillows, said nasal pillows adapted to substantially seal against the nostrils of a user in use, so that substantially the whole of said stream of gases is delivered to said user, a pair of connecting arms extending generally one from each side of said manifold in use and adapted for connection to a headgear or similar, said connecting arms and said pillows each formed from the same or similar materials, so that said connecting arms and said pillows have the same or substantially similar flexibility and suppleness.

In a sixth aspect the invention consists in an interface assembly for use as part of an apparatus for providing a stream of gases to a user, comprising:

a flexible and lightweight interface gases supply tube or conduit having a first or distal end and a second or proximal end, said first or distal end adapted to receive a gases stream from a gases supply apparatus in use, a manifold, including a gases supply aperture, said second end and said gases supply aperture mutually adapted for connection so that in use said manifold receives said stream of gases, a pair of supple and flexible nasal pillows fluidically connected to said manifold so that in use said stream of gases passes through said nasal pillows, said nasal pillows adapted to substantially seal against the nostrils of a user in use, so that substantially the whole of said stream of gases is delivered to said user, a pair of connecting arms extending generally one from each side of said manifold and adapted for connection to a headgear or similar, said connecting arms and said pillows each formed from the same or similar materials, so that said connecting arms and said pillows have the same or substantially similar flexibility and suppleness.

In a seventh aspect the invention consists in an interface for use as part of an apparatus for providing a stream of gases to a user, comprising:

a manifold, including a gases supply aperture adapted for connection to a flexible and lightweight gases supply conduit or tube in use to receive a stream of gases therefrom, a pair of supple nasal pillows fluidically connected to said manifold so that in use said stream of gases passes through said nasal pillows, said nasal pillows adapted to substantially seal against the nostrils of a user in use, so that substantially the whole of said stream of gases is delivered to said user, a pair of connecting arms extending generally one from each side of said manifold in use and adapted for connection to a headgear or similar, said manifold configured so that in use said gases supply aperture is aligned substantially vertically downwards, said manifold and said pillows configured so that said interface will not extend beyond the end of the nose of an average user in use.

Preferably said manifold is formed from a rigid or semi-rigid material, said interface further including a gasket formed from a supple and flexible material, said gasket connected or attached to said manifold in use, said nasal pillows connected to said gasket.

Preferably said manifold includes a substantially open upper portion or face, and said gasket is adapted to connect over the top of said open upper portion.

Preferably said manifold is configured so that in use said gases supply aperture is aligned substantially vertically downwards.

Preferably said manifold, said gasket and said pillows are configured so that said interface will not extend beyond the end of the nose of an average user in use.

Preferably at least said gasket and said connecting arms are formed as a unitary or one-piece item.

Even more preferably said gasket, said connecting arms and said pillows are formed as a unitary or one-piece item.

Preferably said gasket includes an open portion which in use is stretched over the outside of the open upper face of said manifold so that said gasket covers and closes the open face of the manifold, with said gasket sealing against the outer surface of the manifold.

Preferably said gases supply aperture is adapted for connection to a flexible and lightweight gases supply conduit by way of a male-female push-fit connection.

Alternatively said gases supply aperture is adapted for connection to a flexible and lightweight gases supply conduit by way of a ball joint connection.

Preferably each of said arms has an L-shape in profile, one face of the L-shape of each arm resting against the face of a user in use.

Preferably said manifold includes a limited flow outlet for providing gas washout from said interface.

Alternatively said proximal end of said gases supply conduit includes a limited flow outlet for providing gas washout from said interface.

Preferably said gasket includes a lip cushion located on the rear of said interface and resting against a users top lip in use.

Preferably said lip cushion is sealed from said flow of gases.

Alternatively said lip cushion receives part of said flow of gases in use and at least partially inflates.

Preferably said connecting arms are integrally connected with said manifold and said gasket, said connecting arms and said pillows formed as a unitary or one-piece item, said gasket including an open portion which in use is stretched over the outside of the open upper face of said manifold so that said gasket covers and closes the open face of the manifold, with said gasket sealing against the outer surface of the manifold.

Alternatively said gasket and said pillows are integrally connected to said manifold, said arms formed as a unitary or one-piece item, merging at their inner ends into a hollow aperture which is shaped and sized with the outer sides or surfaces of said gasket and said manifold, said manifold in use passed into said hollow aperture so that said manifold, or said gasket, or both wedge into said hollow aperture.

Preferably said gasket includes a flared portion from the outer part towards the inner part closest to a user, and said hollow aperture corresponds to said flared portion, so that when said manifold is passed into the hollow aperture, that part of said manifold which forms the gases supply aperture and the outer part of the manifold which includes the limited flow outlet passes through the aperture and the inner part of said manifold and said gasket wedges into said hollow aperture.

Preferably said interface assembly further includes a lanyard, said lanyard forming a loop, one point on said loop connected at or close to the distal end of said supply conduit.

Preferably said interface assembly further includes a lanyard, said lanyard formed as two separate lengths, the outer ends of said lengths connects at or close to the distal end of said supply conduit, the inner ends of said lengths connected to said headgear.

Preferably said flexible and lightweight interface gases supply tube will not support its own weight when held at one end in such a manner that the main body of the conduit extends outwards from the held end generally horizontally, and over a 20 to 30 cm length of supply conduit having a typical diameter of 1 to 2 cm and a wall thickness at the ribs of 1 to 3 mm and a wall thickness between the ribs of less than 1 mm, the unsupported end of the supply conduit will bend and 'droop' so that the unsupported end points substantially or directly downwards or bends through at least 70 degrees over this length.

In an eighth aspect the present invention consists in a nasal plug for inserting in a patient's nare to supply gases to said patient comprising:
- a foam body with a bore there through for the passage of said gases,
- a skin, substantially covering the exterior surfaces of said foam body.

Preferably said skin is made from a plastics or silicone material.

Preferably said skin extends over the surfaces of said bore.

Preferably said skin is perforated.

Preferably said foam body is tubular with a curved tip.

Preferably said foam body has a tip and an end, with a circumferential flange there between, said flange in use resting against the external surface of said patient nare.

Preferably said nasal plug further comprises a circumferential flap extending downwards from said tip.

Alternatively said nasal plug further comprises a circumferential flap extending upwards from said flange.

In a ninth aspect the present invention consists in a nasal plug for inserting in a patient's nare to supply gases to said patient comprising:
- a foam body with a bore there through for the passage of said gases, said foam body having a tip and an end, with a circumferential flange there between,
- a skin substantially covering the exterior surfaces of said foam body, and
- a circumferential flap extending from one of said tip and said flange.

In a tenth aspect the present invention consists in a nasal plug for inserting in a patient's nare to supply gases to said patient comprising:
- a foam body having an inlet and a bifurcated bore there through for the passage of said gases,
- two nasal members formed in said foam body, in use extending into a patient's nares, one each of said bifurcated branches of said tubular bore extending through each of said nasal member and terminating in an outlet in each of said nasal member, and
- a circumferential flange formed in said foam body between said inlet and said outlets on said nasal members.

Preferably said nasal plug further comprises a coating substantially covering the exterior surfaces of said foam body.

In a further aspect the invention consists in a nasal pillow section for use as part of a system for delivering a stream of gases to a user, said system of the type that includes a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
- a gasket portion, adapted to receive said stream of gases from said supply conduit,
- a pair of pillow portions connected to and extending from said pillow gasket, said pillow portions adapted to receive said stream of gases from said pillow gasket and provide said stream of gases to said user, each of said pillow portions having a stalk, the base of said stalk connected to said pillow gasket, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user,
- said outer cap having at least one and preferably a pair of ribs that extend from the inner surface of said outer cap towards said inner cap, said at least one rib having a height less than the height of said outer cap, said rib located on said inner surface of said outer cap so that said at least one rib does not extend all the way to the top nor all the way to the bottom of said outer cap.

Preferably said at least one rib is rounded, so that the upper and lower ends of said rib blend with said inner surface of said outer cap.

Preferably said at least one rib is located towards the top of said inside wall of said outer cap.

Preferably said at least one rib is a pair of ribs, said pair spaced opposite to one another on the perimeter of said inner surface of said outer cap.

Preferably said rib or ribs are of substantially equal width.

Alternatively the width of said rib or ribs varies over the height of said rib or ribs.

In a another aspect the invention consists in a nasal pillow section for use as part of a system for delivering a stream of gases to a user, said system of the type that includes a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
- a gasket portion, adapted to receive said stream of gases from said supply conduit,
- a pair of pillow portions connected to and extending from said pillow gasket, said pillow portions adapted to receive said stream of gases from said pillow gasket and provide said stream of gases to said user, each of said pillow portions having a stalk, the base of said stalk connected to said pillow gasket, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user,
- said inner cap having at least one and preferably a pair of ribs extending from the outer surface of the wall of said inner cap, said at least one rib not extending the full length or height of said inner cap, said rib not extending to either of the rim or the base of said inner cap.

Preferably said at least one rib is rounded so that the upper and lower ends of said rib blend with said inner surface of said inner cap.

Preferably said at least one rib extends between one fifth and four fifths of the height of said inner cap.

Preferably said rib or ribs is a pair of ribs spaced equidistant around the perimeter of said inside pillow.

Preferably each of said ribs are of equal width.

Alternatively the width of said rib or ribs varies with the height of said rib or ribs.

In a further aspect the invention consists in a nasal pillow section for use as part of a system for delivering a stream of gases to a user, said system of the type that includes a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said pillow gasket, said pillow portions adapted to receive said stream of gases from said pillow gasket and provide said stream of gases to said user, each of said pillow portions having a stalk, the base of said stalk connected to said pillow gasket, and a cap section, said cap connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, each of said pillow portions having at least one and preferably a pair of ribs extending from the rim of said inner cap to the base of said inner cap, said rib tapering in thickness from zero at the top rim of said inner cap to a maximum at the base of said inner cap, and extending across the width of said airgap at said base.

Preferably said at least one rib or ribs are equally spaced apart around the perimeter of said inner cap.

Preferably said at least one rib is a pair of ribs.

Preferably each of said rib or ribs have substantially the same width over their height.

Alternatively the width of said rib or ribs varies with the height of said rib or ribs.

Preferably the base of said rib or ribs is thicker than the upper portion of said rib or ribs.

Alternatively the base of said rib or ribs is thinner than the upper portion of said rib or ribs.

In a further aspect the invention consists in a nasal pillow section for use as part of a system for delivering a stream of gases to a user, said system of the type that includes a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said pillow gasket, said pillow portions adapted to receive said stream of gases from said pillow gasket and provide said stream of gases to said user, each of said pillow portions having a stalk, the base of said stalk connected to said pillow gasket, and a cap section, said cap section connected to the upper end of said stalk, said cap formed from an inner cap and an outer cap, said inner cap and said outer cap arranged substantially concentrically and separated by a cavity when not in use, said outer cap surrounding said inner cap, the outer surface of said outer cap adapted to substantially seal against the nare of said user, each of said pillow portions has at least one rib and preferably a pair of ribs that extend inwards and downwards from the rim of said outer cap to preferably contact and most preferably connect with the rim of said inner cap, said rib contacting and most preferably merging with the outer surface of said inner cap from said rim of said inner cap to the base of said inner cap.

Preferably said at least one rib or said ribs are spaced substantially equidistant from one another around the perimeter of said pillow.

Preferably said at least one rib is a pair of ribs.

Preferably said at least one rib or ribs have substantially the same width over their height.

Alternatively the width of said rib or ribs varies with the height of said rib or ribs.

Preferably the base of said rib or ribs is thicker than the upper portion of said rib or ribs.

Alternatively the base of said rib or ribs is thinner than the upper portion of said rib or ribs.

In a further aspect the invention consists in a nasal pillow section for use as part of a system for delivering a stream of gases to a user, said system of the type that includes a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said pillow gasket, said pillow portions adapted to receive said stream of gases from said pillow gasket and provide said stream of gases to said user, each of said pillow portions having a stalk, the base of said stalk connected to said pillow gasket, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, each of said pillow portions has at least one rib and preferably a pair of ribs which extend inwards and downwards from the rim of said outer cap, said at least one rib extending downwards to the base of said outer cap, in such a manner that there is always an airgap or cavity between that part, side or edge of said rib closest to the outer surface of said inner cap, and the outer surface of said inner cap.

Preferably said at least one rib or ribs are spaced equidistant from each other around the perimeter of said inside wall of said outer cap.

Preferably said at least one rib is a pair of ribs.

Preferably said at least one rib or ribs have substantially the same width over their height.

Alternatively the width of said rib or ribs varies with the height of said rib or ribs.

Preferably the base of said rib or ribs is thicker than the upper portion of said rib or ribs.

Alternatively the base of said rib or ribs is thinner than the upper portion of said rib or ribs.

In a further aspect the invention consists in a nasal pillow section for use as part of a system for delivering a stream of gases to a user, said system of the type that includes a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said pillow gasket and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap section and stalk also forming an airway that acts as a path for said stream of gases to flow through said pillow section and to said user, each of said pillow portions also having at least one fin which extends into said air gap and which runs between the rim of said outer cap and the base of said inner and outer caps, said fin extending across said pillow portion from one side to the other, said fin having a central portion located between the inner sides of said inner cap, the top edge of said central portion substantially aligned with the rim of said outer cap, the lower edge of located above the bases of inner and outer caps.

Preferably said fin has parallel sides.

Preferably said fin tapers in thickness, said fin being thicker at its base than at its rim.

Preferably said fin extends straight across said pillow section.

Preferably said fin curves across the width of said pillow section.

Preferably the vertex of said curve is centrally located.

Alternatively the vertex of said curve is offset from the centre of said pillow section.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said pillow gasket and provide said stream of gases to said user, each of said pillow portions having a stalk, the base of said stalk connected to said pillow gasket, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap and stalk also forming an airway that acts as a path for said stream of gases to flow through said pillow section and to said user, each of said pillow portions having a recess that forms an air gap in said airway, said recess formed at the point where said inner cap attaches to the top of the stalk, said recess following the perimeter of said inner cap, each of said pillow portions having at least one and preferably a series of ribs within the recess.

Preferably said ribs are a series of ribs and are spaced at substantially equal intervals around said perimeter.

Preferably said ribs are a pair of ribs, diametrically opposed on said nasal pillow section.

Preferably said ribs have an inner edge or surface that generally follows and is aligned with the inner wall of said inner pillow and said stalk.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said pillow gasket, and a cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap and stalk also including an airway that acts as a path for said stream of gases to flow through said pillow section and to said user, said inner cap thicker at the top edge or rim than at the bottom edge or base.

Preferably the wall of said outer cap is thinner than the wall of said inner cap.

Preferably said inner cap gradually tapers in thickness, from being thin at the base to thicker at the rim.

Preferably said inner and outer caps are flared in an upward and outward direction from said base, said inner cap flared to a greater extent than said outer cap.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap and stalk also including an airway that acts as a path for said stream of gases to flow through said pillow section and to said user, said inner cap having a bead which extends inward from the top edge of said inner cap, and said outer cap having a bead which extends inward from the top edge of said outer cap.

Preferably said bead extends in an unbroken ring around the entire perimeter of said outer cap and said inner cap.

Preferably said bead is substantially circular in shape.

Preferably the wall of said inner cap tapers in thickness, said wall of said inner cap being thicker at the base than at said rim or top edge.

Alternatively the wall of said inner cap has a uniform thickness.

Preferably said bead is thicker in cross-section than the wall thickness of said outer cap and said inner cap.

Preferably said bead applied to said outer cap is substantially identical to said bead applied to said inner cap.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, said inner and outer caps having a common base which connects to said upper end of said stalk, the outer surface of said outer cap adapted to substantially seal against the nare of said user, said cap and stalk also including an airway that acts as a path for said stream of gases to flow through said pillow section and to said user, said pillow portion having a flange that extends from said common base upwards into said airgap.

Preferably said flange extends upwards substantially parallel to the inner surface of said outer cap or the outer surface of said inner cap, or both.

Preferably said flange is generally triangular in cross-section.

Preferably said flange tapers in cross section, said flange thicker at its base and thinner at its upper extreme.

Preferably said flange is the same or greater thickness than the wall of said inner cap wall.

Preferably said flange is the same or greater thickness than the wall of said outer cap wall.

In yet another aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said pillow gasket, and a cap section, said cap section connected to the upper end of said stalk, said cap formed from an inner cap and an outer cap, said inner cap and said outer cap arranged substantially concentrically, said outer cap surrounding said inner cap, the outer surface of said outer cap adapted to substantially seal against the nare of said user, said cap and stalk also including an airway that acts as a path for said stream of gases to flow through said pillow section and to said user, said outer cap having at least one bead extending inward from the inner surface of the wall of said outer cap and around the perimeter of said outer cap, said bead located below the upper rim of said outer cap.

Preferably said bead is substantially semi-circular in cross section.

Preferably said bead is thicker in cross-section than said outer cap wall.

Preferably the cross-sectional thickness of said bead is substantially twice the thickness of said outer cap wall.

Preferably said bead has a constant thickness and runs around the entire perimeter of said outer cap.

Preferably said bead is located in the top one third of said outer cap.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap and stalk also including an airway that acts as a path for said stream of gases to flow through said pillow section and to said user, said inner cap has at least one bead extending outward from said inner cap and running around the perimeter of said inner cap.

Preferably said bead has a substantially round cross section.

Preferably the cross-sectional thickness of said bead is greater than that of said inner cap wall.

Preferably the wall of said inner cap has a uniform thickness.

Preferably the wall of said outer cap has a uniform thickness.

Preferably said bead is located approximately two thirds of the way up the outer surface of said inner cap.

Alternatively said bead is located at and extends around the rim of said inner cap.

Preferably said bead has a constant thickness around the entire perimeter of said inner cap.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap and stalk also including an airway that acts as a path for said stream of gases to flow through said pillow section and to said user, said outer cap having at least one bead extending outwardly from the rim of said outer cap, and running around the perimeter of said outer cap.

Preferably bead is substantially semi-circular in cross section.

Preferably said bead is thicker in cross-section than the wall of said outer cap.

Preferably said bead has a constant cross section along its perimeter and said bead runs around the entire perimeter of said outer cap.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap and stalk also including an airway that acts as a path for said stream of gases to flow through said pillow section and to said user, said inner cap including at least one bead extending inward from the rim of said inner cap and running around the perimeter of said inner cap.

Preferably said bead has a substantially circular cross section.

Preferably said bead has a substantially constant cross-sectional thickness.

Alternatively said bead differs in thickness at various points along the perimeter of said inner cap.

Preferably the wall of said inner cap is of uniform thickness.

Alternatively the wall of said inner cap tapers, said inner cap being thicker at its base than at its rim.

Preferably said outer cap is of uniform thickness.

Preferably said bead has a thicker cross-section than the wall of said inner cap or said outer cap or both.

More preferably said bead is substantially twice the thickness of the wall of said inner cap.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
- a gasket portion, adapted to receive said stream of gases from said supply conduit,
- a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap and stalk also including an airway that acts as a path for said stream of gases to flow through said pillow section and to said user,
- said outer cap having a bead located on and around the upper rim of said outer cap extending inwards.

Preferably said bead is substantially round in cross section.

Preferably said bead is thicker in cross section than the wall of said outer cap, or said inner cap, or both.

More preferably said bead is substantially twice the thickness of said outer cap.

Preferably said bead has a constant thickness.

Alternatively said bead varies in thickness at various points around the perimeter of said outer cap.

Preferably the wall of said inner cap is of uniform thickness.

Alternatively the wall of said inner cap tapers in thickness, said inner cap being thicker at its base than at its rim.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
- a gasket portion, adapted to receive said stream of gases from said supply conduit,
- a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap and stalk also including an airway that acts as a path for said stream of gases to flow through said pillow section and to said user,
- said inner cap and said outer cap are substantially the same height so that the rim of said outer cap and the rim of said inner cap are substantially aligned and planar.

Preferably the wall of said inner cap has a uniform thickness.

Preferably the wall of said outer cap has a uniform thickness.

Alternatively the wall of said inner cap is tapered in thickness, said inner cap being thicker at its base and thinner at its rim.

Alternatively the wall of said outer cap is tapered in thickness, said outer cap being thicker at its base and thinner at its rim.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
- a gasket portion, adapted to receive said stream of gases from said supply conduit,
- a pair of pillow portions connected to and extending from said pillow gasket, said pillow portions adapted to receive said stream of gases from said pillow gasket and provide said stream of gases to said user, each of said pillow portions formed from an air delivery tube, the base of said air delivery tube connected to said pillow gasket, and a cap section, said cap section connected to and partially surrounding said air delivery tube over at least part of the length or height of said air delivery tube, the outer surface of said cap adapted to substantially seal against the nare of said user,
- said air delivery tube having an inner surface with parallel walls or sides.

Preferably the top edge or rim of said air delivery tube is in line or planar with the rim of said cap.

More preferably said air delivery tube extends above and out of said cap, such that the rim of said air delivery tube is located above the rim of said cap.

Preferably the internal walls of said air delivery tube are parallel, and the outer walls of said air delivery tube taper, being thicker at the base of said air delivery tube than at the rim.

Alternatively said cap has a thinner cross-sectional thickness than said air delivery tube.

Preferably said cap extends above said air delivery tube, such that the rim of said cap is above the rim of said air delivery tube.

Preferably the wall of said cap is of uniform cross-sectional thickness.

Alternatively the wall of said cap tapers in thickness such that said cap is thicker at its base than at its rim.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
- a gasket portion, adapted to receive said stream of gases from said supply conduit,
- a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said stream of gases flowing through said stalk and said cap section to said user, the wall of said outer cap tapered in cross-sectional thickness so that said outer cap wall is thicker at the upper rim of said outer cap than at the base of said outer cap.

Preferably the wall of said inner cap tapers in cross-sectional thickness such that said inner cap wall is thicker at the base of said inner cap than at the rim.

Preferably said outer cap is taller than said inner cap, the base of said inner cap and the base of said outer cap co-located so that the rim of said outer cap is above the rim of said inner cap.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap section and stalk forming an airway that acts as a path for said stream of gases to flow to said user, said inner cap extending at least partially from the upper end of said outer cap.

Preferably the wall of said inner cap is thicker in cross-section than the wall of said outer cap.

Preferably said inner cap has a uniform thickness in cross-section.

Alternatively said inner cap tapers in cross-sectional thickness, the base of said inner cap thicker than the rim of said inner cap.

Preferably said outer cap is of uniform cross-sectional thickness.

Alternatively said outer cap tapers in cross-sectional thickness, the base of said outer cap thicker than the rim of said outer cap.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap section formed from an inner air delivery tube having substantially parallel inner walls that substantially align with the inner wall of said stalk so that said inner air deliver tube extends upwards from the top of said stalk, and an outer cap which surrounds and extends above the top of said inner air delivery tube in such a manner that there is an air gap between said inner air delivery tube and said outer cap, said outer cap having a bead which is formed on and extends substantially inward from the rim of said outer cap.

Preferably said air delivery tube tapers in cross-sectional thickness, the inner wall of said air deliver tube having parallel sides, the outer sides tapering inwards towards the top of said air delivery tube.

Preferably said outer cap has a uniform cross-sectional thickness.

Preferably said bead extends inwards from and around said rim of said outer cap, around the entire perimeter of said outer cap.

Preferably bead is thicker in cross-section than the cross-sectional thickness of said outer cap or air delivery tube or both.

Preferably said bead has a uniform cross-sectional thickness.

Alternatively said bead varies in cross-sectional thickness around the perimeter of said cap.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said cap and stalk forming an airway that acts as a path for said stream of gases to flow through said pillow portion to said user, said pillow section having at least one rib which extends across said airgap between said inner and outer caps, said at least one rib aligned substantially radially.

Preferably said pillow section has a series of ribs, spaced at substantially even or equal distances around said cap.

More preferably said pillow section has four ribs, said ribs spaced around said cap at substantially 90-degree intervals.

Alternatively said pillow section has a pair of ribs extending across said airgap and aligned substantially radially, each of said ribs angled towards the inner side or user side of said pillow section.

Preferably one of said ribs is aligned so that one of said ribs is also angled slightly inwards towards the centreline of said pillow section, and the other of said ribs is also angled outwards away from said centreline towards the outer side of said pillow section.

Alternatively said pillow section has two ribs that extend across said airgap, said ribs aligned such that said ribs are substantially 180 degrees apart or aligned diametrically across said airgap.

In a further alternative said pillow section has three ribs spaced at substantially even or equal distances around said cap, spaced around said cap at substantially 60-degree intervals.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said pillow gasket, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap and extending above said inner cap, the outer surface of said outer cap adapted to substantially seal against the nare of said user, said cap and stalk forming an airway that acts as a path for said stream of gases to flow through said pillow portion to said user, said outer cap having at least one partial rib and more preferably multiple partial ribs extending inward toward said inner cap from said outer cap, and running from the top edge or rim of said outer cap downwards along the surface of the inside wall of said outer cap, said partial rib or partial ribs extending partway from said top edge to the base of said outer cap.

Preferably said pillow section has multiple partial ribs, each of said partial ribs having the same height as each of the other partial ribs.

Alternatively said pillow section has multiple partial ribs, at least one of said partial ribs having a different height to the others.

Preferably said pillow section has multiple partial ribs, each of said partial ribs having the same thickness as each of the other partial ribs.

Alternatively said pillow section has multiple partial ribs, at least one of said partial ribs having a different thickness to the others.

Preferably said partial rib or partial ribs extends from said top edge or rim downwards for substantially one fifth of the height of said outer cap.

Preferably said rib is substantially circular in cross section and has rounded edges that blend into said inside wall of said outer cap.

Preferably said at least one partial rib has a thicker centre than outer extremes.

Preferably the wall of said inner cap and the wall of said outer cap taper in cross sectional thickness, being thicker at their base than at the top or upper edge or rim.

Alternatively the wall of said inner cap and the wall of said outer cap have a constant cross-sectional thickness.

Preferably said pillow section has a pair of identical partial ribs, spaced at substantially 180 degrees from each other on the perimeter of said outer cap.

In a still further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

a gasket portion, adapted to receive said stream of gases from said supply conduit, a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap and extending above said inner cap, the outer surface of said outer cap adapted to substantially seal against the nare of said user, said cap and stalk forming a path for said stream of gases, a fin aligned radially across said pillow portion, said fin having side portions that extend from the bottom of said air gap at radially opposed sides of said pillow portion, up to the rim or top of said outer cap and the rim or top of said inner cap, and a central portion that extends across the width of said pillow portion between said side portions, said central portion extending from the top edge or rim of said inner cap to the top edge or rim of outer pillow, said fin formed integrally with the material of said inner and outer caps.

Preferably said fin has a uniform cross-sectional thickness.

Alternatively said fin tapers in cross-sectional thickness, said fin thicker at the lower end at the base of said outer cap than at the upper end.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
- a gasket portion, adapted to receive said stream of gases from said supply conduit,
- a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap section, said cap section connected to the upper end of said stalk, said cap formed from an inner cap and an outer cap, said inner cap and said outer cap arranged substantially concentrically and separated by an air gap when not in use, said outer cap surrounding said inner cap and extending above said inner cap, the outer surface of said outer cap adapted to substantially seal against the nare of said user, said inner and outer caps and said stalk forming an airway that acts as a path for said stream of gases to flow through said pillow portion to said user,
- each of said pillow portions having at least one fin that extends diametrically across said pillow portion, said fin having a top edge or surface that is substantially aligned with the top edge or rim of said outer pillow, and a lower edge or surface that is substantially aligned with the top edge or rim of said inner cap.

Preferably said fin has a uniform cross-sectional thickness.

Alternatively said fin tapers in cross-sectional thickness, said fin thicker at said lower edge or surface than at said upper edge or surface.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
- a gasket portion, adapted to receive said stream of gases from said supply conduit,
- a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, the outer surface of said cap adapted to substantially seal against the nare of said user, said caps and said stalk forming an airway that acts as a path for said stream of gases to flow through said pillow portion to said user,
- said cap including at least one partial rib extending inward from the inside surface of the cap, and also extending downwards from the top edge or rim of said cap along the inside surface of said cap, said rib or ribs extending partway down the height of said cap from said top edge towards the base of said cap.

Preferably said pillow section has multiple partial ribs, each of said partial ribs having the same height or length as each of the other partial ribs.

Preferably said pillow section has multiple partial ribs, at least one of said partial ribs having a different height or length to the others.

Preferably said nasal pillow section has multiple partial ribs, each of said partial ribs having the same cross-sectional thickness as each other of said partial ribs.

Preferably said nasal pillow section has multiple partial ribs, at least one of said partial ribs having a different cross-sectional thickness to the other partial ribs.

Preferably said partial rib is curved from top to bottom along the inside edge of said rib.

Preferably each one of said partial rib or ribs has a greater cross-sectional thickness at the top of the rib and tapers or curves in such a manner that said partial rib merges with the wall of said pillow portion at the bottom of said rib.

More preferably each one of said partial rib or ribs extends from the top edge or rim of said downwards for substantially one third of the height of said cap.

Preferably said pillow section has two partial ribs diametrically opposed on the perimeter of said cap.

Even more preferably said cap wall is tapered in thickness, said cap wall being thicker at the base of said cap and thinner at the rim of said cap.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
- a gasket portion, adapted to receive said stream of gases from said supply conduit,
- a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, the outer surface of said cap adapted to substantially seal against the nare of said user, said caps and said stalk forming an airway that acts as a path for said stream of gases to flow through said pillow portion to said user,
- said cap including at least one but preferably a series of ribs extending inward from the inner surface of said cap, and extending from a point at or close to the top edge or rim of said cap and a point at or close to the base of said cap.

Preferably said pillow section has multiple ribs, at least one of said ribs having a different cross-sectional thickness to the others of said ribs.

Preferably said rib or ribs follow the contour of the inside surface of said cap wall, the top end and lower end of said rib curved towards the inner surface so as to blend with the inner surface of said cap, the cross-sectional thickness of said rib greatest at the centre of said rib.

Preferably said rib or ribs follow the contour of the inside surface of said cap wall, said rib having a constant cross-sectional thickness along its entire height or profile.

Alternatively said pillow section has a plurality of ribs, said ribs having the same cross-sectional thickness as each other.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
   a gasket portion, adapted to receive said stream of gases from said supply conduit,
   a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, the outer surface of said cap adapted to substantially seal against the nare of said user, said caps and said stalk forming an airway that acts as a path for said stream of gases to flow through said pillow portion to said user,
   said cap further comprising a fin, said fin aligned substantially diametrically across said cap, the top edge of said fin extending downwards from a position at or close to the top edge or rim of said cap to substantially three quarters of the way down the height of said cap.

In one form said fin has a uniform cross-sectional thickness or width at any position over the height of said fin.

In another form said fin tapers in width, said fin thicker at each end towards the inner surface of the wall of said cap than in the centre.

In a further form said fin tapers in thickness over the height of said fin, said fin having a base or lower end which is thicker than the upper end or top.

Preferably the bottom edge of said fin is curved upwards.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
   a gasket portion, adapted to receive said stream of gases from said supply conduit,
   a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, the outer surface of said cap adapted to substantially seal against the nare of said user, said caps and said stalk forming an airway that acts as a path for said stream of gases to flow through said pillow portion to said user,
   said cap having at least one bead which extends outwards from the outer surface of said cap, and which extends around the perimeter of said cap.

Preferably said bead extends in a substantially unbroken ring around the perimeter of said cap.

Preferably said bead is located at or close to the rim of said cap.

Preferably said bead is substantially semi-circular in cross section.

Preferably said bead is of uniform thickness along the entire perimeter of said cap.

Alternatively said bead differs in thickness at various points along the perimeter of said cap.

More preferably said bead is twice as thick as said cap wall.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
   a gasket portion, adapted to receive said stream of gases from said supply conduit,
   a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, the outer surface of said cap adapted to substantially seal against the nare of said user, said caps and said stalk forming an airway that acts as a path for said stream of gases to flow through said pillow portion to said user,
   said cap having a top edge or rim which in use is inserted into the nostril of a user, said top edge or rim having a greater cross-sectional thickness than at least the centre portion of said cap.

Preferably said top edge or rim is formed from the upper one fifth of said cap.

More preferably the cross-section of said cap is uniform, except for said top edge or rim.

Preferably the base of said cap has substantially the same thickness as said top edge or rim, and the middle or centre portion of said cap wall between said base and said top edge or rim is thinner than said top edge or rim and said base.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:
   a gasket portion, adapted to receive said stream of gases from said supply conduit,
   a pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, the outer surface of said cap adapted to substantially seal against the nare of said user, said caps and said stalk forming an airway that acts as a path for said stream of gases to flow through said pillow portion to said user, said cap having a first bead which extends inward from the inner surface of the wall of said cap, said cap having an open top and a rim which forms the perimeter of said open top, said first bead located at or close to the open top of said cap, said first bead hemispherical or semi-circular in cross-section.

Preferably said first bead has a cross-sectional thickness greater than the cross-sectional thickness of said wall of said cap.

Preferably the cross-sectional thickness of said first bead is substantially double that of said wall.

Preferably said first bead forms a substantially unbroken ring around the inner surface of said wall.

More preferably said first bead has a substantially uniform cross sectional thickness.

Preferably said first bead is located at the same vertical position at all points around the perimeter.

Alternatively the vertical position of said first bead may vary around said perimeter.

Preferably said cap has a second, lower bead located below said first bead, said lower bead extending inwards from the inner surface of said wall.

More preferably said lower bead is disposed between 2 and 25 mm below said first bead.

Preferably said lower bead has a cross-sectional thickness greater than the cross-sectional thickness of said wall of said cap.

More preferably the cross-sectional thickness of said lower bead is substantially double that of said wall.

Preferably said lower bead forms a substantially unbroken ring around the inner surface of said wall.

Preferably said lower bead has a substantially uniform cross sectional thickness.

Preferably said lower bead is located at the same vertical position at all points around the perimeter.

Alternatively the vertical position of said lower bead may vary around said perimeter.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

gasket portion, adapted to receive said stream of gases from said supply conduit, pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, said cap formed from an inner cap and an outer cap, said inner cap and said outer cap arranged substantially concentrically and separated by an air gap when not in use, said outer cap surrounding said inner cap, the outer surface of said outer cap adapted to substantially seal against the nare of said user, said caps and said stalk forming an airway that acts as a path for said stream of gases to flow through said pillow section and to said user, aid inner cap having an upper opening, and a bead which extends outwards from the outer wall of said inner cap at or close to the rim of said inner cap, aid inner cap further having at least one and preferably a plurality of openings which pass through the wall of said inner cap.

Preferably said bead forms a continuous ring.

Preferably said bead is semi-circular in cross section and of constant cross sectional thickness all the way around said inner cap.

Preferably said inner cap has four openings.

Preferably said openings are circular.

Preferably said openings are spaced at regular intervals around the outer surface of said inner cap.

Preferably wherein said inner cap further comprises at least one rib extending outward from the outer surface of said inner cap.

More preferably said inner cap further comprises a plurality of ribs arranged around the outer surface of said inner cap extending outwards.

Preferably said rib or ribs are rectangular in cross-section.

Preferably said rib or ribs are curved in cross-section.

Preferably said rib or ribs are twice the thickness of the wall of said outer cap.

Preferably said rib or ribs are placed at regular intervals around the outer surface of said inner cap.

More preferably said ribs are positioned between successive ones of said openings.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

gasket portion, adapted to receive said stream of gases from said supply conduit, pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, the outer surface of said cap adapted to substantially seal against the nare of said user, said caps and said stalk forming an airway that acts as a path for said stream of gases to flow through said pillow portion to said user, said stalk also having at least one rib which extends outwards from the outer surface of said stalk.

Preferably said rib or ribs extend outwards substantially perpendicular to the body of said stalk, from substantially the midpoint of said stalk.

Preferably each of said rib or ribs is an elongate member with a rounded outer end.

Preferably said at least one rib is a pair of ribs at substantially diametrically opposed positions on said stalk.

Preferably said stalk is longer than the height of said rib or ribs.

Preferably the base of said cap is wider than the length of said rib or ribs.

In another form said ribs extend outwards from the base of the stalk.

Preferably said ribs extend upward for substantially one-third of the height of the stalk.

Preferably said ribs are a pair of ribs, the outer edge of one of the ribs curving away from the centre of said stalk, the outer edge of the other of said ribs curving toward the centre of the stalk.

In a further alternative form said ribs extend outwards from the top of the stalk, directly underneath the base of said cap.

Preferably said ribs extend downward from the top of said stalk for substantially one-half of the height of the stalk.

Preferably said rib or ribs extend outwards substantially perpendicular to the body of said stalk.

Preferably each of said rib or ribs is an elongate member with a rounded outer end.

Preferably said at least one rib is a pair of ribs at substantially diametrically opposed positions on said stalk.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

gasket portion, adapted to receive said stream of gases from said supply conduit, pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, the outer surface of said cap adapted to substantially seal against the nare of said user, said caps and said stalk forming an airway that acts as a path for said stream of gases to flow through said pillow portion to said user, aid stalk also having at least one rib which extends outwards from the outer surface of said stalk, said rib substantially curved away from the centre of said stalk.

Preferably said rib has a planar outer face and concave sides.

Preferably said stalk has four ribs arranged at equal intervals around perimeter of said stalk.

Preferably the base of said cap extends outwards further from the sides of said stalk than said ribs.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

gasket portion, adapted to receive said stream of gases from said supply conduit, pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, the outer surface of said cap adapted to substantially seal against the nare of said user, said caps and said stalk forming an airway that acts as a path for said stream of gases to flow through said pillow portion to said user, aid stalk also having at least one rib which extends outwards from the outer surface of said stalk, said rib or ribs extending in a spiral or helical shape around the outer surface of said stalk.

Preferably said rib is at a helical angle suitable to allow said stalk to rotate when loaded.

Preferably said ribs are arranged at equal intervals around the perimeter of said stalk.

Preferably said ribs on each of said pillow portions spiral in opposite directions.

Preferably the helical angle of each of said ribs is the same between separate ribs.

Preferably said nasal pillow section has three ribs on each of said pillow portions.

Preferably said ribs extend from the top of said stalk to the base of said stalk.

Alternatively said ribs extend from the top of said stalk to a position substantially halfway down said stalk.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

gasket portion, adapted to receive said stream of gases from said supply conduit, pair of pillow portions connected to and extending from said gasket portion, said pillow portions adapted to receive said stream of gases from said gasket portion and provide said stream of gases to said user, each of said pillow portions having a base section, the bottom of said base section connected to said gasket portion so that gases can pass from said gasket portion into said base section, and a cap, the bottom end of said cap connected to the upper end of said base section, the outer surface of said cap adapted to substantially seal against the nare or nostril of said user, said base section and said cap forming a gases path for said stream of gases to flow to said user, aid base section extending directly from said gasket portion, said upper end of said base section at least as wide as said bottom end of said cap, said cap extending upwards from said upper end of said base section, said cap substantially funnel shaped, narrowing from said bottom end of said cap.

Preferably said gases path through said base section and said cap is as wide as possible through said base section and at the point of entry to said cap.

Preferably said base section is formed in such a manner that said base section has substantially less flexibility than said cap, said base section shaped and arranged such that said cap deforms downward toward said base section when loaded.

Preferably the wall of said base section is of greater thickness than the wall of said cap.

Preferably the side walls of said base section are substantially straight and extend upwards substantially perpendicularly from the upper surface of said gasket.

Alternatively the side walls of said base section are tapered inwards towards each other from the top of the base section so that the bottom of said base section is narrower than the top of said base section, such that said gases path widens from the bottom of the base section towards the top.

In a further alternative form the side walls of said base section extend upwards from the gasket portion substantially parallel to each other, curving outwards before connecting to the cap so that said pillow portion has a central bulge where the base section and the cap connect.

In another alternative form the side walls of said base section taper or angle inwards towards each other, so that said bottom of said base section is wider than said bottom end of said cap, the sides of said base section angled outward such that the lower portion of the base section is wider than the upper portion of said base section.

In another alternative form said base section is wider at the central portion of said base section than at the upper and lower ends, the walls of said base section rounded outwards between said bottom of said base section and said bottom end of said cap.

Preferably the wall thickness of said base section is substantially constant over the height of said base section, so that said air path through said base section is substantially defined by the contours of the walls of said base section.

Preferably said base section has at least one rib extending inward substantially radially from the inner wall of said base section toward the centre of the said base section.

More preferably said at least one rib extends between the bottom of said base section and a point just above the bottom of the cap.

Further said at least one rib curves inwards towards the central axis of the pillow portion.

Further the maximum inwards extent of said at least one rib is the perimeter of a circle defined by looking straight down the axis of the pillow portion from the top opening of the cap from above.

Preferably said ribs are twice the thickness of the wall of said cap.

Preferably said at least one rib is four ribs spaced at equal intervals around the inner surface of the wall of said pillow portion and extending inwards substantially radially.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

gasket portion, adapted to receive said stream of gases from said supply conduit, pair of pillow portions connected to and extending from said gasket portion, said pillow portions adapted to receive said stream of gases from said gasket portion and provide said stream of gases to said user, each of said pillow portions having a base section, the bottom of said base section connected to said gasket portion so that gases can pass from said gasket portion into said base section, an intermediate section on the top of said base section extending upwards, and a cap located above said base section and said intermediate section, the outer surface of said cap adapted to substantially seal against the nare or nostril of said user, said base section, said intermediate section and said cap forming a gases path for said stream of gases to flow to said user, the bottom of said cap fitting inside the intermediate portion so that the intermediate portion generally forms a boundary wall around the top of said base portion, said bottom of said cap fitting inside said boundary wall, said cap extending upwards above said boundary wall.

Preferably said boundary wall is formed in such a manner that it is substantially flexible and can deform to conform with the shape of a user's nose and form an effective seal.

In a further aspect the invention consists in a nasal pillow section for use as part of a system for delivering a stream of gases to a user, said system of the type that has a gases supply that produces a stream of gases, a supply conduit that is connected to said gases supply and which receives said stream of gases from said gases supply, and a patient interface connected to and in fluid communication with said supply conduit and adapted to deliver said stream of gases to said user via the nares, said pillow section forming part of said patient interface, said pillow section comprising:

gasket portion, adapted to receive said stream of gases from said supply conduit, pair of pillow portions connected to and extending from said gasket portion, said pillow portions adapted to receive said stream of gases from said gasket portion and provide said stream of gases to said user, each of said pillow portions having a stalk, the base of said stalk connected to said gasket portion, and a cap, said cap connected to the upper end of said stalk, the outer surface of said cap adapted to substantially seal against the nare of said user, said caps and said stalk forming an airway that acts as a path for said stream of gases to flow through said pillow portion to said user, said cap having a flange portion around the lower part of said cap, said flange portion sloping downwards and outwards to surround the upper part of the stalk, said flange portion substantially flexible.

Preferably said pillow section also has at least one rib, running between the outer surface of said stalk and the underside of said flange, said at least one rib adapted to support said flange.

More preferably said at least one rib is four ribs arranged around said flange portion and running radially outwards from the outer surface of said stalk.

Preferably the lower edge or surface of said rib or ribs does not extend downwards further than the lower edge of said flange.

Preferably the inside walls of said pillow portion are parallel to each other forming a smooth vertical airway.

Preferably said cap section has an internal cavity with a greater width than the internal width or diameter of said stalk.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

Preferred forms of the present invention will now be described with reference to the accompanying drawings.

FIG. 2b shows the interface of FIG. 2a in use, being worn by a user, viewed from the same angle as FIG. 2a.

FIG. 2d shows a first preferred form of nasal pillow section for use as part of the first preferred embodiment of patient interface assembly, the nasal pillow section comprising a pair of pillow portions connected to a pillow gasket portion.

FIG. 3b shows the functionality of the connection between the supply conduit and the interface core section of the second preferred embodiment of FIG. 3a.

FIG. 3c shows a close-up view of the interface core portion or core section of FIG. 3a.

FIG. 4b shows an exploded perspective view of the interface of FIG. 4a.

FIG. 49a shows a top view of a still further embodiment of nasal pillow section, the nasal pillow section comprising a pair of pillow portions connected to a pillow gasket portion with internal detail also shown, each of the pillow portions having a cap section that consists of an inner and an outer cap separated by an air gap, the inner cap having a bead around the rim extending outwards, and a series of holes passing through the wall of the inner cap, each of the pillow sections also having a number of ribs passing between the inner and outer caps within the air gap, the ribs as being curved in profile, and a pair of section lines X and Y for each of the pillow portions also shown.

FIG. 49b shows the nasal pillow section of FIG. 49a from the point of view of a user or patient, each of the nasal pillow portions shown in cross-section, the cross-section for each pillow taken along the section lines X and Y, the cross section showing the internal detail of the structure of each of the pillow portions.

FIG. 49c shows a detail view of the right hand nasal pillow of FIG. 47b.

FIG. 50a shows a user or rear view of a still further embodiment of nasal pillow section, the nasal pillow section comprising a pair of pillow portions connected to a pillow gasket portion, each of the pillow portions comprising a stalk and a cap, the stalk having a series of ribs extending outwards from the outer surface of the stalk, the ribs located at regular intervals around the perimeter of the stalk, a pair of section lines X and Y which bisect each of the stalks perpendicular to the main axis of the stalk also shown, section line X bisecting the left hand one of the stalks through the ribs on the stalk, section line Y bisecting the stalk below the ribs on the stalk.

FIG. 50b shows a view of the stalks of FIG. 50a through the cross sections along the lines X and Y looking upwards towards the top of the pillow portions.

FIG. 50c shows a detail view of the right hand pillow portion of FIG. 50a.

FIG. 51c shows a detail view of the right hand pillow portion of FIG. 51a.

FIG. 52a shows a user or rear view of a still further embodiment of nasal pillow section, the nasal pillow section comprising a pair of pillow portions connected to a pillow gasket portion, each of the pillow portions comprising a stalk and a cap, the stalk having a series of ribs extending outwards from the outer surface of the stalk at or close to the top of the stalk, the ribs located at regular intervals around the perimeter of the stalk, a pair of section lines X and Y which bisect each of the stalks perpendicular to the main axis of the stalk also shown, section line X bisecting the left hand one of the stalks, section line Y bisecting the right-hand one of the stalks, the ribs generally extending downwards from the top of each of the stalk to approximately the mid point of each of the stalks.

FIG. 52b shows a view of the stalks of FIG. 52a through the section lines X and Y looking upwards towards the top of the pillow portions.

FIG. 52c shows a detail view of the right hand pillow portion of FIG. 52a.

FIG. 53c shows a detail view of the right hand pillow portion of FIG. 53a.

FIG. 54a shows a user or rear view of a still further embodiment of nasal pillow section, the nasal pillow section comprising a pair of pillow portions connected to a pillow gasket portion, each of the pillow portions comprising a stalk and a cap, the stalk having a series of ribs extending outwards from the stalk and spiraling around the stalk, the ribs extending from the top of the stalk to the base, a pair of section lines X and Y which bisect each of the stalks perpendicular to the main axis of the stalk also shown.

FIG. 54b shows a view of the nasal pillow section of FIG. 54a along the lines X and Y looking upwards towards the top of the pillow portions.

FIG. 54c shows a detail view of the right hand pillow portion of FIG. 54a.

FIG. 55a shows a user or rear view of a still further embodiment of nasal pillow section, the nasal pillow section comprising a pair of pillow portions connected to a pillow gasket portion, each of the pillow portions comprising a stalk and a cap, the stalk having a series of ribs extending outwards from the stalk and spiralling around the stalk, the ribs extending from the top of the stalk but not extending all the way to the base of the stalk, a pair of section lines X and Y which bisect each of the stalks perpendicular to the main axis of the stalk also shown, section line X bisecting the left-hand stalk through the ribs and section line Y bisecting the right-hand stalk below the bottom of the ribs.

FIG. 55b shows a view of the nasal pillow section of FIG. 55a along the lines X and Y looking upwards towards the top of the pillow portions.

FIG. 55c shows a detail view of the right hand pillow portion of FIG. 55a.

FIG. 57b shows a detailed view of the pillow portion of FIG. 57a.

FIG. 58b shows a detail view of the stalk and cap from FIG. 58a.

FIG. 59b shows a detail view of one cap from FIG. 59a.

FIG. 60b shows a detail view of one cap from FIG. 60a.

Figure 59A:
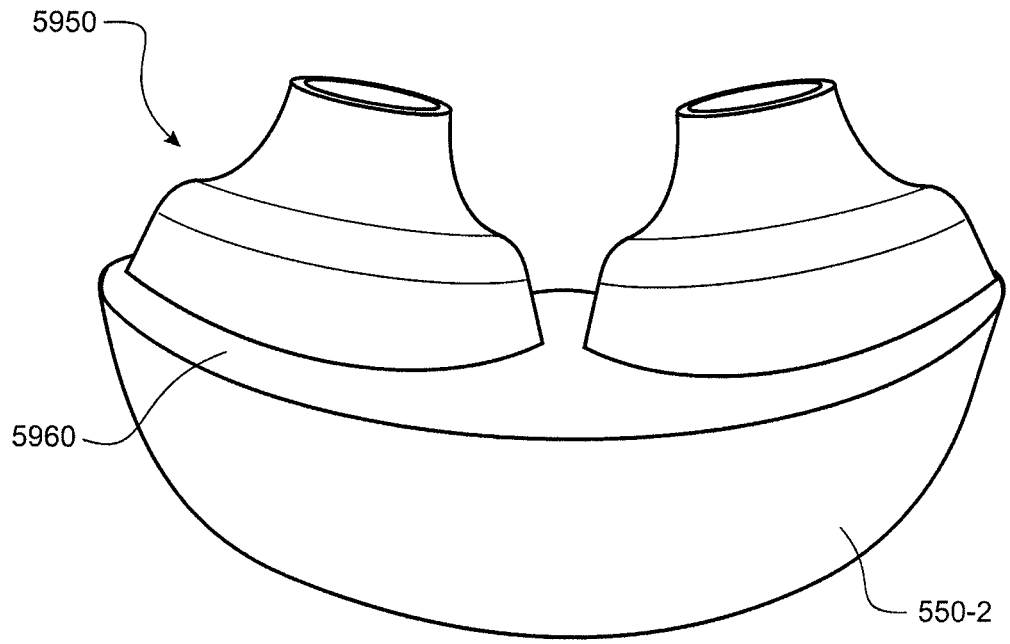
FIG. 59a shows a user or rear view of a still further embodiment of nasal pillow section, similar to that shown in FIGS. 56a-56c, except that in this variation the base section is tapered or angled outwards so that the base section is wider at the point of connection to the nasal gasket portion than at the top.
Figure 59B:
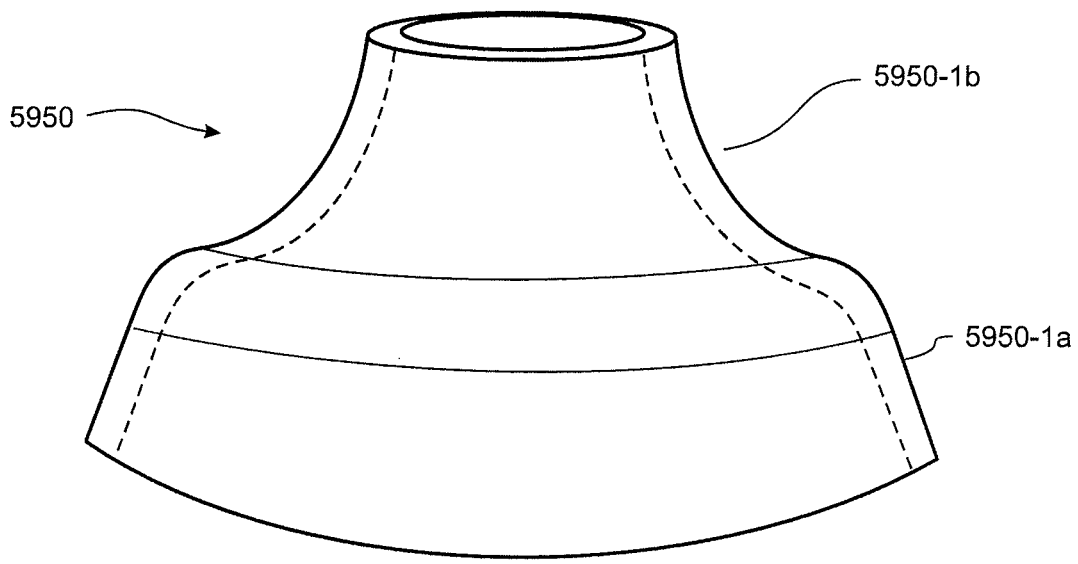
Figure 60A:
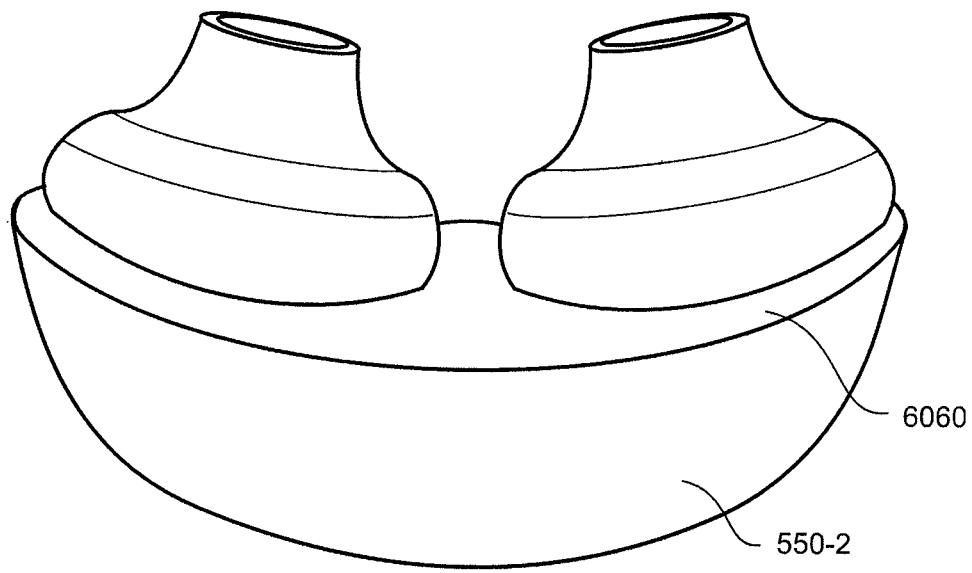
FIG. 60a shows a user or rear view of a still further embodiment of nasal pillow section, similar to that shown in FIGS. 56a-56c, except that in this variation the walls of the base section are rounded outwards so that the centre of the base section is wider than the ends.
Figure 60B:
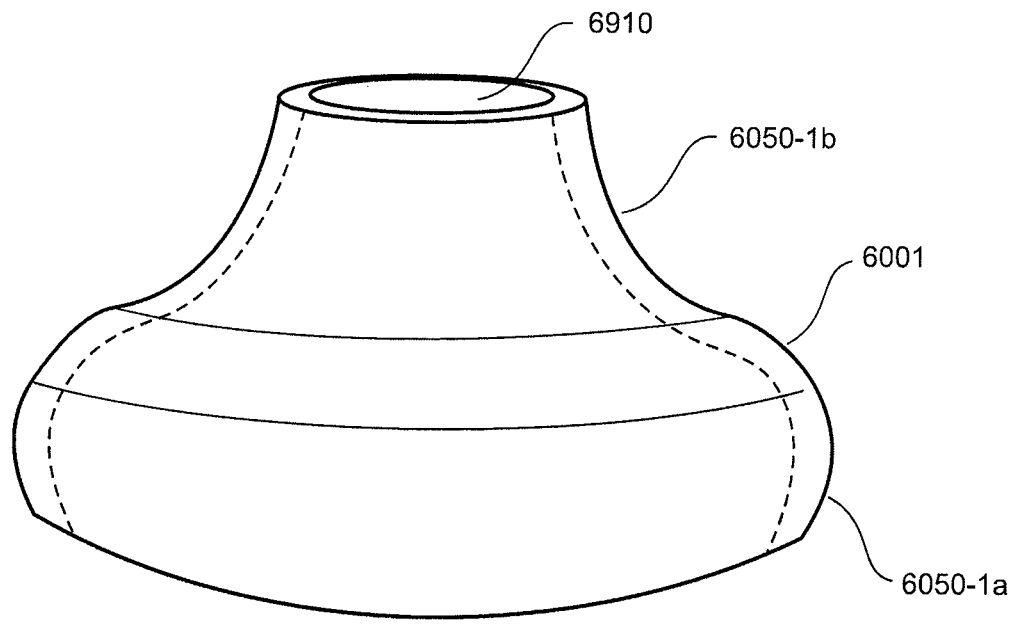
Figure 61A:
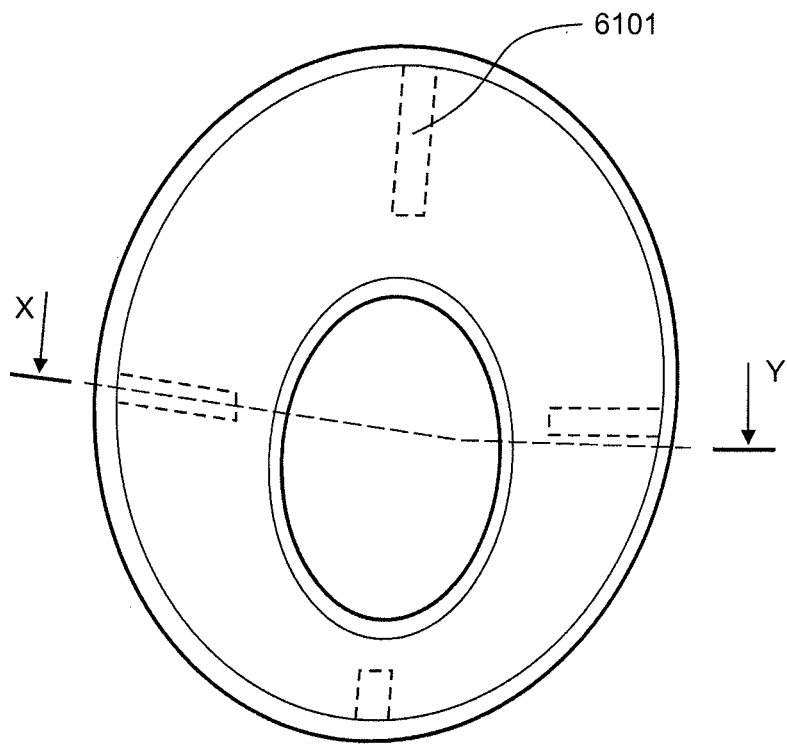

FIG. 61a shows a top view of a further embodiment of the pillow section described and shown in FIGS. 56a to 60b. The figure shows the cap including four ribs arranged at equal intervals around the perimeter of the cap. Each of the ribs is of equal length. The figure shows a line X and Y that bisects the cap. Line X bisects the cap and rib, while line Y bisects the cap to one side of the rib.

Figure 61B:
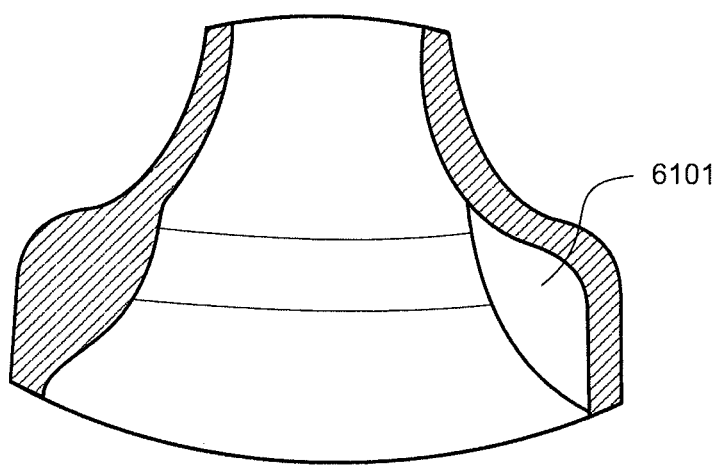

FIG. 61b shows a detail view of the embodiment of the pillow section as shown in FIG. 61a. The figure shows internal details of the cap. The rib extends from the inner wall of the cap. The rib preferably extends from the base of the cap to the point where the cap begins to narrow suddenly. The rib preferably extends inward from the cap and curves inward toward the centre of the cap.

Figure 62A:
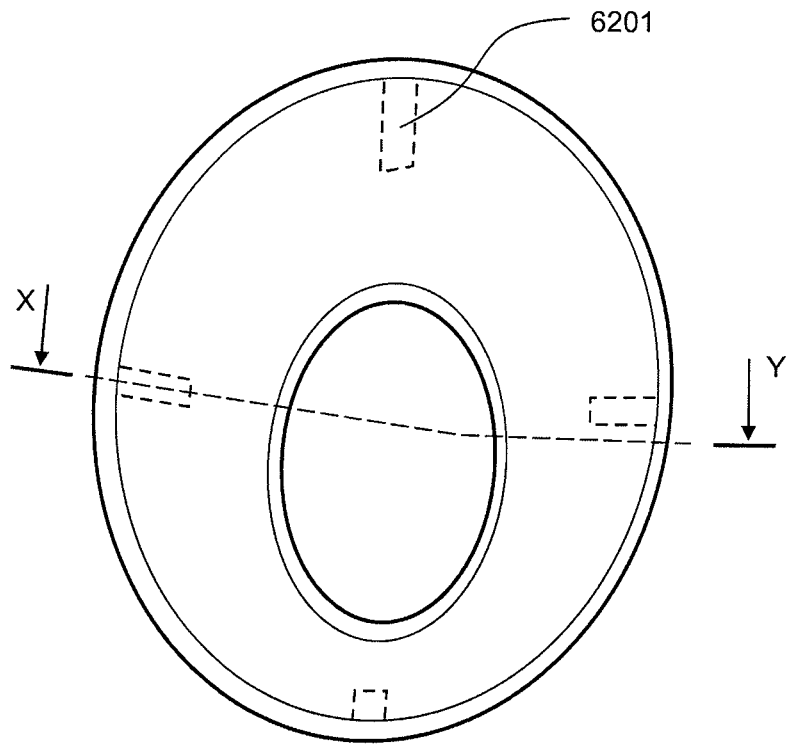

FIG. 62a shows a top view of a further embodiment of the pillow section described and shown in FIGS. 56a to 60b. The figure shows the cap including four ribs arranged at equal intervals around the perimeter of the cap. Each of the ribs is of equal length. The figure shows a line X and Y that bisects the cap. Line X bisects the cap and rib, while line Y bisects the cap to one side of the rib.

Figure 62B:
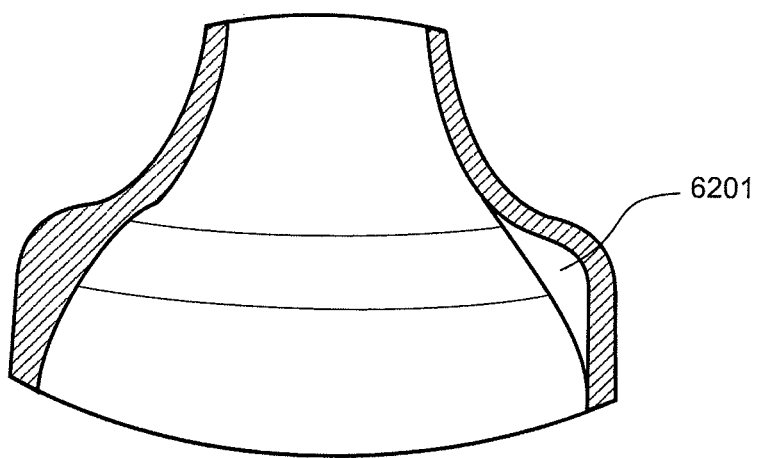

FIG. 62b shows a detail view of the embodiment of the pillow section as shown in FIG. 61a. The figure shows internal details of the cap. The rib extends from the inner wall of the cap. The rib preferably extends from the base of the cap to the point where the cap begins to narrow suddenly. The rib preferably extends to form a smooth internal wall shape.

Figure 63A:
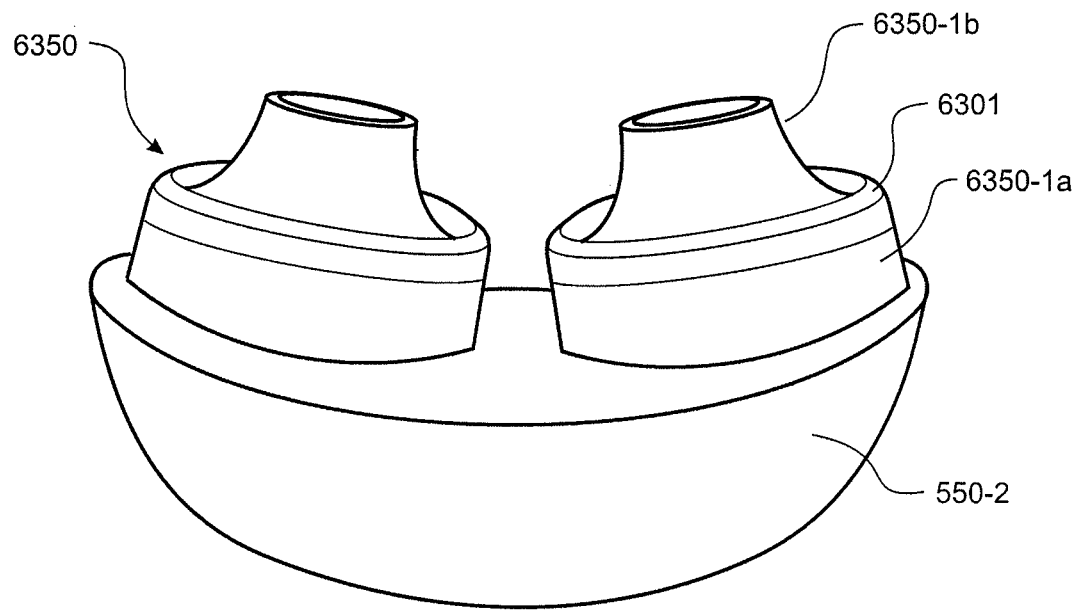

FIG. 63a shows a view of a further embodiment of the nasal pillow section as viewed by the patient. The view shows the nasal section comprising a pillow portion extending from a gasket portion. The pillow portion includes a pair of platforms extending from the gasket portion and a cap extending from each platform. The platforms are of equal height and are substantially identical and substantially rigid. The platforms are of a larger diameter than the caps. The larger diameter of the platform adds an extra edge that acts as a secondary seal around the outside of the patient or user's nostril. This secondary seal makes the pillow portion more adaptive and allows it be used with a variety of nostril shapes. The platform acts as a stop and reduces the amount the cap inserts into the nostril thus increasing the size of the opening in use, leading to reduced pressure drop across the pillow portion in use.

Figure 63B:
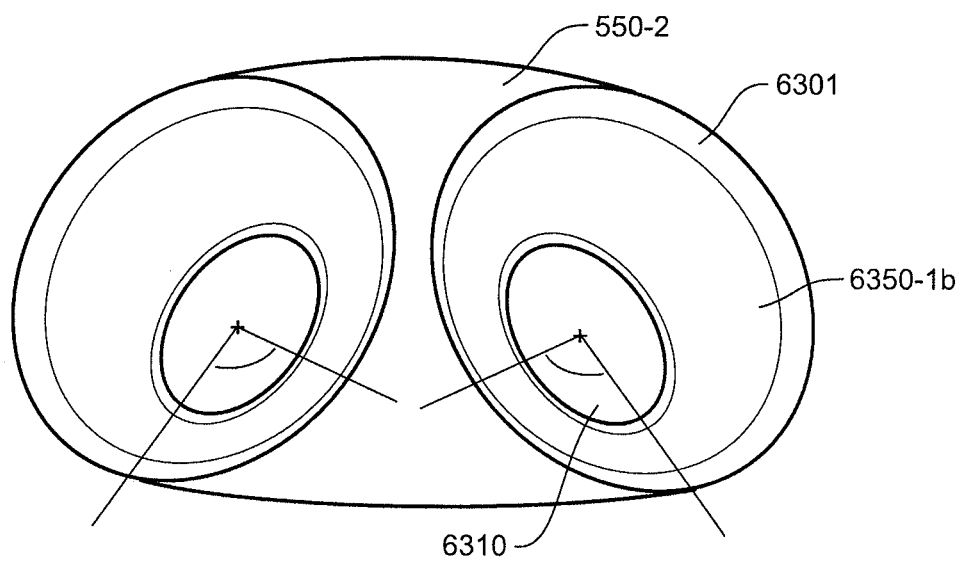

FIG. 63b shows a top view of the nasal pillow section of FIG. 63a. The figure shows the caps are angled inward toward each other.

Figure 64A:
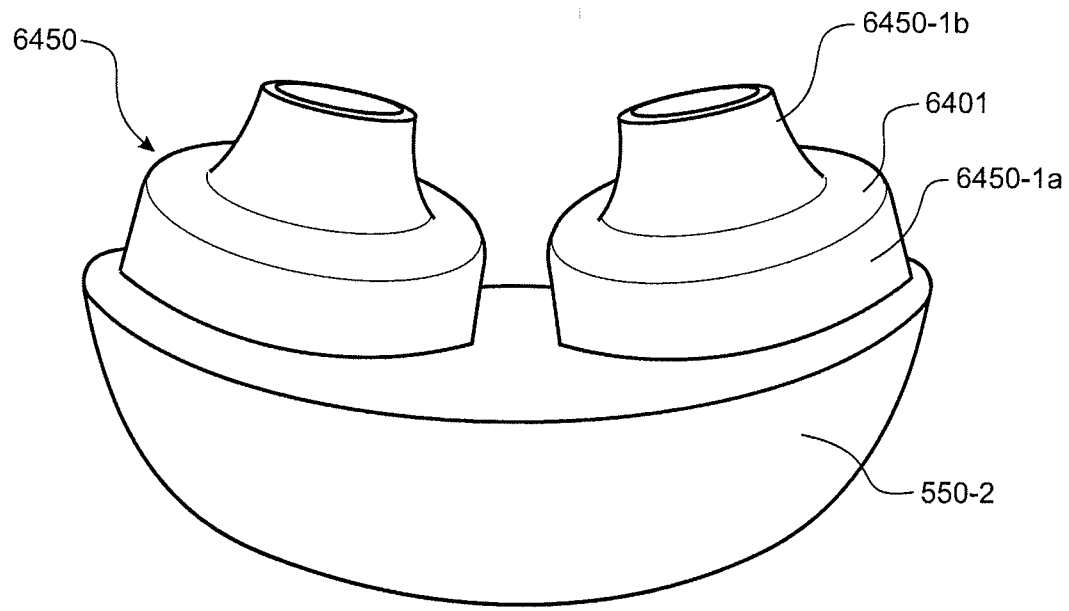

FIG. 64a shows a view of a further embodiment of the nasal pillow section as viewed by the patient. The view shows the nasal section comprising a pillow portion extending from a gasket portion. The pillow portion includes a pair of platforms extending from the gasket portion and a cap extending from each platform. The platforms are of equal height and are substantially identical. Preferably the platforms are pliable, meaning they are deformable. The platforms can adjust in height when in use. The platforms are of a larger diameter than the caps. The larger diameter of the platform adds an extra edge that acts as a secondary seal around the outside of the patient or user's nostril. This secondary seal makes the pillow portion more adaptive and allows it be used with a variety of nostril shapes. The platform acts as a stop and reduces the amount the cap inserts into the nostril thus increasing the size of the opening in use, leading to reduced pressure drop across the pillow portion in use.

Figure 64B:
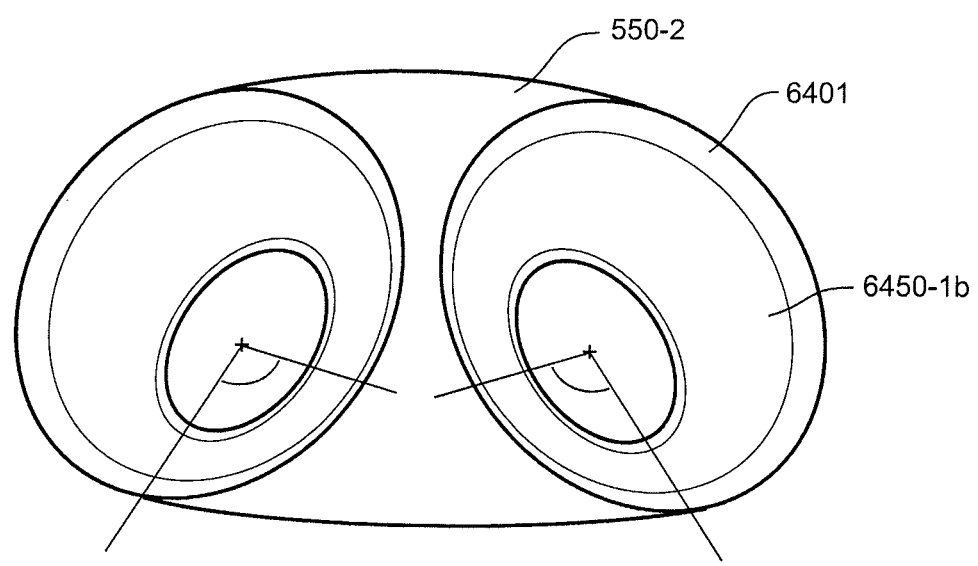

FIG. 64b shows the top view of the embodiment of the nasal pillow section shown in FIG. 64a. The figure shows the caps angled inward toward each other.

Figure 65A:
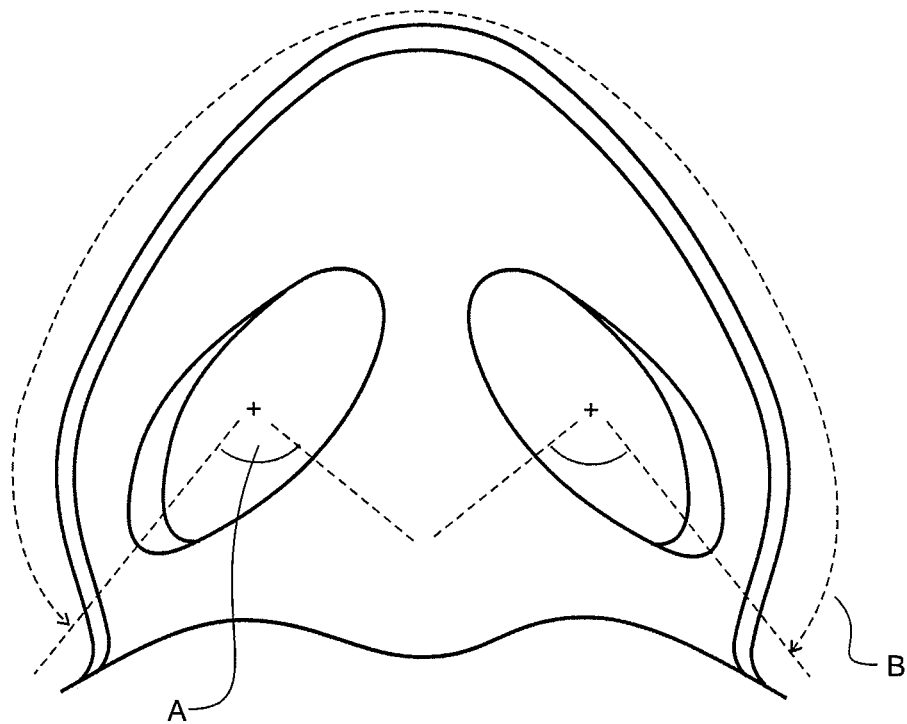

FIG. 65a shows a view of a user's nostrils from below the nostrils. The dotted region shows the region that the platforms of either 63a or 64a engage with. The figure also shows the nostrils of a user are angled.

Figure 65B:
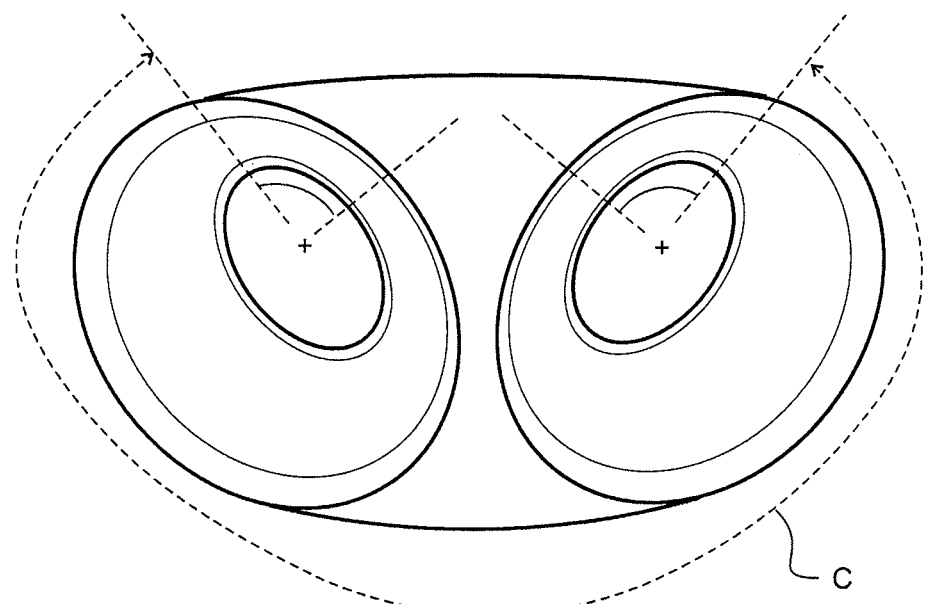

FIG. 65b shows a top view of the nasal pillow section embodiment shown in FIG. 63a or 64a. The figure shows the dotted region occupied by the platforms. The figure also shows how the caps are angled to fit complementarily within the users nostrils shown in FIG. 65a.

Figure 66A:
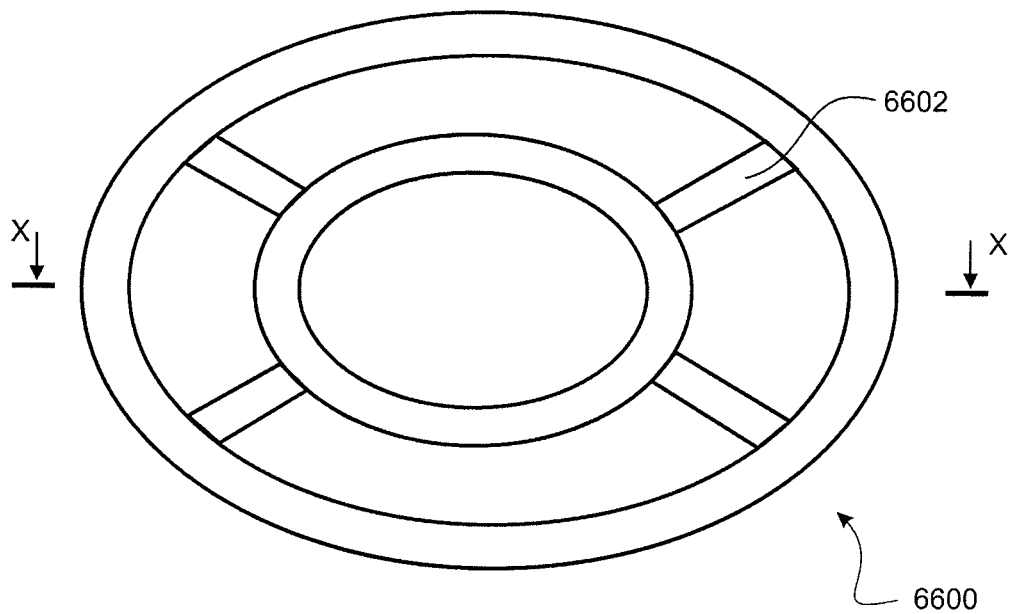

FIG. 66a shows a top view of a cap of a further embodiment of the nasal pillow section. The figure does not show the gasket portion. The figure shows the pillow portion that is connected to the gasket portion. The top view shows the pillow portion comprising four ribs arranged around the perimeter of the cap. The top view shows a line X-X that bisects the cap.

Figure 66B:
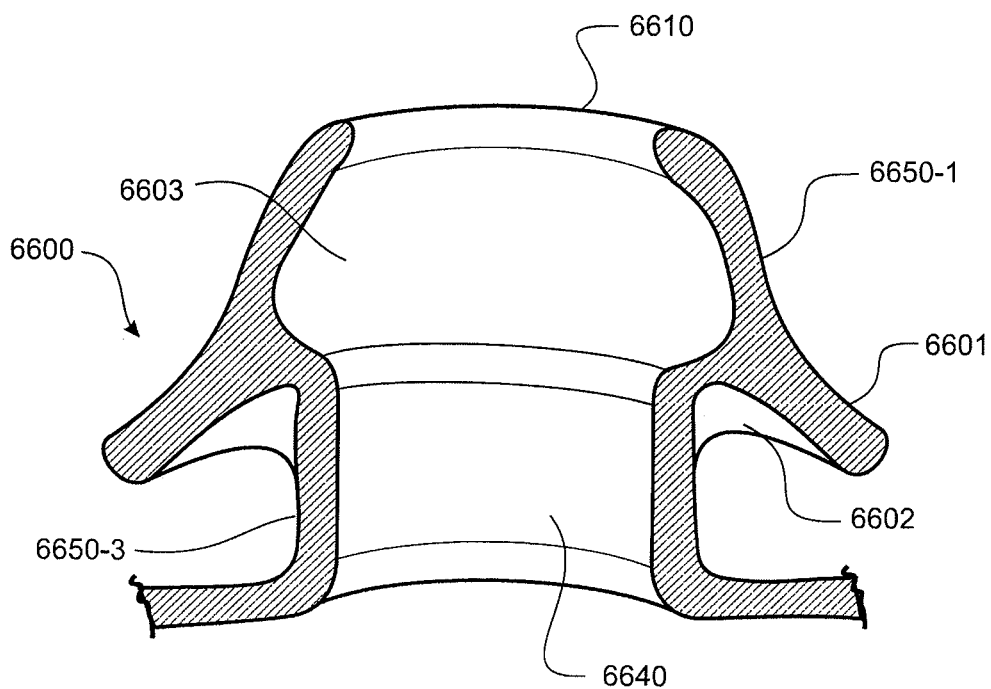

FIG. 66b shows a detail view of the nasal pillow section embodiment of FIG. 66a. The view shows internal detail of the pillow portion shown in FIG. 66a. The figure shows a stalk with a cap extending from the stalk. The inside of the cap has an expanded area as it extends from the cap. The inside of the cap extends outward from the top of the stalk and then extends upward and toward the centre of the cap, culminating in the exit orifice. The cap is wider than the stalk and slopes downward and outward around it to form a flange around the stalk. The figure shows ribs extending from the bottom of the extended cap and connecting with the stalk. The ribs add strength to the cap, minimise leakage from the caps when in use and contribute to reducing the pressure drop across the pillow portion.

Figure 67A:
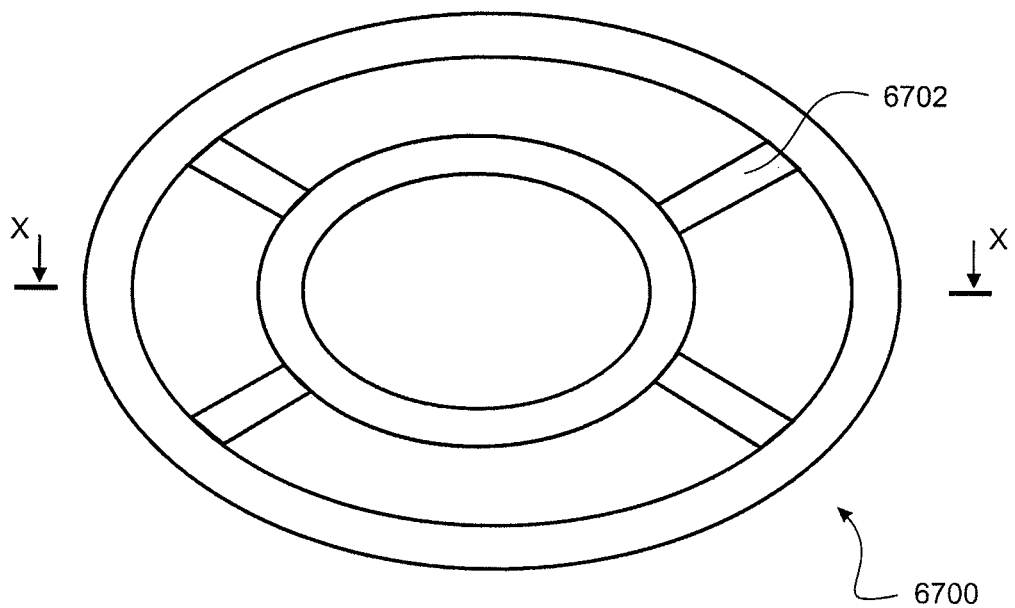

FIG. 67a shows a top view of a cap of a further embodiment of the nasal pillow section. The figure does not show the gasket portion. The figure shows the pillow portion that is connected to the gasket portion. The top view shows the pillow portion comprising four ribs arranged around the perimeter of the cap. The top view shows a line X-X that bisects the cap.

Figure 67B:
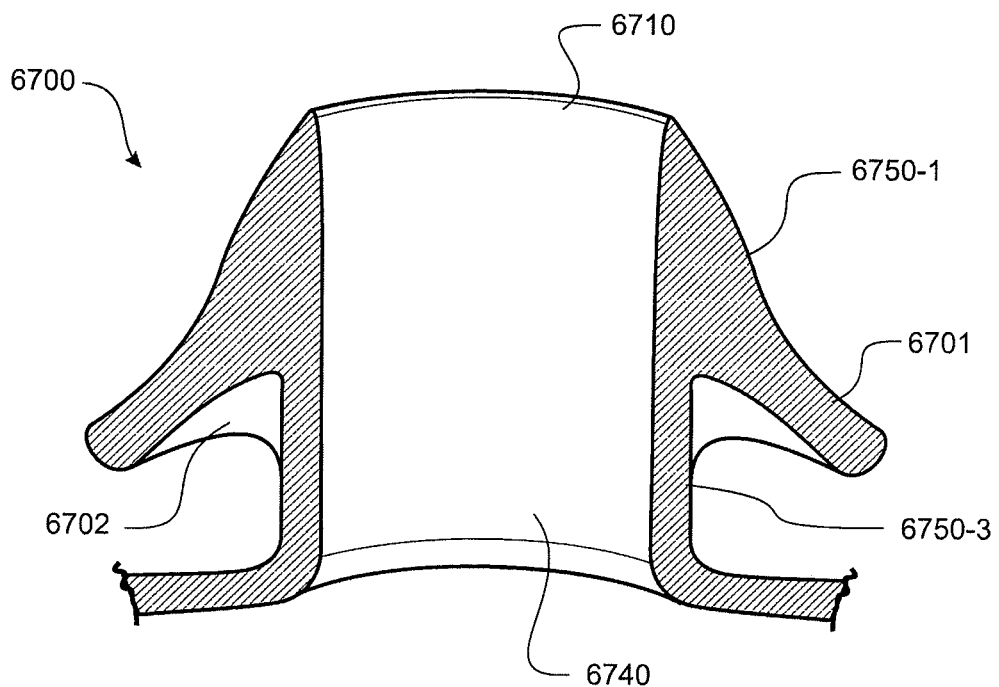

FIG. 67b shows a detail view of the nasal pillow section embodiment of FIG. 66a. The view shows internal detail of the pillow portion shown in FIG. 66a. The figure shows a stalk with a cap extending from the stalk. The inside of the cap extends straight upward from the top of the stalk. The inside of the cap extends to form a substantially straight air delivery path, as seen in the figure. The cap is wider than the stalk and slopes downward and outward around it to form a flange around the stalk. The figure shows ribs extending from the bottom of the extended cap and connecting with the stalk. The ribs add strength to the cap, minimise leakage from the caps when in use and contribute to reducing the pressure drop across the pillow portion.

Figure 68:
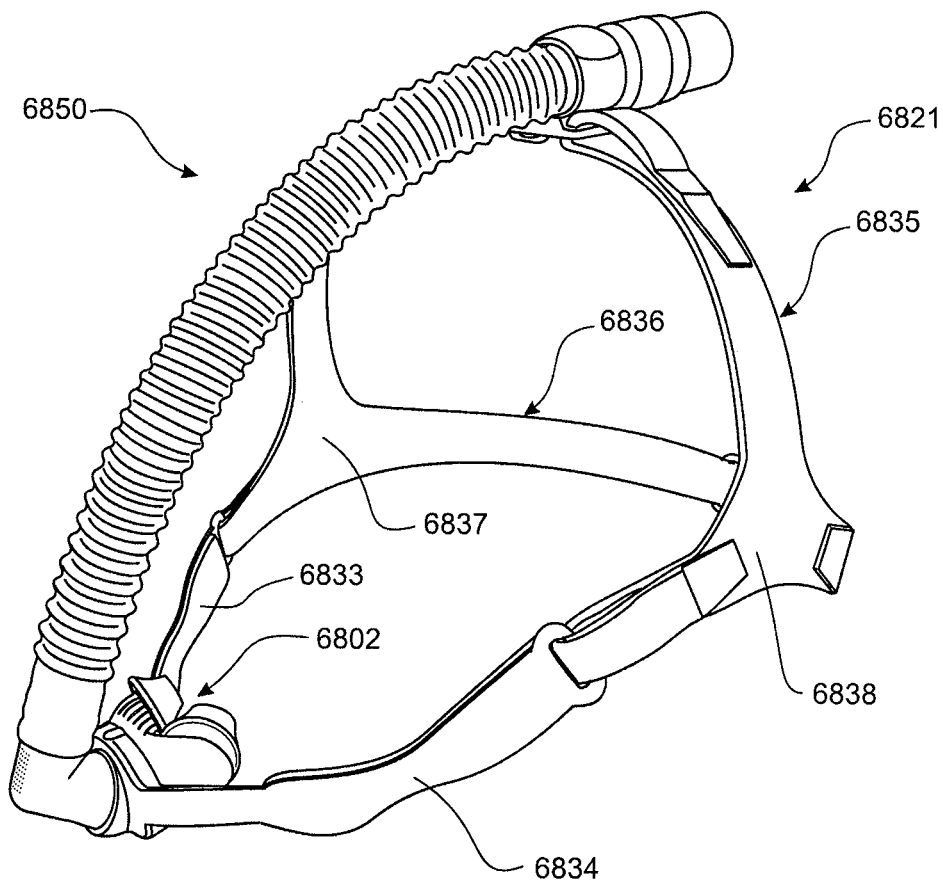

FIG. 68 is a perspective view of one embodiment of a nasal interface of the present invention.

Figure 69A:
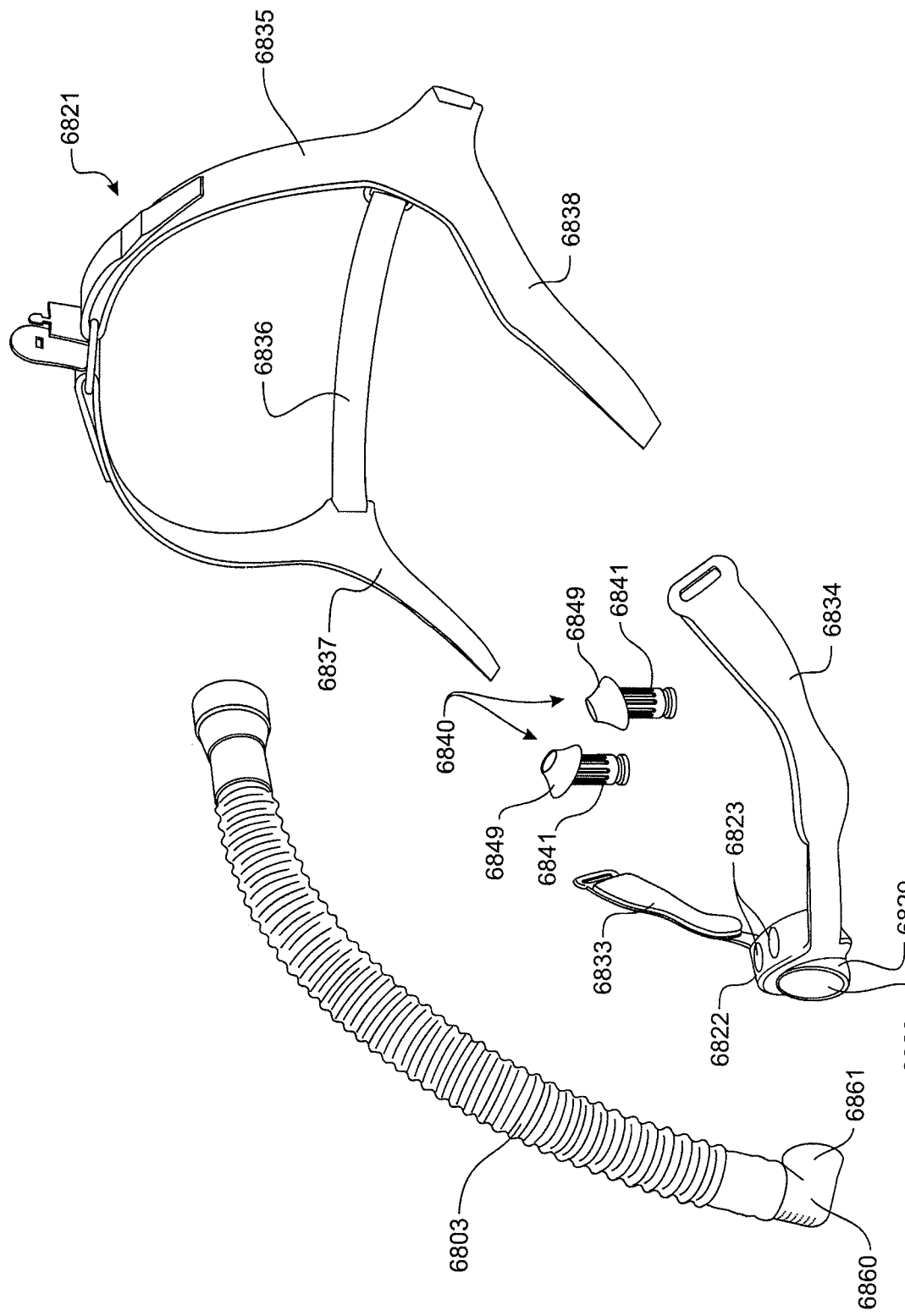

FIG. 69a is an exploded view of a preferred embodiment of a nasal interface of the present invention, showing a nasal cannula assembly and a headgear assembly which together form the nasal interface of the preferred form of the present invention.

Figure 2A:
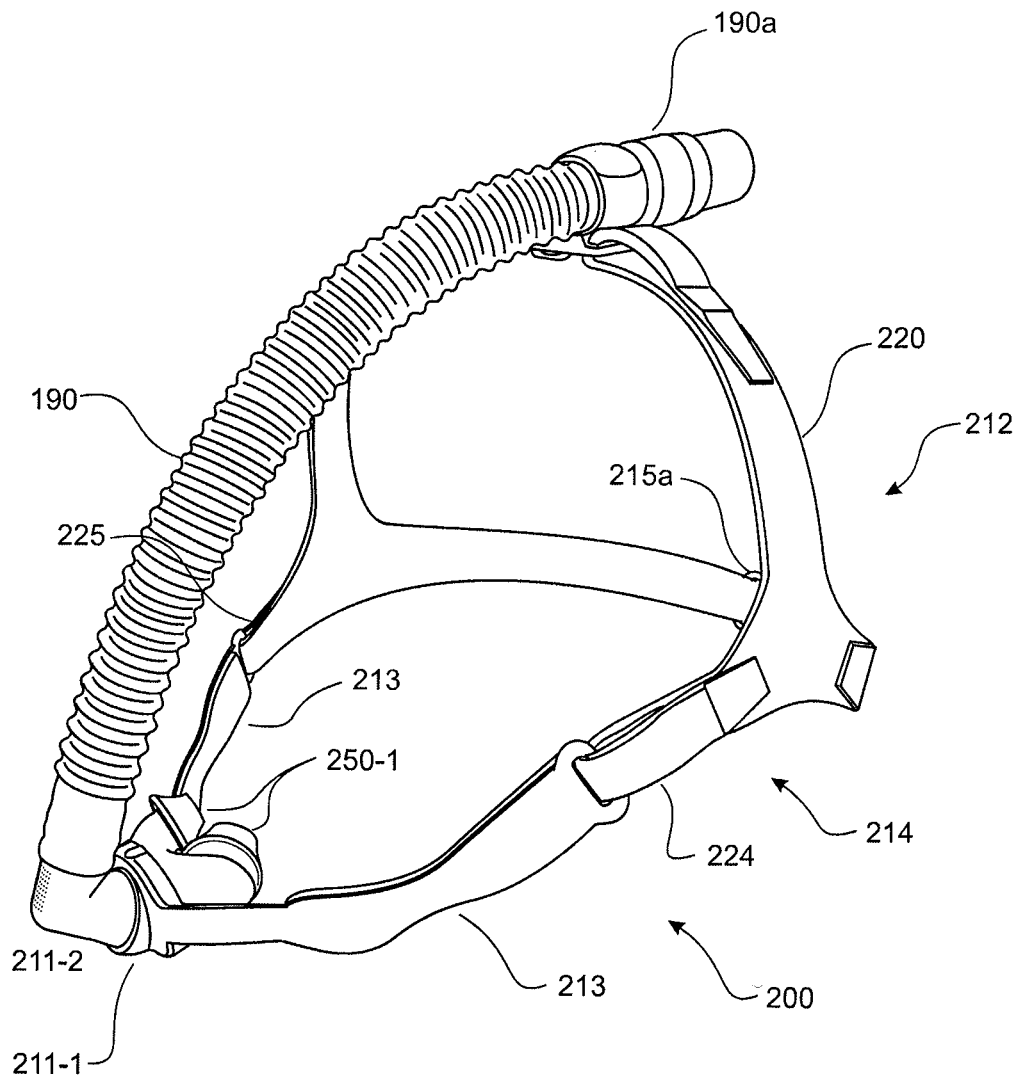
FIG. 2a shows a perspective view from the front and to one side of a first preferred embodiment of the interface assembly of the present invention, showing an interface core portion or core section adapted to connect to the supply conduit so the interface can receive gases from the gases supply unit in use, a nasal pillow section also included as part of the interface core section, and a headgear assembly connected to the core section which is adapted to hold the interface in position on the head of a user.
Figure 2B:
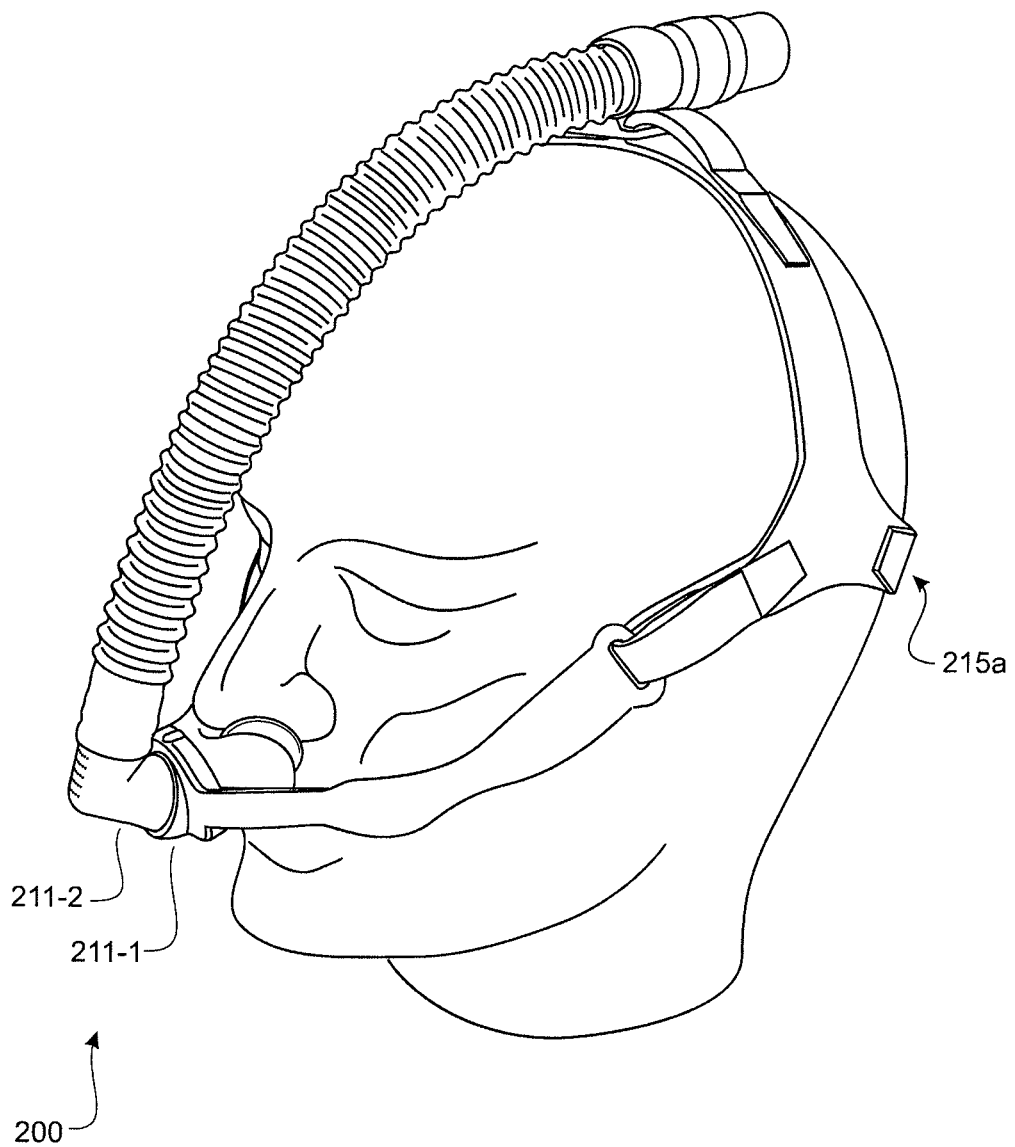
Figure 2C:
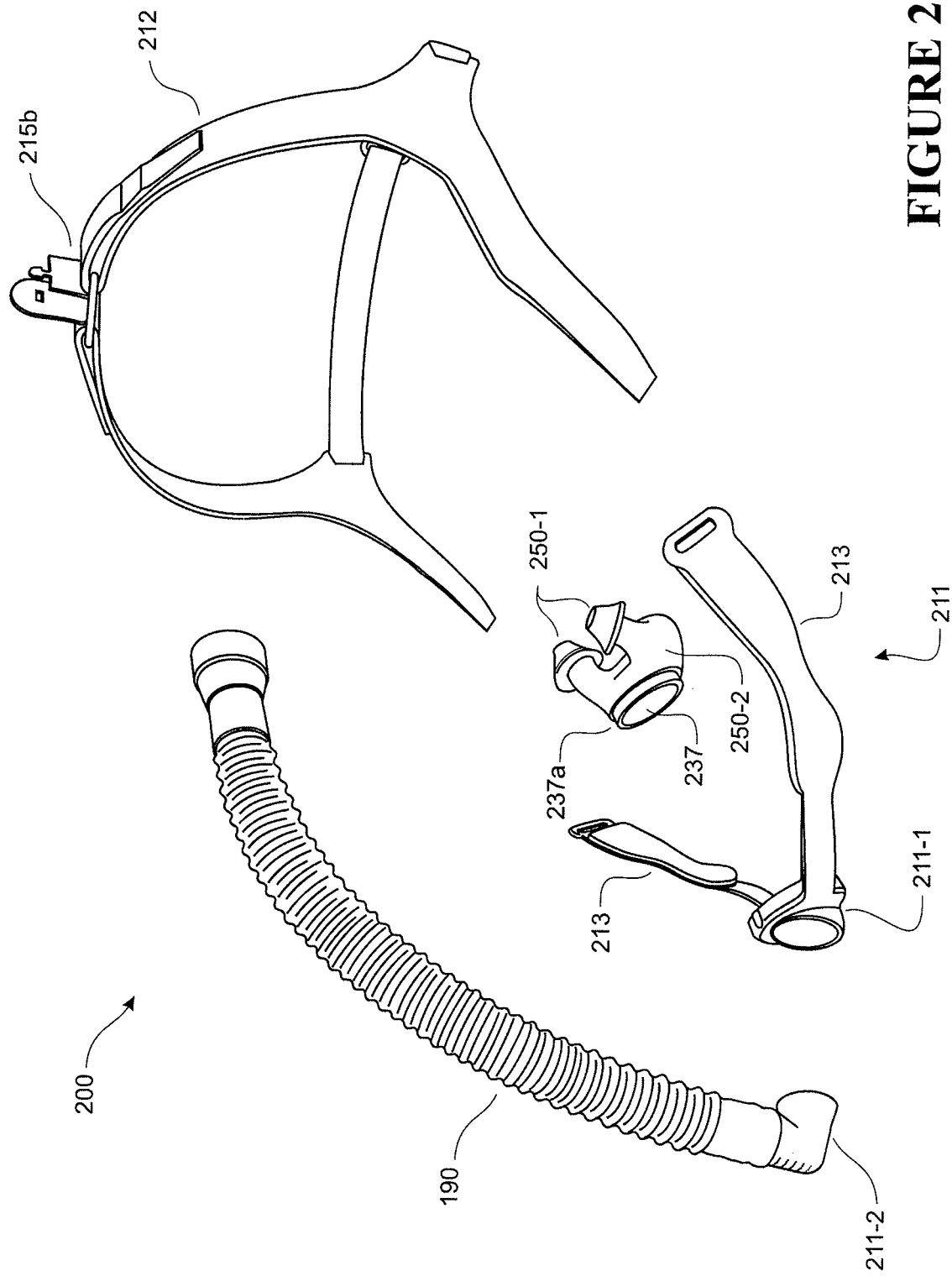
FIG. 2c shows an exploded view of the interface of FIG. 2a or 2b.
Figure 69B:
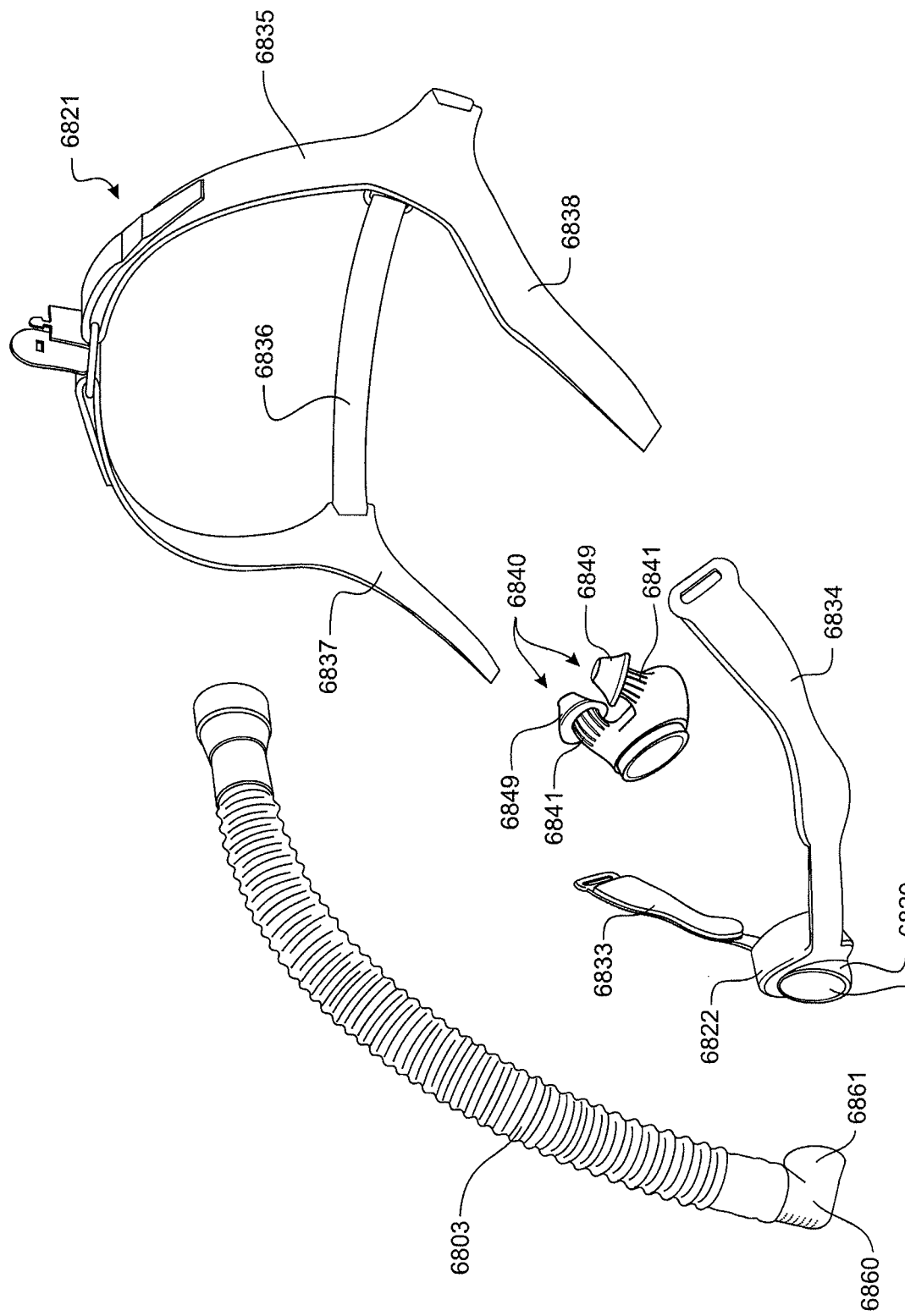

FIG. 69b is an exploded view of the nasal interface of FIG. 2, showing a nasal cannula assembly and a headgear assembly which together form the nasal interface of one embodiment of the present invention.

Figure 70A:
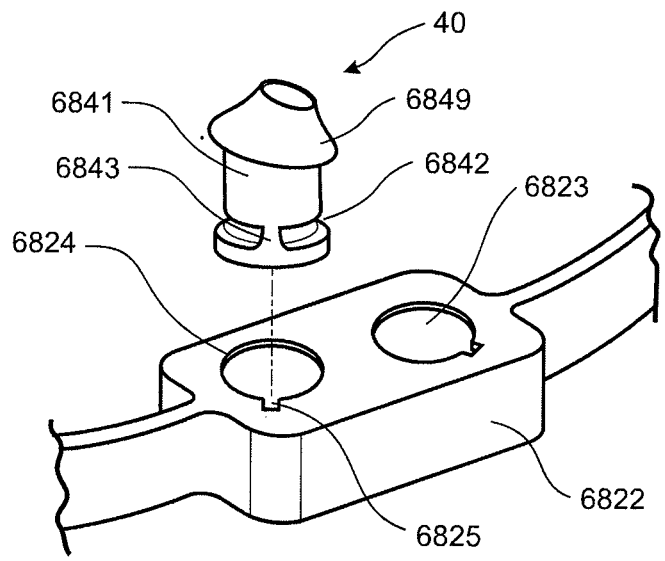
Figure 70B:
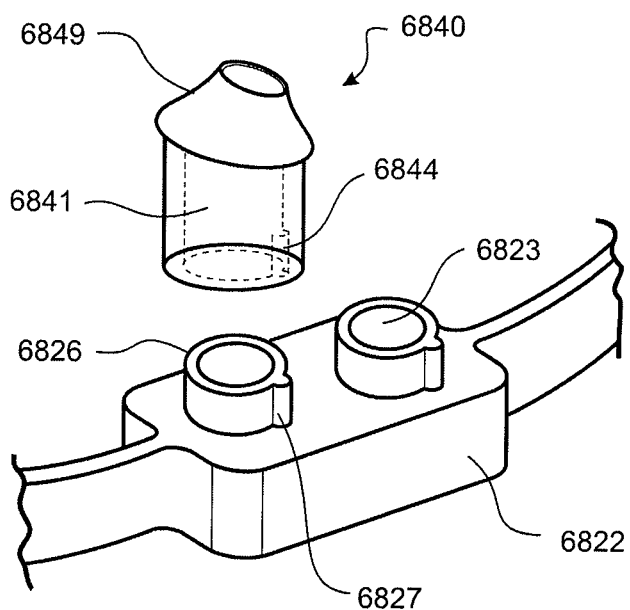

FIGS. 70a and 70b are perspective views of two embodiments of a nasal cannula assembly of the present invention, the preferred form of nasal cannula assembly comprising a manifold and two nasal pillows.

Figure 71:
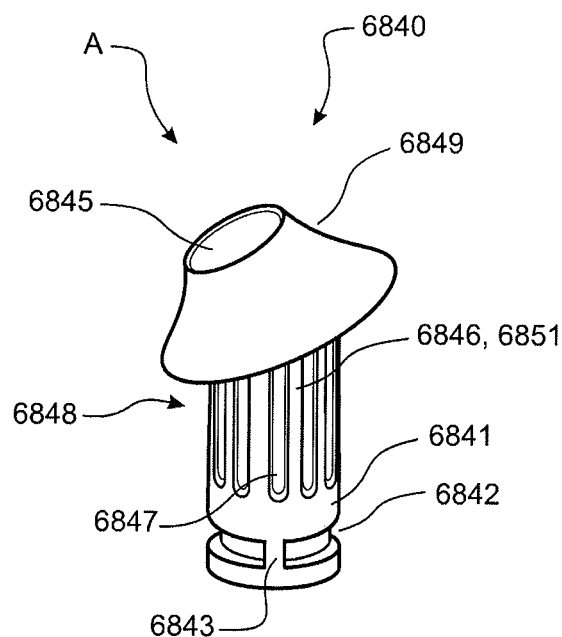

FIG. 71 is a perspective view of the nasal pillow of FIG. 70a, showing detail of a tubular base which in use is attached to the manifold, and a puff which is inserted into the nostril of a user.

Figure 72:
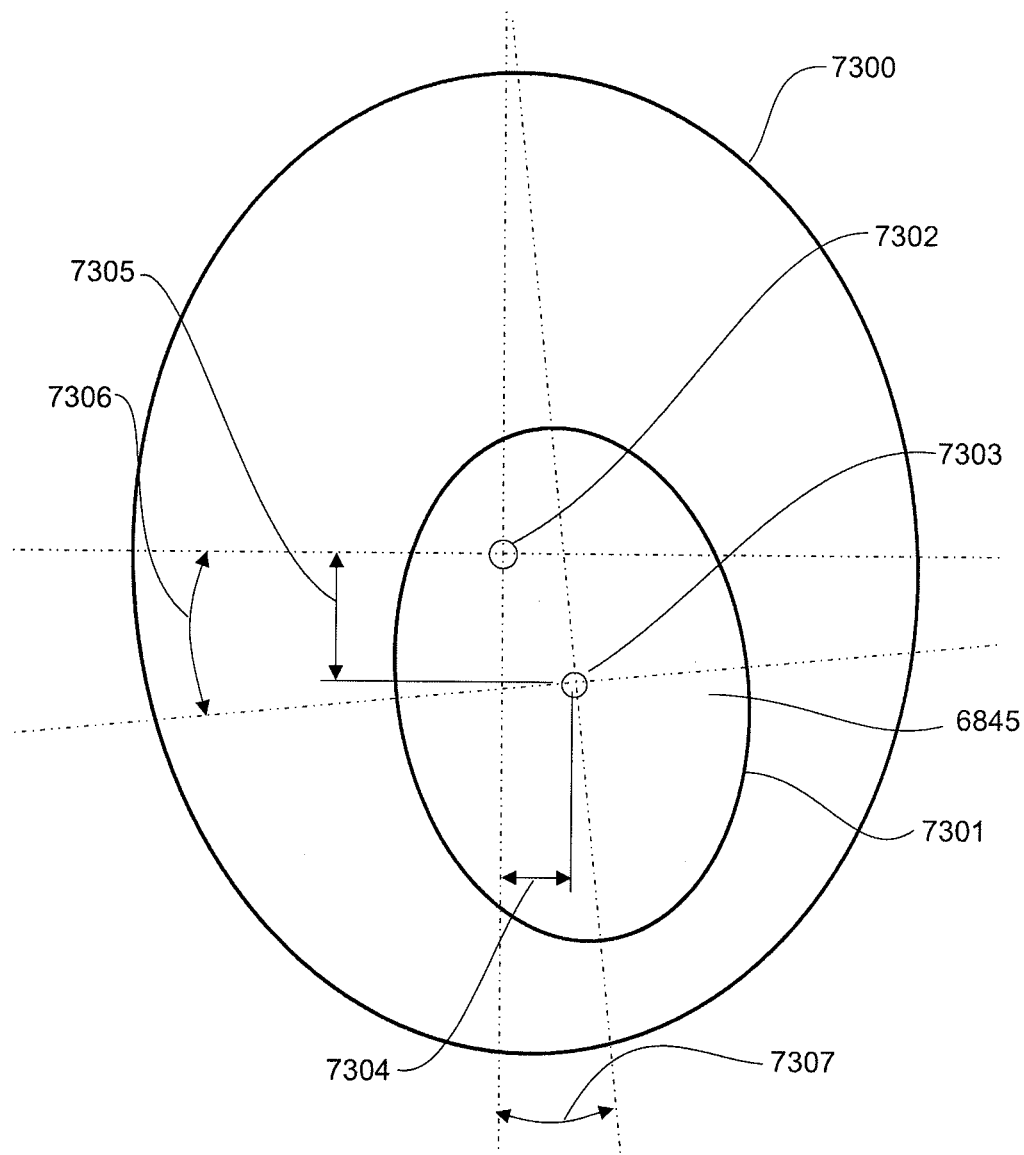

FIG. 72 is an end view of the nasal pillow of FIG. 71 viewed in the direction of arrow A.

Figure 73B:
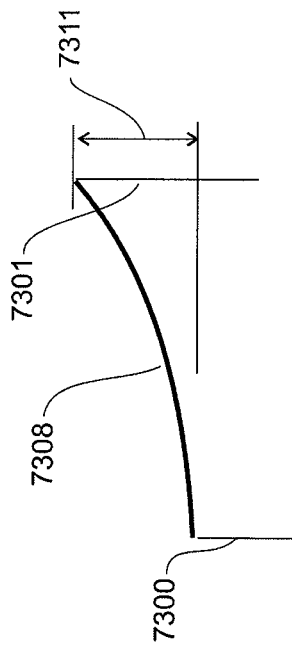
Figure 73C:
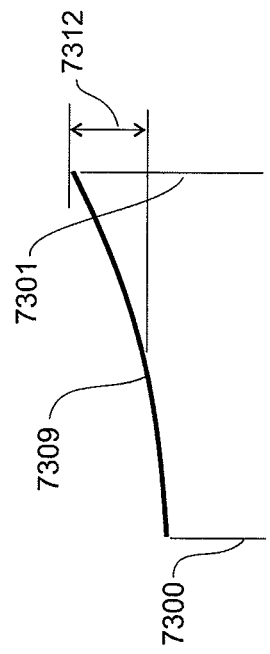
Figure 73D:
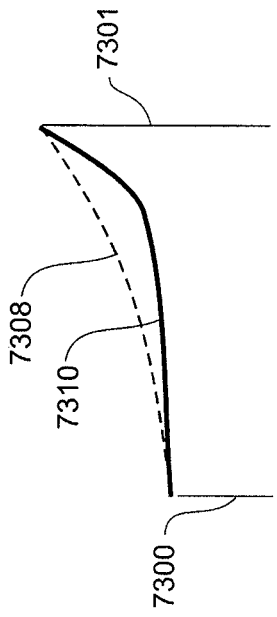
Figure 73A:
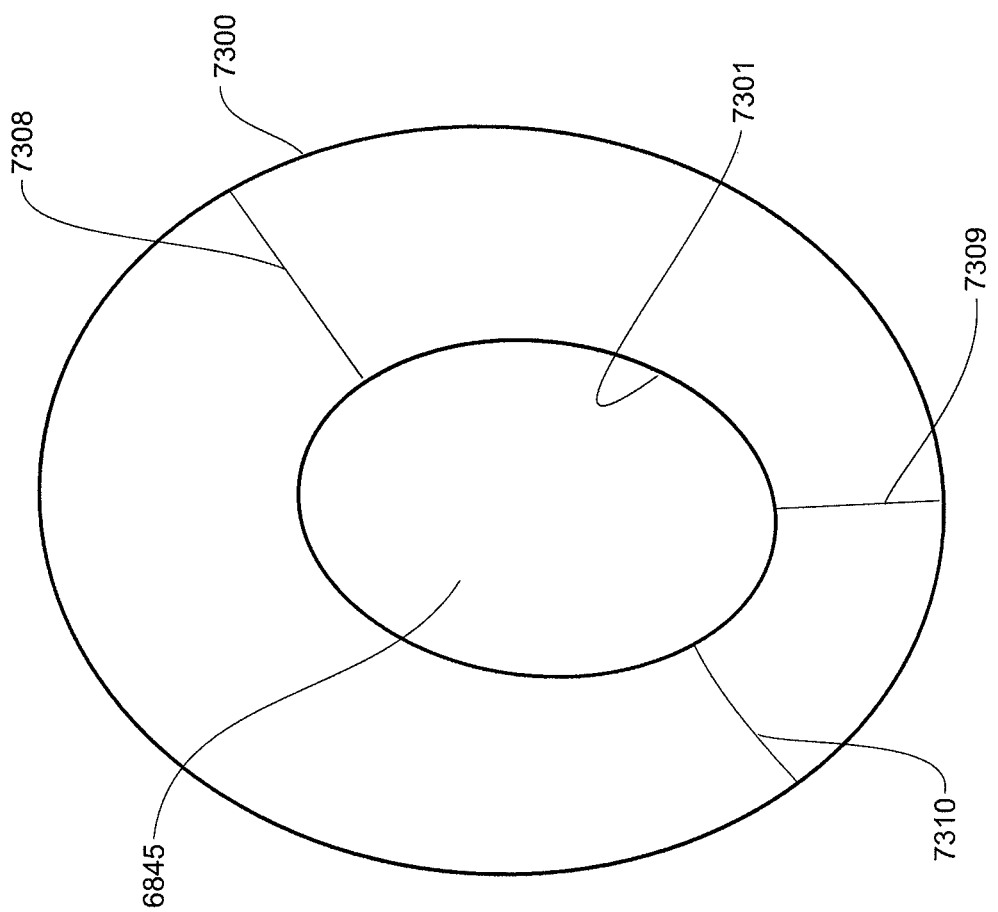

FIG. 73a is an end view of the nasal pillow of FIG. 71 viewed in the direction of arrow A.

FIGS. 73b to 73d are graphs showing the gradients of the nasal pillow connecting surfaces at different cross-sections of the nasal pillow, the cross sections shown in FIG. 73a.

Figure 74:
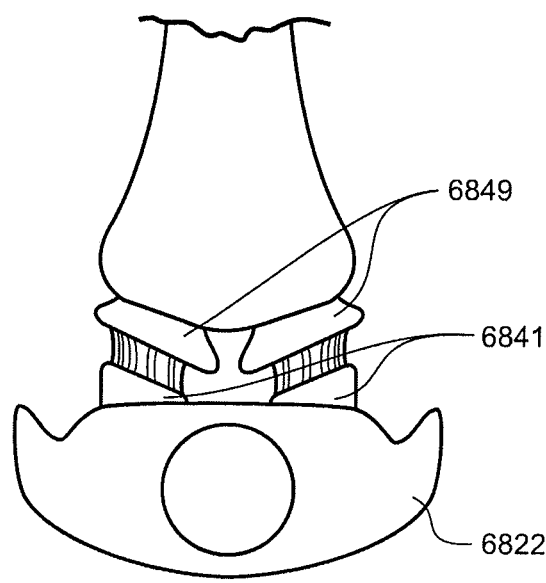

FIG. 74 shows a front view of the nasal interface of the present invention fitted to a user, showing detail of the tubular bases of a pair of nasal pillows connected to the manifold so that in use the tubular bases are parallel to one another.

FIGS. 75a to 75g show various alternative cross sections through a ribbed section of the nasal pillow tubular base.

Figure 76:
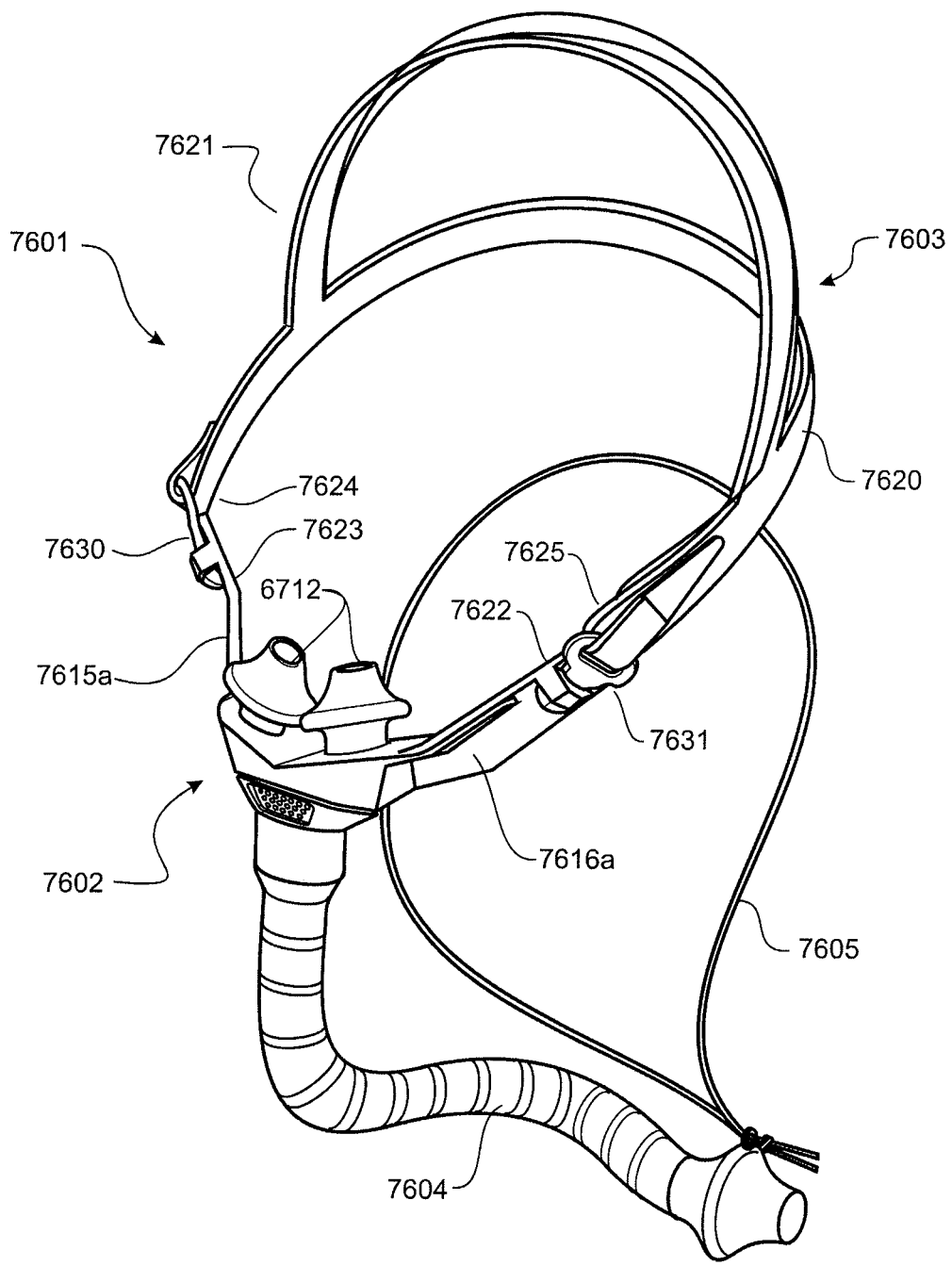

FIG. 76 shows a perspective view from the front and to one side of a preferred embodiment of the interface of the present invention, showing an interface core portion or core section that includes a pair of nasal pillows, with connecting arms extending from each side of the core portion, a headgear connected to the connecting arms, a supply conduit connected to the interface core portion, and a lanyard connected to the supply conduit, the interface ready for use by a patient or user.

Figure 77:
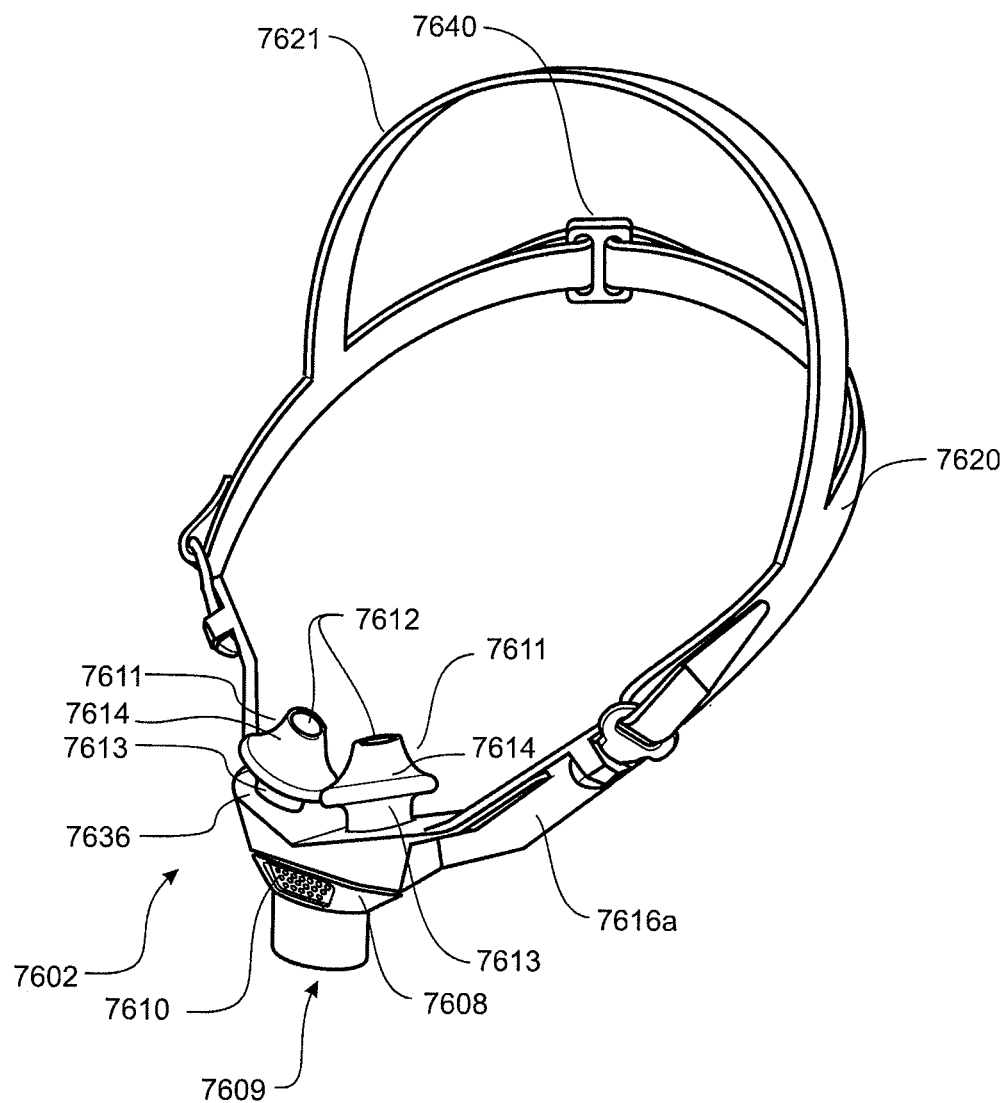

FIG. 77 shows a perspective view from the front and to the side of the interface core portion of FIG. 76, showing detail of the core portion and the connecting arms, with the headgear attached.

Figure 78A:
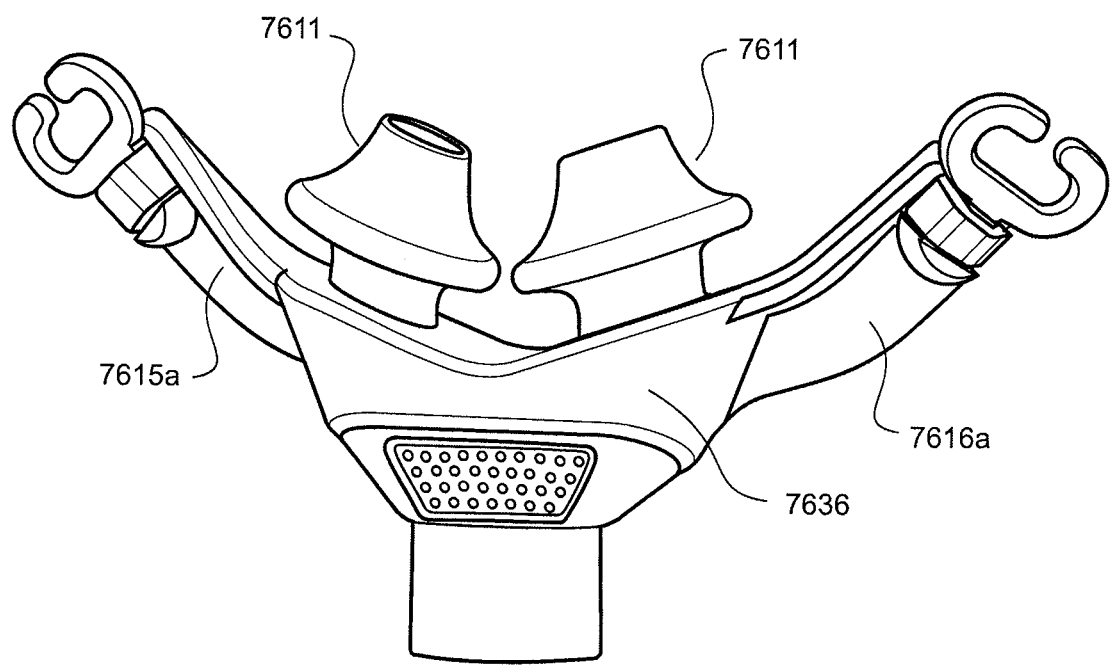

FIG. 78a shows a perspective view from the front and slightly to one side of the preferred form of interface core portion and connecting arms, with the nasal pillows and connecting arms connected to a gasket, the gasket, pillows and arms moulded as a one-piece item from a flexible and supple material, and removably connected to a rigid or semi-rigid manifold which is in use connected to the supply conduit (not shown in this figure), the connecting arms also including removable connector tabs on the outer ends of the connecting arms which are adapted to attach the connector arms to the headgear.

Figure 78B:
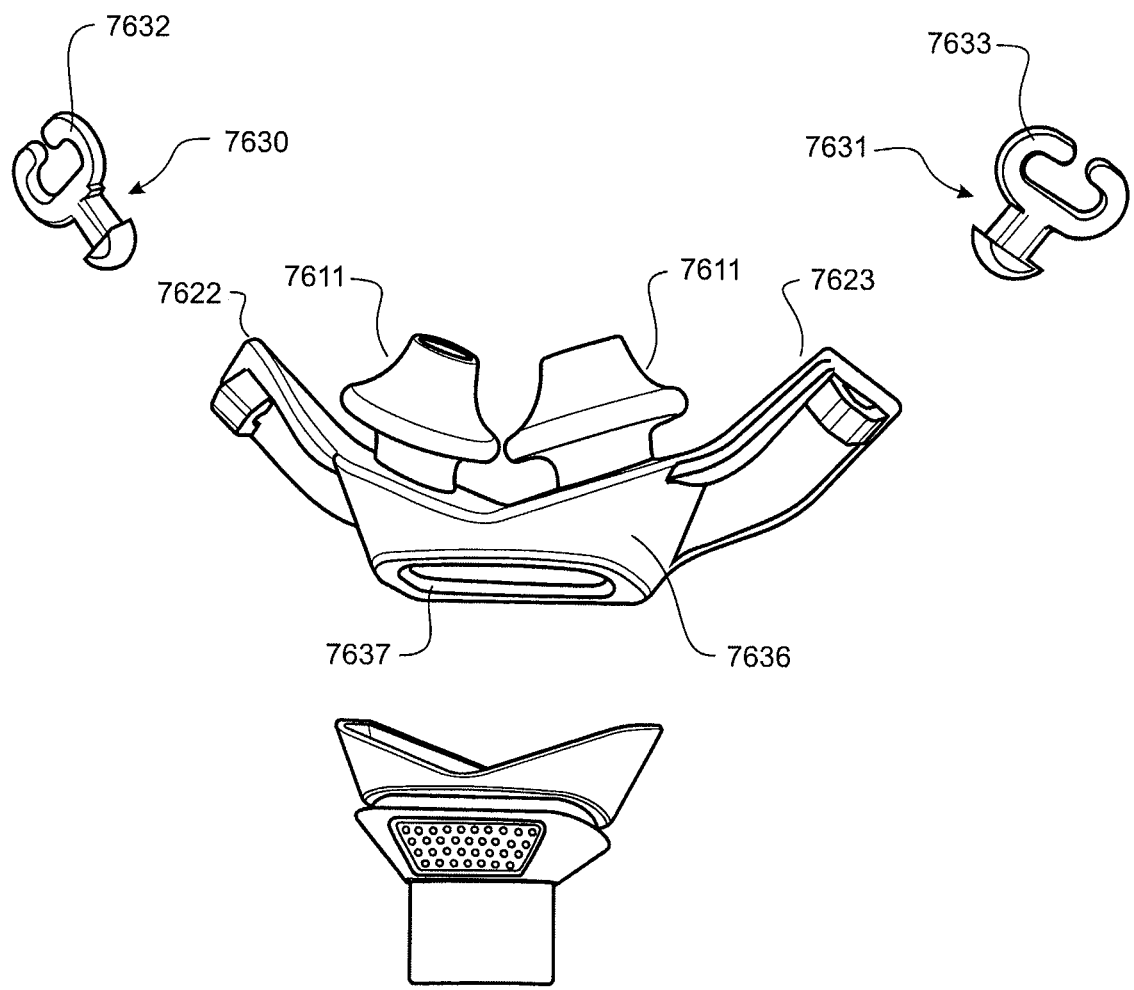

FIG. 78b shows an exploded view of the preferred form of interface core portion and connecting arms of FIG. 78a.

Figure 79:
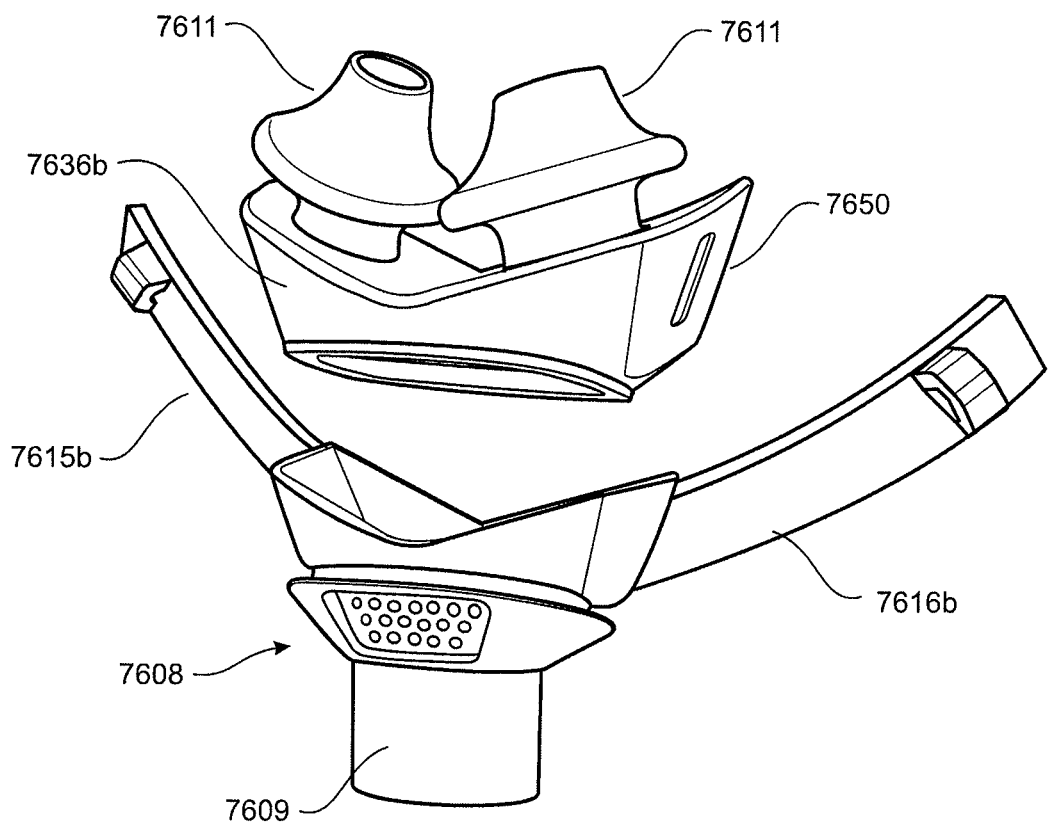

FIG. 79 shows an exploded perspective view from the front and to the side of a first alternative form of interface core portion and connecting arms, with the flexible and supple connecting arms directly connected or moulded to a rigid or semi-rigid manifold, the nasal pillows formed or included as part of a separate element which includes a gasket, and which is removably connected to the rigid or semi-rigid manifold.

Figure 80:
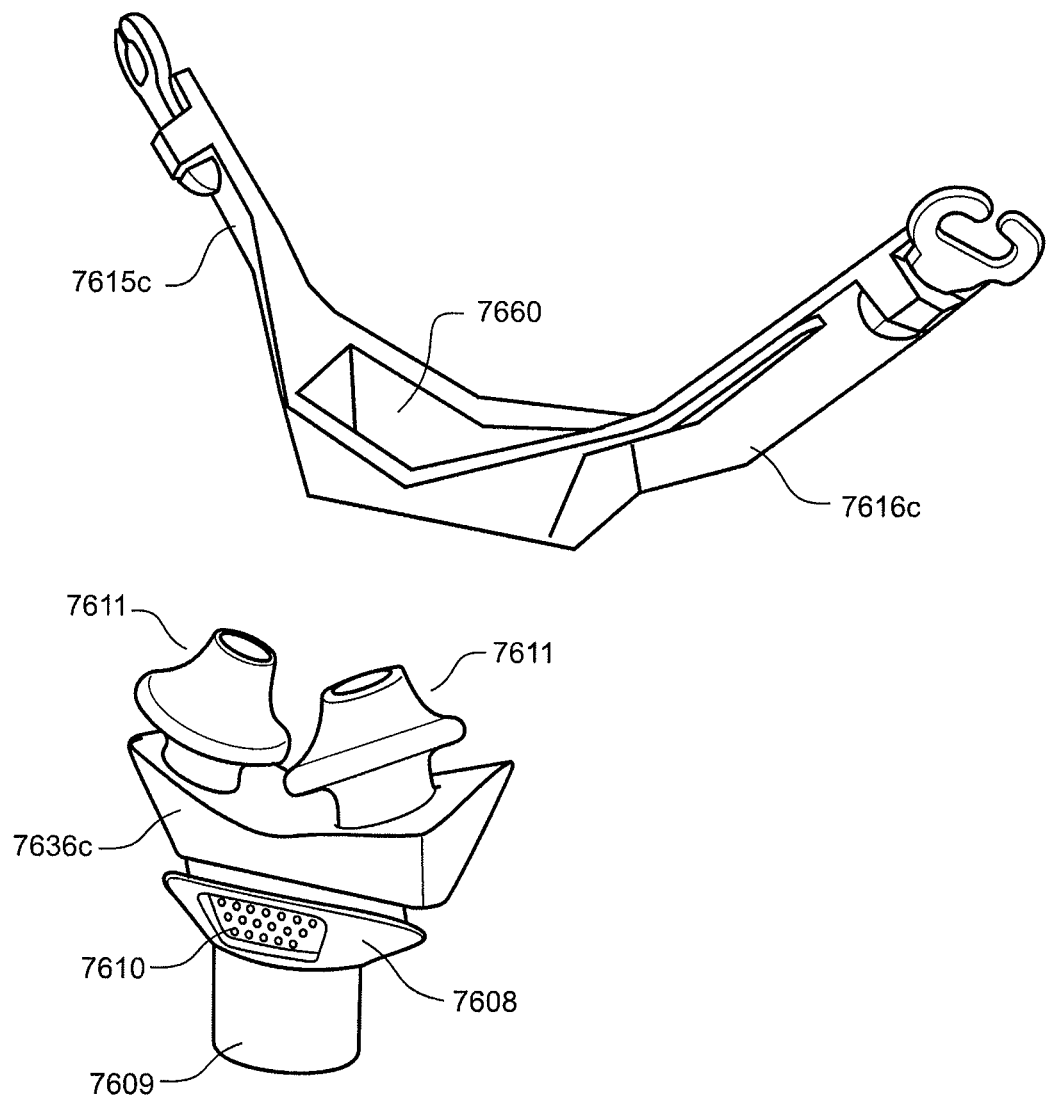

FIG. 80 shows an exploded perspective view from the front and to the side of a second alternative form of interface core portion and connecting arms, with the flexible and supple nasal pillows directly connected or moulded to a rigid or semi-rigid manifold by way of a flexible and supple gasket, the connecting arms removably connected to the rigid or semi-rigid manifold, or formed as part of a separate element which is removably connected to the rigid or semi-rigid manifold.

Figure 81:
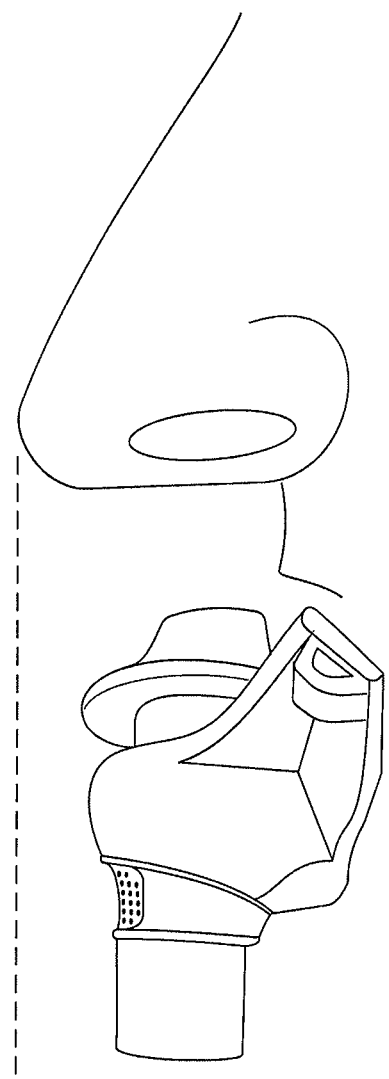

FIG. 81 shows a side view of the nose of a typical user, with the interface core portion and connecting arms of the preferred embodiment located just below the users nose, so that they would only be required to be moved upwards a short distance vertically to be in an 'in use' position, the tip or front-most portion of the users nose extending beyond the front-most portions of the interface core portion.

Figure 82A:
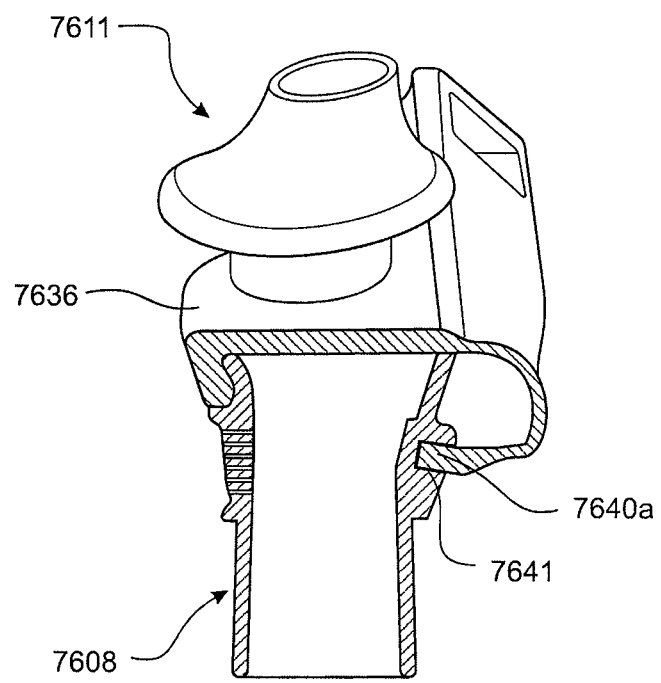

FIG. 82a shows a cut away side view of the preferred form of interface core portion, showing detail of the preferred form of connection between the manifold and the pillows and gasket, with a lip cushion also shown.

Figure 82B:
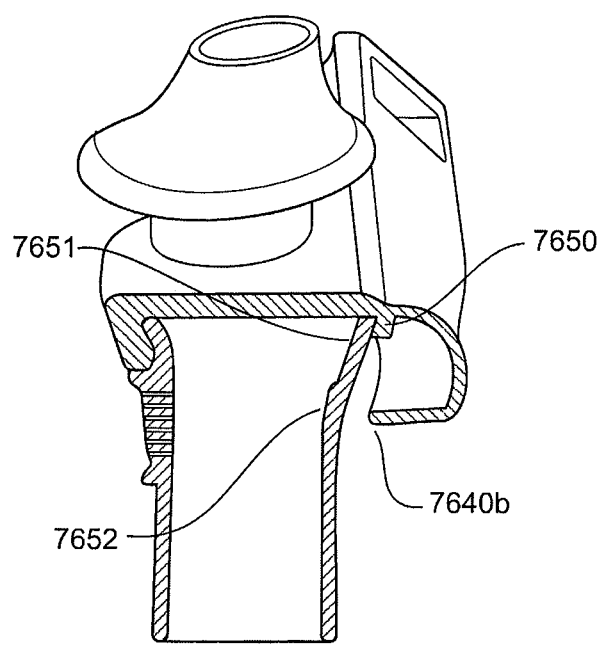

FIG. 82b shows a cut away side view of an alternative form of interface core portion, showing detail of a first alternative form of connection between the manifold and the pillows and gasket and the lip cushion.

Figure 82C:
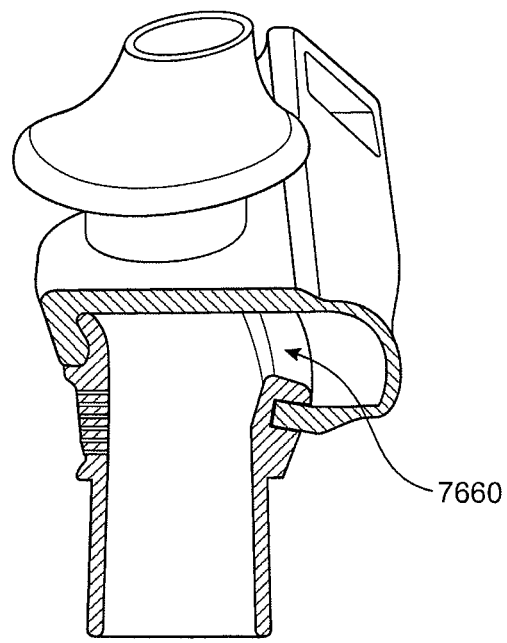

FIG. 82c shows a cut away side view of another alternative form of interface core portion, showing detail of an air passage between the interior of the manifold 8 and the interior of the lip cushion.

Figure 83:
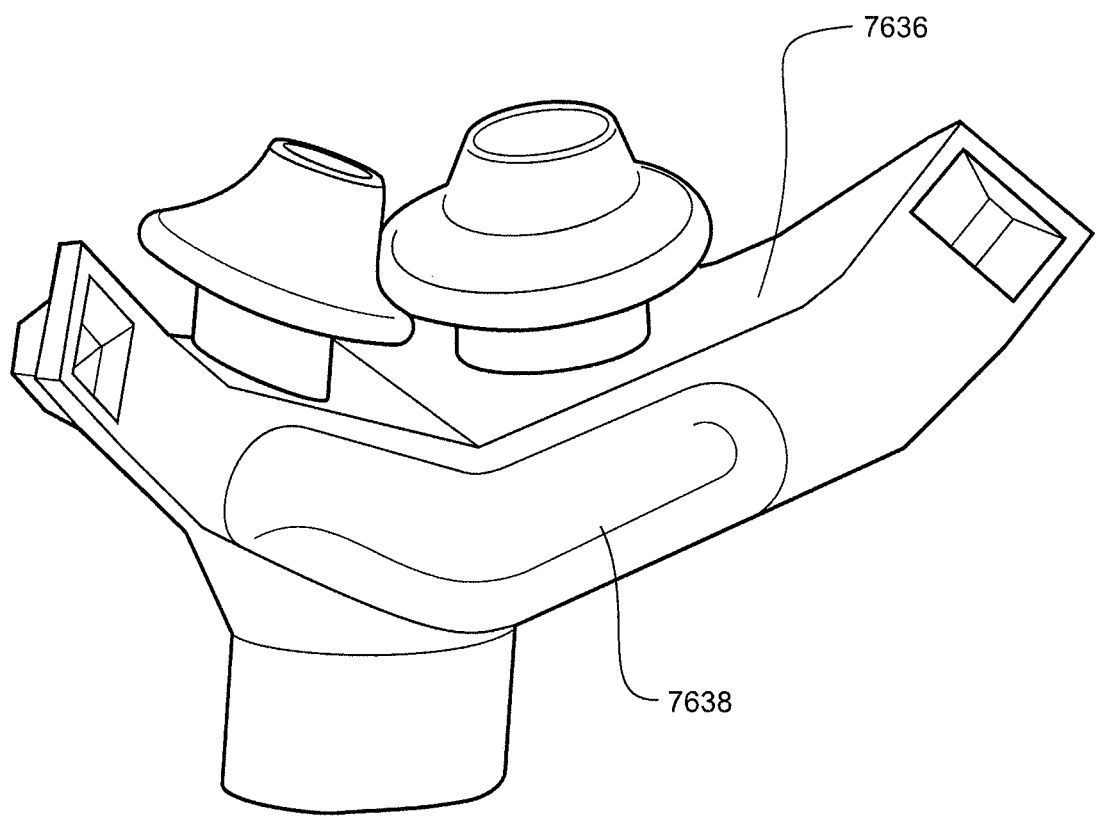

FIG. 83 shows a perspective view from the rear and to the side of the preferred form of interface core portion, showing particular detail of a lip cushion formed on the rear of the interface core portion and which rests on the upper lip of a user in use.

Figure 84A:
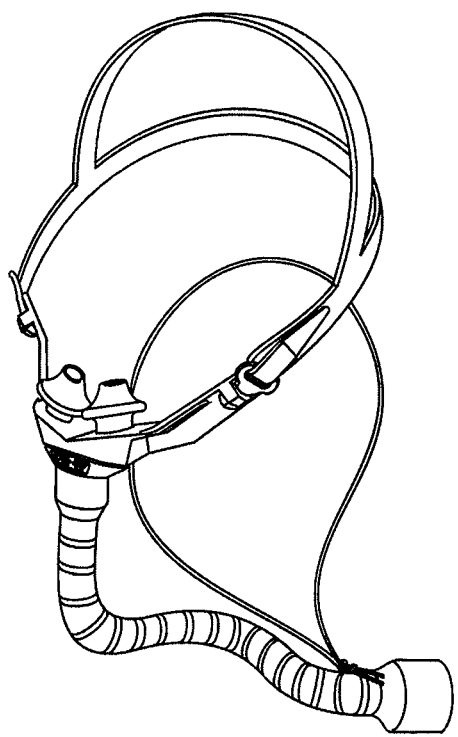
Figure 84B:
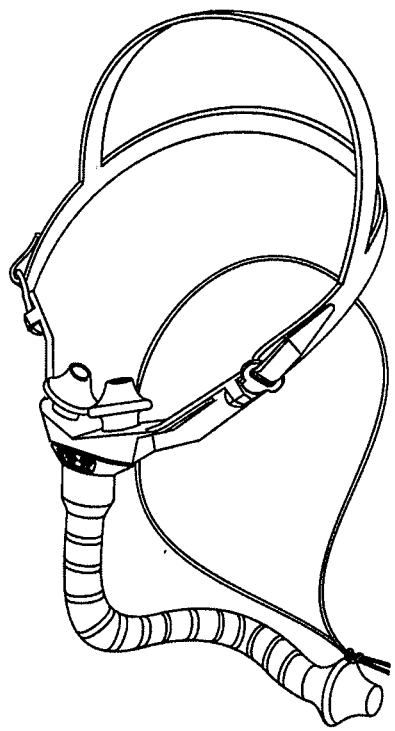
Figure 84C:
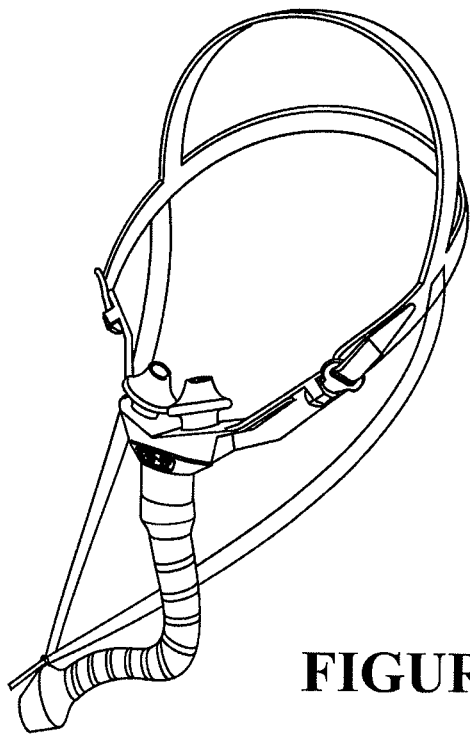

FIGS. 84a to 84c show detail of different alternative forms of connection of the lanyard to the rest of the interface.

Figure 85:
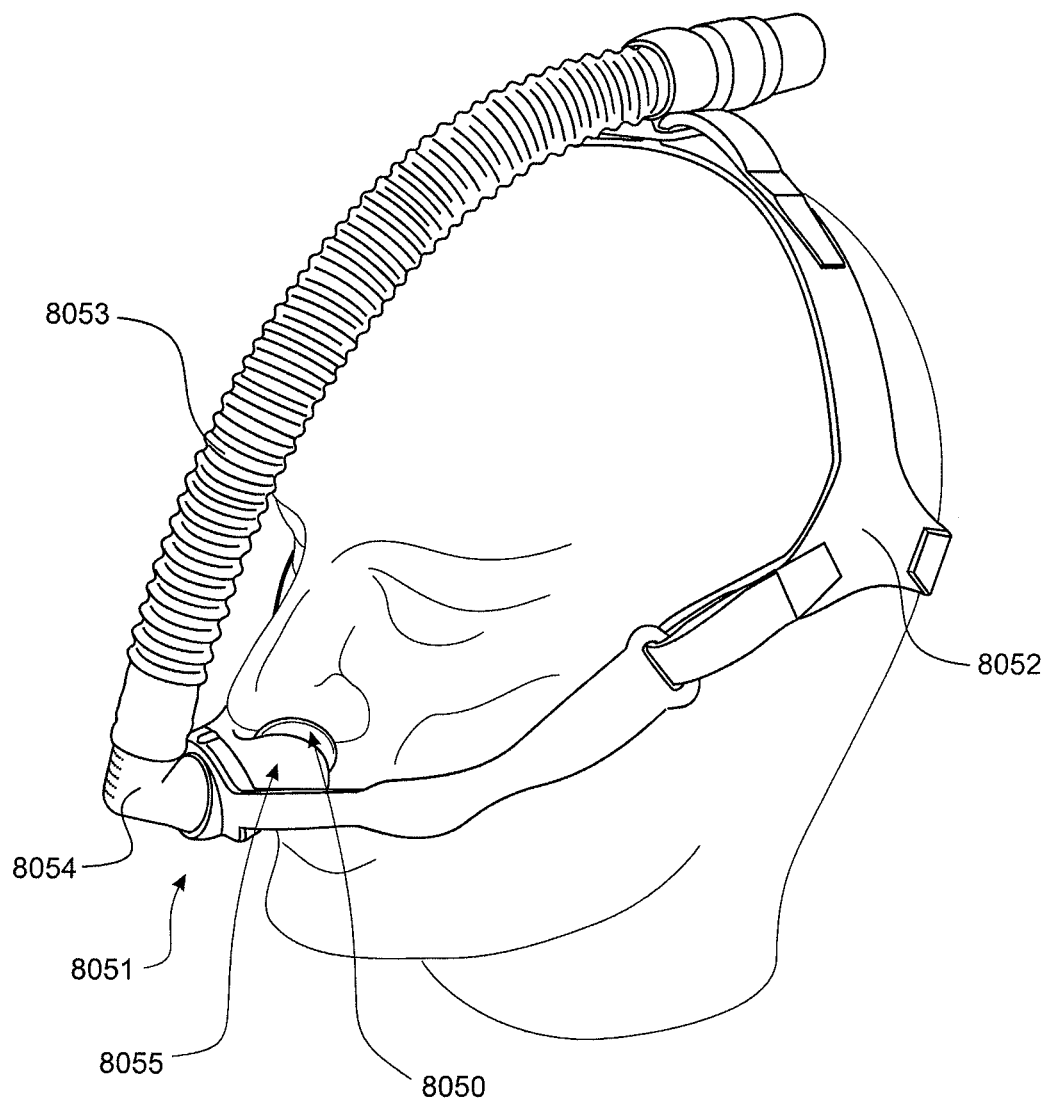

FIG. 85 is a mask and headgear that can be used with any of the embodiments of the nasal plugs of the present invention.

Figures 86, 87, 88:
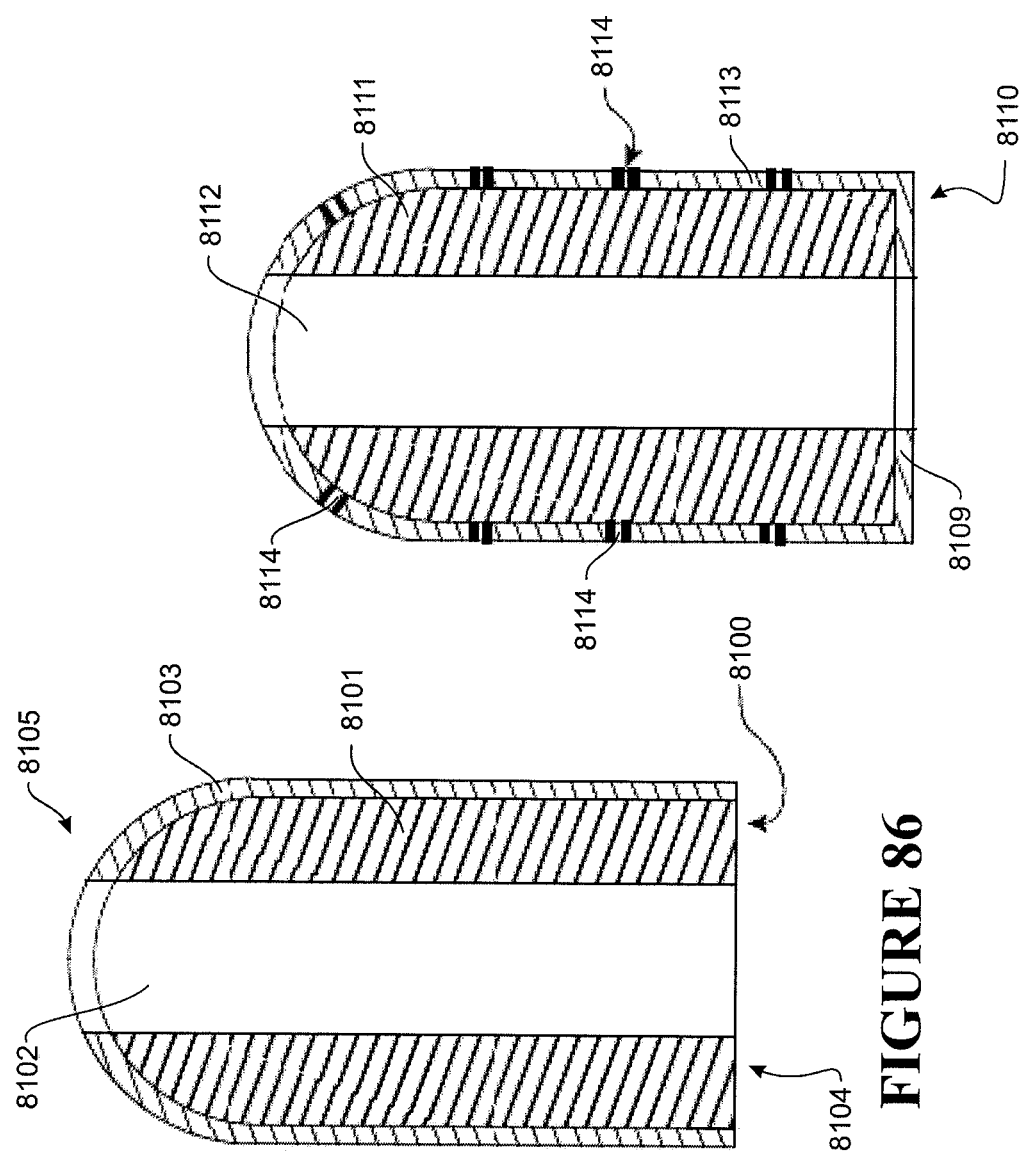

FIG. 86 is a cross-sectional view of a first form of a nasal plugs of the present invention.

FIG. 87 is a cross-sectional view of a second form of a nasal plugs of the present invention.

FIG. 88 is a cross-sectional view of a third form of a nasal plugs of the present invention.

FIG. 89 is a cross-sectional view of a fourth form of a nasal plugs of the present invention.

FIG. 90 is a cross-sectional view of a fifth form of a nasal plugs of the present invention.

FIG. 91 is a cross-sectional view of a sixth form of a nasal plugs of the present invention.

Figure 92:
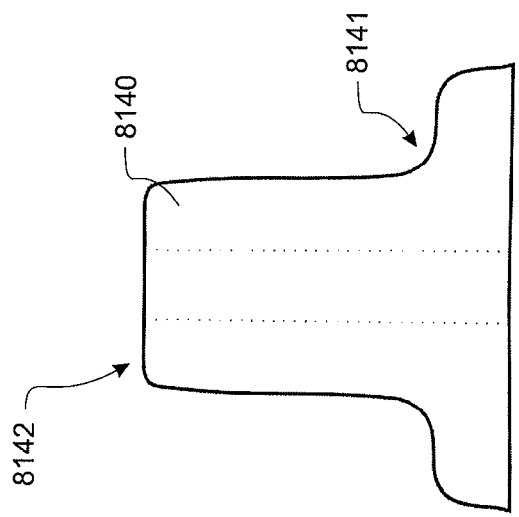

FIG. 92 is a cross-sectional view of a seventh form of a nasal plugs of the present invention.

Figure 93:
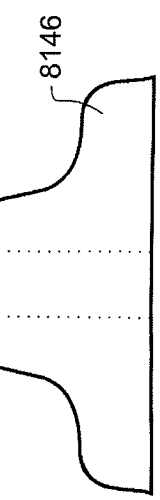

FIG. 93 is a cross-sectional view of an eighth form of a nasal plugs of the present invention.

Figure 94:
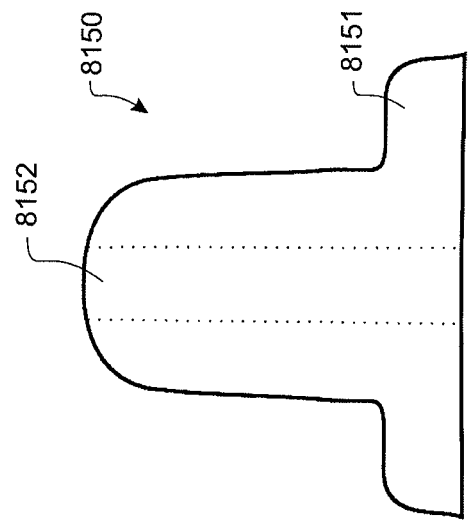

FIG. 94 is a cross-sectional view of a ninth form of a nasal plugs of the present invention.

Figure 95:
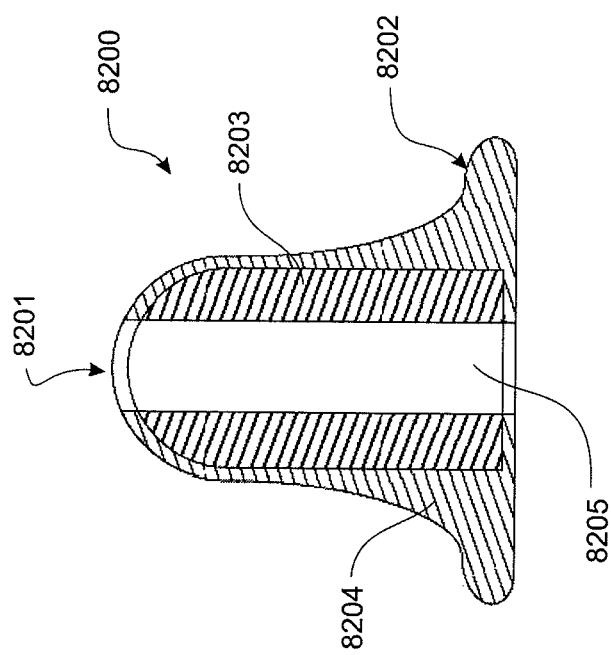

FIG. 95 is a cross-sectional view of a tenth form of a nasal plugs of the present invention.

Figure 96:
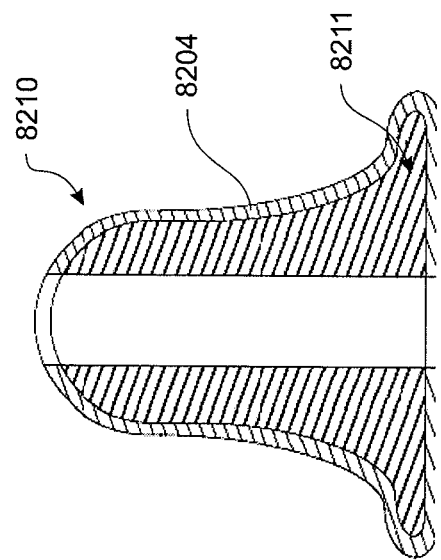

FIG. 96 is a cross-sectional view of an eleventh form of a nasal plugs of the present invention.

FIG. 97 is a cross-sectional view of a twelfth form of a nasal plugs of the present invention.

FIG. 98 is a cross-sectional view of the nasal plugs of FIG. 97 with a different coating layer.

FIG. 99 is a cross-sectional view of the nasal plugs of FIG. 97 with a yet another different coating layer.

FIG. 100 is a cross-sectional view of the nasal plugs of FIG. 98 with a yet another different coating layer.

FIG. 101 is a side view showing hidden detail of the nasal plugs of FIG. 97.

Figure 102:
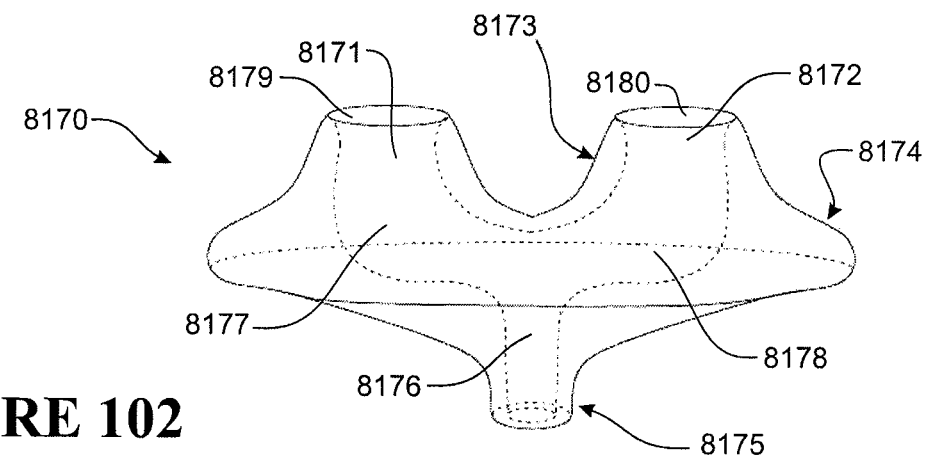

FIG. 102 is a side view showing hidden detail of a thirteenth form of a nasal plugs of the present invention.

Figure 103:
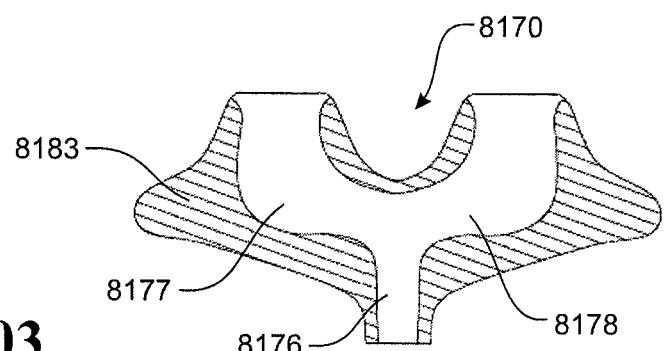

FIG. 103 is a cross sectional view of the nasal plugs of FIG. 102.

Figure 104:
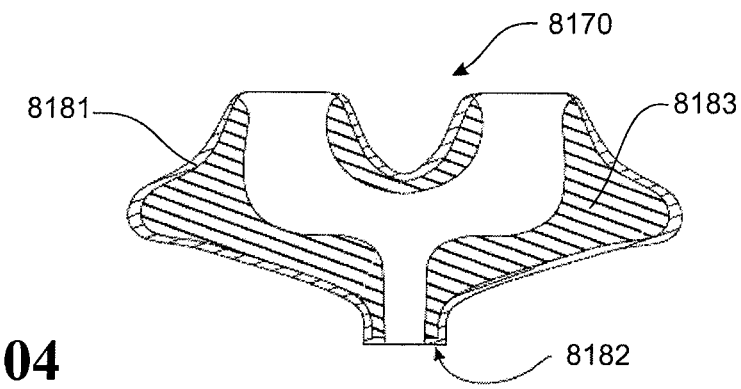

FIG. 104 is a cross sectional view of the nasal plugs of FIG. 102 with a different coating layer.

Figure 105:
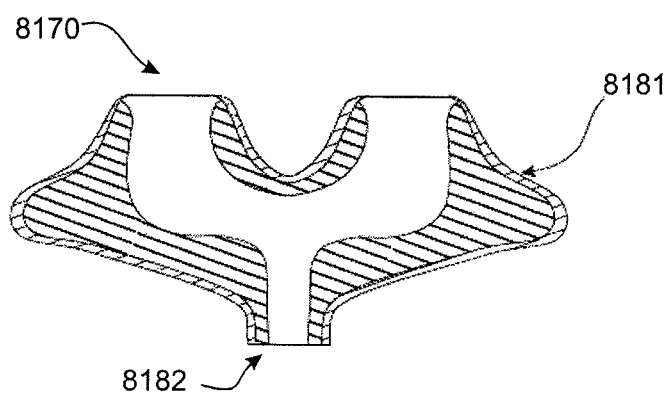

FIG. 105 is a cross sectional view of the nasal plugs of FIG. 102 with a yet another different coating layer.

Figure 106:
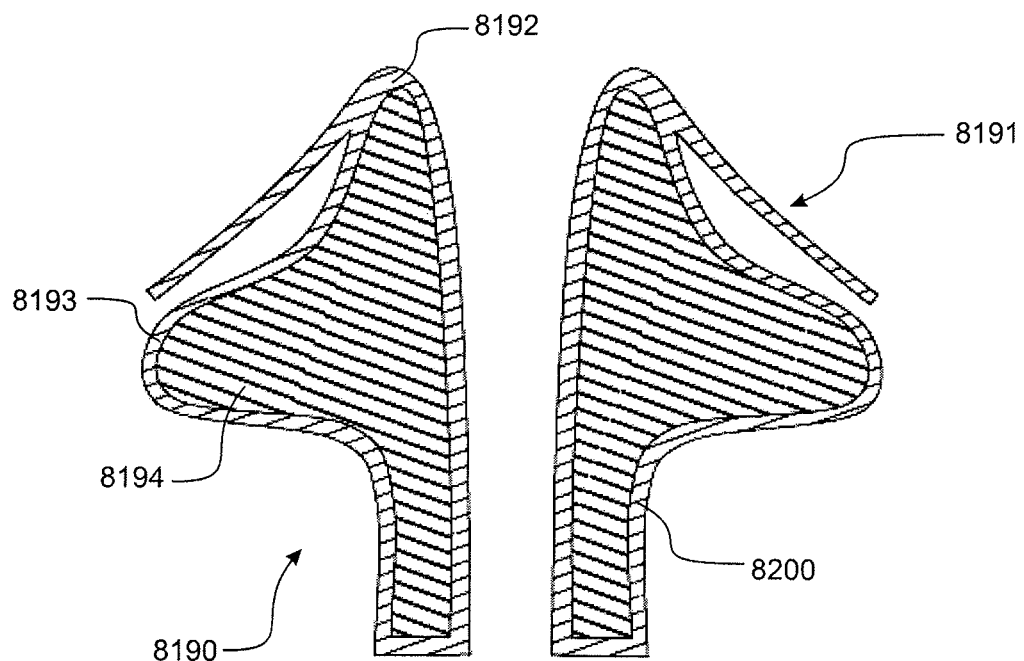

FIG. 106 is a cross sectional view of a fourteenth form of nasal plugs of the present invention.

Figure 107:
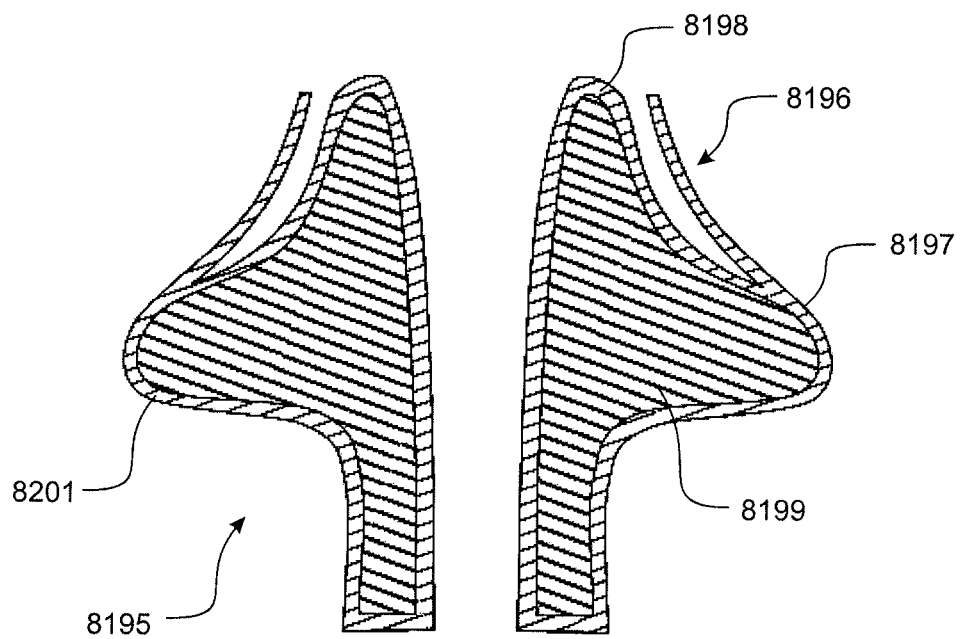

FIG. 107 is a cross sectional view of a fifteenth form of nasal plugs of the present invention.

DETAILED DESCRIPTION OF THE PREFERRED EMBODIMENT

Preferred and alternative forms of an interface for use as part of an apparatus for providing gases to a patient are described below. The preferred and alternative embodiments are for use as part of an apparatus for providing a stream of heated, humidified gases at a pressure above atmospheric pressure to a user for the purposes of CPAP therapy or similar.

It should be noted that the interface is not limited for use as part of an apparatus for providing CPAP therapy. The interface could also be used for Bi-PAP or variable pressure therapy, as part of an apparatus used for an anti-snoring treatment regime, for the treatment of COPD, or as part of any therapy regime where the gases are supplied at a pressure greater than atmospheric is delivered to the breathing passages of a patient or user via an interface assembly. Further it should be noted that the term "patient" or "user" may be interchangeably used. They both have the same meaning in the context of the specification. "User" and "patient" refer to a person who will be using the system and apparatus described in the specification.

The preferred embodiments will now be described in detail with reference to the Figures. However, it should be noted that many variations are possible which have not been specifically described, without departing from the intended scope.

1. Gases Supply System

Figure 1:
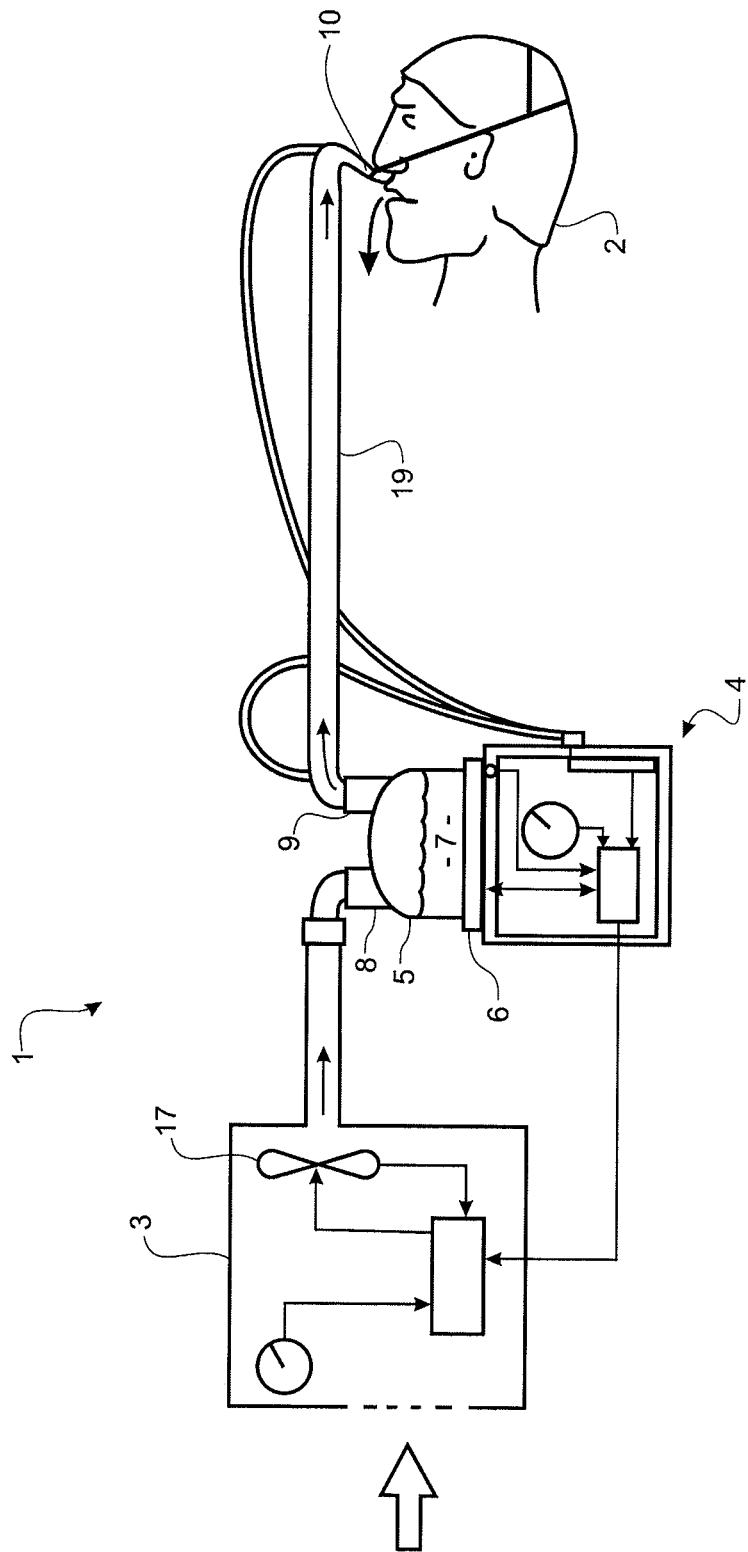
FIG. 1 shows a schematic view of a system for supplying a stream of heated humidified gases to a user via an interface assembly, the system including a gases supply unit or blower, a humidifier chamber gaseously or fluidically connected to the gases supply unit, and a supply conduit connecting the humidifier chamber to an interface assembly.

FIG. 1 shows a schematic view of a typical system 1 for providing a stream of heated humidified gases at a pressure above atmospheric to a user 2. The system 1 includes a gases supply unit or blower unit 3 which in use receives gases from atmosphere and passes these through a fan unit 17 or similar inside the blower unit so that when the gases leave the blower unit 3, they are at a pressure above atmospheric, and are flowing at a certain flow rate. A humidifier unit 4 is located downstream from the blower unit 3, and in use receives the flow of pressurised gases from the blower unit 3. The humidifier unit 4 includes a water chamber 5 which in use contains a volume of water 7. The volume of water 7 in the chamber 5 is in use heated—in the embodiment shown in FIG. 1, the water 7 is heated by a heater plate 6 located underneath the chamber 5. The gases from the blower unit 3 pass into the chamber 5 via an entry port 8, the gases passing through the chamber 5 and across the surface of the water 7, becoming heated and humidified as they do so. The gases then pass out of the humidifier chamber 5 via a humidifier outlet port 9.

It should be noted that a modular humidification system has been described above—that is, a system where the humidifier unit 4 is a separate unit to the blower unit 3. An integrated humidification system could also be used—that is, a system where the blower unit and the humidifier unit are two integral parts of a single unit, or where the blower unit and the humidifier unit are rigidly attached or connected together in use.

Furthermore, it is preferable, although not necessary, that the overall respiratory system have a modular configuration. In the preferred embodiment the individual components are releasably interconnected to form the complete respiratory system. The modularity of the preferred system allows individual components to be maintained and replaced as necessary. It also permits components to be interchanged to meet individual user requirements. This is particularly useful in institutional applications, where a base unit (such as the blower and humidifier unit) can be used for different recipients at different times while the patient interface is interchanged to suit the particular user.

In use, a main supply conduit 19 is connected to the humidifier outlet 9. The heated and humidified gases stream exits the humidifier unit 4 via the humidifier outlet 9 and enters the main supply conduit 19, passing along the supply conduit 19 to an interface assembly 10 which is connected to the user end of the supply conduit 19. The supply conduit 19 can either be directly connected to the interface assembly 10, as shown in FIG. 1, or an intervening interface conduit 190 can be used to connect between the main supply conduit 19 and the interface assembly 10, as shown in the embodiments of FIGS. 2, 3 and 4. Where the supply conduit 19 is referred to below, this should be taken to mean either the supply conduit 19 by itself, or in combination with the interface conduit 190.

2. Supply Conduit and Interface Conduit

In the preferred embodiment, the supply conduit 19 is a flexible tube formed from a plastic type material, many different variations of which are known in the art. One end of the supply conduit 19 is connected to the humidifier outlet port 9, with the other end connected either directly to the interface assembly 10, or connected to the distal end 190a of the interface conduit 190, the interface conduit 190 connected to the interface core section 11. The most preferred form of interface conduit 190 is approximately 30 cm or 1 foot in length, with an external diameter of between 1-2 cm and a thin ribbed wall, the ribs being approximately 2-3 mm thick and the wall between the ribs being significantly less that 1 mm thick. However, it should be noted that variations from these dimensions are possible without departing from the scope of the invention, and for example a non-ribbed conduit could be used if required. It should further be noted that 'flexible tube' as it is used in this specification should be taken to mean that the tube or conduit is flexible enough so that it is capable of being bent or deformed repeatedly (for example, by bringing the two ends of the conduit together, or by tying a loose knot in the conduit if it is long enough, say, approximately 30 cm or more in length), with the tube or conduit returning to its original undeformed shape with little to no plastic deformation occurring, every single time the tube or conduit is bent or deformed in this manner.

In the most preferred form, neither of the supply conduit 19 or the interface conduit 190 will rigidly support their own weight when held at one end so that the main body of the conduit extends outwards generally horizontally from the held end. Over a 20-30 cm length of supply conduit (which has a diameter of 1-2 cm and a wall thickness at the ribs of 1-3 mm and a wall thickness between the ribs of less than 1 mm), the unsupported end of the interface conduit will bend to face substantially directly downwards. For example, the interface conduit of the Swift LT™ interface is formed in such a manner that over a 20-30 cm length, the unsupported end will bend downwards so that it points substantially vertically downwards. The interface conduit used in the Opus is somewhat stiffer, but will still bend through an angle of around 45 degrees. Both of these conduits are flexible for the purposes of this specification, and should not be thought of as 'rigid' or 'semi-rigid' (see Lexicon section for more details). The main supply conduit 19 is of similar flexibility to both of these items.

The conduits 19, 190 connect to each other, or to the interface assembly 10, or both, by a friction push fit, a bayonet connection or similar, or by any other suitable connection as might be known in the art.

3. Nasal Pillow Variations 3.1 Interface Assembly

Specific preferred forms of an interface assembly 10 are shown in FIGS. 2, 3, and 4 as interface assembly 200, interface assembly 300 or interface assembly 400. The interface assemblies 200, 300, 400 have a number of common elements and differences as will be described below. In the description below, the element numbering conforms to the following convention: For the embodiment of FIG. 2, the elements unique to that embodiment will be numbered e.g. 201, 210, etc. The equivalent unique elements on the embodiments shown in FIGS. 3 and 4 will be numbered e.g. 301, 310 and 401, 410 respectively. If the element is being referred to in a general sense, it will be referred to as e.g. 1, 10 etc to show that the description is applicable to all the embodiments shown in FIGS. 2, 3, 4, and could also be applied as a general description to other, general, embodiments not specifically shown.

The interface assembly 10 (e.g. assemblies 200, 300, 400) are assembled from two main parts: an interface core portion or interface core section 11, and a headgear assembly 12.

The interface core section 11 and the supply conduit 19 (either including or excluding the interface conduit 190) are mutually adapted so that one end (the patient end or proximal end) of the supply conduit 19 is fluidically or gaseously connected to the interface core section 11 in use, the interface core section 11 adapted so that the supply of heated, humidified gases is provided to the interior of the interface core portion 11 from the supply conduit 19 via this connection. The preferred forms of this connection will be described in detail below.

3.2 Headgear Assembly

The headgear assembly 12 is formed from two main items: a set of arms 13 that extend in use one from each side of the interface core portion 11, and a set of headgear straps 14. In the preferred embodiments, the arms 13 are formed from either a flexible or a semi-rigid plastic, backed with neoprene, foam, or similar to form a cushion portion, the cushion portion resting against the face of a user in use.

The arms 13 can be connected to the interface core portion 11 in a number of ways. For example, arms 213 could be integrally formed with the interface core portion 211, as shown in the embodiment of FIG. 2.

Figure 3A:
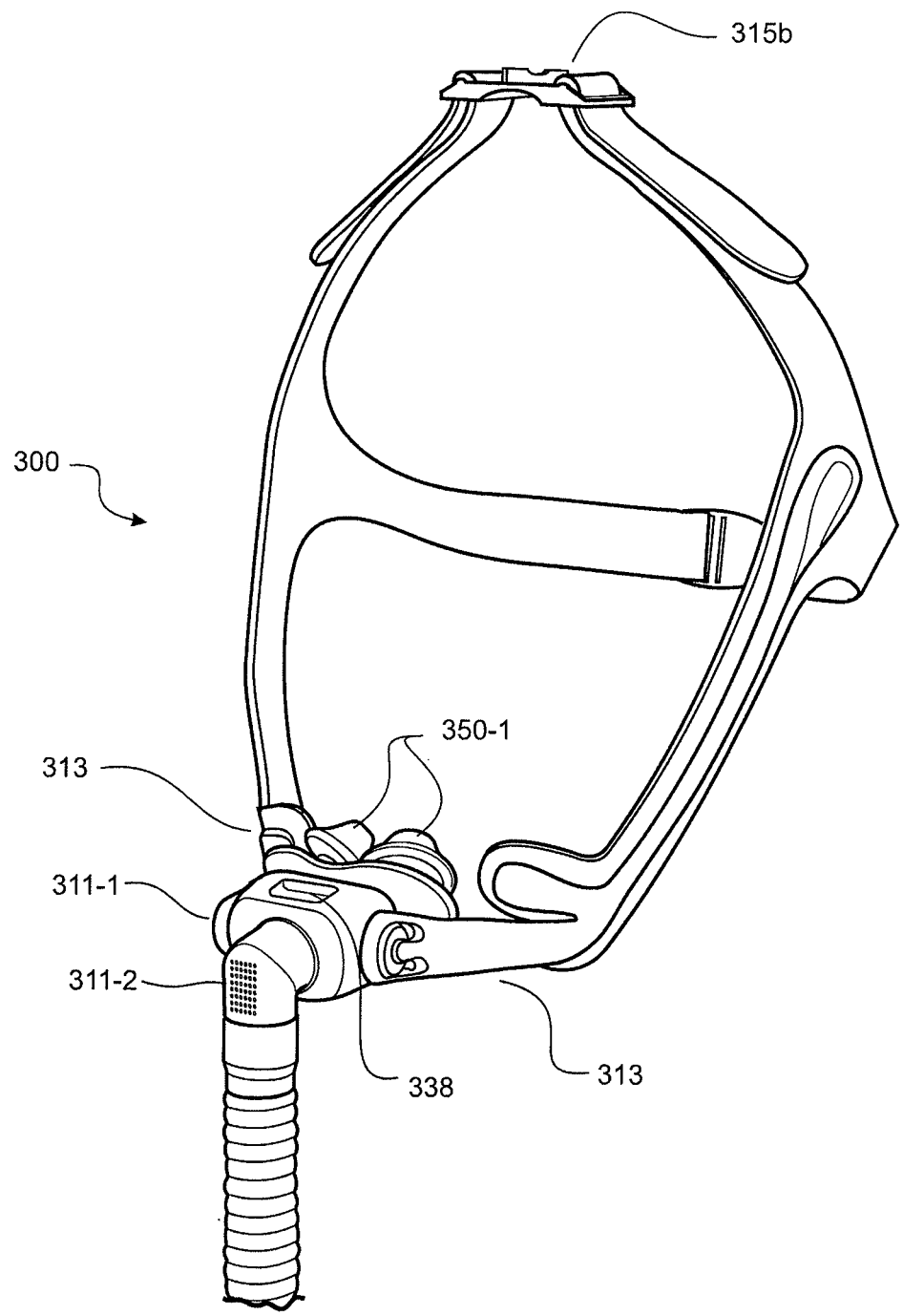
FIG. 3a shows a second preferred embodiment of the interface assembly of the present invention, the second preferred embodiment containing similar elements to those of the first preferred form of FIG. 2 but configured differently.
Figure 4A:
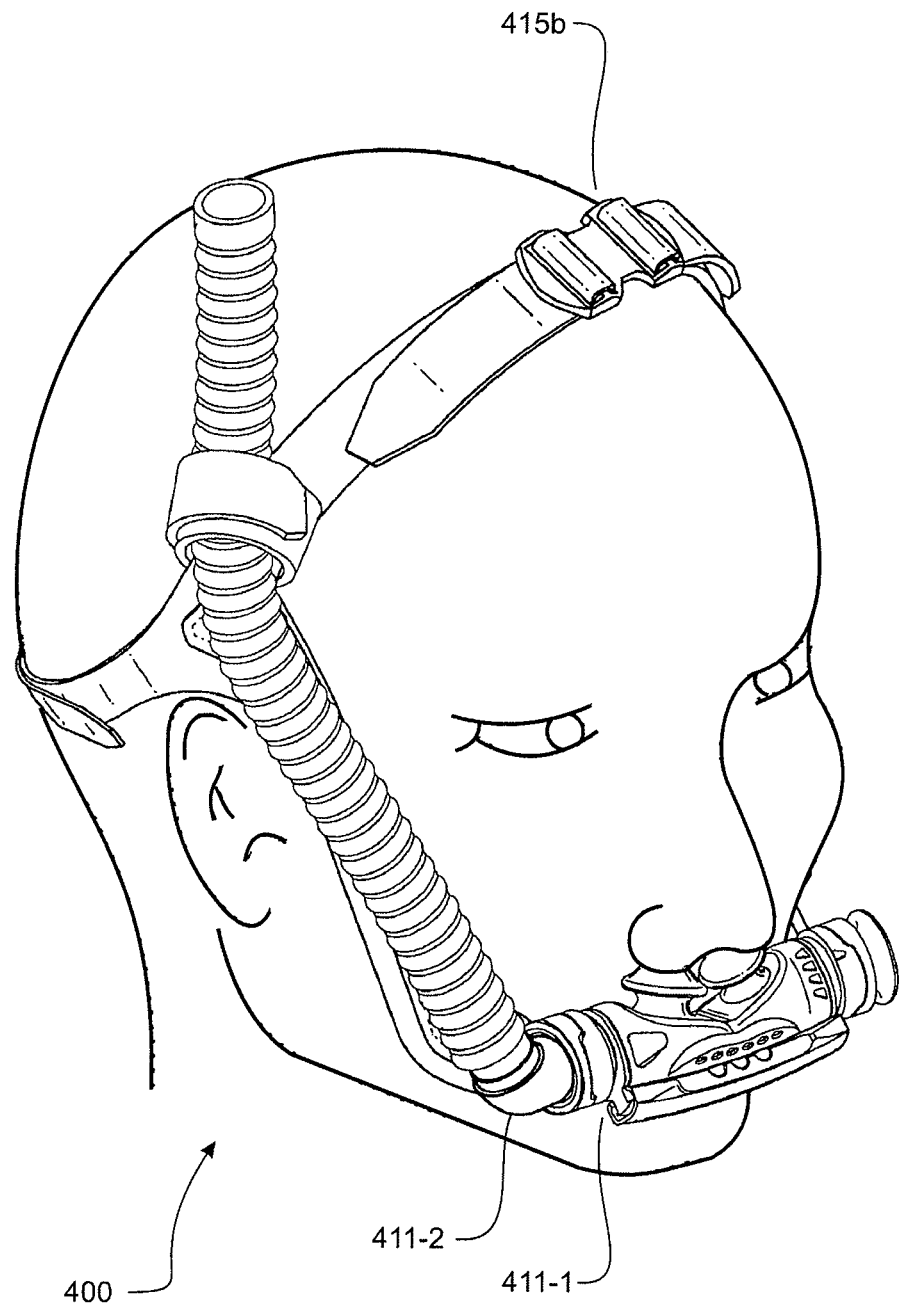
FIG. 4a shows a third preferred embodiment of the interface assembly of the present invention being worn by a user, the interface assembly of this third preferred form having similar elements to those of the preferred embodiments of FIGS. 2 and 3, but configured differently.

Alternatively, arms 313 could be connected to the interface core portion 311 as shown in the embodiment of FIG. 3a, the connection made in such a manner as to allow the arms 313 to be rotatably adjusted with respect to the interface core portion 311. The embodiment of FIG. 3a with the adjustable arms shows an interface assembly 300 that has an interface core portion 311 and arms 313. The interface ends of the arms 313 are rotatably connected to the interface core portion 311 by way of a 'rotating barrel' connection as on the ResMed Swift™ LT, which allows the arms 313 to rotate relative to the interface core portion 311, and still remain connected. The mutual connection is formed so that when the connection is made, the arm 313 will remain in the position to which a user rotates it once it is rotated to that position—it will not freely rotate unless manipulated by a user.

For all of the preferred forms, the headgear straps 14 extend around the rear, or over the top of a user's head (or both) in use, to support the interface assembly 10 in position in use. In the embodiment of FIG. 2, the ends of the arms 213 in use co-locate with the ends of the headgear straps 214, with the ends of the arms 213 and the ends of the headgear straps 214 mutually adapted to connect together in use to hold the interface assembly 200 in position. In this form, the ends of the main strap 214 include two patches of Velcro™ on the outer surface at each end—one 'hook' patch and one 'loop' patch. When each of the ends is doubled back on itself to form a loop, the Velcro™ patches engage to hold this loop together. In use, the ends 224, 225 are passed one each through slots on the ends of the arms 213 and then doubled back on themselves to engage the headgear assembly 212 with the core section 211. This arrangement could be used on other embodiments if required.

In alternative embodiments, such as those shown in FIGS. 3 and 4, the headgear straps 314, 414 could be formed as an extension of the cushion portion, with the headgear straps 314, 414 formed from neoprene or similar.

It is preferred that all the different embodiments of headgear straps 13 include a secondary upper strap 20 which passes across the top of a user's head, as well as the main strap 14 which passes behind the user's head. The secondary upper strap 20 is arranged so that it passes across the top of a users head, with each end of the secondary strap 20 connecting to the main strap 14 just behind the ears of a user. Each of these straps 14, 20 includes an adjustment mechanism such as buckles 15a, 15b or similar. These could be Velcro™ adjusters or buckles as preferred. The headgear secondary upper strap 20 could also be independently formed and connected to the main strap 14. The adjustments could be at any location on the strap that is convenient—sides, front or rear. The straps 14, 20 could be of different widths or thicknesses as required for user comfort. For example, in the most preferred form, the main strap 14 is wider than the secondary strap 20.

Suitable strap materials may include a woven elastic strip or a narrow strip of foam and fabric, such as Breathoprene™. Alternatively, the headgear could be formed from silicone, or coated with silicone. The headgear arms could be padded or cushioned on their inside surfaces if they are formed from silicone, in order to increase user comfort. Padding could also be added to the preferred form of arms—those made from Breathoprene™ or similar.

3.3 Interface Core Section—General

The interface core section 11 of the preferred forms functions as a supply manifold inlet, receiving breathing gases from the breathing gas conduit 19.

Preferably the interface core section incorporates a connector junction adapted to engage with a reciprocal connector junction on another breathing system component. Such components may include an elbow connector, the interface conduit or the supply conduit 19.

Preferably the respective connector junctions incorporate a reciprocal snap or push fit inter-engagement. However alternate connection mechanisms are also known and are equally as applicable.

When the connector junctions are appropriately engaged, an interface connection is formed between the respective breathing system components. The resulting interface connection locates and seals the respective breathing system components relative to each other.

Preferably the interface connection is capable of adapting to changes in the users position. Generally the interface connection compensates for user movements by permitting the respective components on either side of the interface connection to move in defined paths relative to each other. One example is the swivel connection pictured in FIG. 3.

The interface core section 11 can be formed as a single component which receives the supply conduit 19 directly, or as separate components that are inter-connected after fabrication.

The integrated embodiment of the interface core section 11 incorporates a connector junction which is adapted to receive the patient end of the supply conduit 19. In this form, the end of the supply conduit 19 is connected directly to the one-piece interface core section 11, for example, by direct interconnection with the interface core section 11 connection junction.

In the alternative, modular embodiment, the supply conduit 19 connects to a sub-component or sub-assembly (such as an elbow connector) which is in turn connected to the interface connection junction. The sub-component is preferably incorporated as part of the interface core portion 11 when the interface core section 11 is assembled; but is generally fabricated as a separate item.

3.4 Interface Core Section—First Preferred Form

An example of a modular interface core section 211 is pictured in FIG. 2. The interface core section 211 includes a manifold inlet section 211-1 and an elbow connector 211-2.

One end of the elbow connector 211-2 is fabricated into a hollow ball segment. The manifold section 211-1 includes a complimentary socket adapted to receive the ball segment. In the assembled core section 211 the ball segment and socket combine to form a ball and socket connection or a ball joint.

The ball joint connection permits the manifold inlet 211-1 three-dimensions of movement (movement in three planes) relative to the elbow connector 211-2.

The connection allows unrestrained relative rotation (swivel) of the manifold inlet 211-1 and the elbow connector 211-2 about the axis of the socket. In the embodiment particularly shown in FIG. 2c, the socket axis on the manifold inlet 211-1 is aligned with the exterior aperture on the elbow connector 211-2 from which the ball segment protrudes.

The ball joint connector of the preferred form shown in FIG. 2 also permits restricted motion of the components transverse to the socket axis. This motion equates to up/down and side/side rotation of the elbow connector 211-2 when viewed by a user wearing the interface in the intended orientation.

3.5 Interface Core Section—Second Preferred Form

Figure 3B:
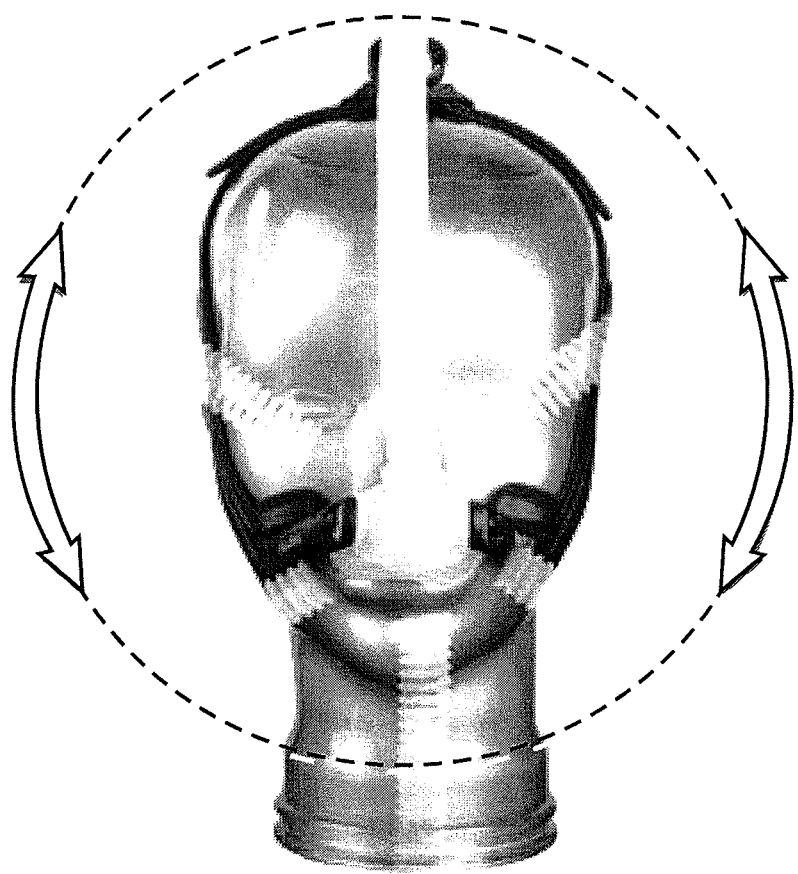

An example of a second preferred form of interface core section 311 that includes an elbow connector is shown in FIG. 3a. A manifold portion or manifold section 311-1 is shown, the manifold section 311-1 including an aperture located at the front of the manifold section 311-1. An elbow connector 311-2 is connected to the manifold section 311-1 via the aperture, with one end of the elbow connector 311-2 locating into or connected to the aperture. The manifold section 311-1 and the elbow connector 311-2 are mutually adapted to provide a 360 degree swivel—the elbow connector 311-2 and the manifold section 311-1 can swivel or rotate relative to one another in use, as shown in FIG. 3b. The manifold section 311-1 and the elbow connector 311-2 are assembled together to form part of the interface core section portion 311 of the embodiment of FIG. 3.

3.6 Interface Core Section—Third Preferred Form

Yet another example of an interface core section that includes an elbow connector is shown in FIG. 4. The manifold section 411-1 includes an aperture at one side of the manifold section 411-1. This aperture receives one end of an elbow connector 411-2 in use, the elbow connector 411-2 adapted to rotate freely relative to the manifold section 411-1, the plane of rotation of the elbow connector aligned back-front of a user 2 in use, rather than side-side as in the embodiment of FIG. 3 or FIG. 2.

3.7 Interface Core Section—Pillow Section

The interface core section 11 further includes a nasal pillow section 50 (e.g. nasal pillow section 250 as shown in FIG. 2d).

The nasal pillow section 50 incorporates nasal pillow portions which include caps 50-1 that are adapted to substantially seal against the nares of a user, the heated, humidified gases stream entering the pillow section 50 and passing through the pillow caps 50-1 into the nasal cavity of a user. 'Substantially seals' as it is used in this specification should be taken to mean that perfectly sealing against the nares with no leaks is the most desirable outcome. However, a small degree of leakage in use is almost certainly inevitable, and a person skilled in the art will understand that the phrase 'substantially sealing' is intended to indicate that a very small amount of leakage may sometimes, but not always, occur. As the pillow caps 50-1 are substantially sealed against the nares of a user, all or substantially all of the stream of gases which passes through the manifold section 11 and the nasal pillow section 50 will be delivered to a user.

As shown in the preferred embodiments of FIGS. 2, 3 and 4, the pillow section 50 is composed of two main sub-parts that form a continuous or integrated whole in use: a pillow portion, which is itself formed from a pair of stems 50-3 and a pair of associated pillow caps 50-1, the caps 50-1 locating into the nares of the user or patient 2 in use, and a pillow manifold section or pillow gasket 50-2, which is connected to the interface core section 11 in use, so that gases passing through the core section 11 in use then pass into the pillow gasket 50-2 and then into the pillows.

In order to aid in sealing the nasal pillow caps 50-1 against the nares of a wide variety of users, each of whom will have differently shaped and sized nostrils, the pillow caps 50-1 and stems 50-3 are in the preferred form formed from a soft and supple material with a high degree of flexibility, such as silicone or similar. Preferred forms of the nasal pillow section 50 are described in detail below.

The nasal pillow section 50 can either be formed separately from the rest of the core portion 11, or integrally formed with the core portion 11. In the preferred embodiments as shown in FIGS. 2, 3 and 4, the nasal pillow section

50 is separate from the core portion 11. The nasal pillow section is formed from two main parts: a base portion or nasal pillow gasket portion 50-2 and a nasal pillow portion composed of stems 50-3 and caps 50-1. The attachment or connection of the nasal pillow portion to the remainder of the core portion 11 is achieved by attaching the gasket portion 50-2 to the manifold portion 11-1, with the pillow portion preferably (although not always) integrally formed with the gasket portion 50-2. The embodiments of FIGS. 2, 3 and 4 show this integral form of connection.

In the preferred embodiments, at least the pillow caps and stalks 50-1, 50-3 are formed from a supple and flexible material, such as silicone rubber.

3.8 Pillow Gasket—First Preferred Form

The first preferred form of pillow gasket portion 250-2 shown in FIG. 2 shall now be described with particular reference to FIG. 2*d*.

The pillow gasket portion 250-2 includes an open lower face or open lower portion 237 which corresponds in use to the open rear face (not shown) of the manifold section 211-1. In use, the perimeter of the open lower portion 237 of the pillow gasket portion 250-2 is connected to the open rear face of the manifold section 211-1. The wall 237*a* which surrounds the open lower portion 237 slots or locates into the open rear face of the manifold section 211-1. It can be seen that all of the gases passing through the manifold section 211-1 will pass into the pillow gasket portion 250-2 and from there into the caps 250-1 of the nasal pillows. It should be noted that the pillow gasket portion 250-2 can be attached and removed repeatedly from the manifold portion 211-1 as required by a user. Optionally, if required, a key 238 can be formed into the wall section 237, the key 238 slotting into a corresponding slot in the manifold section 211-1 to ensure the pillows are correctly oriented in use.

In the first preferred form of pillow gasket portion 250-2, the pillow gasket 250-2 is shaped so that the two side portions are slightly angled towards one another. That is, the top surface which covers the open rear face of the manifold 8 appears to have a V-shape when viewed from the front, with the stems 250-3 of the pillows mounted one on each of the two sub-surfaces or inner faces of the 'V'. The angle of the 'V' is not acute—each edge or plane of the 'V' of the pillow gasket portion 250-2 is raised by a few degrees only (e.g. 5-10 degrees). The stems 250-3 of the pillows are mounted one on each of the two planes, and are in this manner angled inwards towards one another slightly in the most preferred form (although there are of course many other ways in which this could be achieved without creating a 'V'-shape).

In the preferred form, as described above, the nasal pillows and the gasket portion 250-2 are formed as a one-piece item. However, the pillow portions could be removably connected to the gasket portion 250-2, either individually or as a pair. For example, the gasket portion 250-2 could include a pair of stub bases to which the pillows are press-fitted in use, the stub base and the base of the stem 250-3 being mutually adapted to connect together by way of a press-fit, a keyed connection, or similar. This would potentially allow pillows which are of different shapes or sizes to be fitted to the pillow gasket portion 250-2. This would be advantageous if a user required pillows moulded specifically to the shape of their nares, or pillows of different sizes. This would also allow a range of standard pillows to be manufactured, the range having different sizes or different shapes, or both. This would provide a range of off-the-shelf adjustment.

The rear of the pillow gasket portion 250-2 can include a lip cushion 239, which is a rounded elongate surface on the rear of the pillow gasket portion 250-2, the lip cushion 239 resting on the upper lip of a user in use. In the most preferred form the lip cushion 239 is hollow and formed from the same supple and flexible material as is used to form the gasket and pillows. The lip cushion 239 rests against the top lip of a user in use. The lip cushion could, in alternative forms, be formed from foam or similar.

Alternatively, the pillow gasket portion 250-2 can be formed so that it does not contact the upper lip of a user 2. Instead of being rounded outwards or bulging outwards convexly to contact the users lip as a lip cushion as described above, the inner surface of the pillow gasket portion 250-2 is either straight or concave, so that contact with the users face occurs only at the caps 250-1 of the nasal pillows and there is no contact between the face of a user 2 and the pillow gasket portion 250-2—contact only takes place at the caps 250-1 of the nasal pillows.

3.9 Pillow Gasket—Second Preferred Form

Figure 3C:
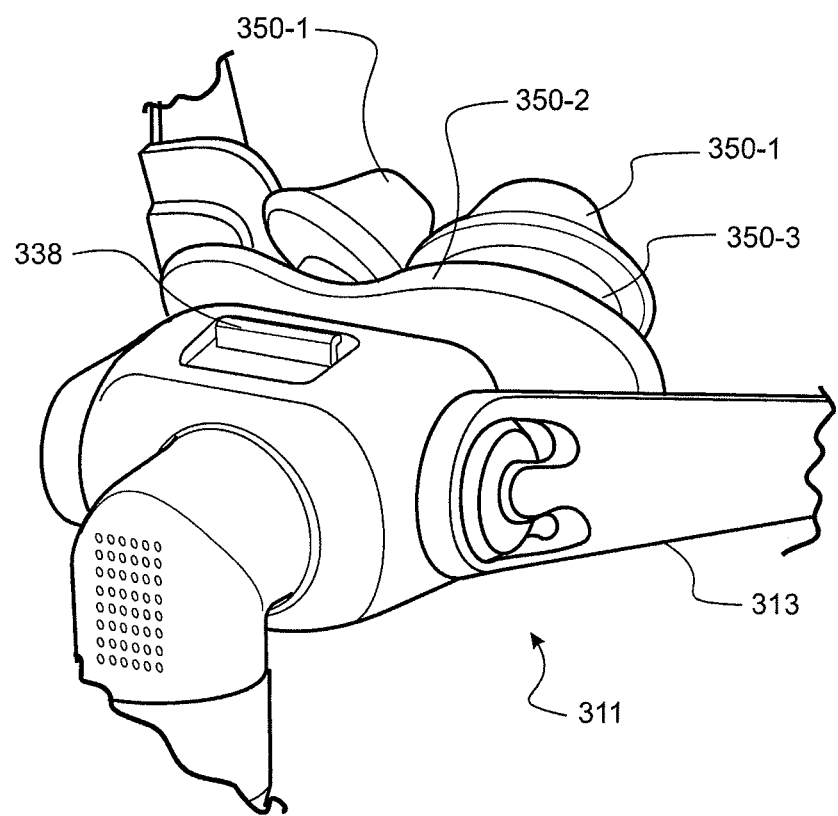

The second preferred form of pillow gasket is shown in FIG. 3, and is described below with particular reference to FIG. 3*c*. This second preferred form shares many of the features of the first preferred form. The main difference is that the pillow gasket portion 350-2 is held in position on the manifold section 311-1 by a pair of protrusions 338 on the gasket portion 350-2 which slot into corresponding apertures on the manifold section 311-1. In the form shown in FIG. 3*a*, the protrusions 338 and the apertures are aligned centrally on the top and bottom surfaces of the manifold section 311-1 and the gasket portion 350-2. However, this potentially allows the gasket portion 350-2 to be fitted upside-down on the manifold section 311-1, so these can be offset to the sides if required, so that the gasket portion 350-2 can only be connected in one (correct) orientation.

3.10 Pillow Gasket—Third Preferred Form

Figure 4B:
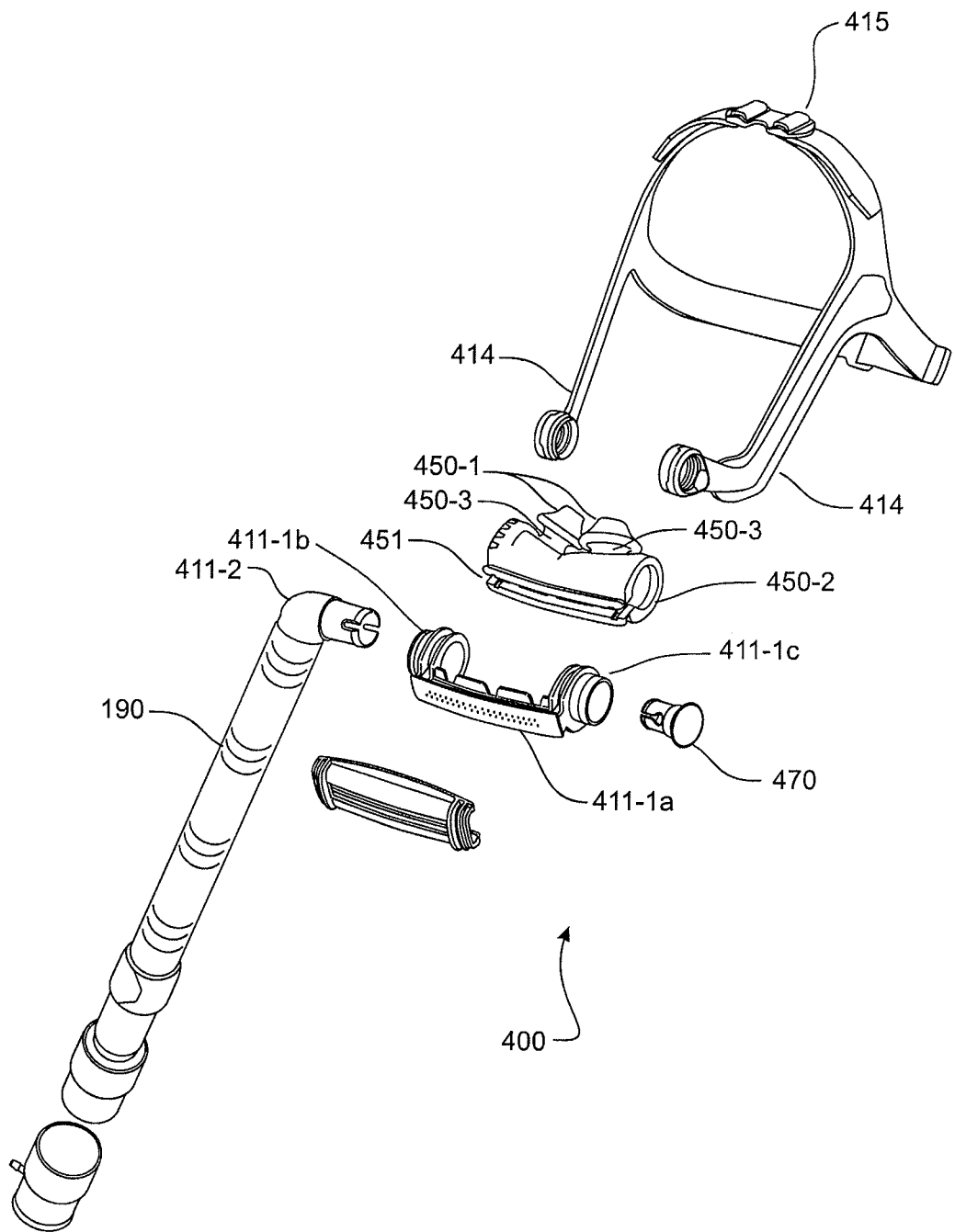

A third preferred form of pillow gasket is shown in FIG. 4, and is described below with particular reference to FIG. 4*b*. As with the previous forms, the third preferred form has a manifold section and a gasket section—manifold section 411-1 and gasket section 450-2 in this third preferred form. The manifold section 411-1 is formed from a semi-rigid plastic, with a central cross-brace body section 411-1*a*, and two end sections 411-1*b* and 411-1*c*. A cap 470 closes off the other end—end 411-1*c*—in use.

The manifold section 411-1 and the main body of the gasket section 450-2 of the pillow section 450 of this third preferred form in use have the overall general form of a cylinder, which in use is aligned across the top lip of a user. The manifold section 411-1 includes an aperture 411-1*b* at one side of the manifold section 411-1, adapted to receive the elbow connector 411-2 in use. The elbow connector 411-2 and the manifold section 411-1 are adapted to rotate freely relative to each other in use, the plane of rotation of the elbow connector aligned back-front of a user 2 in use, rather than side-side as in the embodiment of FIG. 3 or FIG. 2.

In this third preferred form, the pillow section 450 is removably attached to manifold section 411-1. When the pillow section 450 and the manifold section 411-1 are connected, the pair of nasal pillow stems 450-3 and caps 450-1 extend outwards and upwards from the cylindrical main portion.

The gasket section 450-2 of the pillow section 450 has the general overall form of a cylinder, the gasket section 450-2 and the manifold section 411-1 are mutually sized so that the gasket section 450-2 slots between the end sections 411-1*b* and 411-1*c*. The gasket section 450-2 includes a slit 451 which runs along the length of the cylindrical body, at the bottom front of the cylindrical body, opposite the pillow stems 450-3. In use, the slit 451 in the gasket section 450-2 is held closed by engagement of the edges of the slit with the cross-brace body section 411-1*a*.

The ends of the headgear straps 414 in this third preferred form include connectors 452 which engage with the ends of the manifold section 411-1 to hold the manifold section and pillow section 450 in place on the face of a user in use.

Three preferred forms of interface assembly have been given as examples above, with reference to FIGS. 2, 3 and 4. It should be noted that the invention is not limited to use with these example (or variants thereof), and could be used with any suitable interface. For example, the invention as described herein could also be used with the interface assembly described in U.S. application 61/082,877, the contents of which is herein incorporated by reference.

3.11 Pillow Portion

As described above, there are three particularly preferred forms of interface assembly, which have several common elements and several elements which are unique to that particular preferred form. Several variations of pillow design will now be described with particular reference to particular Figures. It should be noted that these variations or embodiments of pillow design are suitable for use with any of the variations of interface assembly as described above, or other variations of these interfaces.

In the description below, the element numbering follows the following numbering convention: For the embodiment of FIG. 5, the elements within the figures will be numbered 500, 501 and so on. For the embodiment in FIG. 6, the elements within the figures will be numbered 600, 601, 650-1*a* and so on. This numbering convention is followed in FIG. 5 onwards. The pillow portion is generally comprised of stalks 50-3 and caps 50-1. The pillow portions described earlier, and indicated by stalks 50-3 and pillow caps 50-1 indicate a 'general' pillow portion. The pillow portion may take two general forms, which are described later. The pillow portions described in FIGS. 5 to 38*c* are specific preferred and alternative forms of the two general forms of the pillow portions, and are numbered 500, 600, and so on. As outlined above, the pillow portions are composed of stems or stalks, and caps. In the preferred and alternative forms of FIGS. 5*a* to 9*c*, the stems/stalks are numbered 550-3, 650-3, etc, and the caps are numbered 550-1, 650-1, etc.

The various forms and embodiments of the pillow portion described below or pillow section described above can be used with face masks also. The pillows, pillow portion or pillow section can be used with any face mask that delivers gases to the nose of patient or user. In particular the pillows, pillow portion or pillow section are suitable for use with a 'hybrid' type face mask. A 'hybrid' face mask is a face mask that delivers gases to the nose and mouth of a patient or user. A typical 'hybrid' face mask generally includes a portion adapted to deliver gases to a user or patient's nasal passages. The 'hybrid' face mask also generally includes a portion adapted to deliver gases to a user or a patient's mouth or oral passage. The various forms and embodiments of the pillows, pillow portion or pillow section as described in this specification can be used with a face mask to deliver a portion of gases to a user or patient's nasal passages.

3.12 Pillow Portion—First General Form

An example of the first general form of the pillow portion is shown in FIG. 5. In the first general form of the pillow portion, the pillow portion comprises two main parts: a stalk 50-3 that connects the pillow portion to the gasket (as described earlier) and a cap section 50-1. Gases pass through the gasket portion and into the pillow portion at the base of the stalks 50-3, exiting at the top of the stalk 50-3. The second part of the pillow portion comprises a cap 50-1, the base of which is connected to the top of the stalk 50-3 and the top of which is inserted into a patient or user's nostril or nare, the outer surface of the cap sealing around the perimeter of the user's nostril or nare. The cap 50-1 is generally much wider at its base than at the top end of the cap 50-1.

In this first general form the cap comprises an outer cap 50-1*a* and an inner cap 50-1*b*, with the outer cap 50-1*a* sealing against the nare or nostril of the user. The lower ends of the caps 50-1*a* and 50-1*b* are generally co-located or congruent where they are located on the top of the stalk 50-3. The caps 50-1*a* and 50-1*b* are generally concentrically nested—meaning the inner cap 50-1*b* is nested inside the outer cap 50-1*a*, with the outer cap 50-1*a* surrounding or enveloping the inner cap 50-1*b*. Generally the upper rims of the inner 50-1*b* and outer 50-1*a* cap are aligned vertically, meaning generally the outer cap 50-1*a* and the inner cap 50-1*b* are at the same height. The gasket includes 2 stalks and caps extending from it. The two caps are angled inwards towards each other on the gasket portion, as can be seen in FIGS. 5*a*, 6*a*, 7*a*, 8*a*, 9*a*, 10*a*, 11*a* and so on. Since the caps are angled toward each other the outer cap 50-1*a* usually extends further upward than the inner cap 50-1*b*, when in use.

Figure 10A:
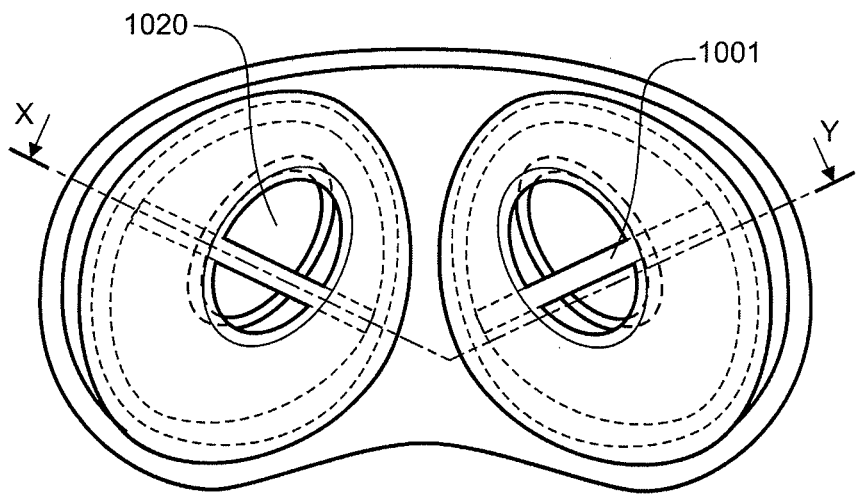
FIG. 10a shows a top view of a still further embodiment of the nasal pillow section, the nasal pillow section comprising a pair of pillow portions connected to a pillow gasket portion with internal hidden detail including an internal solid fin within each of the pillow portions shown, and section lines X and Y which bisect each of the pillows also shown, section line X bisecting the pillows and the fin within one of the pillows, and section line Y bisecting the other of the pillows to one side of the fin.
Figure 10B:
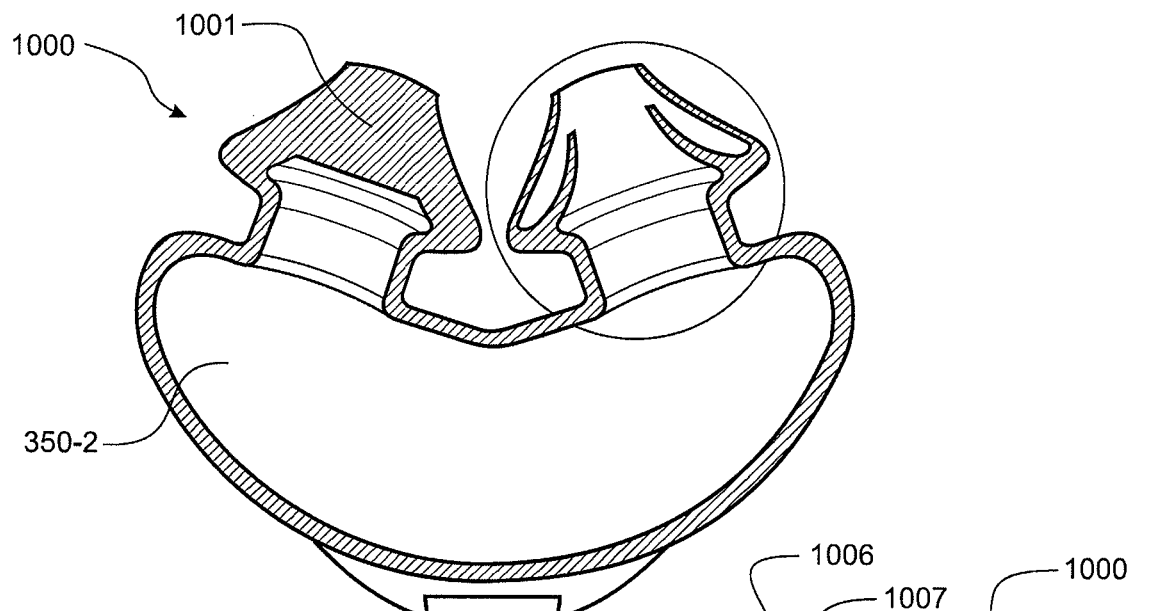
FIG. 10b shows a view of the nasal pillow section of FIG. 10a from the point of view of a user or patient, each of the nasal pillow portions shown in cross-section, the cross-sectional view for each pillow portion taken along the section lines X and Y, the cross section showing the internal detail of the structure of each of the pillow portions.
Figure 10C:
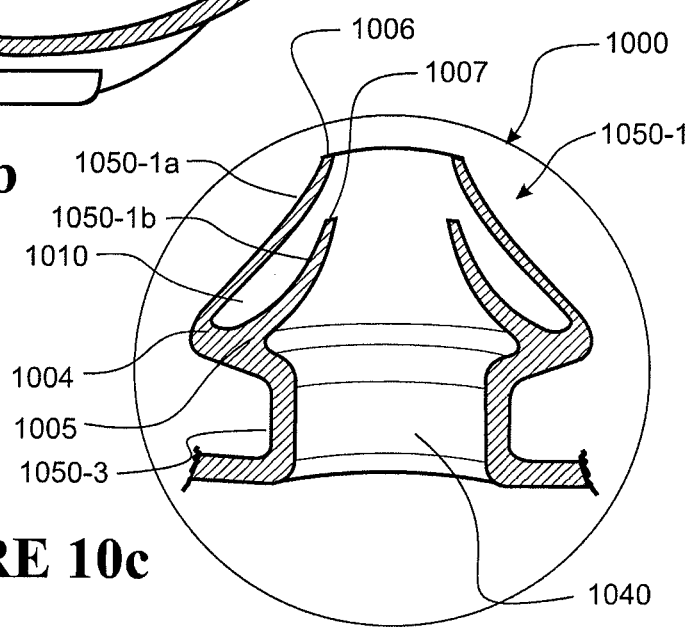
FIG. 10c shows a detail view of the right hand nasal pillow of FIG. 10b, bisected by section line Y.
Figure 20:
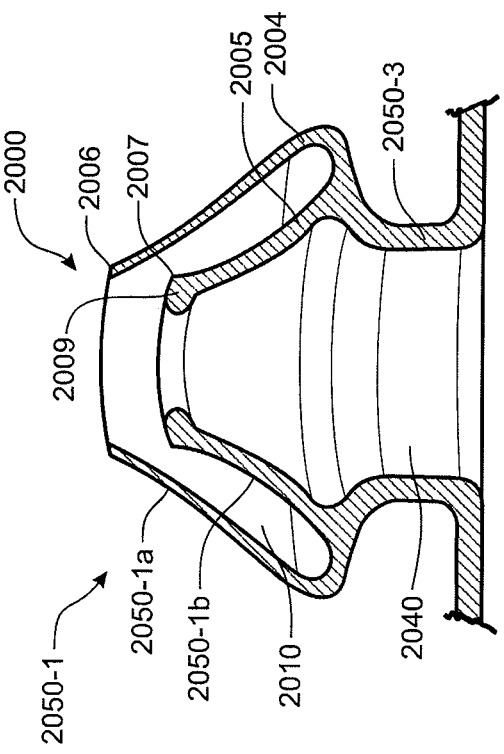
FIG. 20 shows a detail view of a further embodiment of a nasal pillow portion in cross section, the pillow portion comprising a stalk, an outer cap and an inner cap, and a bead which extends from the inside wall of the inner cap, the bead extending inwards from the rim of the inner cap and around the perimeter of the inner cap, the inner cap wall thicker than the outer cap wall.

The inner cap 50-1*b* and outer cap 50-1*a* are generally arranged concentrically with a common central axis, as can be seen in the respective figures (for example FIG. 10*c*, 12*c*, 20 and so on). The cap 50-1 is wider at its base than the stalk 50-3. The outer cap 50-1*a* and inner cap 50-1*b* merge at their bases, with the base extending from outwards almost perpendicular to the axis of the stalk 50-3 before angling upwards and inwards. The shape of the inner and outer caps allows the caps to form a substantial seal with the nostril of the user, when in use. The walls of the inner 50-1*b* and outer 50-1*a* caps are curved upwards and outwards to help the cap conform to a user's nostril and to assist in guiding a stream of gases from the pillow portions to the nostrils of a user. Preferably the walls of the inner 50-1*b* and outer 50-1*a* caps are curved along a parabolic arc.

Figure 13:
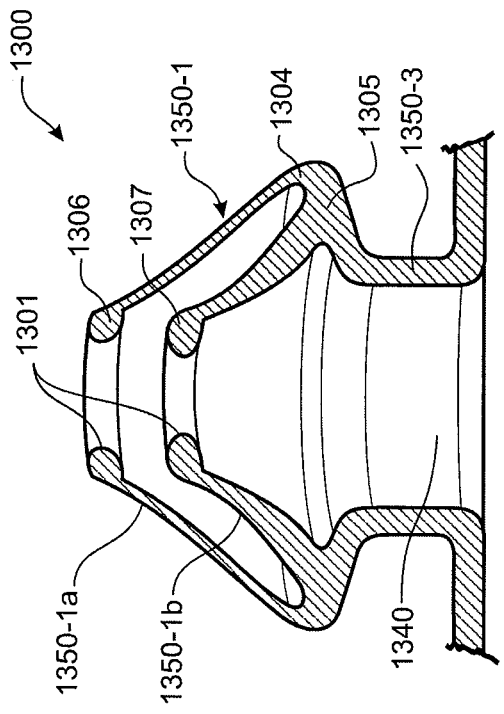
FIG. 13 shows a detail view of a further embodiment of a nasal pillow portion in cross section, the pillow portion comprising a stalk, an outer cap and an inner cap, the inner cap wall tapering in thickness such that the wall is thicker at the base than at the rim, a first bead extending inwards from the top edge or rim of the inner cap and a second bead extending inwards from the top edge or rim of the outer cap.
Figure 12:
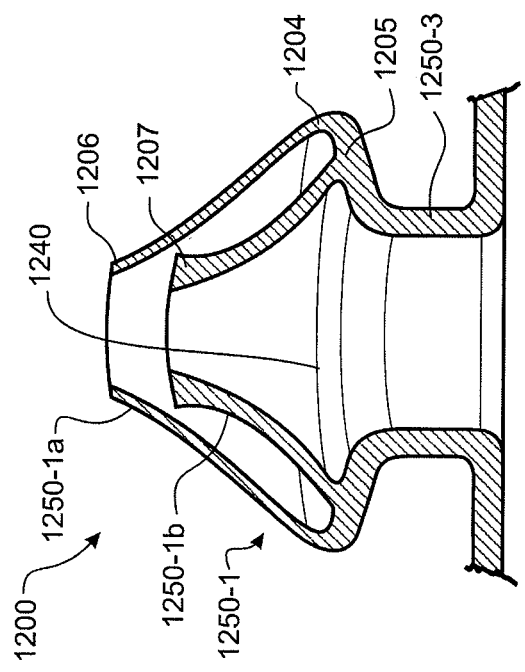
FIG. 12 shows a detail view of a further embodiment of a nasal pillow portion in cross-section, the pillow portion comprising a stalk, an outer cap and an inner cap, the inner cap thicker at the rim and thinner at the base.

The numbering of the stalks and caps changes from figure to figure and embodiment to embodiment while maintaining the common numbering elements identified above. For example the stalk in FIG. 12 is 1250-3 and in FIG. 13 is 1350-3 and so on. The inner cap in FIG. 12 is 1250-1*b* and in FIG. 13 is 1350-1*b* and so on. The outer cap in FIG. 12 is 1250-1*a* and in FIG. 13 is 1350-1*a* and so on.

3.13 Pillow Portion—Second General Form

Figure 25:
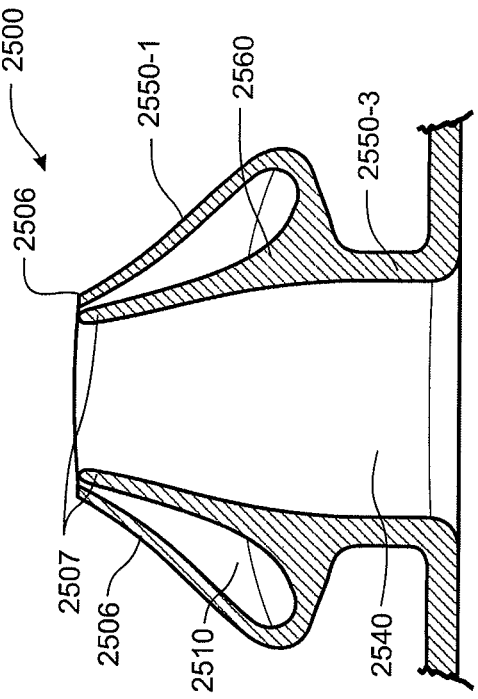
FIG. 25 shows a detail view of a further embodiment of a nasal pillow portion in cross section, the pillow portion comprising a stalk and a cap, the pillow portion also comprising a slightly tapered air delivery tube within the cap, the rim of the air delivery tube in line with the rim of the cap, the air delivery tube extending through the cap and through the stalk to form a passageway for a stream of gases to travel to the patient or user.

An example of the second general form of the pillow portion is shown in FIG. 25. In the second general form of the pillow portion, the pillow portion comprises two main parts: a stalk 50-3 that connects the pillow portion to the gasket (as described earlier) and a cap section 50-1. Gases pass through the gasket portion and into the pillow portion at the base of the stalks 50-3, exiting at the top of the stalk 50-3. The second part of the pillow portion comprises a cap 50-1, the base of which is connected to the top of the stalk 50-3 and the top of which is inserted into a patient or user's nostril or nare, the outer surface of the cap sealing around the perimeter of the user's nostril or nare. The cap 50-1 is generally much wider at its base than at the top end of the cap 50-1.

The second general form of the pillow portion, the cap comprises an outer cap 50-1*a* and an internal air delivery tube 60, with the outer surface of the outer cap 50-1a sealing against the nostrils of a user. The lower end of the outer cap 50-1a is joined to the tube 60. The outer cap 50-1a and tube 60 are generally concentrically nested—meaning the tube 60 is nested inside the outer cap 50-1a, with the outer cap 50-1a surrounding or enveloping the tube 60.

Preferably the air delivery tube 60 is substantially rigid and stiffer than the outer cap 50-1a. This means the air delivery tube 60 does not flex or bend as much as the more flexible outer cap 50-1a does. Preferably the outer cap 50-1a is flexible and supple enough to undergo elastic deformation while in use and return to its original position when not in use.

The cap 50-1 is wider at its base than the stalk 50-3. The outer cap 50-1a and air delivery tube 60 merge at their bases, with the base extending from outwards almost perpendicular to the axis of the stalk 50-3 before angling upwards and inwards. The shape of the air delivery tube 60 outer cap allows the caps to form a substantial seal with the nostril of the user, when in use. The walls of the outer 50-1a cap are curved upwards and outwards to help the cap conform to a user's nostril and to assist in guiding a stream of gases from the pillow portions to the nostrils of a user. Preferably the walls of outer 50-1a cap flare outwards and upwards such that the flare may allow the outer cap 50-1a to form a substantial seal with the nostril of the user, when in use.

Figure 27:
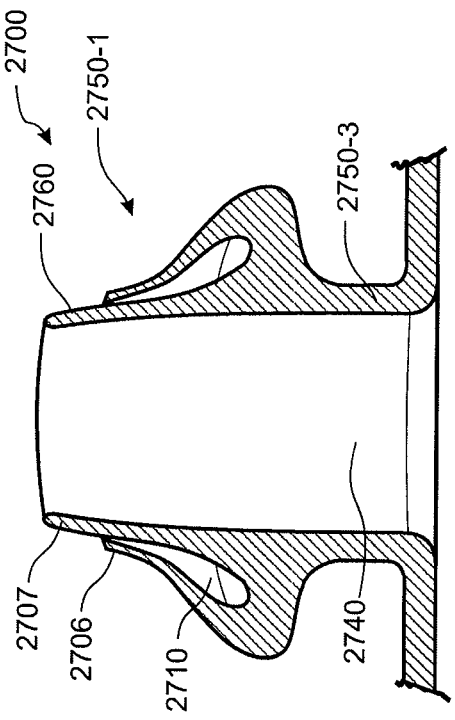
FIG. 27 shows a detail view of a further embodiment of a nasal pillow portion in cross section, the pillow portion comprising a stalk and a cap, the pillow portion also comprising an air delivery tube within the cap, the air delivery tube extending through the cap and stalk to form a passageway for a stream of gases or air to travel to a patient or user and the air delivery tube extending past the rim of the cap.
Figure 26:
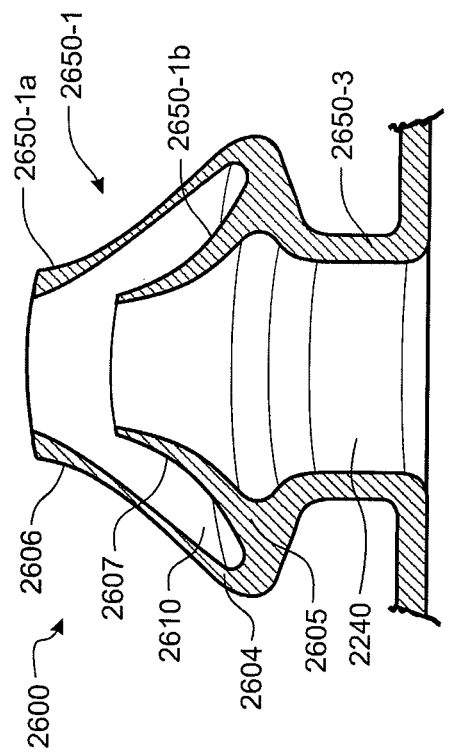
FIG. 26 shows a detail view of a further embodiment of a nasal pillow portion in cross section, the pillow portion comprising a stalk, an outer cap and an inner cap, the inner cap tapering in thickness so that the inner cap is thicker at the base and thinner at the rim, the wall of the outer cap being tapered in thickness and the wall of the outer cap being thicker at the rim than at the base.

The numbering of the stalks, caps and air tube changes from figure to figure while maintaining the common cumbering element identified here. For example the stalk in FIG. 25 is 2550-3 and the stalk in FIG. 26 is 2650-3 and so on. The cap in FIG. 25 is 2550-1 and in FIG. 26 is 2650-1 and so on. The air delivery tube in FIG. 25 is 2560 and in FIG. 27 is 2760 and so on.

3.14 Pillow Portion—Third General Form

An example of a third general form of the pillow portion is shown in FIG. 39. In the third general form the pillow portion comprises two parts: a stalk 50-3 (3950-3 in the specific embodiment shown in FIG. 39) which connects the pillow portion to the pillow gasket 50-2 (250-2 in the specific embodiment shown in FIG. 39) and a cap 50-1 (3950-1 in the specific embodiment shown in FIG. 39) that extends from the top of the stalk 50-3. Gases pass through the pillow gasket and into the pillow portion at the lower end of or base of the stalk 50-3. Preferably the stalks curve upward and outward. The numbering of the stalks changes from embodiment to embodiment and figure to figure, but follows the general convention outlined above. That is, for example, the stalk in FIG. 39 is numbered 3950-3, in FIG. 40 the stalk is 4050-3 and so on. The gasket numbering has been described earlier.

The second part of the pillow portion is the cap 50-1, the base of cap 50-1 being connected to the top of the stalk 50-3. The top of the cap is inserted into a user or patient's nares or nostrils, with the outer surface of the cap 50-1 sealing against a user's nostrils or nares. The gasket portion includes a pair of caps extending from it. The cap 50-1 is generally wider at its base than at its top end, where the gases exit. The rims of the two caps are generally aligned. The caps are angled inward toward each other on the gasket portion.

The cap 50-1 is wider at its base than the stalk 50-3. The shape of the cap 50-1 allows the cap to form a substantial seal with the nostril of the user, when in use. The cap 50-1 preferably curves upwards and outwards to help conform to a user or patient's nostril and assist in guiding a stream of gases from the pillow portion into the nostrils of a user. The walls of the cap 50-1 preferably curve along an arc. The cap 50-1 preferably flares upwards and outward from the base such that in use the flare of the cap 50-1 allows the cap 50-1 to form a substantial seal with the nostril of the user. The numbering of the cap is altered from embodiment to embodiment and figure to figure while maintaining a common element—50-1. For example, the cap shown in FIG. 40 is numbered 4050-1, the cap in FIG. 39 is numbered 3950-1 and so on.

3.15 Specific Pillow Portion Embodiments

Figure 5A:
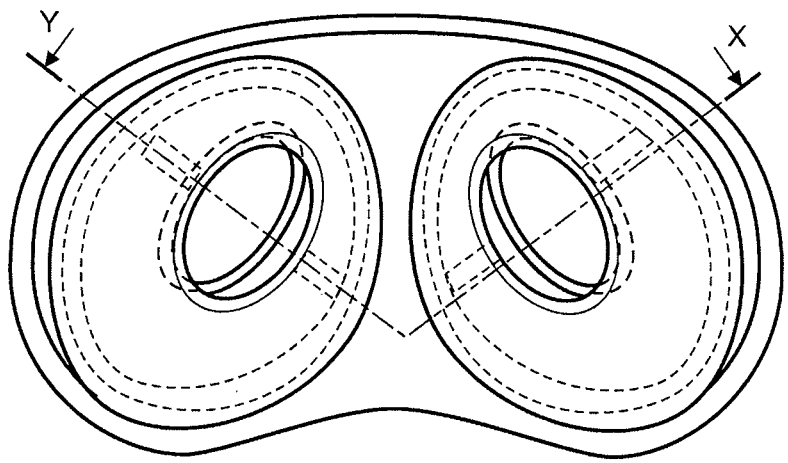
FIG. 5a shows a top view of the first preferred embodiment of nasal pillow section, the nasal pillow section comprising a pair of pillow portions connected to a pillow gasket portion with internal hidden detail including internal ribs of the pillow portions shown, and section lines X and Y which bisect each of the pillows also shown, section line Y bisecting the pillows and the ribs within the pillows, and section line X bisecting the pillows to one side of the ribs.
Figure 5B:
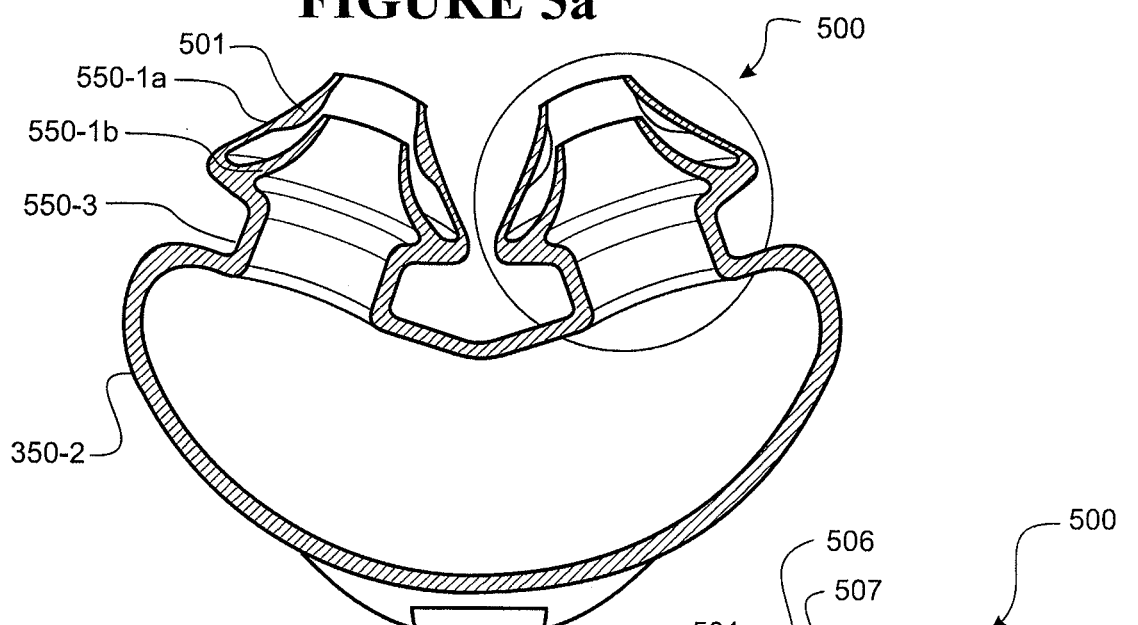
FIG. 5b shows a view of the nasal pillow section of FIG. 5a from the point of view of a user, each of the nasal pillow portions shown in cross-section, the cross-section for each pillow portion taken along the section lines X and Y, the cross-section showing internal detail of the structure of each of the nasal pillow portions.
Figure 5C:
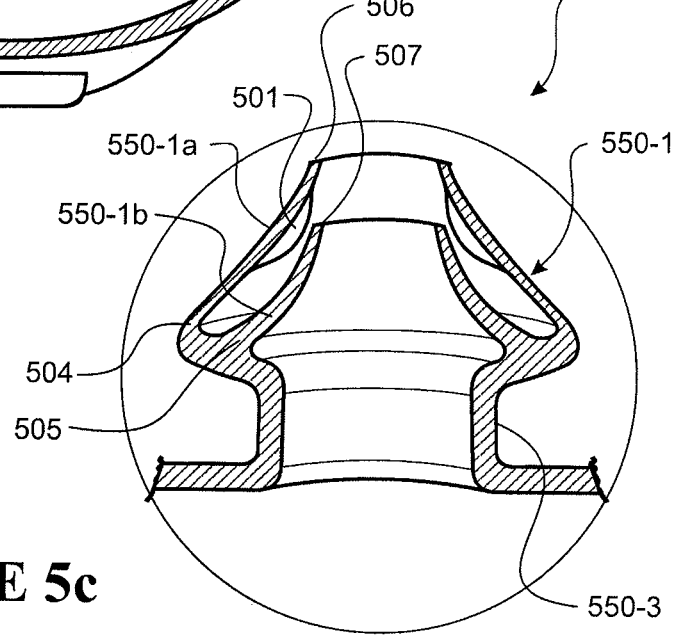
FIG. 5c shows a detail view of the right-hand nasal pillow of FIG. 5b.

An embodiment of nasal pillow portion is shown in FIGS. 5a, 5b and 5c. In this variation, the pillow portion is shown as being used with the pillow gasket portion 350-2 (although as outlined above, these could be used with pillow gasket portion 250-2 or pillow gasket portion 450-2). In this embodiment, the pillow section is formed from the pillow portions and the pillow gasket portion.

As seen in FIGS. 5a-5c, the embodiment of the nasal pillow portion is made up of the first general form of the pillow portion (described above).

In the preferred form of this embodiment, the walls of the inner cap 550-1b and the outer cap 550-1a taper in cross sectional thickness as best seen in FIG. 5c. The walls of the inner cap 550-1b and the outer cap 550-1a are thicker at the lower end. The wall of the outer cap 550-1a is thicker at the base 504 of the outer cap 550-1a than at the rim 506 of the outer cap 550-1a, and the wall of the inner cap 550-1b is thicker at the base 505 of the inner cap 550-1b than at the rim 507 of the inner cap 550-1b. Alternatively the thickness of the walls of the inner and outer cap may be constant or the wall thickness of one of the walls may taper while the wall thickness of the other wall may remain constant.

The inside surface of the wall of the outer cap 550-1b contains at least one and preferably a pair of ribs 501. In alternate embodiments, the inner or inside surface of the wall of the outer cap 550-1a may contain three or more ribs 501. If a series of ribs is used, the ribs 501 can be positioned at regular or differing intervals around the perimeter of the inside surface of the wall of the outer cap 550-1a. The pair of ribs 501 extend only a partial length along the height of the inside wall of the outer cap. Preferably the height of the rib is less than the height of the outer cap 550-1a. The ribs can have the same height as one another, or different heights. The ribs can also have different thicknesses, or the same thickness.

The rib could also be positioned at any location along the inside wall of the outer cap 550-1a—for example, with the lower end of the rib at the base 504 of the outer cap 550-1a or at the base 505 of the inner cap 550-1b, near the air gap. A further alternative is that the upper end of the rib is at the rim 506 of the outer cap 550-1a. However, preferably the rib does not extend all the way to the top or the bottom of the outer cap 550-1a. As shown in FIG. 5c, in this embodiment, each of the pair of ribs 501 is around two-thirds to three-quarters of the way up the inner surface of the wall of the outer cap 550-1a. However, each one of the pair could be in different positions in alternative embodiments.

It should particularly be noted that the ribs 501 of this embodiment are rounded so that their ends blend into the inner surface of the outer cap 550-1a—that is, they do not have 'cornered' or 'sharp' upper and lower edges or surfaces. The rib 501 is thicker in the middle than it is at its extremes, and generally the majority of the profile shape follows an arc or curve from end to end. The width of the ribs 501 is preferably constant, ('Thicker' in this context means that the central portion of the rib extends further inwards towards the inner cap 550-1b than the ends. 'Width' in this context is the side-side dimension of the rib 501—that is, the dimension into and out of the page in FIG. 5c. In this embodiment, the width of the pair of ribs is constant).

It should be particularly noted that the ribs 501 do not run the entire length of the wall 550-1a: the rib or ribs 501 only run around one-third to one-half of the total length or height of the wall 550-1a.

It should also be noted that in the preferred form shown in FIG. 5, the rib or ribs 501 are located towards the top of the wall 550-1a, and not towards the base.

Surprisingly, it has been found that a rib or ribs 501 in this form act to increase the strength of the outer pillow wall 550-1a in certain areas to control and manipulate the collapse of the outer pillow wall 550-1a when this is inserted into the nostril of a user. By controlling the collapse, the pillow wall 550-1a will have more movement in some areas rather than others. This is advantageous as pillows can be produced which are both more comfortable and which also offer good sealing properties against the nares of a user.

The addition of a pair of ribs 501 spaced equidistant around the perimeter of the inner surface of the outer cap 550-1a helps to improve the strength of the rim 506 of the outer cap 550-1a in order to minimise the collapse of the rim 506 into the air path. However, it has surprisingly been found that having a rib 501 that does not extend all the way to the top of the wall or all the way to the base of the wall 550-1a still provides strength, helps to maintain structure of the caps 550-1a and 550-1b in use and at the same time helps to ensure that the rim 506 of the outer cap 550-1a is still flexible to a degree, and comfortable for a user when inserted into the nostril of a user The addition of the rib 501 also helps to improve the feel of positive affirmation of the pillow 500 being correctly inserted into the nostril, from the user's point of view, to reduce the occurrence of the pillow 500 being incorrectly fitted.

Figure 6A:
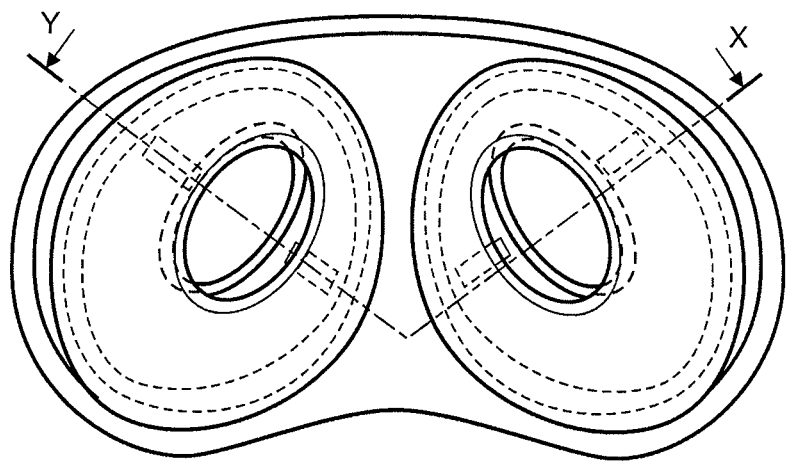
FIG. 6a shows a top view of an alternative embodiment of nasal pillow section, the nasal pillow section comprising a pair of pillow portions connected to a pillow gasket portion with internal hidden detail including internal ribs of the pillow portions shown, and section lines X and Y which bisect each of the pillows also shown, section line Y bisecting the pillows and the ribs within the pillows, and section line X bisecting the pillows to one side of the ribs.
Figure 6B:
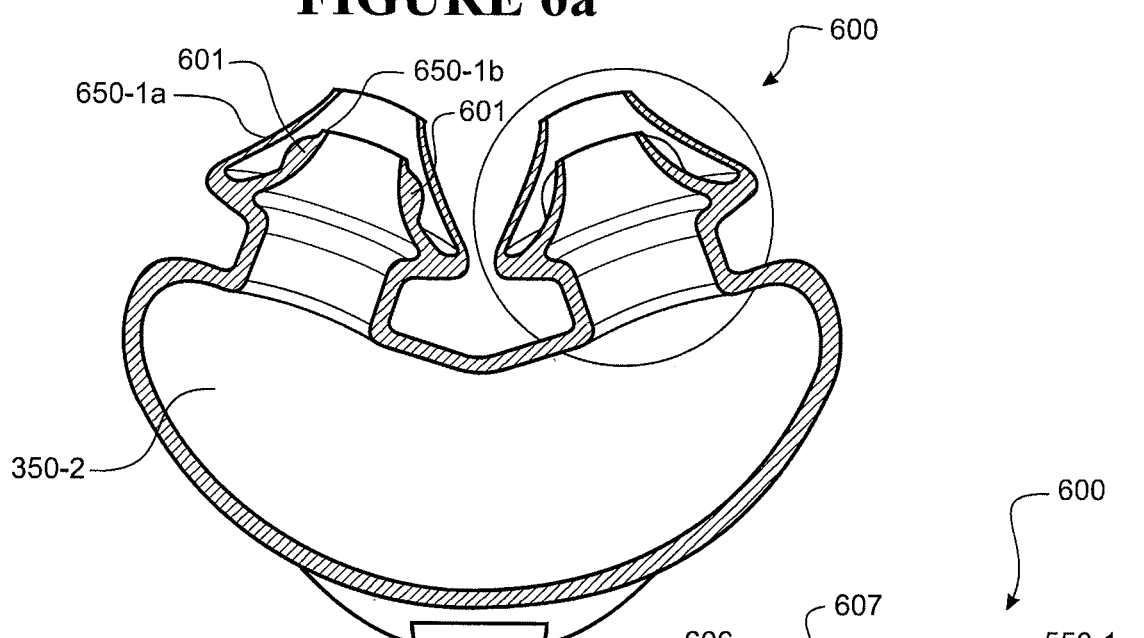
FIG. 6b shows a view of the nasal pillow section of FIG. 6a from the point of view of a user, each of the nasal pillow portions shown in cross-section, the cross-section for each pillow portion taken along the section lines X and Y, the cross-section showing internal detail of the structure of each of the nasal pillow portions.
Figure 6C:
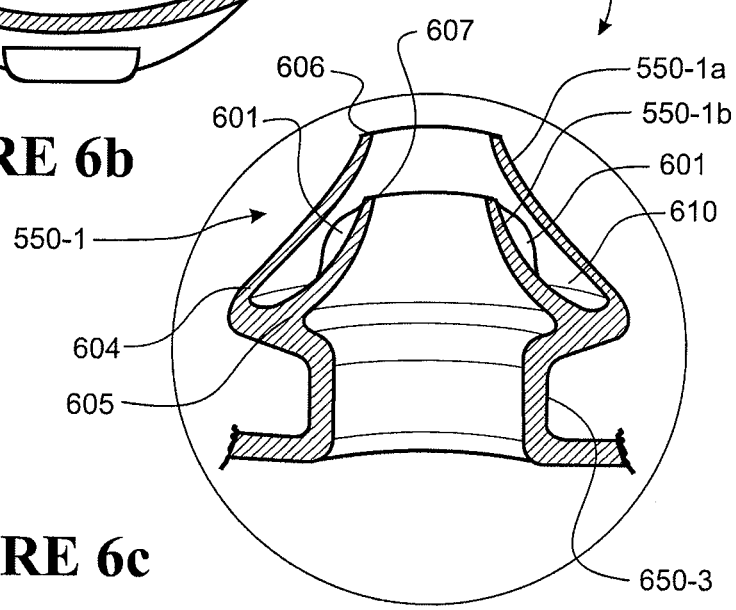
FIG. 6c shows a detail view of the right hand nasal pillow of FIG. 6b.

A further embodiment of the pillow portion is shown in FIGS. 6a, 6b and 6c. In this variation, the pillow portion is shown as being used with the pillow gasket portion 350-2 (although as outlined above, these could be used with pillow gasket portion 250-2 or pillow gasket portion 450-2). In this embodiment the pillow section is formed from the pillow portions and the pillow gasket portion.

As seen in FIGS. 6a-6c the embodiment of the nasal pillow portion is made up of the first general form of the pillow portion. There are specific variations that will be described below.

In the preferred form of this embodiment the wall of the inner cap 650-1b and the outer cap 650-1a taper in cross sectional thickness, as best seen in FIG. 6c. The walls of the inner cap 650-1b and the outer cap 650-1a are thicker at the lower end. This means the thickness of the wall of the outer cap 650-1a is thicker at the base 604 of the outer cap 650-1a than at the outer rim 606 of the outer cap 650-1a, and that the thickness of the wall of the inner cap 650-1b is thicker at the base 605 of the inner cap 650-1b than at the rim 607 of the inner cap 650-1b. Alternatively the thickness of the walls of the inner and outer cap may be uniform or the thickness of one of the walls may taper while the other wall has uniform wall thickness. The walls of the inner and outer caps are curved to help them conform to the nostrils of a user. This helps to provide an effective seal with the user's nostril and to guide a stream of gases from the pillow portions into a users nostrils.

The outer surface of the wall of the inner cap 650-1b includes a rib and preferably a pair of ribs 601. In alternate embodiments, the outer surface of the wall of the inner cap 650-1b may contain three or more ribs 601. If a series of ribs are used, the ribs 601 may be positioned at regular or differing intervals around the perimeter of the outer surface of the wall of the inner cap 650-1b. All the ribs may be of identical length. Alternatively the rib or ribs may have varying lengths. The length may also vary from rib to rib. The pair of ribs 601 extend only a partial length along the height of the outer wall of the inner cap 650-1b.

The rib or ribs 601 could be positioned at any location along the outside wall of the inner cap 650-1b—for example, with the lower end of the rib at the base 605 of the inner cap 650-1b or at the base 604 of the outer cap 650-1a, near the air gap 610. A further alternative is that the upper end of the rib is at the rim 607 of the inner cap 650-1b. The rib or ribs 601 preferably extends between the rim and the base of the inner cap 650-1b. As shown in FIG. 6c, in this embodiment, each of the pair of ribs 601 are located substantially in the middle of the outer wall of the inner cap 650-1b and do not join to the rim 607 or the base 605 of the inner cap 650-1b, as illustrated in FIG. 6c. The rib may extend between one fifth and four fifths of the height of the inner cap 650-1b. Preferably the rib extends approximately three quarters of the height of the inner cap 650-1b. However, each one of the pair could be in different positions in alternative embodiments.

It should be particularly noted the ribs 601 of this embodiment are rounded so that the ends of the ribs blend into the outer surface of the inner cap 650-1b—that is, they do not have 'cornered' or sharp upper and lower edges or surfaces. The rib is thicker in the middle than at its extremes. The width of the rib 601 is preferably constant, ('thicker' in this context means that the central portion of the rib extends further towards the outer cap 600a that the ends. 'Width' in this context is the side-side dimension of the rib 601—that is, the dimension into and out of the page in FIG. 6c.)

Surprisingly it has been found that positioning the rib or ribs 601 along the outer wall of the inner cap 650-1b provides an upper pivot for the outer cap 650-1a. The rib or ribs 601 act as pivot or a support and reduces the inwards collapse of the top rim 606 of the outer cap 650-1a as the pillow portion 600 is inserted into a user's nostril. Preventing the total collapse of the top rim 606 of the outer cap 650-1a helps in preventing the outer cap 650-1a from completely or partially sealing the orifice of the inner cap 650-1b. The sealing of the exit orifice of the inner cap 650-1b can prevent the optimal delivery of therapy gases. The addition of the rib or ribs 601 could prevent the rim 606 of the outer cap 650-1a from collapsing and sealing the exit orifice.

A common problem with pillow portion comprising two caps is the outer cap can collapse and bear on to the inner cap to distort the shape of the inner cap, resulting in reduced gases being delivered and an uncomfortable fit for the user. The rib or ribs 601 prevent the outer cap 650-1a from collapsing and bearing on the inner cap 650-1b, and hence prevent the inner cap 650-1b from distorting in shape, resulting in a more comfortable fit, a better seal formed with the user's nostrils and correct amount of gases being delivered to the user.

The addition of the rib or ribs 601 can allow the outer cap 650-1a to retain its initial flexibility until enough load is applied to force contact of the outer cap 650-1a onto the rib or ribs 601 of the inner cap 650-1b. This characteristic improves the strength of the inner cap 650-1b while maintaining the flexibility of the outer cap 650-1a.

The locations of the rib or ribs 601 may be varied along the outer wall of the inner cap 650-1b in order to accommodate shape variations of nostrils. The ribs support the outside cap 650-1a deforming in non-uniform directions as the nasal pillow portion 600 is inserted into a user's nasal passage. The rib or ribs 601 can support non uniform forces applied to the inner and outer caps when the pillow portions 600 are in use. This may improve the fit of the pillow portions 600 for differing nostrils of various users'.

The rib or ribs 601 on the inner cap 650-1b help to prevent or reduce the deformation of the inner cap 650-1b. This reduces or prevents the inner cap 650-1b from deforming and closing off the orifice in the inner cap 650-1b. The prevention of the inner cap 650-1b deforming may result in a more comfortable fit and improved therapy to the user. The rib or ribs 601 on the inner cap 650-1b also help to reduce or prevent the inner cap 650-1b from folding into the stalk 650-3. This assists in creating and maintaining a seal on the nostril wall of the user.

Figure 7A:
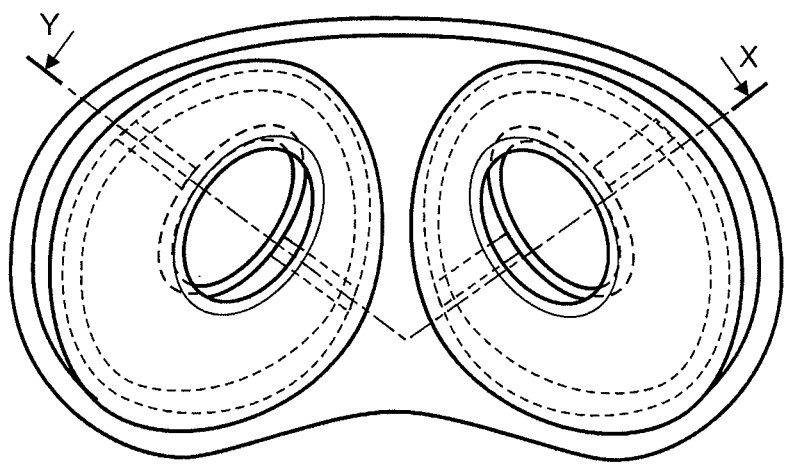
FIG. 7a shows a top view of a further alternative embodiment of nasal pillow section, the nasal pillow section comprising a pair of pillow portions connected to a pillow gasket portion with internal hidden detail including internal ribs of the pillow portions shown, and section lines X and Y which bisect each of the pillows also shown, section line Y bisecting the pillows and the ribs within the pillows, and section line X bisecting the pillows to one side of the ribs.
Figure 7B:
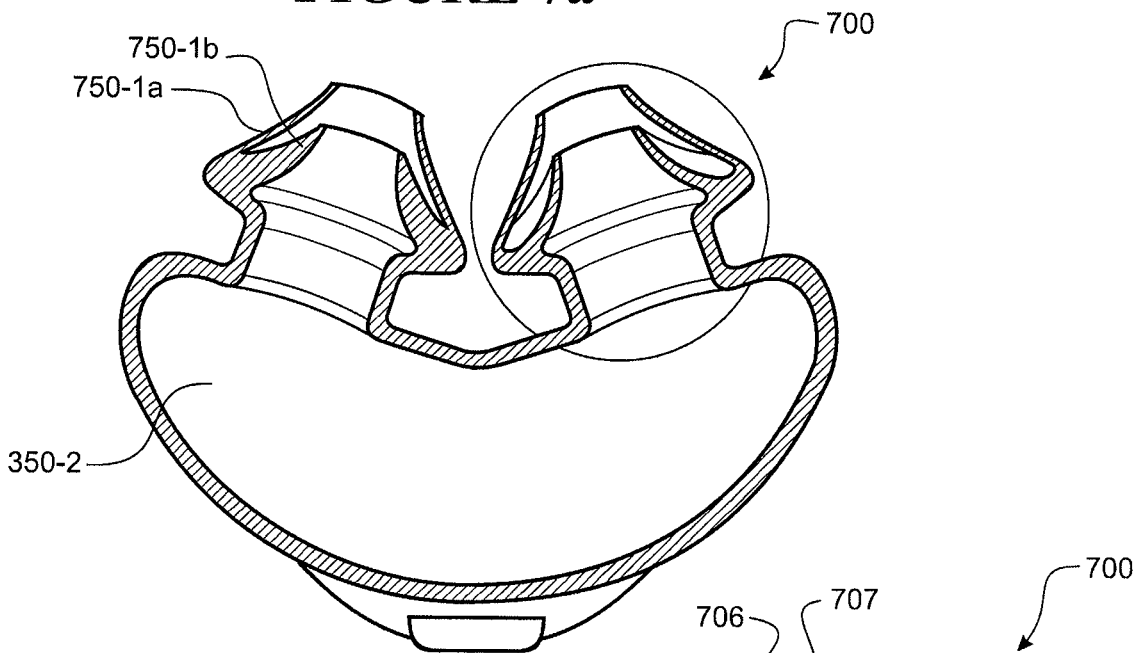
FIG. 7b shows a view of the nasal pillow section of FIG. 5a from the point of view of a user, each of the nasal pillow portions shown in cross-section, the cross-section for each pillow portion taken along the section lines X and Y, the cross-section showing internal detail of the structure of each of the nasal pillow portions.
Figure 7C:
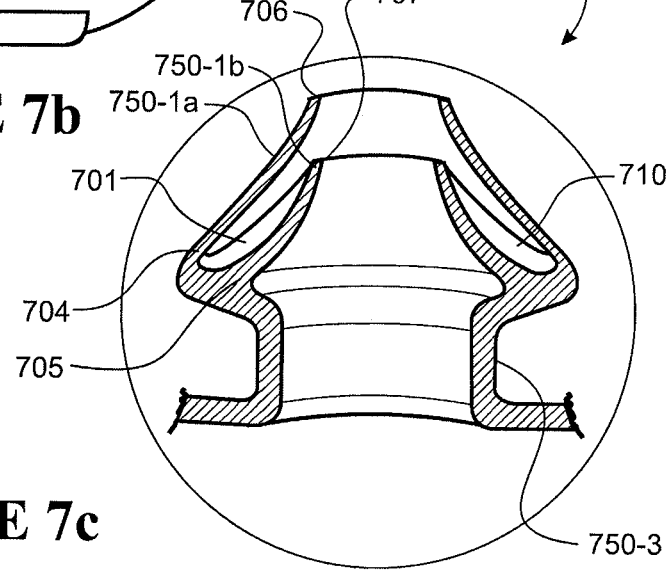
FIG. 7c shows a detail view of the right hand nasal pillow of FIG. 7b.

A further embodiment of the pillow portions is shown in FIGS. 7a, 7b and 7c. In this variation, the pillow portions 700 are shown as being used with the pillow gasket portion 350-2 (although as outlined above, these could be used with pillow gasket portion 250-2 or pillow gasket portion 450-2).

As seen in FIGS. 7a-7c this embodiment is made up of the first general form of the nasal pillow portion (described above). The specific variations will be described below. In the preferred form of this embodiment the wall of the inner and outer cap taper in cross sectional thickness as best seen in FIG. 7c. The walls of the inner cap 750-1b and the outer cap 750-1a are thicker at the base 705 of the inner cap 750-1b and the base 704 of the outer cap 750-1a, than at the rim 706 of the outer cap 750-1a and the rim 707 of the inner cap 750-1b. Alternatively the thickness of the walls may be uniform or the thickness of one of the walls may taper while the thickness of the other wall may remain uniform.

The outer surface of the inner cap 750-1b contains at least one but preferably a pair of ribs 701. In alternate embodiments the outer surface of the wall of the inner cap 750-1b may contain 3 or more ribs. The rib or ribs 701 can be positioned at regular or differing intervals around the perimeter of the outer surface of the wall of the inner cap 750-1b. Preferably the rib or ribs 701 are formed integral to the outer wall of the inner cap 750-1b. The ribs can be of the same width as each other (the width being the dimension horizontally across or through the rib at any location on the rib) or varying width to one another. It should also be noted that the width could vary along the height of the rib—for example, one or both of the ribs could be flared (horizontally) towards their bases, and conversely be tapered (horizontally) towards the top of the rib. It should also be noted that these variable dimensions could vary from one rib to another. It should still further be noted that the ribs as shown in FIGS. 7a-c are shown having an increasing thickness from the top (where the ribs blend with the inner cap 750-1b) to the base. This thickness could in alternative forms be more uniform along the height or length of the rib.

The location of the rib or ribs could also be positioned at any location along the outer surface of the wall of the inner cap 750-1b. The distance between each rib 701 could vary or remain in the same along the perimeter of the outer surface of the wall of the inner cap 750-1b. The rib 701 extends from the top rim 707 of the inner cap 750-1b to the base 704 of the outer cap 750-1a as shown in FIG. 7c. It should be noted the rib is preferably sloped toward the base 704 of the outer cap 750-1a from the top rim 707 of the inner cap 750-1b. The angle of the slope can be any acute angle relative to the inner cap 750-1b. Preferably the rib 701 follows the curvature of the outer surface of the wall of the inner cap 750-1b and the rib may follow a parabolic arc similar to that of the walls of the inner and outer caps. The rib 701 tapers in thickness from nothing at the top rim 704 of the inner cap 750-1b to its thickest point at the base 704 of the inside wall of the outer cap 750-1a. Preferably the rib 701 is thinner at the top rim 707 of the inner cap 750-1b than at the base 704 of the outer cap 750-1a. Preferably the rib 701 gets progressively thicker from the top rim 707 of the inner cap 750-1b to the base 704 of the outer cap 750-1a. The thickness, taper and progression of thickness may vary from rib to rib. The rib 701 extends into the air gap 710 but does not completely fill the air gap 710.

Surprisingly, it has been found that the addition of the rib or ribs 701 helps to improve the seal created in the patient's nostrils when in use. The ribs further provide strengthening of the inner cap 750-1b. The inner cap 750-1b folding back in the stalk 750-3 can reduce the effectiveness of the seal created by the pillow portions 700, with the user's nostrils, when in use. The addition of the rib or ribs 701 reduces and helps to eliminate the folding of the inner cap 750-1b back into the stalk 750-3 when there is load on it from the user's nostrils pushing against the inner and outer caps. The addition of the ribs 701 provides the surprising effect of improving the seal created by the pillow portions 700 when in use.

The rib or ribs 701 also strengthen the inner cap 750-1b and provide rigidity to the inner cap 750-1b. This provides more support to the outer cap 750-1a and prevents the outer cap from deforming too much when depressed by a user's nostril in use. The ribs help to control or limit the amount of deformation the inner and outer caps 750-1b and 750-1a, undergo when in use. The rib or ribs 701 help to make the outer and inner cap more rigid and hence create a better seal with a user's nostrils.

The addition of the rib or ribs 701 maintains the flexibility of the outer cap 750-1a or inner cap 750-1b while providing strength and support against permanent bending and deformation to the inner cap 750-1b and outer cap 750-1a. This flexibility of the outer cap 750-1a or the inner cap 750-1b or both makes the pillow portions 700 suitable for use with a wide range of users and a variety of nostril shapes since the inner or outer cap or both can flex to take the shape of any nostril and create a substantial seal with the nostril.

Figure 8A:
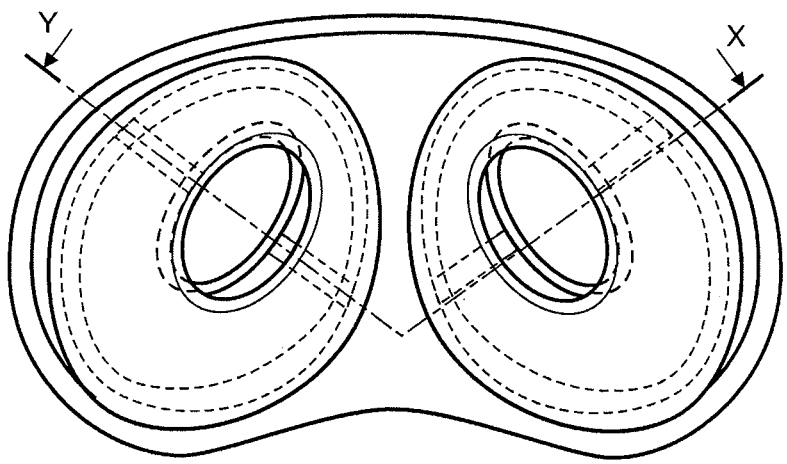
FIG. 8a shows a top view of yet another embodiment of nasal pillow section, the nasal pillow section comprising a pair of pillow portions connected to a pillow gasket portion with internal hidden detail including internal ribs of the pillow portions shown, and section lines X and Y which bisect each of the pillows also shown, section line X bisecting the pillows and the ribs within the pillows, and section line Y bisecting the pillows to one side of the ribs.
Figure 8B:
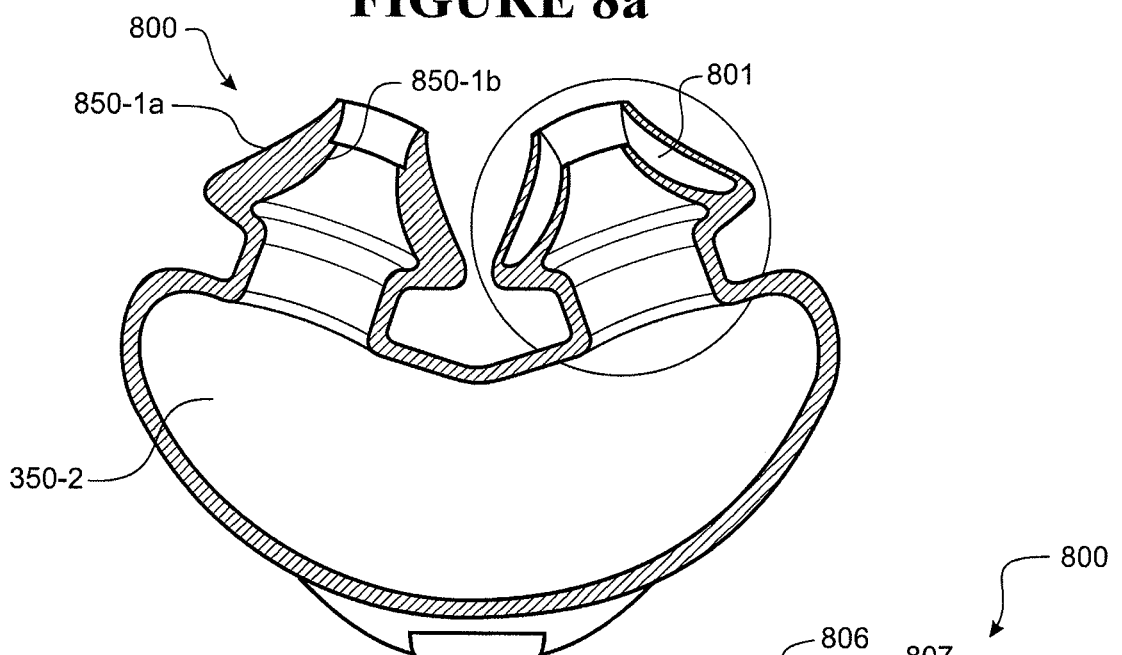
FIG. 8b shows a view of the nasal pillow section of FIG. 8a from the point of view of a user, each of the nasal pillow portions shown in cross-section, the cross-section for each pillow portion taken along the section lines X and Y, the cross-section showing internal detail of the structure of each of the nasal pillow portions.
Figure 8C:
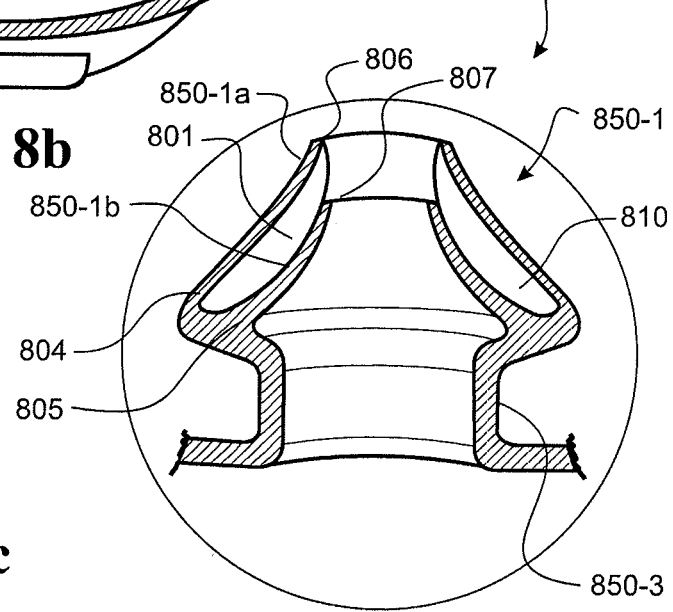
FIG. 8c shows a detail view of the right hand nasal pillow of FIG. 8b.

A further embodiment of the pillow portions is shown in FIGS. 8a, 8b and 8c. In this variation, the pillow portions are shown as being used with the pillow gasket portion 350-2 (although as outlined above, these could be used with pillow gasket portion 250-2 or pillow gasket portion 450-2).

As can be seen from FIGS. 8a-8c this embodiment is made up of the first general form of the pillow portion as described above. The specific variations of this embodiment will be described below.

In the preferred form of this embodiment the walls of the inner cap 850-1b and the outer cap 850-1a taper in cross sectional thickness, as best seen in FIG. 8c. The wall of the inner cap 850-1b is thicker at the base of the inner cap 805 than at the rim 807 of the inner cap 850-1b. The wall of the outer cap 850-1a is thicker at the base 804 of the outer cap 850-1a than at the rim 806 of the outer cap 850-1a. Alternatively the thickness of the walls of the outer 850-1a and inner 850-1b caps may be uniform thickness. As a further alternative the wall thickness of one of the walls may taper while the other wall does not, for example the wall thickness of the wall of the outer cap 850-1a may taper while the wall thickness of the inner cap 850-1b may remain constant. The inner and outer caps flare upwards and outwards in a similar manner as has already been described for the previous embodiment of FIG. 7.

There is a cavity or air gap 810 formed between the outside surface of wall of the inner cap 850-1b and the inside surface of the wall of the outer cap 850-1a. The cavity 810 is out of the direct air path of the caps 850-1a and 850-1b, meaning the cavity 810 is not formed in the path of the stream of gases being delivered to the user.

The cavity 810 between the inner 850-1b and outer cap 850-1a contains at least one but preferably a pair (or more) of ribs 801 that extend into the cavity 810. The rib or ribs 801 may be positioned at regular or differing intervals around the perimeter of the outer surface of the wall of the inner cap 850-1b or the inner surface of the wall of the outer cap 850-1a. The rib or ribs 801 can be attached or formed integral to the outer surface of the wall of the inner cap 850-1b or to the inner surface of the wall of the outer cap 850-1a or both. Preferably the rib 801 is positioned on the inside surface of the wall of the outer cap 850-1a. The rib or ribs 801 can be positioned at any position along the inside surface of the wall of the outer cap 850-1a. Preferably the ribs 801 are equally spaced along the perimeter of the inner surface of the wall of the outer cap 850-1a. Alternatively the spacing between successive ribs could vary and could be irregular.

Preferably the rib or ribs 801 extend from the top rim 806 of the inside surface of the wall of the outer cap 850-1a or are formed along the inside surface of the wall of the outer cap 850-1a and preferably extend all the way to the common base 804 of the inner and outer caps. The rib conforms to the shape of the cavity 810 and follows the general curve of the walls of the inner cap 850-1b and outer cap 850-1a.

The rib or ribs 801 generally curves outwards from the rim 806 and downwards to the outer edge of the rim 807 of the inner cap 850-1b, where it merges with the rim 807, with the rib 801 then extending downwards to the common base 804 merged with or at least contacting the inner cap 850-1b all the way along the outer wall of the inner cap 850-1b.

Surprisingly, it has been found the addition of the rib or ribs 801 helps to reduce or eliminate the folding of the inner cap 850-1b back on the stalk 850-3. This allows a more effective seal to form with the user's nostrils when in use and stops the inner cap 850-1b from blocking the exit orifice and leads to the correct amounts of therapy gases being delivered to the user.

The rib or ribs 801 are also intended to add strength to the outer cap 850-1a to stop the outer cap or the rim 806 of the outer cap from completely collapsing onto the inner cap 850-1b, the stalks 850-3 or the exit orifice. The rib or ribs 801 provide strengthening by acting like a splint and resisting the forces exerted on the inner and outer caps when the pillow portions 800 are in use. The addition of the rib or ribs 801 provides the advantage of making it easier to correctly fit the pillow portions 800 into a user's nostrils. The addition of a rib or ribs 801 adds strength but also maintains some degree of flexibility of the outer cap 850-1a. The flexibility of the outer cap 850-1a allows the outer cap 850-1a to flex and conform to the shape of a user's nostrils in order to create an effective seal with the user's nostrils.

The inner cap 850-1b without any rib or ribs 801 may often collapse when in use and cover or partially cover the exit orifice of the inner cap 850-1b. The collapsing of the inner cap may result in pressure drop across the pillow portion 800 during the exhale cycle of the user, resulting in an increase in the effort needed by the user to exhale. This increased effort by the user may cause harm to the user and could damage the user's respiratory system.

Surprisingly it has been found that the addition of the rib or ribs 801 can strengthen the inner cap 850-1b and reduces or minimises the collapse of the inner cap 850-1b on to itself because the rib 801 acts like a splint and absorbs the forces exerted upon the inner cap. If the inner cap begins to collapse or fold the rib resists that movement and exerts an opposite force to force the inner cap 850-1b to maintain its position. This provides the advantage of being comfortable for the user since the user may not need to use as much effort to exhale.

Figure 9A:
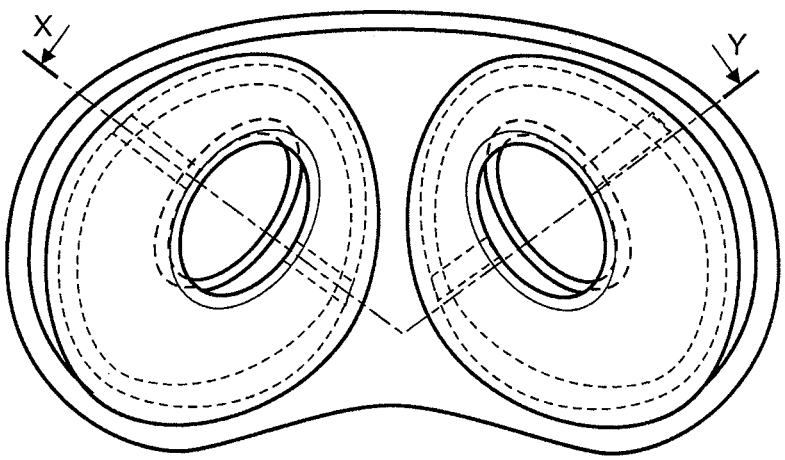
FIG. 9a shows a top view of a still further embodiment of nasal pillow section, the nasal pillow section comprising a pair of pillow portions connected to a pillow gasket portion with internal hidden detail including internal ribs of the pillow portions shown, and section lines X and Y which bisect each of the pillows also shown, section line X bisecting the pillows and the ribs within the pillows, and section line Y bisecting the pillows to one side of the ribs.
Figure 9B:
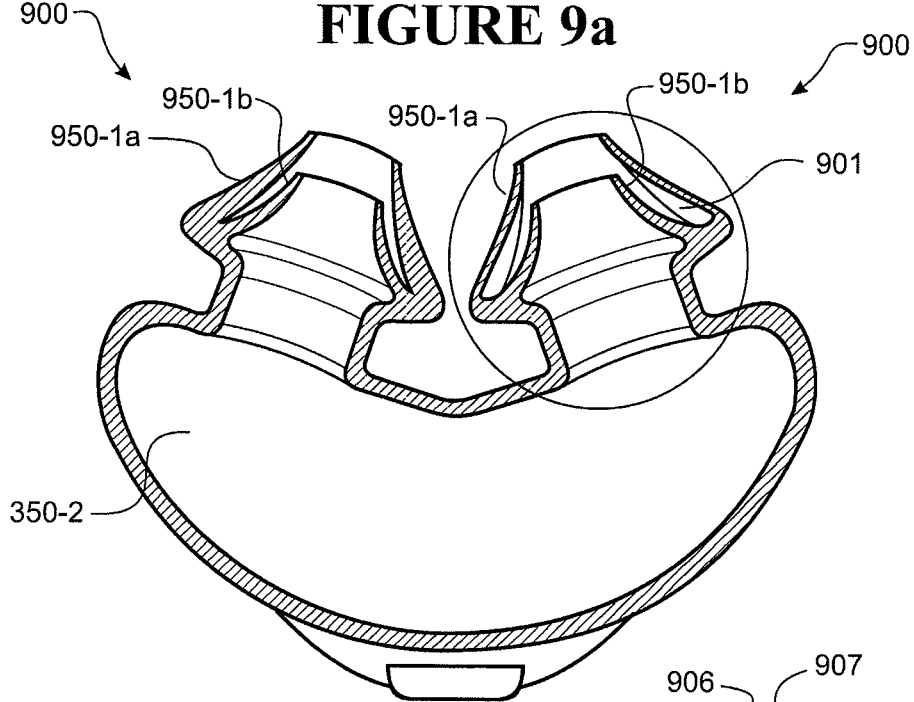
FIG. 9b shows a view of the nasal pillow section of FIG. 9a from the point of view of a user, each of the nasal pillow portions shown in cross-section, the cross-section for each pillow portion taken along the section lines X and Y, the cross-section showing internal detail of the structure of each of the nasal pillow portions.
Figure 9C:
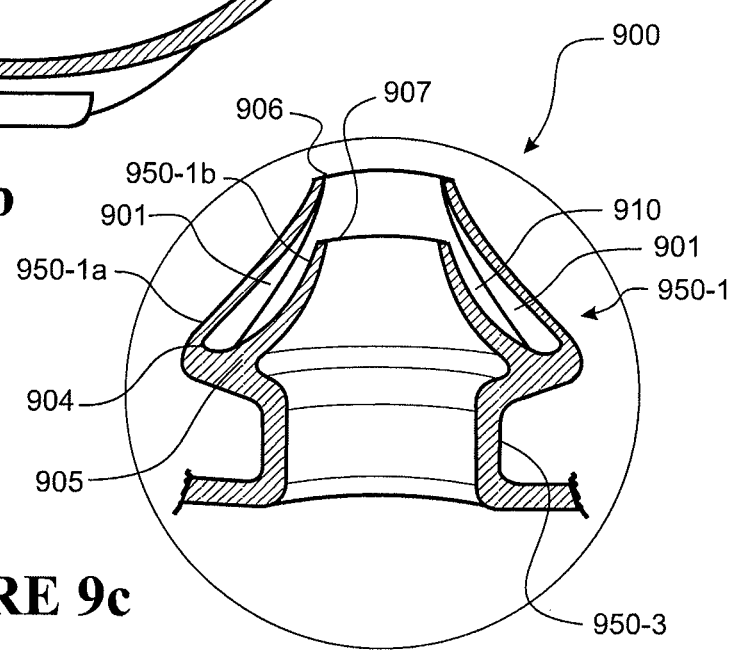
FIG. 9c shows a detail view of the right hand nasal pillow of FIG. 9b.

A further embodiment of the pillow portions is shown in FIGS. 9a, 9b and 9c. In this variation, the pillow portions are shown as being used with the pillow gasket portion 350-2 (although as outlined above, these could be used with pillow gasket portion 250-2 or pillow gasket portion 450-2).

As seen in FIGS. 9a-9c this embodiment is made up of the first general form of the nasal pillow portion 9 (described above). The specific variations of this embodiment are described below.

In the preferred form of this embodiment the walls of the inner cap 950-1b and the outer cap 950-1a taper in cross sectional thickness as best seen in FIG. 9c. The wall of the inner cap 950-1b is preferably thicker at the base 905 of the inner cap 950-1b than at the rim 907 of the inner cap 950-1b. The wall of the outer cap 950-1a is preferably thicker at the base 904 of the outer cap 950-1a than at the rim 906 of the outer cap 950-1a. Alternatively the thickness of walls of the inner 950-1b and outer 950-1a caps may be uniform. As a further alternative the thickness of the wall of one of the caps may taper while the thickness of the other cap may remain uniform—for example the thickness of the wall of the inner cap 950-1b may taper while the thickness of the wall of the outer cap 950-1a may be constant. There is a cavity 910 or air gap formed between the outer cap 950-1a and the inner cap 950-1b (except where they are connected at their bases to the stalk and to each other). This cavity 910 is not in the direct air path of the stream of gases, as best seen in FIG. 9c.

The inside surface of the wall of the outer cap 950-1a contains at least one and preferably two ribs 901. Alternatively the inside surface of the wall of the outer cap may contain 3 or more ribs 901. Preferably the rib or ribs 901 are located along the inside surface of the wall of the outside cap 950-1a, extending from the rim 906 into the cavity 910 between the inner 950-1b and outer cap 950-1a and connecting to either the base 904 of the outer cap 950-1a or to the base 905 of the inner cap 950-1b as shown in FIG. 9c. Preferably the rib partially fills the volume of the cavity 910, extending and curving outwards from the rim 906 of the outer cap 950-1a and into the airgap or cavity 910, but not contacting the outer surface of the inner cap 950-1b when the caps are in a non-deformed state. There is a gap 911 between the rib 901 and the outer surface of the wall of the inner cap 950-1b, as seen in FIG. 9b. Preferably the rib extends between one quarter and three quarters of the way across the airgap 911 from the inner surface of the outer cap 950-1a to the outer surface of the inner cap 950-1b.

If a plurality of ribs 901 is used the ribs 901 may be positioned at regular or differing intervals around the perimeter of the inner or outer cap. The distance between ribs 901 may very from rib to rib, for example the distance between a first pair of ribs may be similar or different to the distance between a second pair of ribs 901. The ribs preferably are thicker at the base of the rib than at the top of the rib, as seen in FIG. 9c. This means the ribs may be thicker at the base 904 of the outer cap 950-1a or at the base 905 of the inner cap 950-1b, than at the rim 906 of the outer cap 950-1a. The ribs 901 may all have the same rate of change of thickness or the rate of change of thickness may vary from rib to rib. Alternatively the ribs may all be the same thickness or the ribs may be thicker at the rim 906 of the outer cap 950-1*a* and thinner at the base 904 or 905 of the outer or inner cap respectively. Each of the arrangements described above may vary between each individual rib feature. Furthermore, the width (side-side or horizontal dimension through the rib) may vary—i.e. not be constant. The rib width could be greater at the base than at the top of the rib, for example.

Surprisingly, it has been found that the addition of the rib 901 results in strengthening the outer cap. The addition of the rib 901 helps to add stiffness to the outer cap 950-1*a* and hence the outer cap does not collapse completely and hold its shape better. Since the outer cap 950-1*a* can hold its shape, this provides the advantage that the pillow portions 900 can be correctly fitted into a patient's nostrils and the pillow portions, in particular the outer surface of the wall of the outer cap forms a better seal with a user's nostrils. The rib 901 acts to support the outer cap and resists forces applied to the outer cap 950-1*a* as the pillow portions 900 are inserted into a user's nostrils.

The flexibility of the outer cap 950-1*a* allows the outer cap to deform enough to fit into a nostril and the rib ensures that the outer cap 950-1*a* has sufficient strength to assist in providing a seal with the user's nostrils.

It has also surprisingly been found that the tapered rib thickness helps to provide the outer cap 950-1*a* with maximum strength and rigidity without compromising flexibility of the outer cap 950-1*a*. The combination of flexibility and rigidity allow the pillow portion 900 to form a substantial seal and a correct fit within the user's nostrils. This can provide the advantage of a more effective therapy being delivered to a user.

A further embodiment of the pillow portions is shown in FIGS. 10*a*, 10*b*, and 10*c*. In this variation, the pillow portions are shown as being used with the pillow gasket portion 350-2 (but as outlined above, the pillow portions may be used with the pillow gasket portion 250-2 or pillow gasket portion 450-2).

As seen in FIGS. 10*a*-10*c*, this embodiment of the nasal pillows is generally made up of the first general form of the pillow portion (described above). However, specific to this embodiment, the inner cap 1050-1*b* extends above the outer cap 1050-1*a*, in order to provide a better fit in the users nostrils and helps to provide a better seal, as shown in FIG. 10*c*. Further variations of this embodiment will be described below.

In the preferred form of this embodiment the walls of the inner cap 1050-1*b* and the outer cap 1050-1*a* taper in cross sectional thickness, as best seen in FIG. 10*c*. The wall of the inner cap 1050-1*b* is preferably thicker at the base 1005 of the inner cap 1050-1*b* than at the rim 1007 of the inner cap 1050-1*b*. The wall of the outer cap 1050-1*a* is preferably thicker at the base of the 1004 of the outer cap 1050-1*a* than at the rim 1006 of the outer cap 1050-1*a*. Alternatively the wall thickness of the inner cap 1050-1*b* and the outer cap 1050-1*a* may be uniform. As another alternative the wall thickness of the inner and outer caps may be equal to each other—meaning the wall of the inner cap 1050-1*b* is the same thickness as the wall of the outer cap 1050-1*a*. Further to this the wall cross section of the inner and outer cap may be identical to each other. As a further alternative the thickness of the wall of one of the caps may taper while the thickness of the other cap wall may be uniform—for example the thickness of the wall of the inner cap 1050-1*b* may taper while the thickness of the wall of the outer cap 1050-1*a* may be uniform.

The cap 1050-1 includes at least one "rib" feature within the cap. Preferably this rib feature is a solid fin 1001 that passes through the entire cap 1050-1. Preferably the fin 1001 is a thin element with parallel sides which passes in a planar fashion across the cap 1050-1. The fin 1001 could also be described as passing diametrically across the pillow section, although it should be noted that 'diametrically' as it is used in this context and in the specification generally should not be taken as meaning that the caps are circular. The fin 1001 joins the inner cap 1050-1*b* with the outer cap 1050-1*a*, as seen in FIGS. 10*a* and 10*b*. Preferably part of the fin 1001 lies within the path of the stream of gases delivered to the user or patient, as seen in FIG. 10*a*. The fin 1001 extends from the rim 1006 of the outer cap 1050-1*a* to the point where the cap 1050-1 joins the stalk 1050-3, as best seen in the left cap of FIG. 10*b*. The fin 1001 extends from the rim 1006 of the outer cap 1050-1*a* to the point where the bases of the inner 1050-1*b* and outer 1050-1*a* caps join each other. The fin 1001 preferably fills the air gap 1010 completely, at the cross-section X. The fin 1001 extends from one side of the cap to the other side of the cap, meaning the fin 1001 extends across the entire diameter of the cap 1050-1, as best seen in FIG. 10*b*. Preferably the fin 1001 follows the contours of the overall cap shape. Preferably the fin 1001 extends vertically from the inner cap 1050-1*b* to the outer cap 1050-1*a*.

As described above, in the preferred embodiment the sides of the fin are straight to form the planar fin. Alternatively the fin 1001 could be curved in shape (not shown) as it passes from one side of the pillow section to the other, instead of being straight as shown in FIGS. 10*a* and 10*b*, and form a gentle curved plane, preferably an inverted parabola as it passes through the entire cap 1050-1. As a further alternative the fin 1001 could be even angled about a central or offset vertex point. For example, the central vertical axis of the exit orifice 1020 of the cap 1050-1, as seen in FIG. 10*a*, or alternatively the fin 1001 may be offset about the vertex point. The vertex point preferably is situated in the middle of the exit orifice 1020 of the cap 1050-1. However, the vertex point may be at any point along the width of the cap 1050-1.

As described above, the fin 1001 is parallel-sided, with the sides aligned vertically in use, and thin. However, in alternative embodiments, the fin 1001 can taper in thickness. The fin 1001 can be thicker at the base of the inner and outer caps than at the rim 1006 of the outer cap 1050-1*a*. Alternatively the fin 1001 may be thicker at the rim 1006 of the outer cap 1050-1*a* than at the base of the caps. This tapering thickness helps to direct airflow from the stalks out of the orifice 1020 and out of the cap 1050-1. The addition of the fin and the tapered cross section of the fin help in reducing the velocity of the delivered gases to a velocity that is comfortable for a user to accept the stream of gas. The possible reduction in velocity may also help prevent air jetting effects that can annoy or damage the nasal passages of a user. The fin 1001 also helps to maintain a low level of pressure drop across the nasal interface when the interface is in use. This again increases comfort for the user.

As a further alternative the fin 1001 may have uniform thickness along its profile. In the preferred form the cap 1050-1 only includes one fin 1001 per cap 1050-1, but each cap may include multiple fins 1001 spaced at varying or constant distances from one another. The fin is preferably made from the same materials as the cap portion 1050-1.

Surprisingly it has been found that adding a fin 1001 to the cap 1050-1 results in strengthening the entire cap 1050-1 structure. The addition of the fin 1001 adds stiffness to the cap 1050-1 and strengthens both the inner and outer caps. The fin helps to prevent the inner and outer caps from folding and permanently deforming in use. Since the cap 1050-1 is stiffer and can resist permanent deformation, this provides the advantage that the cap 1050-1 and hence the pillow portions 1000 can be correctly fitted into a patient's nostrils.

While strengthening the cap 1050-1 structure the addition of the fin 1001 still allows the cap to maintain flexibility on either side of the fin 1001. This flexibility allows the cap 1050-1 to elastically deform as the cap conforms to the nostrils of the user and allows the cap to provide a better seal with the nostrils of the user.

It has also surprisingly been found that the addition of the fin 1001 helps to prevent the collapse of the outer cap 1050-1*a* into the path of the stream of gases and closing of the orifice 1020 of the caps. The closing or partial closing of the orifice 1020 increases pressure drop across the cap 1050-1 and increases the effort needed by the user or patient to exhale through the nasal interface. The addition of the fin 1001 aids in preventing the outer cap 1050-1*a* from collapsing into the orifice 1020 and into the path of the stream gases, thus improving comfort and safety for the user. The fin 1001 also provides the advantage of delivering more effective therapy since the addition of the fin 1001 provides a better seal and helps in preventing the outer cap 1050-1*a* from collapsing into the path of the stream of gases and from sealing up the orifice 1020.

Figure 11A:
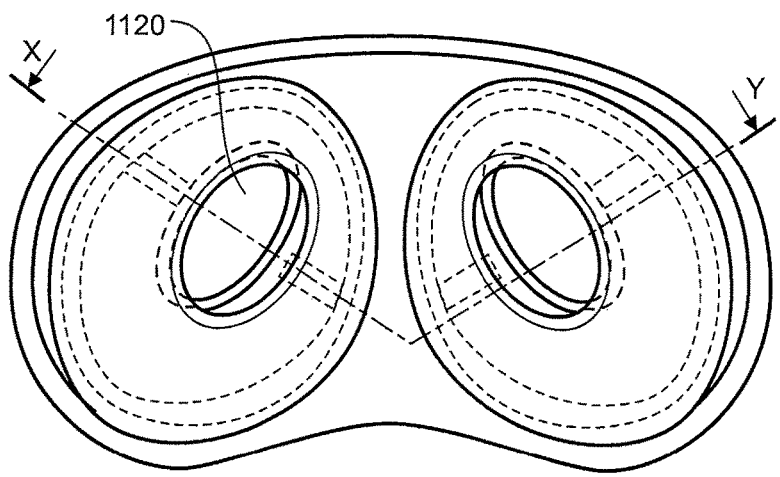
FIG. 11a shows a top view of a still further embodiment of nasal pillow section, the nasal pillow section comprising a pair of pillow portions connected to a pillow gasket portion with internal hidden detail including internal ribs of the pillow portions shown, and section lines X and Y which bisect each of the pillow portions also shown, section line X bisecting the ribs within one of the pillow sections, and section line Y bisecting the other pillow section to one side of the ribs.
Figure 11B:
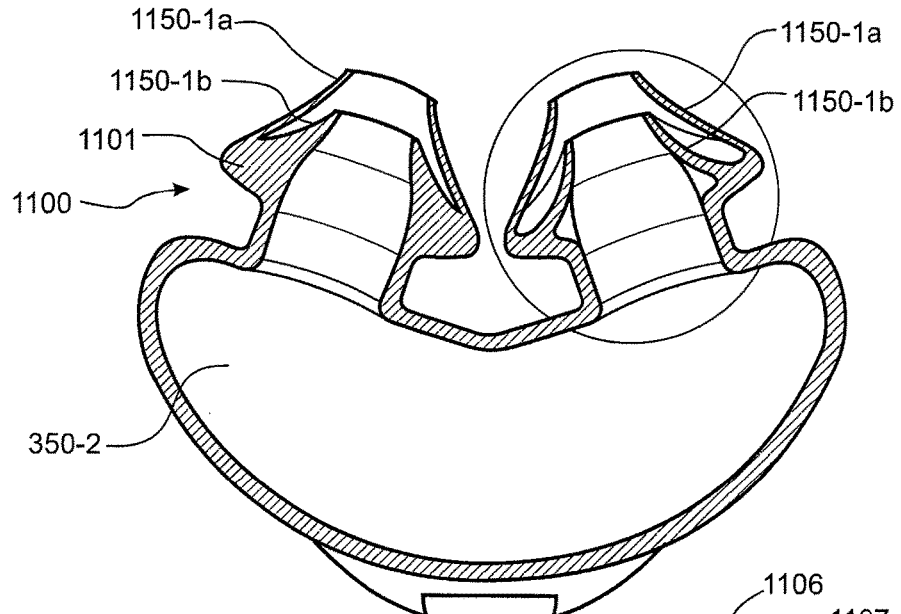
FIG. 11b shows a view of the nasal pillow section of FIG. 11a from the point of view of a user, each of the nasal pillow portions shown in cross-section, the cross-section for each pillow portion taken along the section lines X and Y, the cross-section showing internal detail of the structure of each of the nasal pillow portions, including the ribs.
Figure 11C:
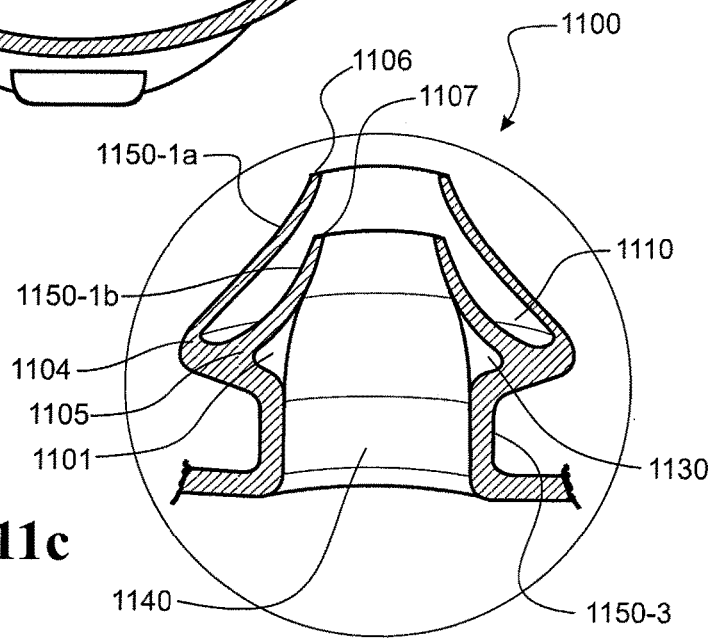
FIG. 11c shows a detail view of the right hand nasal pillow portion of FIG. 11b showing detail of the rib or ribs.

A further embodiment of the pillow portion is shown in FIGS. 11*a*, 11*b* and 11*c*. In this variation, the pillow portion is shown as being used with the pillow gasket portion 350-2 (although as outlined above, the pillow portion could be used with pillow gasket portion 250-2 or pillow gasket portion 450-2). In this embodiment the pillow section is formed from the pillow portions and the pillow gasket portion.

As seen in FIGS. 11*a*-11*c* this embodiment is made up of the first general form of the pillow portion (described above). Specific variations of this embodiment will now be described.

In the preferred form of this embodiment the walls of the inner cap 1150-1*b* and the outer cap 1150-1*a* taper in cross sectional thickness as best seen in FIG. 11*c*. The walls of the inner cap 1150-1*b* and the outer cap 1150-1*a* are thicker at the lower end. The wall of the outer cap 1150-1*a* is thicker at the base 1104 of the outer cap 1150-1*a* than at the rim 1106 of the outer cap 1150-1*a*. The wall of the inner cap 1150-1*b* is thicker at the base 1105 of the inner cap 1150-1*b* than at the rim 1107 of the inner cap 1150-1*b*. Alternatively the thickness of the walls of the inner and outer cap may be constant or the wall thickness of one of the walls may taper while the wall thickness of the other wall may remain constant—for example the thickness of the wall of the outer cap 1150-1*a* may taper while the thickness of the wall of the inner cap 1150-1*b* may remain constant. As another alternative the wall of one or both caps may be thicker at the top near the rim than at the base.

The inner cap 1150-1*b* is shaped such that a recess 1130 is created at the point where the inner cap 1150-1*b* attaches to the top of the stalk 1150-3. The recess is formed due to the shape of the inner cap and the flare of the inner cap, as best seen in FIG. 11*c*. The recess 1130 is an air gap formed in the path the stream of gases follow as they flow from the gasket portion, through the pillow portion and out through the orifice 1120 in the pillow portion. The recess 1130 follows the perimeter of the inner cap 1150-1*b*. An air gap 1110 is formed between the inner wall of the outer cap 1150-1*a* and the outer wall of the inner cap 1150-1*b*, best seen in FIG. 11*c*. The air gap 1110 is not formed in the path of the gases being delivered to the user.

The inner surface of the inner cap 1150-1*b* includes at least one, but preferably a plurality of ribs 1101. The rib or ribs 1101 are preferably housed within the recess 1130. Preferably the rib 1101 is housed only within the recess 1130. However, alternatively the rib 1101 may be housed within the recess 1130 and extend through the inner cap 1150-1*b* to the base 1104 of the outer cap 1150-1*a*. In a further alternative the rib 1101 may be formed of two sections, a first section housed within the recess 1130 and a section housed within the lower part of the air gap 1110.

If a plurality of ribs 1101 is used the ribs 1101 may be positioned at regular intervals around the perimeter of the recess 1130, the ribs being attached to the inside surface of the inner cap 1150-1*b*. Alternatively the ribs 1101 may be positioned at varying intervals around the perimeter of the inner cap 1150-1*b* and within the recess 1130 which also runs the perimeter of the inner cap 1150-1*b*. The spacing between ribs may also very from rib to rib. Preferably all the ribs 1101 are of the same thickness and width. Alternatively each rib 1101 may be of different thickness and width from each other rib 1101.

The rib 1101 follows the same profile as the stalk and the inner surface of the inner cap 1150-1*b*, so as to provide a smooth passageway for gases to pass through the pillow portion 1100, as best seen in FIG. 11*c*.

Surprisingly it has been found that the addition of the rib 1101 into the recess 1130 formed within the inner cap 1150-1*b* provides several advantages. Firstly the addition of the rib reduces and helps to stop the inner cap 1150-1*b* from folding into the stalk 1150-3. The inner cap 1150-1*b* folding back into the stalk 1150-3 causes the stalk and hence the entire cap 1100 structure to deform or collapse, thus reducing the effectiveness of the seal created with the nose. Sealing with nasal cavities is vital for delivering a stream of gases and allows for effective therapy for the patient or user. The addition of the ribs 1101 helps in creating an effective seal with the users' nostrils or nares.

It has also surprisingly been found that the addition of a rib or ribs 1101 into the recess 1130 adds strength to the inner cap 1150-1*b* that in turn provides added support for the outer cap 1150-1*a* when the pillow portion 1100 is in use and the outer cap 1150-1*a* is placed into a users' nostril. This improves the effectiveness of the seal created between the outer cap 1150-1*a* and the users' nostril. It has also surprisingly been found that the addition of the rib 1101 allows the outer cap 1150-1*a* to be substantially flexible while providing support and strength to the inner cap 1150-1*b*. The flexibility of the outer cap 1150-1*a* and the support added to the outer cap 1150-1*a* by the rib 1101 allows the outer cap 1150-1*a* to seal with a variety of different nostril shapes. It allows the pillow portion 1100 to be used by a variety of users.

An further embodiment of a pillow portion 1200 is shown in FIG. 12. A cap 1250-1 forms part of the pillow portion 1200 that is preferably used with the pillow gasket 350-2 (not shown). The pillow portion 1200 is similar to pillow portion 800, with specific differences as outlined below. As outlined above in the specification, the pillow portion 1200 could be used with pillow gasket portion 250-2 or pillow gasket portion 450-2. In this embodiment the pillow section is formed from a pair of the pillows portions 1200 and a pillow gasket portion such as gasket section 350-2 (but as outlined above, the pillow portions may be used with the pillow gasket portion 250-2 or pillow gasket portion 450-2). FIG. 12 only shows one of the pair of pillow portions.

FIG. 12 shows that this embodiment is made up of the first general form of the pillow portion (described above). The specific variations of the pillow portion are described below.

In the preferred form of this embodiment the walls of the inner cap 1250-1*b* taper in cross sectional thickness as best seen in FIG. 12. The walls of the inner cap 1250-1*b* are thicker at the rim 1207 of the inner cap 1250-1*b* than at the base 1205 of the inner cap 1250-1*b*. In the preferred form the inner cap 1250-1*b* also has a sharp edge at the rim 1207 of the inner cap 1250-1*b*, as seen in FIG. 12. In an alternate form the rim 1207 of the inner cap 1250-1*b* may be slightly rounded to improve manufacturability and comfort for the user when the pillow portion 1200 is in use. In the preferred form the cross sectional thickness of the inner cap 1250-1*b* wall may be thicker than the cross sectional thickness of the outer cap 1250-1*a* wall. This means the thinnest part of the inner cap 1250-1*b* wall may be thicker than the outer cap 1250-1*a* wall. The wall of the outer cap 1250-1*a* may be constant in thickness or may taper in thickness. In the preferred form the wall of the outer cap 1250-1*a* has a constant cross sectional thickness, as seen in FIG. 12. Alternatively the cross sectional thickness of the wall of the outer cap 1250-1*a* may be thicker at the base 1204 of the outer cap 1250-1*a* and thinner at the rim 1206 of the outer cap 1250-1*a*. As a further alternative the cross sectional thickness of the wall of the outer cap 1250-1*a* may be thicker at the rim 1206 than at the base 1204 of the outer cap 1250-1*a*.

Surprisingly it has been found that having a larger cross sectional wall thickness at the rim 1207 of the inner cap 1250-1*b* helps to improve the strength of the inner cap 1250-1*b* and the rim 1207 section of the inner cap 1250-1*b*. A common problem that occurs when the pillow portion 1200 is in use is that the outer cap 1250-1*a* is depressed by the user's nostrils. The outer cap 1250-1*a* can bear onto the inner cap 1250-1*b* and cause the inner cap to collapse and possibly block the path of the gases being delivered to the user through the pillow portion 1200. The thicker rim 1207 of the inner cap 1250-1*b* helps to prevent the rim 1207 from collapsing when the rim 1207 is depressed by the outer cap 1250-1*a*. Preventing the inner cap 1250-1*b* from blocking the gases from exiting the pillow portion 1200 helps to prevent an increase in the pressure drop across the pillow and prevents the user from exerting excessive effort to exhale through the pillow portion 1200. This particular advantage leads to the delivery of more effective therapy.

It has also surprisingly been found that a thicker wall section at the rim 1207 of the inner cap assists in maintaining the airway 1240 open, which can partially collapse when the user or patient is exhaling. The thicker wall section adds strength to the inner cap 1250-1*a*, in particular the rim section 1207 of the inner cap 1250-1*a* and helps to stop the rim section or the inner cap 1250-1*a* from collapsing. It has also surprisingly been found that the thicker rim 1207 section results in the outer cap 1250-1*a* and inner cap 1250-1*b* being substantially flexible and supple allowing the pillow portion 1200 to form an effective seal with the user's nostril.

A further embodiment of a pillow portion 1300 is shown in FIG. 13. A cap 1350-1 forms part of the pillow portion 1300 that is preferably used with the pillow gasket 350-2 (not shown) as one of a pair of pillow portions. The pillow portion 1300 is similar to pillow portion 800, with specific differences as outlined below. As outlined above in the specification, the pillows portion 1300 could also be used with pillow gasket portion 250-2 or pillow gasket portion 450-2. FIG. 13 shows one pillow portion.

As seen from FIG. 13, this embodiment is made up of the first general form of pillow portion (described above). The specific variations of this embodiment are described below.

In the preferred form of this embodiment the cross sectional thickness of the wall of the inner cap 1350-1*b* tapers in thickness, as seen in FIG. 13. The wall of the inner cap 1350-1*b* is thicker at the base 1305 of the inner cap 1350-1*b* than at the rim 1307 of the inner cap 1350-1*b*. Alternatively the wall of the inner cap 1350-1*b* may be constant in cross-sectional thickness. In a further alternative form the wall of the inner cap 1350-1*b* may be thinner in cross sectional thickness at the base 1305 and thicker at the rim 1307. In the preferred form the cross sectional thickness of the wall of the outer cap 1350-1*a* may be constant along the entire outer cap 1350-1*a*. However, in an alternative form the wall thickness of the outer cap 1350-1*a* may taper in thickness—for example the wall of the outer cap may be thicker at the base 1304 of the outer cap 1350-1*a* and thinner at the rim 1306 of the outer cap 1350-1*a*.

Surprisingly it has been found that the tapering cross sectional wall thickness of the inner cap 1350-1*b* assists in improving the overall stiffness and in particular the flexural stiffness of the inner cap. The tapering cross sectional wall thickness of the inner cap 1350-1*b* also helps to strengthen the inner cap 1350-1*b* walls. A common problem that may occur when the pillows are in use is that the outer cap 1350-1*a* depresses as it tries to conform to the shape of the user's nostril in order to form a seal. The outer cap 1350-1*a* can bear on the inner cap 1350-1*b* as it depresses. The added stiffness from the tapered cross section of the inner cap 1350-1*b* helps to prevent the inner cap 1350-1*b* from collapsing into the airway 1340 (path of gases) when the inner cap 1350-1*b* is depressed by the outer cap 1350-1*a*. This helps to prevent the inner cap 1350-1*b* from collapsing and blocking the exit of gases from the pillows. Blocking the exit of the gases from the pillows can increase the pressure drop across the pillows 1300 and increase the effort required by a patient to breath out of the pillow portion 1300. The added stiffness of the inner cap 1350-1*b* wall also helps to prevent the inner wall from collapsing and blocking the exit of gases thus reducing the effort required by a patient to breath out through the pillow portion 1300 and reduces the pressure drop across the pillow portion 1300. This leads to more effective therapy delivered to a patient and makes the pillow portion 1300 and system more comfortable to use.

In the preferred form both the rim 1307 of the inner cap 1350-1*b* and the rim 1306 of the outer cap 1350-1*a* also include a round bead 1301 extending around the perimeter of the rims, as seen in FIG. 13. The outer cap rim 1306 has a first bead 1301*a* extending inwards and running around the perimeter, while the inner cap rim 1307 has another, second separate bead 1301*b* extending inwards and running around the perimeter. Alternatively only one of the caps may have a bead 1301 extending around its rim—for example on the inner cap 1350-1*b* may have the bead 1301 extending around its rim 1307 or vice versa. Preferably the bead is formed integral to the inner and outer caps. The beads are formed as part of the manufacturing process.

Surprisingly it has been found that the addition of the beads 1301*a* and 1301*b* strengthens the rims 1306, 1307 of the outer and inner caps and adds stiffness to the rims 1306, 1307. As the patient exhales through the caps 1350-1*a*, 1350-1*b*, the caps or at least part of the caps can partially collapse. The inner cap or outer cap or both caps can also partially collapse when the cap section 1350-1 is depressed into a user's nostrils during the fitting of the pillow portion 1300. The increased stiffness of the rims 1306, 1307 of the inner and outer caps prevent the rims from collapsing as the patient is exhaling or as the pillow portion 1300 is being fitted into a patient's nostrils thus maintaining the airway 1340 in an open position. This can also reduce the effort the patient requires as he or she exhales through the pillow portion 1300, leading to increased comfort and more effective therapy for the patient. Adding a bead to both the inner and the outer rims has been found to have this surprisingly beneficial effect.

It has also surprisingly been found that the addition of the beads 1301*a* and 1301*b* in combination with the tapering cross section of inner cap 1350-1*b* results in the inner cap 1350-1*b* and outer cap 1350-1*a* in being flexible and supple to allow the pillow portion to form an effective seal with the user's nostril and deliver effective therapy to the user, and yet having a structural stability and strength sufficient to help prevent collapse in use.

Figure 14:
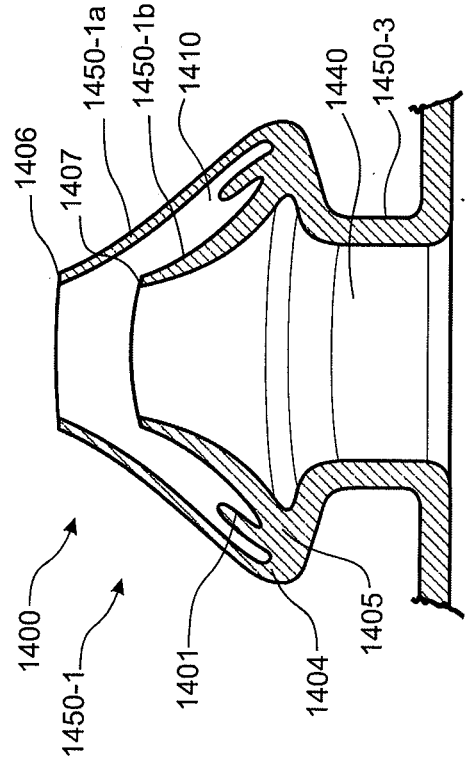
FIG. 14 shows a detail view of a still further embodiment of a nasal pillow portion in cross section, the pillow portion comprising a stalk, an outer cap and an inner cap, the pillow portion also comprising a small flange which extends upwards from between the join of the outer and inner cap.

A further embodiment of a pillow portion 1400 is shown in FIG. 14. A cap 1450-1 forms part of the pillow portion. The cap 1450-1 is preferably used with the pillow gasket 350-2 (not shown), but can be used with either of the other two pillow gaskets specifically described above, or any other suitable pillow gasket. The pillow portion 1400 has similar features to pillow portion 800, with specific differences as outlined below. As outlined above in the specification, the pillows portion 1400 could be used with pillow gasket portion 250-2 or pillow gasket portion 450-2. FIG. 14 shows one pillow portion.

As seen from FIG. 14, this embodiment is made up of the first general form of the pillow portion (described above). The specific variations of this embodiment will be described below.

In the preferred form of this embodiment the walls of the inner cap 1450-1*b* and the outer cap 1450-1*a* taper in cross sectional thickness as best seen in FIG. 14. The wall of the inner cap 1450-1*b* is preferably thicker at the base 1405 of the inner cap 1450-1*b* than at the rim 1407 of the inner cap 1450-1*b*. The wall of the outer cap 1450-1*a* is preferably thicker at the base 1404 of the outer cap 1450-1*a* than at the rim 1406 of the outer cap 1450-1*a*. Alternatively the thickness of walls of the inner 1450-1*b* and outer 1450-1*a* caps may be uniform. As a further alternative the thickness of the wall of one of the caps may taper while the thickness of the other cap may remain uniform—for example the thickness of the wall of the inner cap 1450-1*b* may taper while the thickness of the wall of the outer cap 1450-1*a* may be constant. There is a cavity 1410 or air gap formed between the outer cap 1450-1*a* and the inner cap 1450-1*b* (except where they are connected at their bases to the stalk and to each other). This cavity 1410 is not in the direct air path of the stream of gases, as best seen in FIG. 14.

In the preferred form of this embodiment a continuous flange 1401 extends upward from the point where the base 1304 of the outer cap 1450-1*a* meets the base 1305 of the inner cap 1450-1*b*. The flange extends around the perimeter of the cap 1450-1. The flange extends upwards from the base into the air gap 1410 between the inner and the outer caps as seen in FIG. 14. In the preferred form the flange 1401 is generally approximately triangular in cross section. Alternatively the flange may be of any other appropriate cross section—for example a rectangular cross section or oval. The cross sections described here are only examples and should not be construed as limiting in any way. Preferably the flange 1401 extends upward into the air gap 1410, anywhere up to half the height of the inner cap 1450-1*b*.

More preferably the flange 1401 extends upward into the air gap 1410, one seventh to one quarter of the total height of the inner cap 1450-1*b*. Preferably the height of the flange 1401 is constant around the perimeter of the inner cap 1450-1*b*. In an alternative form the flange 1401 height may vary along the perimeter of the inner cap 1450-1*b*—meaning the height of the flange 1401 may vary at various points along the perimeter of the inner cap 1450-1*b*. This variation in the height of the flange aims to strategically add strength to the outer cap 1450-1*a* in specific areas that are weaker. Therefore, for example the height of the flange may be increased at the weaker points along the outer cap 1450-1*a* to strengthen them. In still further embodiments, there may be gaps in the flange around the perimeter—that is, the flange is discontinuous around its perimeter.

Surprisingly it has been found that the addition of the flange 1401 acts to strengthen the lower parts of the outer cap 1450-1*a* and helps add rigidity and support to the lower part of the outer cap 1450-1*a*. The addition of the flange also allows the outer cap 1450-1*a* to exert a larger force on a patient's nostril when the caps 1450-1 and pillow portion 1400 are in use, due to the additional rigidity and strength added to the lower portion of the outer cap 1450-1*a* by the flange 1401. This helps to improve the seal formed between the outer cap 1450-1*a* and the user's nostril allowing for more effective therapy to be delivered. The flange also acts as a support for the outer cap 1450-1*a*—for example as the outer cap 1450-1*a* bends and is depressed while being fitted into a user's nostrils the flange acts against the bending of the outer cap 1450-1*a* and thus allows the outer cap 1450-1*a* to exert a larger force against the nostril of the user to form a more effective seal.

It has also surprisingly been found that by adding the flange 1401, this allows the upper part of the outer cap 1450-1*a* to maintain flexibility, while providing strength and rigidity for the lower part of the outer cap 1450-1*a*. The flexibility of the upper part of the outer cap 1450-1*a* allows the upper part of the outer cap 1450-1*a* to flex and bend in order to conform to the shape of a user's nostril and form an effective seal with the nostril. The flexibility of the upper part of the outer cap 1450-1*a* allows the pillow portion 1400 to be used with a variety of users and allows the pillow portion to conform to a variety of nostril shapes.

Figure 15:
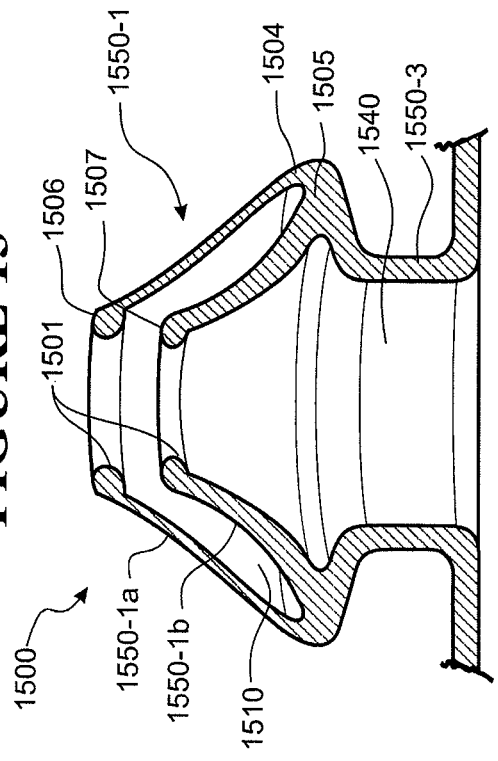
FIG. 15 shows a detail view of a further embodiment of a nasal pillow portion in cross section, the pillow portion comprising a stalk, an outer cap and an inner cap, the inner cap and outer cap walls of uniform (but different) thicknesses, a first bead extending inwards from the top edge or rim of the inner cap and a second bead extending inwards from the top edge or rim of the outer cap, the beads extending around the perimeter of their respective caps.

FIG. 15 shows a further embodiment of a pillow portion 1500. This embodiment is substantially similar to the embodiment described above with respect to FIG. 13. This embodiment is generally made up of the first general form of the pillow portion.

This embodiment is made up of the first general form of the pillow portion (described above). The eleventh embodiment also includes a bead 1501*a* on the rim 1506 of outer cap 1550-1*a* and a bead 1501*b* on the rim 1507 of the inner cap 1550-1*b*. This is very similar to embodiment nine described above.

The key difference between this embodiment and the embodiment shown in FIG. 13, is that in this embodiment, the inner cap wall has a uniform cross sectional thickness. The beads 1501*a* and 1501*b* extending from the rims 1506 and 1507 are substantially similar in shape and properties to the beads 1301*a* and 1301*b* described in the ninth embodiment.

Surprisingly it has been found that adding the beads to both the inner and the outer caps provides additional strength and stiffness, in particular flexural stiffness to the rims 1506, 1507 of the outer and inner caps respectively. A patient or user generally inhales and exhales through the nasal pillow portions 1500 when in use. A common problem that can occur is the rim of the outer cap or inner cap or both can collapse partially and partially or completely block the airway 1540 the therapy gases pass through. This can lead to increased pressure drop across the nasal pillow portion 1500 and cause the user to exert extra effort to exhale. The bead 1501 strengthens the rims 1506, 1507 of the outer and inner caps and helps to prevent the rims from collapsing into the airway 1540 and closing the airway 1540. This allows the airway 1540 to stay open and thus the user exerts less effort to exhale through the nasal pillow portion 1500. This makes the nasal pillows more comfortable to use for a patient as the patient can breathe naturally and does not have to exert extra effort to exhale through the pillows portion 1500. The rims 1506, 1507 can also collapse partially or completely into the airway 1540 as the cap 1550-1 is depressed while fitting the cap 1550-1 into a patient's nostrils. The bead 1501 reinforces the rims 1506, 1507 and may stop them from collapsing while the cap 1550-1 is being fitted into a patient's nostril allowing for a more comfortable fit and a more effective seal being formed.

Figure 16:
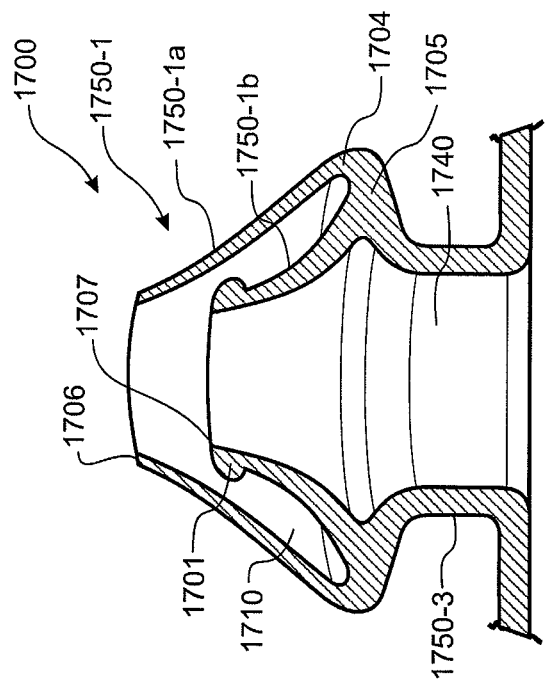
FIG. 16 shows a detail view of a further embodiment of a nasal pillow portion in cross section, the pillow portion comprising a stalk, an outer cap and an inner cap, a bead extending from the inside wall of the outer cap, the bead located in the upper third of the outer cap profile and the bead extending around the perimeter of the outer cap.

A further embodiment of a pillow portion 1600 is shown in FIG. 16. A cap 1650-1 forms part of a pillow portion 1600 that is preferably used as one of a pair of pillow portions with the pillow gasket 350-2 (not shown). The pillow portion 1600 is similar to pillow portion 800, with specific structural differences as outlined below. As outlined above in the specification, the pillows portion 1600 could be used with pillow gasket portion 250-2 or pillow gasket portion 450-2. FIG. 16 shows only one nasal pillow portion As can be seen from FIG. 16, this embodiment is made up of the first general form of the pillow portion (described above). The specific variations of the pillow portion of this embodiment are described below.

In the preferred form the cap 1650-1 is wider at the base than the stalk 1650-3. The outer 1650-1a and inner 1650-1b caps merge at their bases, with the base extending outwards almost perpendicular to the axis of the stalk 1650-3 before angling upwards and inwards. The shape of the inner and outer caps allows the caps to form a substantial seal with the nostril of the user, when in use. The inner and outer caps flare upwards and outward in a similar manner as has already been described for the embodiments shown in FIGS. 7, 8 and 14.

In the most preferred form the cross sectional thickness of the wall of the inner cap 1650-1b is uniform along the height of the inner cap 1650-1b, as seen in FIG. 16. In a less preferred form the thickness of the wall of the inner cap 1650-1b may taper in any direction. In the preferred form the cross sectional thickness of the wall of the outer cap 1650-1a is uniform along the length of the outer cap 1650-1a as seen in FIG. 16. Alternatively the cross sectional thickness of the outer cap 1650-1a wall may vary along the height of the outer cap 1650-1a—meaning the thickness of the wall may be different at different points along the wall.

The inside wall of the outer cap 1650-1a has a bead 1601 that extends around the perimeter of the outer cap 1650-1a, as seen in FIG. 16. Preferably the bead 1601 has a semicircular cross section. However, the bead 1601 may have any other shaped cross section for example a rectangular or oval cross section. These examples of bead 1601 cross sections are to be treated as examples only and are not limiting in any way as many variations will suggest themselves to a person skilled in the art on reading this specification. In the preferred form the cross sectional shape of the bead 1601 is constant along the entire perimeter of the outer cap 1650-1a. Alternatively the shape of the bead 1601 cross section may vary along different parts of the bead 1601 and the perimeter of the outer cap 1650-1a—for example one section of bead may have a circular cross section while another part of the same bead may have a rectangular cross section.

The bead 1601 is preferably located near the top of the outer cap 1650-1a on the inner surface of the outer cap 1650-1, and in the preferred form of this embodiment running in an unbroken ring around the inside surface of the outer cap 1650-1. More preferably the bead 1601 is located between the top and two thirds along the outer cap height 1650-1a. Alternatively the bead may be placed anywhere along the inside wall of the outer cap 1650-1a. As a further alternative the bead may vary in location as it extends or runs around the perimeter of the outer cap 1650-1a—for example the bead 1601 may be located half way up along the height of the inside wall of the outer cap 1650-1a at one point along the perimeter, while at another point along the perimeter the bead may be located at the top of the inside wall of the outer cap 1650-1a and so on. The placement of the bead may vary randomly or the bead may be placed at specific weak points along the inside wall of the outer cap 1650-1a.

The thickness of the bead 1601 may be constant along the entire perimeter of the outer cap 1650-1a. Preferably the thickness of the bead 1601 from its innermost point where it is joined to the surface of the outer cap to its outermost point is approximately twice the wall thickness of the outer cap 1650-1a. However, the thickness of the bead may be any thickness required for the particular type of patient and load conditions of the cap 1650-1. In a further alternative form the thickness of the bead 1601 may vary along the perimeter of the outer cap 1650-1a. Preferably the bead 1601 follows a symmetrical path around the outer cap 1650-1a, as shown in FIG. 16. Alternatively the bead may follow any varying path along the inside wall of the outer cap 1650-1a, as outlined above.

Surprisingly it has been found that the addition of the bead 1601 to the inside wall of the outer cap 1650-1a helps to strengthen and stiffen the section and surrounding sections of the outer cap 1650-1 along which the bead 1601 is placed. In the most preferred form the bead is placed around the inside surface of the outer cap 1650-1, close to the top edge of the inside wall of the outer cap 1650-1a. The bead helps to strengthen the particular area of the outer cap 1650-1a that the bead 1601 is placed at. The addition of the bead 1601 can stop or at least reduce the amount the outer cap 1650-1a collapses while being fitted into a patient's nostril. The added stiffness of the outer cap 1650-1a, due to the bead 1601, allows for a more effective seal to form between the outer cap and the patient's nostril. Surprisingly it has also been found that the location of the bead 1601 in the most preferred form, as shown in FIG. 16, allows the upper part of the outer cap 1650-1a to hold its shape while maintaining the flexibility of the lower part of the outer cap 1650-1a. This allows the outer cap 1650-1a to conform to a variety of nostril shapes and sizes.

The bead is purposely located out of the airway 1640 so that the bead is not in the path of the gases delivered to the user. The bead 1601 is placed out of the airway 1640 in order to minimise the pressure drop across the pillows portion 1600 and reduce the effort required for user to exhale or breath through the pillows portion 1600. This provides the advantage of making the use of the pillows portion 1600 more comfortable for a user.

Surprisingly it has been found that a tapered inner cap 1650-1b wall thickness helps to strengthen the inner cap 1650-1b and stiffen the inner cap 1650-1a. This is advantageous since in some circumstances in use the inner cap 1650-1b supports the outer cap 1650-1a as it flexes and bends while fitting the caps into a patient's nose. This allows for a more effective seal being formed with the user's nostril. This also stops the cap 1650-1 from collapsing into the airway 1640, stopping the delivery of gases and making the pillows portion 1600 uncomfortable for a user to wear.

Surprisingly it has been found that the bead 1601 acts as a pivot point for the outer cap 1650-1a when the outer cap 1650-1a is depressed against the inner cap 1650-1b during fitting of the outer cap 1650-1a into a user's nostrils. As the outer cap is being fitted into a user's nostrils the outer cap 1650-1a flexes, bends and is depressed, bearing onto the inner cap 1650-1b. The bead 1601 acts as a pivot point by bearing onto the inner cap 1650-1b and allowing the top portion of the outer cap 1650-1a to bend away from the airway 1640. This provides the advantage of maintaining an open airway 1640 as the outer cap 1650-1a is being fitted into a patient's nose. This is advantageous because it continuously allows the user to be supplied with therapy gases and provides a comfortable seal for the user.

Figure 17:
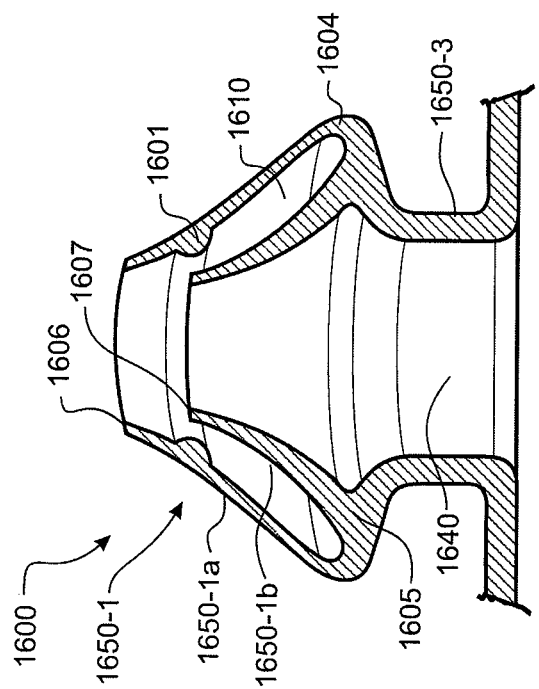
FIG. 17 shows a detail view of a further embodiment of a nasal pillow portion in cross section, the pillow portion comprising a stalk, an outer cap and an inner cap, a bead extending outwards from the outer wall of the inner cap, the bead extending from the top edge or rim of the inner cap and around the perimeter of the inner cap.

A further embodiment of a pillow portion 1700 is shown in FIG. 17. A cap 1750-1 forms part of the pillow portion 1700. A pair of the pillow portions 1700 are preferably used with the pillow gasket 350-2 (not shown). The pillow portion 1700 is similar to pillow portion 800, with specific structural differences as outlined below. As outlined above in the specification, the pillows portion 1700 could be used with pillow gasket portion 250-2 or pillow gasket portion 450-2.

This embodiment has generally the same or similar elements to the first general form of the pillow portion (as described above). The specific variations associated with this embodiment are described below.

In the most preferred form of this embodiment the cross sectional thickness of the wall of the inner cap 1750-1b is uniform along the height of the inner cap 1750-1b, as seen in FIG. 17. In a less preferred form the thickness of the wall of the inner cap 1750-1b may taper in any direction— meaning for example either the wall thickness at the base 1705 may be greater than at the rim 1707 or vice versa. In the preferred form the cross sectional thickness of the wall of the outer cap 1750-1a is uniform along the length of the outer cap 1750-1a as seen in FIG. 17. Alternatively the cross sectional thickness of the outer cap 1750-1a wall may vary along the height of the outer cap 1750-1a—meaning the thickness of the wall may be different at different points along the wall.

The outer surface of the inner cap 1750-1b includes a bead 1701. The bead 1701 is preferably located at the rim 1707 and extends around the perimeter of the inner cap 1750-1b. Preferably the bead 1701 has a circular cross section. Alternatively the bead may have any other shaped cross section, for example a rectangular cross section or triangular or oval cross section. The bead 1701 cross section shapes mentioned are only examples and should not be construed as limiting in any way. The bead 1701 is placed at the top or rim of the inner cap 1750-1b, and most preferably the bead extends around the rim 1707 of the inner cap 1750-1b. The bead 1701 extends symmetrically around the rim 1707 of the inner cap 1750-1b. Alternatively the bead 1701 may be placed at varying locations along the top third of the inner cap 1750-1b—that is, not just at or around the rim 1707, but dipping lower down the outer surface of the inner cap 1750-1b. The bead may also be discontinuous—that is, not a closed loop. As a further alternative the bead 1701 may be placed at specific weak points along the top part of the inner cap 1750-1b. In this particular description 'top part' should be taken to refer to the upper sixth of the inner cap 1750-1b.

Preferably the bead 1701 is thicker than the wall thickness of the inner cap 1750-1b. Even more preferably, the bead 1701 is twice the thickness of the wall thickness of the inner cap 1750-1b. In an alternative form the bead 1701 may be thinner than the wall of the inner cap 1750-1b. The thickness of the bead 1701 may be any thickness necessary for the specific patient and loading conditions experienced by the inner cap 1750-1b. Preferably the thickness of the bead 1701 is uniform at all points along its perimeter. Alternatively the bead 1701 thickness may vary from point to point along its perimeter. The variations in thickness may be deliberately created to strengthen certain weak points along the top part of the inner cap 1750-1b.

Surprisingly it has been found that adding the bead 1701 to the outer surface of the inner cap 1750-1b helps to strengthen and add stiffness, particularly flexural stiffness, to the top part and rim 1707 of the inner cap 1750-1b. Strengthening the top part of the inner cap 1750-1b can reduce the amount the inner cap or the top part of the inner cap collapses while fitting the pillows portion 1700 into a patient's nostrils. Strengthening the top part of the inner cap 1750-1b helps keep the airway 1740 open and doesn't force the patient to exert extra effort to exhale through the cap 1750-1 and pillows portion 1700. This leads to added comfort for the patient and may help to enhance the effectiveness of the therapy delivered to the patient.

Surprisingly the added strength of the inner cap 1750-1b also provides more support to the outer cap 1750-1a. The outer cap 1750-1 can often collapse inwards toward the inner cap 1750-1b while fitting the cap 1750-1 and the nasal pillows portion into a patient's nostril. The outer cap 1750-1a collapsing can cause the inner cap 1750-1b to deform or collapse into the airway 1740, thus completely or partially blocking the flow of gases to a patient. This can increase the pressure drop across the pillows portion 1700 and make it difficult for a patient to exhale out of the pillows portion 1700. The blocking of the airway also reduces the effectiveness of the therapy delivered to a patient. The bead 1701 acts as a "bump stop" for the outer cap 1750-1a. This means the outer edge of the bead 1701 acts as a support or limit for the outer cap 1750-1a as it is depressed. The outer edge of the bead 1701 will bear the load of the outer cap 1750-1a and can prevent the outer cap 1750-1a from collapsing into the airway 1740 and blocking the gases from being delivered to a patient. This limits the amount the outer cap 1750-1a will collapse while being fitted into a patient's nostril. This provides the advantage of making the pillows portion 1700 more comfortable to use since there is not a large pressure drop across the pillow portion 1700 and the patient does not have to exert too much effort to exhale. Further the gases delivery to the patient is not blocked and thus the therapy delivered to the user is more effective. Limiting the depression and flexing of the inner and outer caps also ensures a more effective seal is formed with a patient's nostrils and allows the pillows portion 1700 and caps 1750-1 can be used with a variety of different shaped nostrils.

Figure 18:
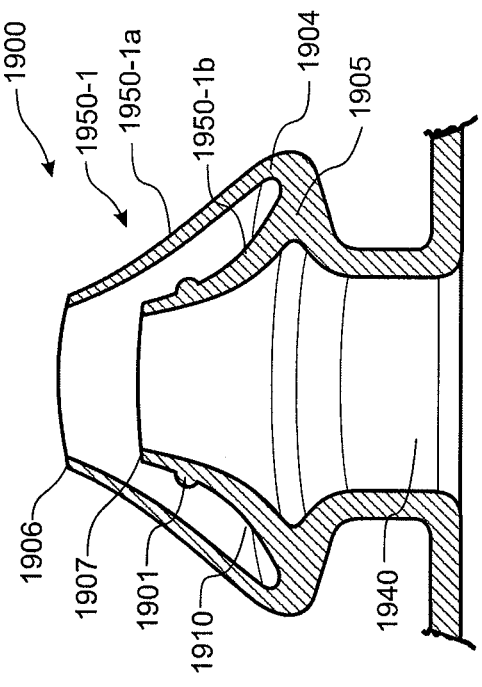
FIG. 18 shows a detail view of a further embodiment of a nasal pillow portion in cross section, the pillow portion comprising a stalk, an outer cap and an inner cap, and a bead which extends outwards from the rim of the outside wall of the outer cap, the bead extending around the perimeter of the outer cap, the inner cap wall being thicker at the base and thinner at the rim.

A further embodiment of pillow portion 1800 is shown in FIG. 18. A pair of pillow portions 1800 are preferably used with the pillow gasket 350-2 (not shown). The pillow portion 1800 is similar to pillow portion 800, with specific structural differences as described below. As outlined above in the specification, the pillows portion 1800 could be used with pillow gasket portion 250-2 or pillow gasket portion 450-2.

This embodiment has generally the same or similar elements as the first general form of the nasal pillow portion (described above). The specific variations associated with this embodiment are described below.

In the most preferred form of this embodiment the cross sectional thickness of the wall of the inner cap 1850-1b is uniform along the height of the inner cap 1850-1b, as seen in FIG. 18. In a less preferred form the thickness of the wall of the inner cap 1850-1b may taper in any direction—meaning for example either the wall thickness at the base 1805 may be greater than at the rim 1807 or vice versa. In the preferred form the cross sectional thickness of the wall of the outer cap 1850-1a is uniform along the length of the outer cap 1850-1a as seen in FIG. 18. Alternatively the cross sectional thickness of the outer cap 1850-1a wall may vary along the height of the outer cap 1850-1a—meaning the thickness of the wall may be different at different points along the wall.

The outer surface of the outer cap 1850-1a includes a bead 1801 that extends around the perimeter at the rim of the outer cap 1850-1a. Preferably the bead 1801 is located around the rim of the outer cap 1850-1a. However, the bead 1801 may be located in the upper third of the outer surface of the outer cap 1850-1a. In the most preferred form the bead 1801 extends outwards from and around the rim 1806 of the outer cap 1850-1a, as seen in FIG. 18. Alternatively the bead 1801 may be located at any point along the top third of the outside surface of the outer cap 1850-1a and extend around the perimeter of the outer cap 1850-1a. As a further alternative, (not illustrated), the bead 1801 may be placed at the top of the rim 1806, such that the centre point of the wall is located at the centre of the bead 1801—meaning the centre point of the wall cross section is on the same vertical axis as the centre point of the bead cross section. Preferably the bead 1801 is thicker than the cross sectional wall thickness of the outer cap 1850-1a. Even more preferably the bead is twice the thickness of the cross sectional wall thickness of the outer cap 1850-1a. As an alternative the bead thickness may be thinner than the thickness of the wall of the outer cap 1850-1a, however, this form is not preferred. Preferably the thickness of the bead is uniform along its perimeter. Alternatively the thickness of the bead may vary along its perimeter, the thickness of the bead being different from point to point along its perimeter. The variation in thickness may be random due to manufacturing conditions or the variation in thickness may be deliberate and the bead may be thicker or thinner at specific points along the perimeter of the outer cap 1850-1a.

The bead 1801 is most preferably circular in cross section. However, the bead 1801 may be any other cross section the manufacturer intends it to be—for example the bead 1801 may have a rectangular cross section or an oval or triangular cross section. It should be noted that the cross section shapes are only examples and should not be construed as limiting in any way, they are simply examples. The bead 1801 preferably follows a symmetrical path around the entire perimeter of the outer cap 1850-1a. Alternatively the bead 1801 may follow any path along the outer cap 1850-1a perimeter—that is, not strictly following the upper rim, but dipping below this if required. Furthermore, the bead may be formed discontinuously around the perimeter or rim if required.

Surprisingly it has been found that the addition of the bead 1801 to the outer cap 1850-1a helps to strengthen or add stiffness to the top part or the rim 1806 of the outer cap 1850-1a. The added stiffness, in particular flexural stiffness, to the top part or rim 1806 helps prevent the rim 1806 or to part of the outer cap 1850-1a from collapsing and blocking the airway 1840 and restricting the flow of gases out of the airway 1840 and pillows portion 1800, while fitting the outer cap 1850-1a into a patient's nostrils. This provides the advantage of keeping the exit opening as big as possible while the outer cap 1850-1a is being fitted into a patient's nostrils. Preventing the airway 1840 from being blocked reduces the amount of pressure drop across the pillows portion 1800, and reduces the effort a patient has to exert in order to exhale through the cap 1850-1 and pillows portion 1800. This provides the advantage of added comfort for the patient while using and fitting the pillows portion 1800.

The bead 1801 is purposely placed on the outer surface of the outer cap 1850-1a so that the bead is out of the path of the gases travelling through the airway 1840. This helps to reduce the amount of pressure drop across the pillows portion 1800 and cap 1850-1. Reduced pressure drop across the cap 1850-1 or pillows portion 1800 is advantageous as it makes it easier for a patient to breath through the cap 1850-1 once it is inserted into a patient's nostril. This allows the patient to breath normally and makes using the pillow portion 1800 and cap 1850-1 more comfortable.

Surprisingly while the bead 1801 may strengthen or stiffen the top part or rim 1806 of the outer cap 1850-1a, the lower part of the outer cap 1850-1a remains substantially flexible and supple. This flexibility and suppleness allows the outer cap 1850-1a to distort to fit into a variety of nostril shapes and form an effective seal. This allows this particular type of pillows portion 1800 and caps 1850-1 to be used with a variety of users to create an effective seal, while delivering therapy gases.

Figure 19:
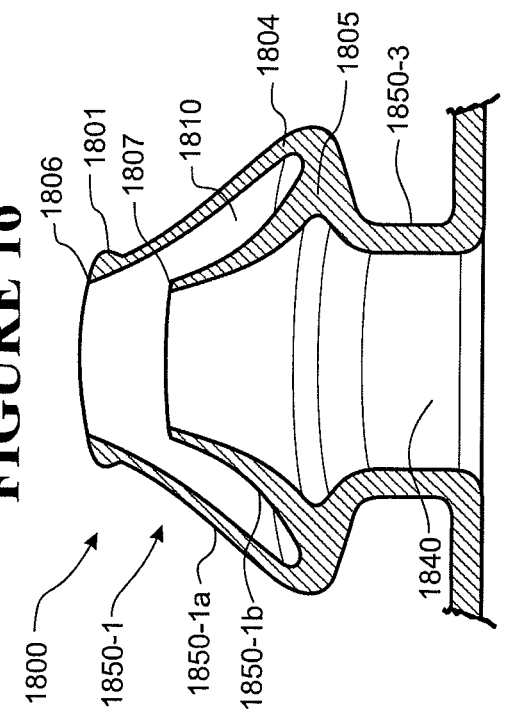
FIG. 19 shows a detail view of a further embodiment of a nasal pillow portion in cross section, the pillow portion comprising a stalk, an outer cap and an inner cap, and a bead which extends from the outer wall of the inner cap, the bead located in the upper region of the inner cap but below the rim.

A further embodiment of the pillow portion is shown as pillow portion 1900 in FIG. 19. Pillow portion 1900 is preferably used as one of a pair with the pillow gasket 350-2 (not shown). The pillow portion 1900 is similar to pillow portion 800, with specific structural differences as outlined below. As outlined above in the specification, the pillows portion 1900 could be used with pillow gasket portion 250-2 or pillow gasket portion 450-2. In this embodiment the pillow section is formed from a pair of pillow portions and a pillow gasket portion.

This embodiment has generally the same or similar elements as the first general form of the nasal pillow portion (described above). Specific variations associated with this embodiment are described below.

In the most preferred form of this embodiment the cross sectional thickness of the wall of the inner cap 1950-1b is uniform along the height of the inner cap 1950-1b, as seen in FIG. 19. In a less preferred form the thickness of the wall of the inner cap 1950-1b may taper in any direction—meaning for example either the wall thickness at the base 1905 may be greater than at the rim 1907 or vice versa. In the preferred form the cross sectional thickness of the wall of the outer cap 1950-1a is uniform along the length of the outer cap 1950-1a as seen in FIG. 19. Alternatively the cross sectional thickness of the outer cap 1950-1a wall may vary along the height of the outer cap 1950-1a—meaning the thickness of the wall may be different at different points along the wall.

The outer wall of the inner cap 1950-1b includes a bead 1901. The bead 1901 extends around the perimeter of the inner cap 1950-1b. The bead 1901 may be located at any point vertically on the inner cap, except the rim 1907. In the most preferred form the bead 1901 is located approximately between the rim and two thirds of the way along the height of the inner cap 1950-1b, when measured from the base 1905 of the inner cap 1950-1b. However the bead 1901 may be located at any other point along the inner cap 1950-1b.

The bead 1901 most preferably has a circular cross section. Alternatively the bead 1901 may have any other cross sectional shape that can be manufactured—for example the bead may be rectangular in cross section or oval in cross section. Preferably the cross section of the bead is constant along the entire perimeter of the inner cap 1950-1*b*. However, in some forms the cross section of the bead 1901 may change shape at various points along the perimeter. Preferably the bead 1901 is thicker in cross section that the wall of the inner cap 1950-1*b*, as seen in FIG. 19. Most preferably the bead 1901 is between approximately one third to two times the thickness of the wall thickness of the inner cap 1950-1*b*. Preferably the thickness of the bead is constant along the perimeter of the inner cap 1950-1*b*. In an alternative form the thickness of the bead 1901 may vary from point to point along the perimeter of the inner cap 1950-1*b*. This variation may be deliberate in order to perhaps strengthen wear points along the inner cap or this variation in thickness may be caused due to other factors, for example manufacturing equipment faults.

Surprisingly it has been found the addition of the bead 1901 to the outer wall of the inner cap 1950-1*b* may strengthen or add stiffness to the upper section of the inner cap 1950-1*b*. The bead helps to add stiffness against bending and deforming, in particular flexural stiffness. The possible added strength and stiffness helps to reduce the tendency of the inner cap 1950-1*b* to collapse into the airway 1940 while fitting the cap 1950-1 or pillows portion 1900 into a patient's nostrils. During the fitting process the inner cap 1950-1*b* may often deform and bend to fit into a patient's nostril to create an effective seal. This bending and the forces acting on the inner cap 1950-1*b* cause it to collapse into the airway 1940, thus blocking or at least partially blocking the airway 1940. The addition of the bead helps to reduce or stop the inner cap from collapsing into the airway 1940 thus not restricting the delivery of gases to a patient. Blocking the airway 1940 can lead to increased pressure drop across the cap 1950-1 and leads to increased effort by the patient to breathe through the cap 1950-1 and pillows portion 1900. Reducing or preventing the inner cap 1950-1*b* from collapsing and blocking the airway ensures the patient can breathe normally through the cap 1950-1 or pillows portion 1900, making the cap and pillows portion 1900 more comfortable to use.

Surprisingly it has been found the addition of bead 1901 to the inner cap 1950-1*b* also provides support to the outer cap 1950-1*a* and helps to reduce or prevent the outer cap 1950-1*a* from collapsing. The outer cap 1950-1*a* deforms and bends more than the inner cap 1950-1*b* while fitting the pillows portion 1900 and cap 1950-1 into a patient's nostrils. As the outer cap 1950-1*a* deforms and bends it usually bears onto the inner cap 1950-1*b* thus causing the inner cap 1950-1*b* to bend or collapse into the airway 1940. The outer cap and inner cap bending or collapsing into the airway 1940 can block or partially block the airway 1940 and the flow of gases out of the airway. 1940. This can lead to an increased pressure drop across the cap 1950-1 and increased breathing effort by the patient to breathe through the cap 1950-1. The bead 1901 acts as a travel limit "stop" or support for the outer cap 1950-1*a* as it flexes and bears onto the inner cap 1950-1*b*. The bead 1901 supports the weight of the bent or collapsed outer cap 1950-1*a* and stops or reduces the deformation or collapse of the inner cap 1950-1*b* due to the stiffness the bead 1901 adds to the inner cap 1950-1*b*. The bead 1901 limits the amount the inner cap 1950-1*b* flexes, bends or collapses. The bead 1901 also limits the amount the outer cap 19501-1*a* bends or collapses and limits the load the outer cap 1950-1*a* places on the inner cap 1950-1*b* when the outer cap 1950-1*a* is in its flexed or bent or collapsed state. This provides the advantage of keeping the airway 1940 open, reducing the pressure drop across the cap 1950-1 or pillows portion 1900 and reducing the amount of breathing effort for the patient, allowing the patient to breathe normally. The bead 1901 also contributes to allowing the cap 1950-1 to form a more effective seal by reducing the amount the inner and outer caps deform.

A further embodiment of the pillow portion 2000 is shown in FIG. 20. A pair of the pillow portions 2000 are preferably used with the pillow gasket 350-2 (not shown). The pillow portion 2000 is similar to pillow portion 800 with specific structural differences as described below. As outlined above in the specification, the pillows portion 2000 could be used with pillow gasket portion 250-2 or pillow gasket portion 450-2.

This embodiment has generally the same or similar elements as of the first general form of the pillow portion (described above). The specific variations associated with this embodiment are described below.

In the most preferred form of this embodiment the cross sectional thickness of the wall of the inner cap 2050-1*b* is uniform along the height of the inner cap 2050-1*b*, as seen in FIG. 20. In a less preferred form the thickness of the wall of the inner cap 2050-1*b* may taper in any direction—meaning for example either the wall thickness at the base 2005 may be greater than at the rim 2007 or vice versa. In the preferred form the cross sectional thickness of the wall of the outer cap 2050-1*a* is uniform along the length of the outer cap 2050-1*a* as seen in FIG. 20. Alternatively the cross sectional thickness of the outer cap 2050-1*a* wall may vary along the height of the outer cap 2050-1*a*—meaning the thickness of the wall may be different at different points along the wall.

The inner wall of the inner cap 2050-1*b* includes a bead 2001 located on the inner wall of the inner cap 2050-1*b*. The bead is preferably located at and extends inwardly around the rim 2007 of the inner cap 2050-1*b*. Alternatively the bead 2001 may be located at any point along the height of the inner cap 2050-1*b* on the inside wall, meaning the bead may be located anywhere between the base 2005 and the rim 2007 of the inner cap 2050-1*b*. The bead 2001 still extends around the perimeter of the inner cap 2050-1*b*. Preferably the bead 2001 is symmetrical around the perimeter of the inner cap 2050-1*b*, meaning in cross section the bead is a mirror image about a vertical axis in the centre of the cap 2050-1 and stalk 2050-3, as seen in FIG. 20. In alternative arrangements the bead may follow any asymmetrical path around the perimeter of the inner cap 2050-1*a*.

FIG. 20 shows the preferred form of the bead 2001, in which the bead 2001 has a substantially circular cross section. Alternatively the bead 2001 may have any other cross section shape, for example a rectangular or oval cross section. The cross section shapes identified are only examples and should not be construed as limiting, since on reading the above description, a number of different possible cross-sections would suggest themselves to a person skilled in the art. Preferably the bead 2001 is thicker in cross sectional thickness than the cross sectional thickness of the wall of the inner cap 2050-1*b*, as best seen in FIG. 20. Even more preferably the bead 2001 is twice as thick as the wall of the inner cap 2050-1*b*. Alternatively the thickness of the bead may be thinner than the thickness of the wall of the inner cap 2050-1*b*. Preferably the thickness of the bead 2001 is uniform along the entire perimeter of the inner cap 2050-1*b*. Alternatively the bead thickness may vary from point to point along the perimeter of the inner cap 2050-1b. As a further alternative the bead 2001 may be thicker at one end of the rim and thinner at the other end.

It has surprisingly been found that the addition of the bead 2001 to the inside wall of the inner cap 2050-1b adds strength and increased stiffness to the upper section of the inner cap 2050-1b, in particular the rim 2001 and the surrounding area of the rim 2007. The additional stiffness due to the bead 2001 helps to stop or reduce the amount the inner cap 2050-1b collapses into the airway 2040, while fitting the cap 2050-1 into a patient's nostrils. The inner cap 2050-1b flexes while fitting the cap 2050-1 into a patient's nostrils. The load on the inner cap 20050-1b may cause the inner cap 2050-1b to partially or completely collapse or bend and block the airway 2040. Blocking the airway restricts the amount of gases being delivered to a patient, increases the pressure drop across the cap 2050-1 and increases the difficulty of breathing through the cap 2050-1 for the user. The bead 2001 assists in reducing or stopping the inner cap 2050-1b from collapsing into the airway 2040. Hence sufficient amount of therapy gases are delivered to the patient, there is less of a pressure drop across the cap 2050-1 and the difficulty of breathing through the cap 2050-1 and pillows portion 2000 is reduced. This leads to added comfort for the patient and effective therapy for the patient.

Figure 21:
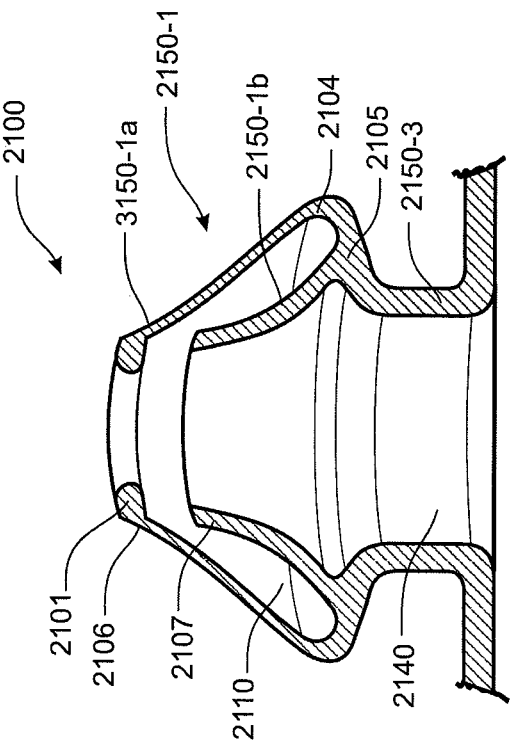
FIG. 21 shows a detail view of a further embodiment of the nasal pillow portion in cross section, the pillow portion comprising a stalk, an outer cap and an inner cap, a bead extending from the inside wall of the outer cap, the bead extending from the rim of the outer cap and around the perimeter of the outer cap, the inner cap wall thicker than the outer cap wall.

A further embodiment of the pillow portion 2100 is shown in FIG. 21. A pair of the pillow portions are used with the pillow gasket 350-2 (not shown). The pillow portion 2100 is similar to pillow portion 800, with specific structural differences as outlined below. As outlined above in the specification, the pillows portion 2100 could be used with pillow gasket portion 250-2 or pillow gasket portion 450-2. In this embodiment the pillow section is formed from a pair of the pillows portions and a pillow gasket portion.

This embodiment has generally the same or similar elements as the first general form of the pillow portion (described above). The specific variations associated with this embodiment are identified below.

In the most preferred form of this embodiment the cross sectional thickness of the wall of the outer cap 2150-1a is uniform along the height of the outer cap 2150-1a, as seen in FIG. 21. In a less preferred form the thickness of the wall of the outer cap 2150-1a may taper in any direction—meaning for example either the wall thickness at the base 2104 may be greater than at the rim 2106 or vice versa. In the preferred form the thickness of the wall of the inner cap 2050-1b is uniform along the length of the inner cap 2050-1b, as seen in FIG. 21. Alternatively the cross sectional thickness of the inner cap 2150-1b wall may vary along the height of the inner cap 2150-1b—meaning the thickness of the wall may be different at different points along the wall.

The outer cap 2150-1a includes a bead 2101 located on the inner wall of the outer cap 2150-1a. The bead is preferably located at and extends around the rim 2106 of the outer cap 2150-1a. Alternatively the bead 2101 may be located at any point along the height of the outer cap 2150-1a on the inside wall, meaning the bead may be located anywhere between the base 2104 and the rim 2106 of the outer cap 2150-1a. The bead 2101 still extends around the perimeter of the outer cap 2150-1a. Preferably the bead 2101 is symmetrical around the perimeter of the outer cap 2150-1a, meaning in cross section the bead is a mirror image about a vertical axis in the centre of the cap 2150-1 and stalk 2150-3, as seen in FIG. 21. In alternative arrangements the bead may follow an asymmetrical path around the perimeter of the inner cap 2150-1a.

FIG. 21 shows the preferred form of the bead 2101, in which the bead 2101 has a substantially circular cross section. Alternatively the bead 2101 may have any other cross section shape, for example a rectangular or oval cross section. The cross section shapes identified are only examples and should not be construed as limiting, since many shapes for the bead 2101 would suggest themselves to a person skilled in the art once they have read the description above. Preferably the bead 2101 is thicker in cross sectional thickness than the cross sectional thickness of the wall of the outer cap 2150-1a, as best seen in FIG. 21. Even more preferably the bead 2101 is twice as thick as the wall of the outer cap 2150-1a. Alternatively the thickness of the bead may be thinner than the thickness of the wall of the outer cap 2150-1a. Preferably the thickness of the bead 2101 is uniform along the entire perimeter of the outer cap 2150-1a. Alternatively the bead thickness may vary from point to point along the perimeter of the outer cap 2150-1a. As a further alternative the bead 2101 may be thicker at one end of the rim and thinner at the other end.

It has surprisingly been found that the addition of the bead 2101 to the inside wall of the outer cap 2150-1a adds strength and increased stiffness to the upper section of the outer cap 2150-1a, in particular the rim 2101 and the surrounding area of the rim 2107. The additional stiffness due to the bead 2101 helps to stop or reduce the amount the outer cap 2150-1a collapses into the airway 2140, while fitting the cap 2150-1 into a patient's nostrils. The outer cap 2150-1a flexes during fitting of the cap 2150-1 into a patient's nostrils. The load on the outer cap 2150-1a from the patient's nostril causes the outer cap 2150-1a to partially or completely collapse or bend and block the airway 2140. Blocking the airway restricts the amount of gases being delivered to a patient, increases the pressure drop across the cap 2150-1 and increases the difficulty of breathing through the cap 2150-1 for the user. The bead 2101 helps to reduce or stop the outer cap 2150-1a from collapsing into the airway 2140. Hence sufficient amount of therapy gases are delivered to the patient, there is less of a pressure drop across the cap 2150-1 and reduces the difficulty of breathing through the cap 2150-1 and pillows portion 2100. This leads to added comfort for the patient and effective therapy for the patient.

Figure 22:
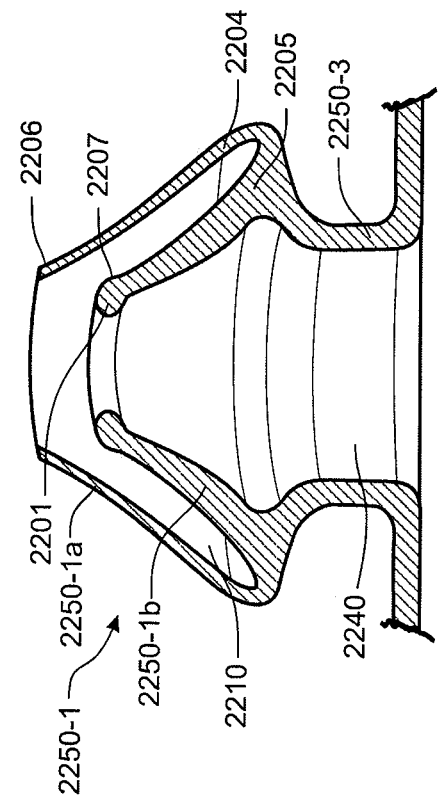
FIG. 22 shows a detail view of a further embodiment of a nasal pillow portion in cross section, the pillow portion comprising a stalk, an outer cap and an inner cap, and a bead which extends inwards from the inside wall of the inner cap, the bead extending from the rim and around the perimeter of the cap, the inner cap wall tapering in thickness, and being thicker at the base than at the rim.

An further embodiment of pillow portion 2200 is shown in FIG. 22. The cap 2250-1 is part of a pillow portion 2200 (not shown) that is preferably used with the pillow gasket 350-2 (not shown). The pillow portion 2200 is similar to pillow portion 800. As outlined above in the specification, the pillows portion 2200 could be used with pillow gasket portion 250-2 or pillow gasket portion 450-2. In this embodiment the pillow section is formed from the pillows portion and pillow gasket portion.

This embodiment has generally the same or similar elements as the first general form of the pillow portion (described above). The specific variations associated with this embodiment are described below. This embodiment is similar to the sixteenth embodiment with a few minor differences that are identified below.

In the most preferred form the cross sectional thickness of the wall of the inner cap 2250-1b tapers along the height of the inner cap 2250-1b, as seen in FIG. 22. The wall of the inner cap is preferably thicker at the base 2205 than at the rim 2207 of the inner cap 2250-1b. However, the wall of the inner cap 2250-1b may be thicker at the rim 2207 than at the base 2205. In a less preferred form the thickness of the wall of the inner cap 2250-1b may be uniform along the height of the inner cap 2250-1b. In the preferred form the cross sectional thickness of the wall of the outer cap 2250-1*a* is uniform along the length of the outer cap 2250-1*a* as seen in FIG. 22. Alternatively the cross sectional thickness of the outer cap 2250-1*a* wall may vary along the height of the outer cap 2250-1*a*—meaning the thickness of the wall may be different at different points along the wall.

The inner wall of the inner cap 2250-1*b* includes a bead 2201 located on the inner wall of the inner cap 2250-1*b*. The bead is preferably located at and extends around the rim 2207 of the inner cap 2250-1*b*. Alternatively the bead 2201 may be located at any point along the height of the inner cap 2250-1*b* on the inside wall, meaning the bead may be located anywhere between the base 2205 and the rim 2207 of the inner cap 2250-1*b*. The bead 2201 still extends around the perimeter of the inner cap 2250-1*b*. Preferably the bead 2201 follows a symmetrical path around the perimeter of the inner cap 2250-1*b*, meaning in cross section the bead is a mirror image about a vertical axis in the centre of the cap 2250-1 and stalk 2250-3, as seen in FIG. 22. In alternative arrangements the bead may follow any asymmetrical path around the perimeter of the inner cap 2250-1*a*.

FIG. 22 shows the preferred form of the bead 2201, in which the bead 2201 has a substantially circular cross section. Alternatively the bead 2201 may have any other cross section shape, for example a rectangular or oval cross section. The cross section shapes identified are only examples and should not be construed as limiting, since a number of different alternatives would suggest themselves to a person skilled in the art on reading the above description. Preferably the bead 2201 is thicker in cross sectional thickness than the cross sectional thickness of the wall of the inner cap 2250-1*b*, as best seen in FIG. 22. Even more preferably the bead 2201 is twice as thick as the wall of the inner cap 2250-1*b*. Alternatively the thickness of the bead may be thinner than the thickness of the wall of the inner cap 2250-1*b*. Preferably the thickness of the bead 2201 is uniform along the entire perimeter of the inner cap 2250-1*b*. Alternatively the bead thickness may vary from point to point along the perimeter of the inner cap 2250-1*b*. As a further alternative the bead 2201 may be thicker at one end of the rim and thinner at the other end.

It has surprisingly been found that the addition of the bead 2201 to the inside wall of the inner cap 2250-1*b* may add strength and increased stiffness to the upper section of the inner cap 2250-1*b*, in particular the rim 2201 and the surrounding area of the rim 2207. The additional stiffness due to the bead 2201 may stop or reduce the amount the inner cap 2250-1*b* collapses into the airway 2240, while fitting the cap 2250-1 into a patient's nostrils. The inner cap 2250-1*b* flexes during while fitting the cap 2250-1 into a patient's nostrils. The load on the inner cap 22050-1*b* may cause the inner cap 2250-1*b* to partially or completely collapse or bend and block the airway 2240. Blocking the airway restricts the amount of gases being delivered to a patient, increases the pressure drop across the cap 2250-1 and increases the difficulty of breathing through the cap 2250-1 for the user. The bead 2201 can reduce or stop the inner cap 2250-1*b* from collapsing into the airway 2240. Hence sufficient amount of therapy gases are delivered to the patient, there is less of a pressure drop across the cap 2250-1 and reduces the difficulty of breathing through the cap 2250-1 and pillows portion 2200. This leads to added comfort for the patient and effective therapy for the patient.

Figure 23:
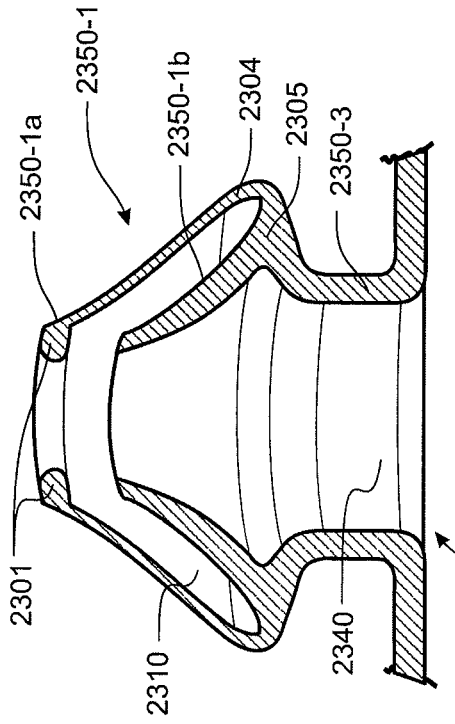
FIG. 23 shows a detail view of a further embodiment of a nasal pillow portion in cross section, the pillow portion comprising a stalk, an outer cap and an inner cap, the pillow portion also comprising a bead which extends inwards from the inside wall of the outer cap, the bead extending from the rim of the outer cap and around the perimeter of the outer cap, the inner cap wall tapering in thickness, and being thicker at the base than at the rim.

A further embodiment of pillow portion 2300 is shown in FIG. 23. The cap 2350-1 is part of a pillow portion 2300 (not shown) that is preferably used with the pillow gasket 350-2 (not shown). The pillow portion 2300 is similar to pillow portion 800. As outlined above in the specification, the pillows portion 2300 could be used with pillow gasket portion 250-2 or pillow gasket portion 450-2. In this embodiment the pillow section is formed from the pillows portion and pillow gasket portion.

This embodiment has generally the same or similar elements as the first general form of the pillow portion (as described earlier). The specific variations associated with this embodiment are described below. The pillow portions of the nineteenth embodiment are substantially similar to those described in the seventeenth embodiment. The general structure and differences are described below.

In the most preferred form the cross sectional thickness of the wall of the outer cap 2350-1*a* is uniform along the height of the outer cap 2350-1*a*, as seen in FIG. 23. In a less preferred form the thickness of the wall of the outer cap 2350-1*a* may taper in any direction—meaning for example either the wall thickness at the base 2304 may be greater than at the rim 2306 or vice versa. In the preferred form the thickness of the wall of the inner cap 2050-1*b* tapers along the length of the inner cap 2050-1*b*, as seen in FIG. 23. Preferably the inner cap 2350-1*b* wall is thicker at the base 2305 than at the rim 2307. However, the thickness of the wall of the inner cap 2350-1*b* may be thicker at the rim 2307 than at the base 2305, and the wall tapers in thickness.

The outer cap 2350-1*a* includes a bead 2301 located on the inner wall of the outer cap 2350-1*a*. The bead is preferably located at and extends around the rim 2306 of the outer cap 2350-1*a*. Alternatively the bead 2301 may be located at any point along the height of the outer cap 2350-1*a* on the inside wall, meaning the bead may be located anywhere between the base 2304 and the rim 2306 of the outer cap 2350-1*a*. The bead 2301 still extends around the perimeter of the outer cap 2350-1*a*. Preferably the bead 2301 follows a symmetrical path around the perimeter of the outer cap 2350-1*a*, meaning in cross section the bead is a mirror image about a vertical axis in the centre of the cap 2350-1 and stalk 2350-3, as seen in FIG. 23. In alternative arrangements the bead may follow any asymmetrical path around the perimeter of the inner cap 2350-1*a*.

FIG. 23 shows the preferred form of the bead 2301, in which the bead 2301 has a substantially circular cross section. Alternatively the bead 2301 may have any other cross section shape, for example a rectangular or oval cross section. The cross section shapes identified are only examples and should not be construed as limiting, since many different shapes of bead would suggest themselves to a person skilled in the art once they have read the description above. Preferably the bead 2301 is thicker in cross sectional thickness than the cross sectional thickness of the wall of the outer cap 2350-1*a*, as best seen in FIG. 23. Even more preferably the bead 2301 is twice as thick as the wall of the outer cap 2350-1*a*. Alternatively the thickness of the bead may be thinner than the thickness of the wall of the outer cap 2350-1*a*. Preferably the thickness of the bead 2301 is uniform along the entire perimeter of the outer cap 2350-1*a*. Alternatively the bead thickness may vary from point to point along the perimeter of the outer cap 2350-1*a*. As a further alternative the bead 2301 may be thicker at one end of the rim and thinner at the other end.

It has surprisingly been found that the addition of the bead 2301 to the inside wall of the outer cap 2350-1*a* may add strength and increased stiffness to the upper section of the outer cap 2350-1*a*, in particular the rim 2301 and the surrounding area of the rim 2307. The additional stiffness due to the bead 2301 may stop or reduce the amount the outer cap 2350-1*a* collapses into the airway 2340, while fitting the cap 2350-1 into a patient's nostrils. The outer cap 2350-1a flexes during fitting of the cap 2350-1 into a patient's nostrils. The load on the outer cap 2350-1a from the patient's nostril may cause the outer cap 2350-1a to partially or completely collapse or bend and block the airway 2340. Blocking the airway restricts the amount of gases being delivered to a patient, increases the pressure drop across the cap 2350-1 and increases the difficulty of breathing through the cap 2350-1 for the user. The bead 2301 can reduce or stop the outer cap 2350-1a from collapsing into the airway 2340. Hence sufficient amount of therapy gases are delivered to the patient, there is less of a pressure drop across the cap 2350-1 and reduces the difficulty of breathing through the cap 2350-1 and pillows portion 2300. This leads to added comfort for the patient and effective therapy for the patient.

Figure 24:
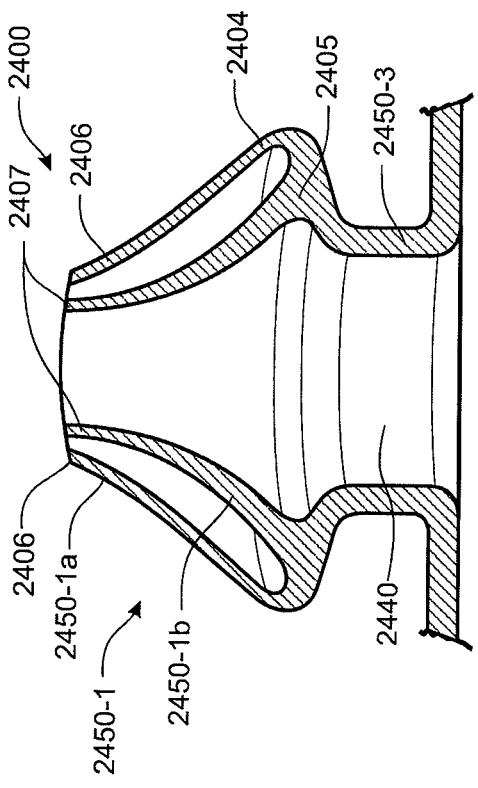
FIG. 24 shows a detail view of a further embodiment of a nasal pillow portion in cross section, the pillow portion comprising a stalk, an outer cap and an inner cap, the inner cap being the same height as the outer cap and the rims of the inner and outer cap being aligned in the same plane, as shown in the figure.

A further embodiment of pillow portion 2400 is shown in FIG. 24. The cap 2450-1 is part of the pillow portion 2400 that is preferably used with the pillow gasket 350-2 (not shown). The pillow portion 2400 is similar to pillow portion 800. As outlined above in the specification, the pillows portion 2400 could be used with pillow gasket portion 250-2 or pillow gasket portion 450-2. In this embodiment the pillow section is formed from the pillows portion and pillow gasket portion.

This embodiment has generally the same or similar elements as the first general form of the pillow portion (as described earlier). The specific variations associated with this embodiment of the pillow portion are described below.

In the most preferred form the cross sectional thickness of the wall of the outer cap 2450-1a is uniform along the height of the outer cap 2450-1a, as seen in FIG. 24. In a less preferred form the thickness of the wall of the outer cap 2450-1a may taper in any direction—meaning for example either the wall thickness at the base 2404 may be greater than at the rim 2406 or vice versa. In the preferred form the thickness of the wall of the inner cap 2050-1b tapers along the length of the inner cap 2050-1b, as seen in FIG. 24. Preferably the inner cap 2450-1b wall is thicker at the base 2405 than at the rim 2407. However, the thickness of the wall of the inner cap 2450-1b may be thicker at the rim 2407 than at the base 2405, and the wall tapers in thickness. Preferably the wall of the outer cap 2450-1a is thinner than the wall of the inner cap 2450-1b. Preferably the inner cap rim 2407 and outer cap rim 2406 are the same height as each other.

It has surprisingly been found that the inner cap 2450-1b and outer cap 2450-1a rims being the same height may make it easier for a patient or user to breathe through the pillows portion 2400 and cap 2450-1. The outer cap 2450-1a rim 2406 extends to the same height as the inner cap 2450-1b rim 2407. It has been found that if the inner cap 2450-1b and outer cap 2450-1a are of the same vertical height, the outer cap 2450-1a collapses and rests against the inner cap 2450-1b as the patient or user exhales. The outer cap 2450-1a collapsing and depressing against the inner cap 2450-1b causes the inner cap 2450-1b rim 2407 to protrude out above the rim 2406 of the outer cap 2450-1a. The rim 2407 of the inner cap 2450-1b protruding above the rim 2406 of the outer cap eliminates any other alternate pathways for the air to travel out of when a user is exhaling. The exhaled air is exhaled solely from airway 2440 since the rim 2407 of the inner cap 2450-1b protrudes above the rim of the outer cap. This reduces the effort a user has to exert while breathing through and using the pillows portion 2400, thus making the pillows portion 2400 more comfortable and safer to use.

A further embodiment of pillow portion 2500 is shown in FIG. 25. The cap 2550-1 is part of the pillow portion 2500 that is preferably used with the pillow gasket 350-2 (not shown). The pillow portion 2500 is similar to pillow portion 800. As outlined above in the specification, the pillows portion 2500 could be used with pillow gasket portion 250-2 or pillow gasket portion 450-2. In this embodiment the pillow section is formed from the pillows portion and pillow gasket portion.

This embodiment has generally the same or similar elements as of the second general form of the nasal pillow portion (described earlier). The specific details of this embodiment are described below.

As can be seen in FIG. 25, the outer cap 2550-1a and the air delivery tube 2560 are generally arranged with a common central axis. As can also be seen in FIG. 25, the outer cap 2550-1a and air delivery tube 2560 are of equal height. The rim 2506 of the outer cap 2550-1a and the rim 2507 of the air delivery tube 2560 are preferably in line and lie on the same horizontal axis. However, the upper rims 2506 and 2507 are generally vertically aligned if the cap is fully upright. Preferably the pillow portions 2500 will be angled inwards towards each other on the gasket portion, similar to that as shown in FIGS. 11a and 11b. The upper rims are not vertically aligned as the pillow portions 2500 are angled inwards towards each other.

In the preferred form the cap 2550-1 is wider at the base than the stalk 2550-3. The outer cap 2550-1a and air delivery tube 2560 merge at their bases, with the base extending outwards almost perpendicular to the axis of the stalk 2550-3 before angling upwards and inwards. The shape of the outer cap and the air delivery tube 2560 allows the cap 2550-1a or the air delivery tube 2560 or both to form a substantial seal with the nostril of the user, when in use. The walls of the outer 2550-1a cap are curved to help the cap to conform to a user's nostril and may assist in guiding a stream of gases from the pillow portions to the nostrils of a user. The outer cap may curve or flare upwards such that in use the flare of the cap allows the cap 2550-1a to form a substantial seal with the nostril of the user, when in use. Preferably the walls of the outer 2550-1a cap are curved along a parabolic arc. The outer cap flares upwards and outward in a similar manner as has already been described for the embodiments shown in FIGS. 7, 8, 14 and 15.

In the most preferred form the cross sectional thickness of the wall of the outer cap 2550-1a is uniform along the height of the outer cap 2550-1a, as seen in FIG. 25. In a less preferred form the thickness of the wall of the outer cap 2550-1a may taper in any direction—meaning for example either the wall thickness at the base 2504 may be greater than at the rim 2506 or vice versa. Preferably the wall of the outer cap 2550-1a is thinner in cross sectional thickness than the wall of the air delivery tube 2560, as seen in FIG. 25. Preferably the air delivery tube 2560 tapers in thickness, meaning the thickness of the wall of the air delivery tube 2560 tapers, but that the inner sides or walls are parallel. Preferably the wall of the air delivery tube 2560 is thicker at its base 2505 than at its rim 2507. Alternatively the thickness of the wall of the air delivery tube 2560 may be thicker at the rim and thinner at its base. In a further alternative form the wall of the air delivery tube 2560 may be of uniform thickness along its height.

Surprisingly it has been found adding an air delivery tube 2560 with internal straight-sides into the cap 2550-1 better directs airflow to patient's nostril, aides in sealing against the nostrils of a patient and reduces the breathing effort required by the patient to breathe through the pillows portion 2500 (not shown). The flexibility of the outer cap 2550-1a allows the outer cap to bend and deform to fit any shaped nostril. This allows the pillows portion to be used with a variety of nostril shapes. The thinner and more flexible outer cap also flexes such that the stiffer air delivery tube is positioned substantially in the centre of a patient's nostrils when in use. The air delivery tube 2560 being in the centre of a patient's nostrils better directs air flow and gases into a patient's nostrils. The air delivery tube 2560 being rigid helps the outer cap 2550-1a to form a better seal with the patient's nostrils, because the air delivery tube 2560 does not deform and acts as a support for the outer cap 2550-1a.

Surprisingly it has been found that air delivery tube directs air into a patient's nostrils with a minimal pressure drop across the pillows portion 2500 and the cap 2550-1. This reduced pressure drop makes it easier for a user to breathe through the cap 2550-1 since there is a lower resistance to the air flowing through the air delivery tube. Further there is less resistance to the air flowing through the air delivery tube 2560 because the air delivery tube does not collapse or deform when in use. This means the airway 2540 (the path of the gases or air) is unhindered and obstacle free, thus reducing the pressure drop across the pillows portion 2500 and the cap 2550-1. The reduced pressure drop makes it easier for a patient to breathe through the pillows portion 2500 and cap 2550-1 when in use, leading to more effective therapy and added comfort for the user.

Surprisingly it has been found that the addition of the air delivery tube 2560 to the cap 2550-1 reduces the effort a patient has to apply to exhale and breathe through the pillows portion and the cap 2550-1. A common problem that may occur is exhaled air being trapped within the cap or exhaled air flowing into various gaps within the cap—for example the exhaled air commonly flows into the gap 2510 between the outer cap 2550-1a and the air delivery tube 2560. The air becomes trapped there when the outer cap 2550-1a is in use. The stiff air delivery tube 2560 offers a support for the outer cap 2550-1a to lean against as the outer cap depresses when in use. The outer cap 2550-1a leans against the air delivery tube 2550-1a causing the rim 2507 of the air delivery tube 2560 to protrude above the rim of the outer cap, thus sealing off the gap 2510. This restricts the exhaled air to flow out of the air delivery tube 2560 only, reducing the effort the user has to apply to breathe through the pillows portion 2500 and the cap 2550-1 since the exhaled air has a clear unhindered pathway to exit.

A further embodiment of pillow portion 2600 is shown in FIG. 26. The cap 2650-1 is part of a pillow portion 2600 that is preferably used with the pillow gasket 350-2 (not shown). The pillow portion 2600 is similar to pillow portion 800. As outlined above in the specification, the pillows portion 2600 could be used with pillow gasket portion 250-2 or pillow gasket portion 450-2. In this embodiment the pillow section is formed from the pillows portion and pillow gasket portion.

This embodiment has generally the same or similar elements as the first general form of the pillow portion (described earlier). The specific variations associated with this embodiment are described below.

In the preferred form of this embodiment the walls of the inner cap 2650-1b taper in cross sectional thickness as best seen in FIG. 26. The walls of the inner cap 2650-1b are thicker at the base 2605 of the inner cap 2650-1b than at the rim 2607 of the inner cap 2650-1b. In the preferred form the cross sectional thickness of the inner cap 2650-1b wall may be thicker than the cross sectional thickness of the outer cap 2650-1a wall. This means the thinnest part of the inner cap 2650-1b wall may be thicker than the outer cap 2650-1a wall. Alternatively the wall of the inner cap 2650-1b may be uniform in thickness. Preferably the wall of the outer cap 2650-1a is tapered in thickness. The wall of the outer cap 2650-1a is thicker at the rim 2606 of the outer cap 2650-1a than at the base 2604 of the outer cap 2650-1a, as seen in FIG. 26, with a sharp edge, as seen in FIG. 26. Alternatively the edge of the rim 2606 may be slightly rounded to make it easier to manufacture.

Surprisingly it has been found that having a larger cross sectional wall thickness at the rim 2606 of the outer cap 2650-1a improves the strength and stiffness of the outer cap 2650-1a and the rim 2606 section of the outer cap 2650-1a. A common problem that occurs when the pillow portion 2600 is in use is that the outer cap 2650-1a is depressed by the user's nostrils. The outer cap 2650-1a may collapse or deform and possibly block the path of the gases being delivered to the patient through the pillow portion 2600. The thicker rim 2606 of the outer cap 2650-1b may prevent the rim 2606 from collapsing when the rim 2606 is depressed by the patient's nostrils as the rim 2606 is inserted into a patient's nostrils. Preventing the outer cap 2650-1a from collapsing and blocking the gases from exiting the pillow portion 2600 may prevent an increase in the pressure drop across the pillow and prevents the patient from exerting excessive effort to exhale through the pillow portion 2600. This particular advantage leads to more effective therapy, added comfort and safety for the patient.

It has also surprisingly been found that a thicker wall section at the rim 2606 of the outer cap 2650-1a assists in maintaining the airway 2640 open, which can partially collapse when the user or patient is exhaling. The thicker wall section adds strength and stiffness to the outer cap 2650-1a, in particular the rim section 2606 of the outer cap 2650-1a and may stop the rim section or the outer cap 2650-1a from collapsing. It has also surprisingly been found that the thicker rim 2606 section may result in the outer cap 2650-1a being substantially flexible and supple allowing the pillow portion 2600 to form an effective seal with the user's nostril.

A further embodiment of pillow portion 2700 is shown in FIG. 27. The cap 2750-1 is part of a pillow portion 2700 that is preferably used with the pillow gasket 350-2 (not shown). The pillow portion 2700 is similar to pillow portion 800. As outlined above in the specification, the pillows portion 2700 could be used with pillow gasket portion 250-2 or pillow gasket portion 450-2. In this embodiment the pillow section is formed from the pillows portion and pillow gasket portion.

This embodiment has generally the same or similar elements as the second general form of the pillow portion (described above). The specific variations are described below.

As can be seen in FIG. 27, the outer cap 2750-1a and the air delivery tube 2760 are generally arranged with a common central axis. As can also be seen in FIG. 27, the air delivery tube 2760 extends upward further than the outer cap 2750-1a. The rim 2706 of the outer cap 2750-1a is lower than the rim 2707 of the air delivery tube 2760, meaning the air delivery tube 2760 extends above the rim of the outer cap 2750-1a as seen in FIG. 27.

The outer cap 2750-1a and air delivery tube 2760 merge at their bases, with the base extending outwards almost perpendicular to the axis of the stalk 2750-3 before angling upwards and inwards. The shape of the outer cap and the air delivery tube 2760 allows the cap 2750-1a or the air delivery tube 2760 or both to form a substantial seal with the nostril of the user, when in use. The walls of the outer 2750-1a cap are curved upwards and outwards. Preferably the air delivery tube 2760 extends beyond the upper rim of the outer cap and guides a stream of gases from the pillow portions to the nostrils of a user. The outer cap 2750-1a acts as a cushion for the nostril to sit on when the air delivery tube 2760 is inserted into a patient's nostril. The air delivery tube 2760 may be sized such that it can form a seal with the patient's nostrils. Preferably the walls of the outer 2750-1a cap are curved along a parabolic arc.

In the most preferred form the cross sectional thickness of the wall of the outer cap 2750-1a is uniform along the height of the outer cap 2750-1a, as seen in FIG. 27. In a less preferred form the thickness of the wall of the outer cap 2750-1a may taper in any direction—meaning for example either the wall thickness at the base 2704 may be greater than at the rim 2706 or vice versa. Preferably the wall of the outer cap 2750-1a is thinner in cross sectional thickness than the wall of the air delivery tube 2760, as seen in FIG. 27. Preferably the air delivery tube 2760 tapers in thickness, meaning the thickness of the wall of the air delivery tube 2760 tapers, but that the internal sides or walls are substantially straight or parallel. Preferably the wall of the air delivery tube 2760 is thicker at its base 2705 than at its rim 2707. Alternatively the thickness of the wall of the air delivery tube 2760 may be thicker at the rim and thinner at its base. In a further alternative form the wall of the air delivery tube 2760 may be of uniform thickness along its height.

Surprisingly it has been found that adding the air delivery tube 2760 into the cap 2750-1 better directs airflow to patient's nostril, aides in sealing against the nostrils of a patient and reduces the breathing effort required by the patient to breathe through the pillows portion 2700 (not shown). The flexibility of the outer cap 2750-1a allows the outer cap to bend and deform to fit any shaped nostril. This allows the pillows portion to be used with a variety of nostril shapes. The thinner and more flexible outer cap also flexes such that the stiffer air delivery tube is positioned substantially in the centre of a patient's nostrils when in use. The air delivery tube 2760 being in the centre of a patient's nostrils better directs air flow and gases into a patient's nostrils and may also avoid the air delivery tube 2760 from contacting the soft tissue within a patient's nostrils. The air delivery tube 2760 being stiffer than the outer cap 2750-1a helps the outer cap 2750-1a to form a better seal with the patient's nostrils, because the air delivery tube 2760 does not deform and acts as a support for the outer cap 2750-1a. The flexibility of the outer cap 2750-1a also allows the outer cap to flex and act as a cushion to support the nostrils of a patient.

Surprisingly it has been found that air delivery tube directs air into a patient's nostrils with a minimal pressure drop across the pillows portion 2700 and the cap 2750-1. This reduced pressure drop makes it easier for a user to breathe through the cap 2750-1 since there is a lower resistance to the air flowing through the air delivery tube. Further there is less resistance to the air flowing through the air delivery tube 2760 because the air delivery tube does not collapse or deform when in use. This means the airway 2740 (the path of the gases or air) is unhindered and obstacle free, thus reducing the pressure drop across the pillows portion 2700 and the cap 2750-1. The reduced pressure drop makes it easier for a patient to breathe through the pillows portion 2700 and cap 2750-1 when in use, leading to more effective therapy and added comfort for the user.

Surprisingly it has been found that the addition of the air delivery tube 2760 to the cap 2750-1 reduces the effort a patient has to apply to exhale and breathe through the pillows portion and the cap 2750-1. A common problem that may occur is exhaled air being trapped within the cap or exhaled air flowing into various gaps within the cap—for example the exhaled air commonly flows into the gap 2710 between the outer cap 2750-1a and the air delivery tube 2760. The air becomes trapped there as the outer cap 2750-1a is in use. The air delivery tube 2760 extends above the rim of the outer cap 2750-1a and so an exhaled air from the patient is exhaled through the air delivery tube only, reducing the effort required to breath through the cap 2760-1. Further since the outer cap 2750-1a is also flexible and acts as a cushion, the gap 2710 is sealed due the outer cap 2750-1a bending while in use and supporting a patient's nostrils. This restricts the exhaled air to flow out of the air delivery tube 2760 only, reducing the effort the user has apply to breathe through the pillows portion 2700 and the cap 2750-1 since the exhaled air has a clear unhindered pathway to exit.

Figure 28:
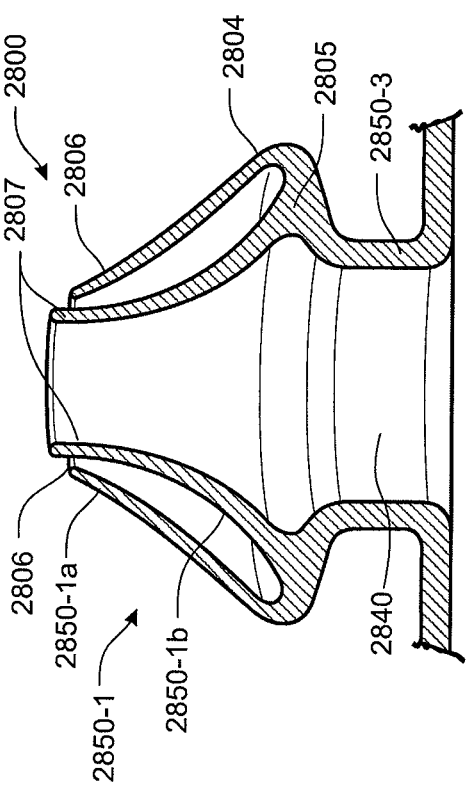
FIG. 28 shows a detail view of a further embodiment of a nasal pillow portion in cross section, the pillow portion comprising a stalk, an outer cap and an inner cap, and the rim of the inner cap extending above the rim of the outer cap.

A further embodiment of pillow portion 2800 is shown in FIG. 28. The cap 2850-1 is part of a pillow portion 2800 that is preferably used with the pillow gasket 350-2 (not shown). The pillow portion 2800 is similar to pillow portion 800. As outlined above in the specification, the pillows portion 2800 could be used with pillow gasket portion 250-2 or pillow gasket portion 450-2. In this embodiment the pillow section is formed from the pillows portion and pillow gasket portion.

This embodiment has generally the same or similar elements as the first general form of the nasal pillow portion (described earlier). This embodiment is substantially similar to the embodiment described above in reference to FIG. 24. Both this embodiment and the twentieth embodiment have the same structural features, except in this embodiment the inner cap rim 2807 extends further vertically than the outer cap rim 2806 when the pillow portion is not in use.

It has surprisingly been found that the inner cap 2850-1b rim extending further upward than the outer cap 2850-1a rim may make it easier for a patient or user to breathe through the pillows portion 2800 (not shown) and cap 2850-1. The inner cap 2850-1b rim 2807 extending higher than the outer cap 2850-1a rim 2806 limits the exhaled air to flow paths. A common problem that can occur is that the exhaled air flows out of the airway 2840 or may flow into the gap 2810 between the outer and inner cap, shown in FIG. 28. This can make breathing difficult for the patient or user since the patient or user has to exert more effort to push any exhaled air trapped in the cap 2850-1, for example air trapped in the gap 2810. This may also make the pillows portion 2800 possibly unsafe to use since it could damage the patient's lungs or diaphragm because the patient has to exert a lot of effort to breathe through the pillows portion 2800. The exhaled air being trapped in the cap 2850-1 or gap 2810 is further compounded by the outer cap 2850-1a collapsing and depressing against the inner cap 2850-1b as the patient exhales. The outer cap 2850-1a collapses because the wall of the outer cap 2850-1a is thinner than the inner cap 2850-1b and cannot support as much load as the wall of the inner cap 2850-1b. Therefore the outer cap 2850-1b collapses and the inner cap 2850-1b remains upright, as the patient exhales. It has been found that if the inner cap 2850-1b extends further than the outer cap 2850-1a eliminates any other alternate pathways for the air to travel out of. The exhaled air is exhaled out of airway 2840 since the rim 2807 of the inner cap 2850-1b protrudes above the rim of the outer cap. This reduces the effort a user has to exert while breathing through and using the pillows portion 2800, thus making the pillows portion 2800 more comfortable and safer to use.

Figure 29:
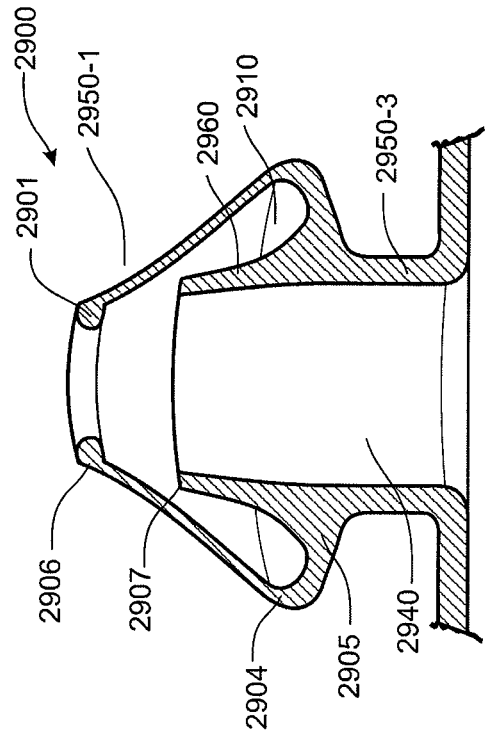
FIG. 29 shows a detail view of a further embodiment of a nasal pillow portion in cross section, the pillow portion comprising a stalk and a cap, the pillow portion also comprising a slightly tapered air delivery tube housed within the cap, the cap covering the air delivery tube, the air delivery tube extending through the stalk to form a passageway for a stream of gases to travel to a patient or user, and the inside wall of the cap having a bead that extends inwards from the rim of the cap.

A further embodiment of pillow portion 2900 is shown in FIG. 29. The cap 2950-1 is part of a pillow portion 2900 that is preferably used with the pillow gasket 350-2 (not shown). The pillow portion 2900 is similar to pillow portion 800. As outlined above in the specification, the pillows portion 2900 could be used with pillow gasket portion 250-2 or pillow gasket portion 450-2. In this embodiment the pillow section is formed from the pillows portion and pillow gasket portion.

This embodiment has generally the same or similar elements as the second general form of the pillow portion (described earlier). The specific variations associated with this embodiment are described below.

As can be seen in FIG. 29, the air delivery tube 2960 and the outer cap 2950-1a are generally arranged concentrically with a common central axis. As can also be seen in FIG. 29, the outer cap 2950-1a extends further upwards than the air delivery tube 2960. The rim 2906 of the outer cap 2950-1a extends above the rim 2907 of the air delivery tube 2960. Preferably the pillow portions 2900 will be angled inwards towards each other on the gasket portion, similar to that as shown in FIGS. 11a and 11b. The upper rims are not vertically aligned as the pillow portions 2900 are angled inwards towards each other.

In the most preferred form the cross sectional thickness of the wall of the outer cap 2950-1a is uniform along the height of the outer cap 2950-1a, as seen in FIG. 29. In a less preferred form the thickness of the wall of the outer cap 2950-1a may taper in any direction—meaning for example either the wall thickness at the base 2904 may be greater than at the rim 2906 or vice versa. In the preferred form the thickness of the wall of the air delivery tube tapers along its height. The air delivery tube 2960 is thicker at its base 2906 than at its rim 2907 or vice versa. The thickness of the delivery tube 2960 may vary from point to point along the height of the delivery tube 2960. Alternatively the cross sectional thickness of the wall of the air delivery tube 2960 may be uniform.

The outer cap 2950-1a includes a bead 2901 located on the inner wall of the outer cap 2950-1a, as seen in FIG. 29. The bead is preferably located at and extends around the rim 2906 of the outer cap 2950-1a. Alternatively the bead 2901 may be located at any point along the height of the outer cap 2950-1a on the inside wall, meaning the bead may be located anywhere between the base 2904 and the rim 2906 of the outer cap 2950-1a. The bead 2901 still extends around the perimeter of the outer cap 2950-1a. Preferably the bead 2901 follows a symmetrical around the perimeter of the outer cap 2950-1a, meaning in cross section the bead is a mirror image about a vertical axis in the centre of the cap 2950-1 and stalk 2950-3, as seen in FIG. 29. In alternative arrangements the bead may follow any asymmetrical path around the perimeter of the inner cap 2950-1a.

FIG. 29 shows the preferred form of the bead 2901, in which the bead 2901 has a substantially circular cross section. Alternatively the bead 2901 may have any other cross section shape, for example a rectangular or oval cross section. The cross section shapes identified are only examples and should not be construed as limiting, since any shape for the bead 2901 cross section would be obvious to a person skilled in the art. Preferably the bead 2901 is thicker in cross sectional thickness than the cross sectional thickness of the wall of the outer cap 2950-1a, as best seen in FIG. 29. Even more preferably the bead 2901 is twice as thick as the wall of the outer cap 2950-1a. Alternatively the thickness of the bead may be thinner than the thickness of the wall of the outer cap 2950-1a. Preferably the thickness of the bead 2901 is uniform along the entire perimeter of the outer cap 2950-1a. Alternatively the bead thickness may vary from point to point along the perimeter of the outer cap 2950-1a. As a further alternative the bead 2901 may be thicker at one end of the rim and thinner at the other end.

It has surprisingly been found that the addition of the bead 2901 to the inside wall of the outer cap 2950-1a may add strength and increased stiffness to the upper section of the outer cap 2950-1a, in particular the rim 2901 and the surrounding area of the rim 2907. The additional stiffness due to the bead 2901 may stop or reduce the amount the outer cap 2950-1a collapses into the airway 2940, while fitting the cap 2950-1 into a patient's nostrils. The outer cap 2950-1a flexes during while fitting the cap 2950-1 into a patient's nostrils. The load on the outer cap 2950-1a from the nostril may cause the outer cap 2950-1a to partially or completely collapse or bend and block the airway 2940. Blocking the airway restricts the amount of gases being delivered to a patient, increases the pressure drop across the cap 2950-1 and increases the difficulty of breathing through the cap 2950-1 for the user. The bead 2901 can reduce or stop the outer cap 2950-1a from collapsing into the airway 2940. Hence sufficient amount of therapy gases are delivered to the patient, there is less of a pressure drop across the cap 2950-1 and reduces the difficulty of breathing through the cap 2950-1 and pillows portion 2900. This leads to added comfort for the patient and effective therapy for the patient. Furthermore since the air delivery tube 2960 is rigid, the air delivery tube 2960 acts as a support and may hold up the outer cap 2950-1a as the outer cap collapses or flexes helping to keep the airway 2940 unblocked or at least partially unblocked. This can lead to reduced pressure drop across the pillow portion 2900, leading to reduced breathing effort and comfort for the patient.

Surprisingly it has been found that adding an air delivery tube 2960 with straight substantially parallel walls into the cap 2950-1 helps to better direct airflow into a patient's nostril and reduces the breathing effort required by the patient to breathe through the pillows portion 2900. The outer cap 2950-1a is preferably more flexible and supple than the air delivery tube 2960. The flexibility of the outer cap 2950-1a allows it to bend and form to fit any shaped nostril. This allows the pillows portion 2900 and cap 2950-1 to be used with a wide variety of nostril shapes. Preferably the outer cap 2950-1a is also thinner than the air delivery tube 2960. The thinner outer cap 2950-1a flexes when engaged with a patient's nostrils such that the air delivery tube is positioned substantially in the centre of the patient's nostrils. The air delivery tube positioned in the middle of a patient's nostrils helps to better direct airflow and gases into the patient's nostrils. The air delivery tube in the centre of the patient's nostrils also may stop the air delivery tube 2960 from contacting the soft tissue inside the patient's nostrils making the cap 2950-1 more comfortable and safer to use.

Surprisingly it has been found that the air delivery tube delivers air or gases to a patient's nostrils with minimal pressure drop across the cap 2950-1 and pillows portion 2900. This reduced pressure drop makes it easier for a user to breathe through the cap 2950-1 since there is a lower resistance to the air flowing through the air delivery tube 2960. Further there is less resistance to the air flowing through the air delivery tube 2960 because the air delivery tube is substantially stiff and does not collapse or deform when engaged with a patient's nostrils. The airway 2940 (the path of the gases or air) is unhindered, thus reducing the pressure drop across the pillows portion 2900 and the cap 2950-1. The reduced pressure drop makes it easier for a patient to breathe through the pillows portion 2900 and cap 2950-1 since the patient does not need to exert extra effort to breathe, leading to safer, more comfortable and more effective therapy.

Figure 30:
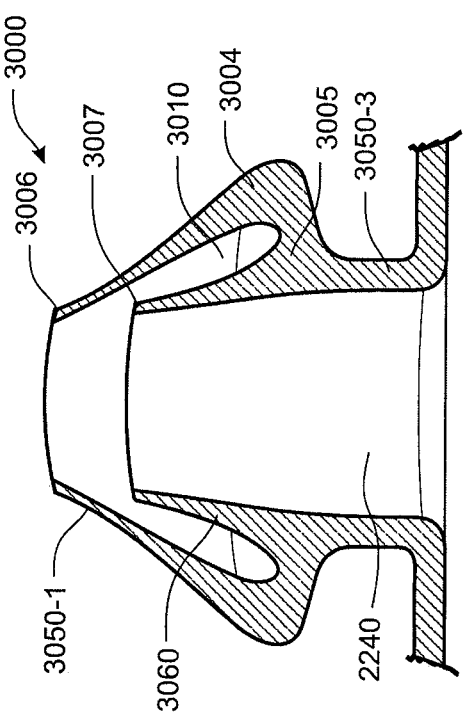
FIG. 30 shows a detail view of a further embodiment of a nasal pillow portion in cross section, the pillow portion comprising a stalk and a cap, and an air delivery tube that is housed within the cap and extends through the stalk to form a passageway to deliver a stream of gases or air to a patient or user, the wall of the cap tapering in thickness so that the wall is thicker at the base than at the rim.

A further embodiment of pillow portion 3000 is shown in FIG. 30. The cap 3050-1 is part of a pillow portion 3000 that is preferably used with the pillow gasket 350-2 (not shown). The pillow portion 3000 is similar to pillow portion 800. As outlined above in the specification, the pillows portion 3000 could be used with pillow gasket portion 250-2 or pillow gasket portion 450-2. In this embodiment the pillow section is formed from the pillows portion and pillow gasket portion.

This embodiment has generally the same or similar elements as the second general form of the pillow portion (described earlier). The specific variations associated with this embodiment are described below.

As can be seen in FIG. 30, the air delivery tube 3060 and the outer cap 3050-1a are generally arranged concentrically with a common central axis. The air delivery tube has a generally straight and parallel-sided internal wall. As can also be seen in FIG. 30, the outer cap 3050-1a extends further upwards than the air delivery tube 3060. The rim 3006 of the outer cap 3050-1a extends above the rim 3007 of the air delivery tube 3060. Preferably the pillow portions 3000 will be angled inwards towards each other on the gasket portion, similar to that as shown in FIGS. 11a and 11b. The upper rims are not vertically aligned as the pillow portions 3000 are angled inwards towards each other.

In the most preferred form the cross sectional thickness of the wall of the outer cap 3050-1a tapers along the height of the outer cap 3050-1a, as seen in FIG. 30. Preferably the wall of the outer cap 3050-1a is thicker at its base 3004 than at its rim 3006, as seen in FIG. 30. Alternatively the wall of the outer cap 3050-1a may be thicker at the rim 3006 and thinner at the base 3004. In the preferred form the thickness of the wall of the air delivery tube 3060 tapers along its height. The air delivery tube 3060 is thicker at its base 3006 than at its rim 3007, as seen in FIG. 30, or vice versa. The thickness of the delivery tube 3060 may also vary from point to point along the height of the delivery tube 3060. Alternatively the cross sectional thickness of the wall of the air delivery tube 3060 may be uniform.

Surprisingly it has been found that adding the air delivery tube 3060 into the cap 3050-1 helps to better direct airflow into a patient's nostril and reduces the breathing effort required by the patient to breathe through the pillows portion 3000. The outer cap 3050-1a is preferably more flexible and supple than the air delivery tube 3060. The flexibility of the outer cap 3050-1a allows it to bend and form to fit any shaped nostril. This allows the pillows portion 3000 and cap 3050-1 to be used with a wide variety of nostril shapes. Preferably the outer cap 3050-1a is also thinner than the air delivery tube 3060. The thinner outer cap 3050-1a flexes when engaged with a patient's nostrils such that the air delivery tube is positioned substantially in the centre of the patient's nostrils. The air delivery tube positioned in the middle of a patient's nostrils helps to better direct airflow and gases into the patient's nostrils. The air delivery tube in the centre of the patient's nostrils also stops the air delivery tube 3060 from contacting the soft tissue inside the patient's nostrils making the cap 3050-1 more comfortable and safer to use.

Surprisingly it has been found that the air delivery tube delivers air or gases to a patient's nostrils with minimal pressure drop across the cap 3050-1 and pillows portion 3000. This reduced pressure drop makes it easier for a user to breathe through the cap 3050-1 since there is a lower resistance to the air flowing through the air delivery tube 3060. Further there is less resistance to the air flowing through the air delivery tube 3060 because the air delivery tube is stiffer than the thin-walled outer cap and does not collapse or deform when engaged with a patient's nostrils. The airway 3040 (the path of the gases or air) is unhindered, thus reducing the pressure drop across the pillows portion 3000 and the cap 3050-1. The reduced pressure drop makes it easier for a patient to breathe through the pillows portion 3000 and cap 3050-1 since the patient does not need to exert extra effort to breathe, leading to safer, more comfortable and more effective therapy.

It has also surprisingly been found that tapering the thickness of the wall of the outer cap 3050-1a helps to strengthen and add stiffness to the outer cap 3050-1a. The stiffness helps the outer cap 3050-1a to maintain its shape when it is in use and engaged with patient's nostrils. The added stiffness helps to stop the amount the outer cap 3050-1a deforms and reduces the amount the outer cap 3050-1a collapses under the load from the patient's nostril. The tapered wall thickness also helps to maintain the flexibility of the upper part of the outer cap 3050-1a. The increased flexibility allows the outer cap 3050-1a to be used with a wide variety of nostril shapes. Reduced deformation and the flexibility of the outer cap 3050-1a helps the outer cap 3050-1a to form an effective seal with a patient's nostrils. The added stiffness can also help to reduce the pressure drop across the pillows portion 3000 and cap 3050-1 since the outer cap does not collapse and block the airway 3040. This leads to added comfort and more effective therapy to a patient.

Figure 31:
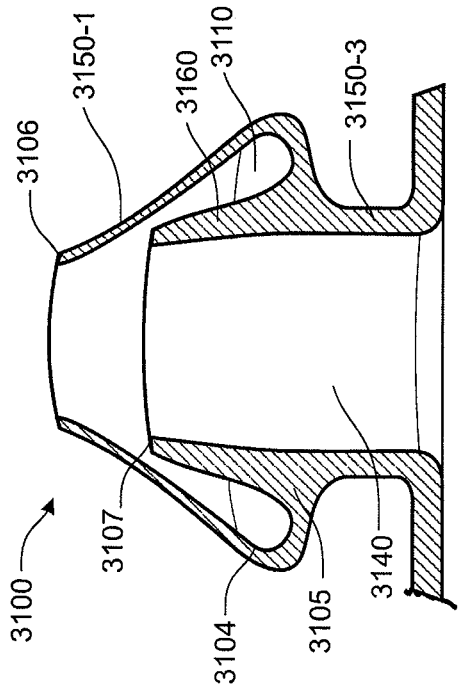
FIG. 31 shows a detail view of a further embodiment of a nasal pillow portion in cross section, the pillow portion comprising a stalk and a cap, and an air delivery tube that is housed within the cap and which extends through the stalk to form a passageway to deliver a stream of gases or air to a patient or user, the wall of the cap being uniform in thickness.

A further embodiment of pillow portion 3100 is shown in FIG. 31. The cap 3150-1 is part of a pillow portion 3100 that is preferably used with the pillow gasket 350-2 (not shown). The pillow portion 3100 is similar to pillow portion 800. As outlined above in the specification, the pillows portion 3100 could be used with pillow gasket portion 250-2 or pillow gasket portion 450-2. In this embodiment the pillow section is formed from the pillows portion and pillow gasket portion.

This embodiment has generally the same or similar elements as the second general form of the pillow portion (described earlier). The specific variations associated with this embodiment are described below. This embodiment is very similar in structure to the embodiment shown in FIG. 30, except that the air delivery tube wall has a constant thickness.

As can be seen in FIG. 31, the air delivery tube 3160 and the outer cap 3150-1a are generally arranged concentrically with a common central axis. As can also be seen in FIG. 31, the outer cap 3150-1a extends further upwards than the air delivery tube 3160. The rim 3106 of the outer cap 3150-1a extends above the rim 3107 of the air delivery tube 3160. Preferably the pillow portions 3100 will be angled inwards towards each other on the gasket portion, similar to that as shown in FIGS. 11a and 11b. The upper rims are not vertically aligned as the pillow portions 3100 are angled inwards towards each other.

In the most preferred form the cross sectional thickness of the wall of the outer cap 3150-1a is thicker at its base 3104 than at its rim 3106. In the preferred form the thickness of the wall of the air delivery tube 3160 tapers along its height, with the internal wall being parallel-sided. The air delivery tube 3160 is thicker at its base 3106 than at its rim 3107, as seen in FIG. 31, or vice versa. The thickness of the delivery tube 3160 may also vary from point to point along the height of the delivery tube 3160. Alternatively the cross sectional thickness of the wall of the air delivery tube 3160 may be uniform. In the preferred form the thickness of the wall of the air delivery tube 3160 is thicker than that of the outer cap 3150-1*a* wall.

Surprisingly it has been found that adding the air delivery tube 3160 into the cap 3150-1 helps to better direct airflow into a patient's nostril and reduces the breathing effort required by the patient to breathe through the pillows portion 3100. The outer cap 3150-1*a* is preferably more flexible and supple than the air delivery tube 3160. The flexibility of the outer cap 3150-1*a* allows it to bend and form to fit any shaped nostril. This allows the pillows portion 3100 and cap 3150-1 to be used with a wide variety of nostril shapes. Preferably the outer cap 3150-1*a* is also thinner than the air delivery tube 3160. The thinner outer cap 3150-1*a* flexes when engaged with a patient's nostrils such that the air delivery tube is positioned substantially in the centre of the patient's nostrils. The air delivery tube positioned in the middle of a patient's nostrils helps to better direct airflow and gases into the patient's nostrils. The air delivery tube in the centre of the patient's nostrils also may stop the air delivery tube 3160 from contacting the soft tissue inside the patient's nostrils making the cap 3150-1 more comfortable and safer to use.

Surprisingly it has been found that the air delivery tube delivers air or gases to a patient's nostrils with minimal pressure drop across the cap 3150-1 and pillows portion 3100. This reduced pressure drop makes it easier for a user to breathe through the cap 3150-1 since there is a lower resistance to the air flowing through the air delivery tube 3160. Further there is less resistance to the air flowing through the air delivery tube 3160 because the air delivery tube is substantially stiff and does not collapse or deform when engaged with a patient's nostrils. The airway 3140 (the path of the gases or air) is unhindered, thus reducing the pressure drop across the pillows portion 3100 and the cap 3150-1. The reduced pressure drop makes it easier for a patient to breathe through the pillows portion 3100 and cap 3150-1 since the patient does not need to exert extra effort to breathe, leading to more effective therapy and makes the pillows portion 3150 more comfortable and safer to use.

Figure 32:
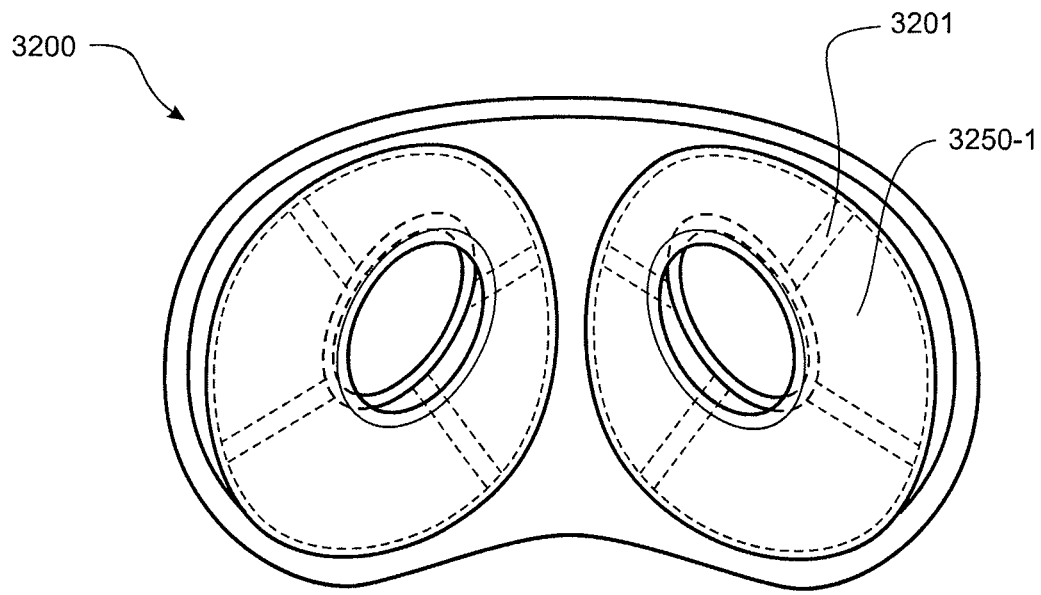
FIG. 32 shows a top view of a further embodiment of a nasal pillow section comprising a pair of pillow portions connected to a pillow gasket portion, with internal hidden detail including internal ribs of the pillow portions shown, the nasal pillow portions of this embodiment having an inner and an outer cap, and four ribs arranged running generally radially outward from a central axis and spaced equidistant around each of the pillow portions, the ribs passing between the inner and the outer caps.

A further embodiment of the pillows portion 3200 is shown in FIG. 32. FIG. 32 shows an alternate configuration of rib arrangement. This embodiment as described below could be applied to any one of the other embodiments described herein. FIG. 32 shows four separate ribs 3201 that are preferably evenly spaced (that is, at substantially equal intervals) around the pillow portion 3250-1, between the inner and the outer caps, or the outer cap and the inner air delivery tube. That is, each of the ribs runs radially outwards and is spaced from the two ribs to each side by substantially a ninety-degree angle.

Surprisingly it has been found that the addition of the ribs 3201 in the configuration shown in FIG. 32 may strategically add strength to the inner or outer caps without compromising the flexibility of the caps. The flexibility of the caps allows them to be fitted and used with a variety of nostril shapes. The added structural strength provided by the ribs helps to reduce the deformation the caps undergo under the loads from a user's nostrils. Further the orientation of the ribs may enhance the characteristics and advantages described for each of the various types of ribs in the embodiments shown in FIGS. 5-9.

Figure 33:
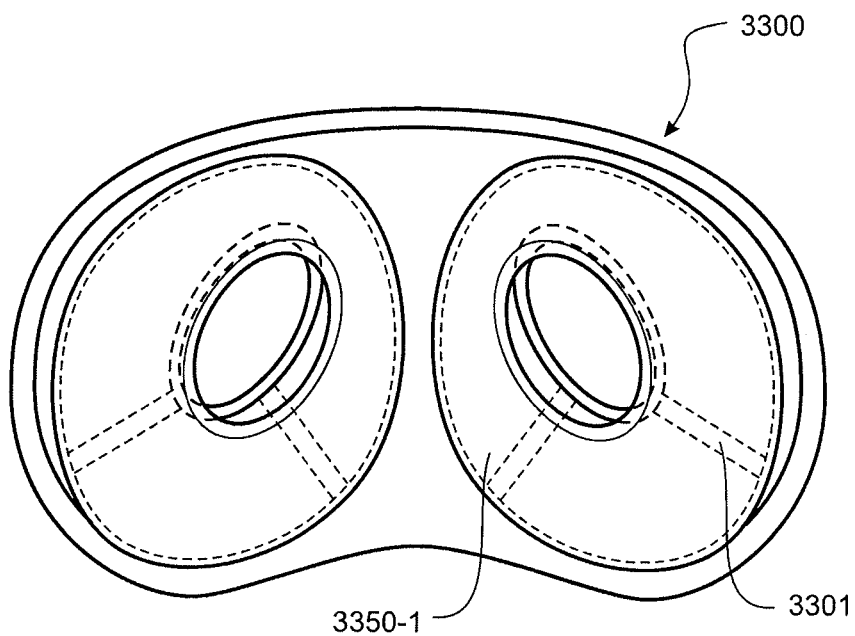
FIG. 33 shows a top view of a further embodiment of a nasal pillow section, the nasal pillow section comprising a pair of pillow portions connected to a pillow gasket portion, each pillow portion having an inner and an outer cap, with internal hidden detail shown, including internal ribs which run between the inner and the outer caps shown, the ribs running generally radially outward from a central axis, each nasal pillow section having two ribs, the two ribs arranged so that they approximately or roughly define a quarter-circle between the lower or inner part of the nasal pillow section and the side.

A further embodiment of the pillows portion 3300 is shown in FIG. 33. FIG. 33 shows an alternate configuration of rib arrangement. This embodiment as described below could be applied to any one of the other embodiments described herein. FIG. 33 shows two separate ribs 3301 that are preferably placed at one end of the cap 3350-1, meaning the ribs are placed in close vicinity to each other. The ribs 3301 are preferably angled at between sixty and one hundred and twenty degrees relative to each other. In the most preferred form the ribs are at ninety degrees to each other. It is most preferred that one of the ribs points backwards and slightly inwards (in use), with the other one of the ribs arranged so that it points outwards to one side and slightly backwards.

Surprisingly it has been found that the addition of the ribs 3301 in the configuration shown in FIG. 33 may strategically add strength to the inner or outer caps without compromising the flexibility of the caps. The flexibility of the caps allows them to be fitted and used with a variety of nostril shapes. The added strength helps to reduce the deformation the caps undergo under the loads from a user's nostrils.

In the embodiments shown in FIGS. 32 and 33, as described above, it is most preferred that the ribs are thin and parallel-sided. The ribs are arranged running radially outwards. It should be noted that 'radially' as used in this context should be taken to mean that the ribs are aligned so that they appear to run outwards from a centre point (although in these embodiments, the ribs do not extend to a central axis of the pillow portion).

Figure 34:
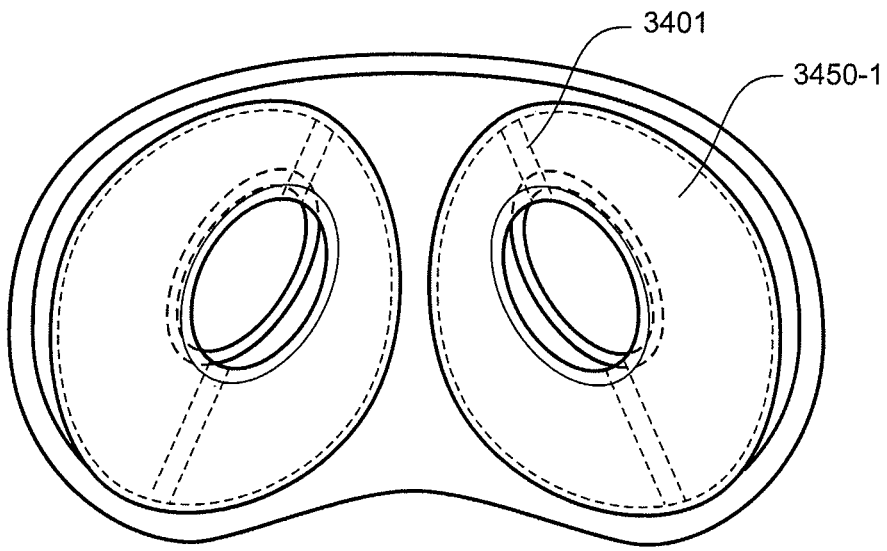
FIG. 34 shows a top view of a further embodiment of a nasal pillow section comprising a pair of pillow portions connected to a pillow gasket portion with internal hidden detail including internal ribs of the pillow portions shown, the nasal pillows section having an inner cap and an outer cap, with two ribs in each pillow portion running between the inner and the outer caps, the ribs in each pillow section arranged diametrically opposite to each other.

A further embodiment of pillows portion 3400 is shown in FIG. 34.

FIG. 34 shows an alternate configuration of rib arrangement. This embodiment as described below could be applied to any one of the other embodiments described herein. FIG. 34 shows two separate ribs 3401, which are located between the outer cap and the inner cap or the inner air delivery tube. Most preferably the two ribs are placed so that they are aligned substantially vertically, and run outwards radially. In the most preferred form the ribs 3401 are at an angle of substantially one hundred and eighty degrees to each other. Alternatively the ribs 3401 may be at angle between one hundred and sixty to two hundred degrees relative to each other. The inner rib (that closest to the user) points slightly outwards and towards the user.

As described above, it is most preferred that the ribs are thin and parallel-sided. The ribs are arranged running radially outwards. It should be noted that 'radially' as used in this context should be taken to mean that the ribs are aligned so that they appear to run outwards from a centre point (although in these embodiments, the ribs do not extend to a central axis of the pillow portion)

Surprisingly it has been found that the addition of the ribs 3401 in the configuration shown in FIG. 34 may strategically add strength to the inner or outer caps without compromising the flexibility of the caps. The flexibility of the caps allows them to be fitted and used with a variety of nostril shapes. The added strength helps to reduce the deformation the caps undergo under the loads from a user's nostrils. Further the orientation of the ribs may enhance the characteristics and advantages described for each of the various types of ribs in the embodiments shown in FIGS. 5-9.

Figure 35:
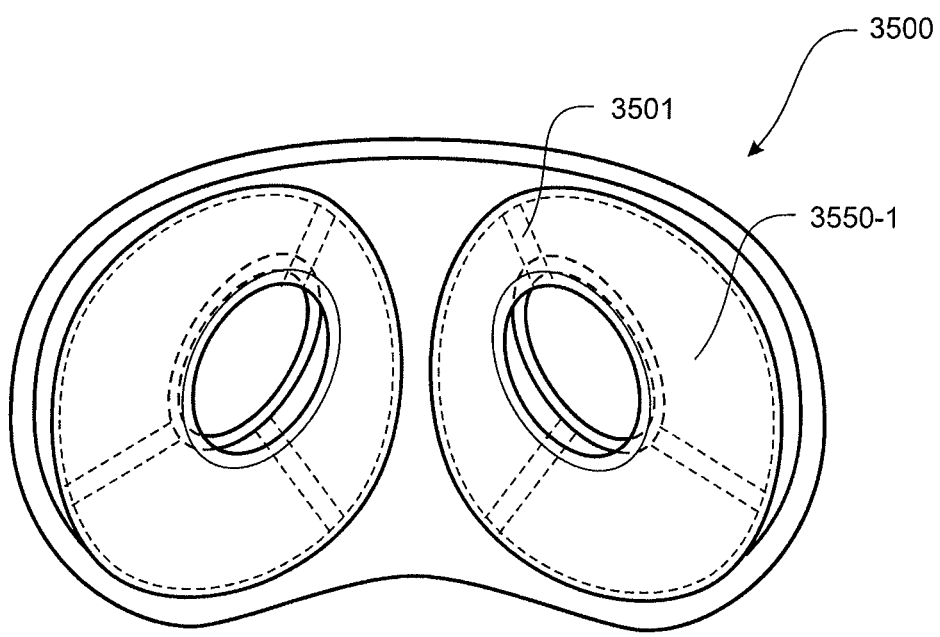
FIG. 35 shows a top view of a further embodiment of a nasal pillow section comprising a pair of pillow portions connected to a pillow gasket portion, each of the pillow portions having an inner cap and an outer cap, the figure also showing hidden detail of internal ribs which run between the inner cap and the outer cap shown, each of the nasal pillow sections having three ribs arranged radially running between the inner cap and the outer cap, and spaced generally equidistant from one another shown.

A still further embodiment of the pillows portion 3500 is shown in FIG. 35.

This embodiment is substantially similar to the embodiments shown in FIGS. 32, 33 and 34, as described above, except that there are three radial ribs arranged spaced at substantially equidistant angles around the circumference of the pillow portion. In the most preferred form, there is one rib on the inner side of the pillow (closest to the user) and this faces slightly inwards. There is one rib on the side of the pillow section, and this faces outwards to the side and slightly towards the user. The third and final rib is aligned substantially at sixty degree to the other tow ribs in the preferred from. However, it should be noted that the three ribs could be rotated around to any point on the circumference as appropriate.

Figure 36A:
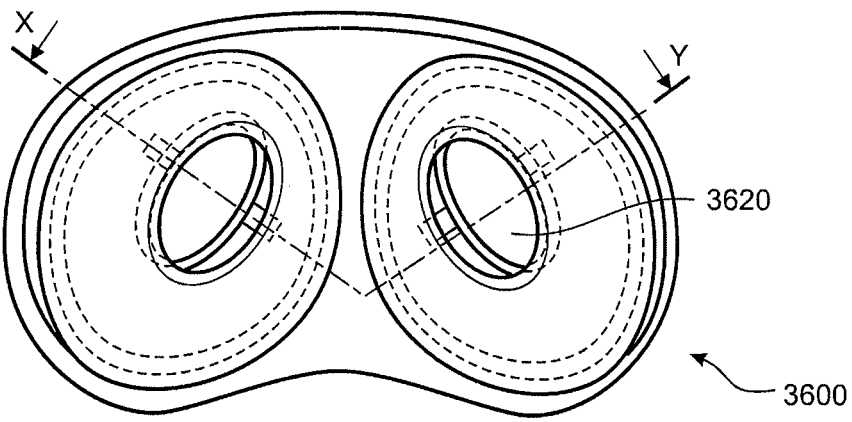
FIG. 36a shows a top view of a further embodiment of nasal pillow section, the nasal pillow section comprising a pair of pillow portions connected to a pillow gasket portion with internal hidden detail including internal ribs of the pillow portions shown, and section lines X and Y which bisect each of the pillows also shown, section line X bisecting one of the pillow portions and the ribs within the pillow portion, and section line Y bisecting the other of the pillow portions to one side of the ribs.
Figure 36B:
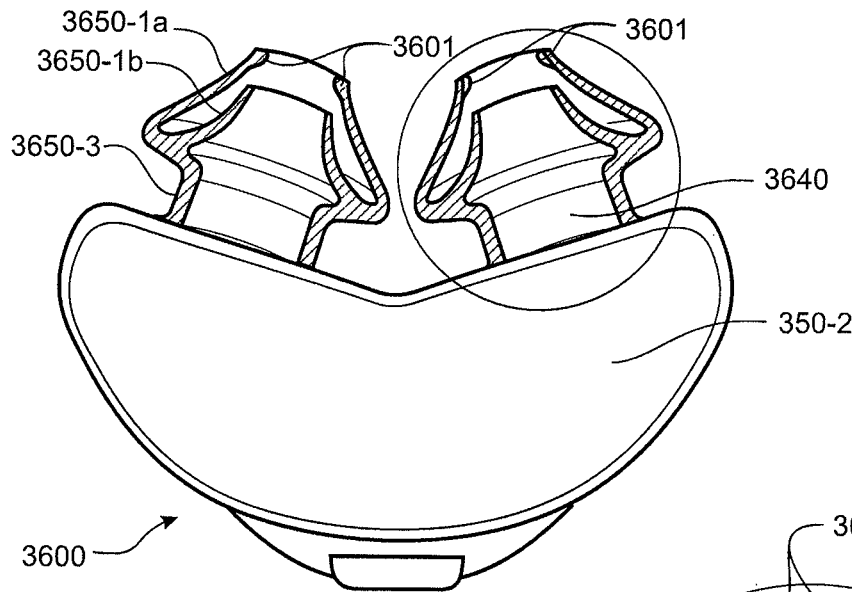
FIG. 36b shows a view of the nasal pillow section of FIG. 36a from the point of view of a user, each of the nasal pillow portions shown in cross-section to show an inner cap and an outer cap, the cross-section for each pillow portion taken along the section lines X and Y, the cross-section showing internal detail of the structure of each of the nasal pillow portions and showing a pair of bumps or protuberances located at the top edge of the outer cap facing inwards at radially opposed positions.
Figure 36C:
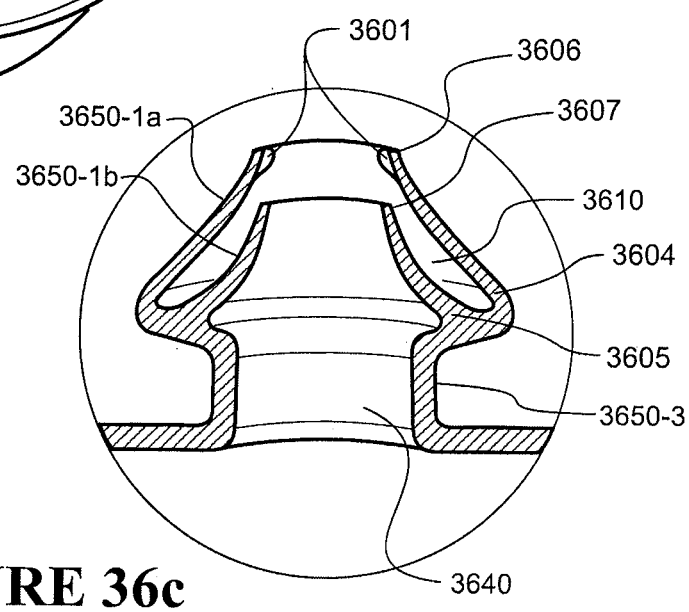
FIG. 36c shows a detail view of the right hand nasal pillow portion of FIG. 36b.

A further embodiment of nasal pillow portion is shown in FIGS. 36a, 36b and 36c. In this variation, the pillow portion is shown as being used with the pillow gasket portion 350-2 (although as outlined above, these could be used with pillow gasket portion 250-2 or pillow gasket portion 450-2. In this embodiment, the pillow section is formed from the pillow portions and the pillow gasket portion.

This embodiment is made up of the first general form of the pillow portion (described earlier). The specific variations associated with this variation are described below.

In the preferred form of this embodiment the walls of the inner cap 3650-1b and the outer cap 3650-1a taper in cross sectional thickness as best seen in FIG. 36c. The walls of the inner cap 3650-1b and the outer 3650-1a are thicker at the lower end. The wall of the outer cap 3650-1a is thicker at the base 3604 of the outer cap 3650-1a than at the rim 3606 of the outer cap 3650-1a, and the wall of the inner cap 3650-1b is thicker at the base 3605 of the inner cap 3650-1b than at the rim 3607 of the inner cap 3650-1b. Alternatively the thickness of the walls of the inner and outer cap may be constant or the wall thickness of one of the walls may taper while the wall thickness of the other wall may remain constant.

The inside surface of the wall of the outer cap 3650-1b contains at least one and preferably a pair of partial ribs 3601. In alternate embodiments, the inner or inside surface of the wall of the outer cap 3650-1a may contain three or more partial ribs 3601. If a series of partial ribs is used, the partial ribs 3601 can be positioned at regular or differing intervals around the perimeter of the inside surface of the wall of the outer cap 3650-1a. The pair of partial ribs 3601 extend only a partial length along the height of the inside wall of the outer cap. Preferably the height of each of the partial ribs is less than the height of the outer cap 3650-1a. The partial ribs can have the same height as one another, or different heights. The partial ribs can also have different thicknesses, or the same thickness. The partial ribs are greater in size than the beads described above, and in the particular embodiment described are located at the top rim, running downwards, of the outer cap. The partial ribs only run part of the height or length of the cap (hence 'partial').

Preferably each of the partial ribs is substantially circular in cross section. However the partial rib may be any other cross sectional shape, for example a square or triangular cross section. The partial rib is preferably placed along the rim 3606 of the outer cap. Most preferably the upper end of the partial rib is at the rim 3606 of the outer cap 3650-1a, with the rest of the partial rib extending down along the inside surface of the outer cap 3650-1a. Preferably the partial ribs 3601 extend downwards up to three quarters of the way down along the inside surface of the outer cap 3650-1a, but not all the way to the bottom or base of the cap sections. Most preferably the upper end of the rib 3601 is at the rim 3606, and the rib extends downwards around one sixth of the height of the inside surface of the outer cap 3650-1a when measured from the rim 3606 of the outer cap 3650-1a, as shown in FIG. 36c. However, each one of the pair could be in different positions along the inside surface of the outer cap 3650-1a.

It should particularly be noted that the ribs 3601 of this embodiment are rounded so that their ends blend into the inner surface of the outer cap 3650-1a—that is, they do not have 'cornered' or 'sharp' upper and lower edges or surfaces. The rib 3601 is thicker in the middle than it is at its extremes. The width of the ribs 3601 is preferably constant. ('Width' in this context is the side-side dimension of the rib 3601—that is, the dimension into and out of the page in FIG. 36c. In this embodiment, the width of the pair of ribs is constant).

It should be noted that in the preferred form shown in FIG. 36c, the rib or ribs 3601 are located towards the top of the wall 3650-1a, and not towards the base. Further it should be noted that one edge of the rib 3601 extends from the rim 3606 of the outer cap 3650-1a.

Surprisingly, it has been found that a rib or ribs 3601 in this form act to increase the strength of the outer pillow wall 3650-1a in certain areas to control and manipulate the collapse of the outer pillow wall 3650-1a when the cap 3650-1 is inserted into the nostril of a user. By controlling the collapse, the pillow wall 3650-1a will have more movement in some areas rather than others. This is advantageous as pillows can be produced which are both more comfortable and which also offer good sealing properties against the nares of a user.

The addition of a pair of ribs 3601 spaced equidistant around the perimeter of the inner surface of the outer cap 3650-1a helps to improve the strength of the rim 3606 of the outer cap 3650-1a in order to minimise the collapse of the rim 3606 into the airway 3640. The addition of the rib 3601 adds stiffness and acts as to support the rim 3606 of the outer cap 3650-1a, to stop it collapsing under the load of a patient's nostril. This keeps the airway 3640 unblocked and reduces the pressure drop across the pillows portion 3600 and cap 3650-1. This reduced pressure drop makes it easier for a user to breathe through the pillows portion 3600 and cap 3650-1, making the cap and pillows portion more comfortable and safer to use.

The addition of the rib 3601 also helps to improve the feel of positive affirmation of the pillow 3600 being correctly inserted into the nostril, from the user's point of view, to reduce the occurrence of the pillow 3600 being incorrectly fitted. The added stiffness of the rim 3606, due to the rib 3601, can stop the rib from completely collapsing and allows the rim to hold its shape while fitting the cap 3650-1 into a patient's nostril. This added stiffness provides the user with an indication of a correct fit and also indicates to the user that the cap 3650-1 has formed an effective seal with the user's nostril.

Figure 37A:
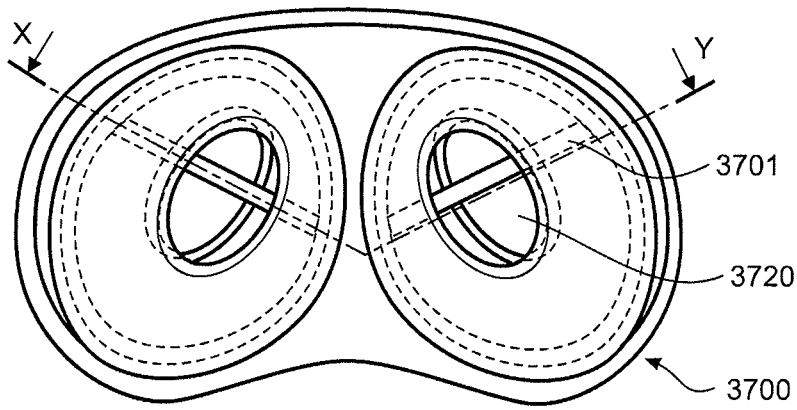
FIG. 37a shows a top view of a still further embodiment of a nasal pillow section, the nasal pillow section comprising a pair of pillow portions connected to a pillow gasket portion with internal hidden detail including an internal solid fin within each of the pillow portions shown, and section lines X and Y which bisect each of the pillows also shown, section line X bisecting one of the pillow portions and the fin within the pillow portion, and section line Y bisecting the other pillow portion to one side of the fin.
Figure 37B:
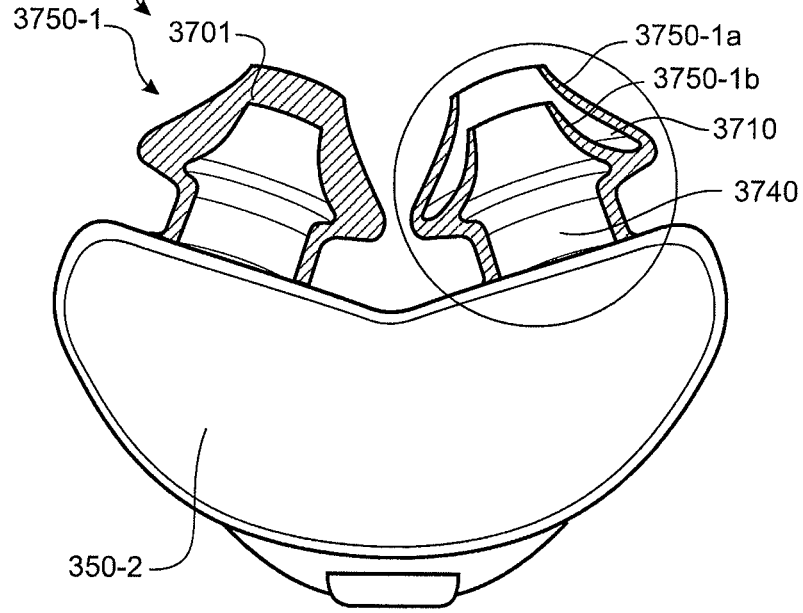
FIG. 37b shows a view of the nasal pillow section of FIG. 37a from the point of view of a user or patient, each of the nasal pillow portions shown in cross-section to show an inner cap and an outer cap, the cross-section for each pillow taken along the section line X and Y, the cross section showing the internal detail of the structure of each of the pillow portions.
Figure 37C:
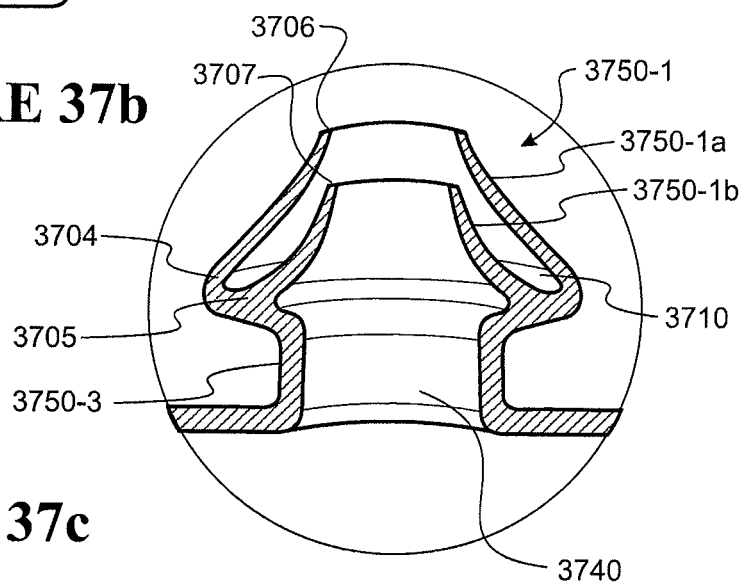
FIG. 37c a detail view of the right hand nasal pillow portion of FIG. 37b.

A further embodiment of nasal pillow section is shown in FIGS. 37a, 37b, and 37c. In this variation, the pillow portions are shown as being used with the pillow gasket portion 350-2, (but as outlined above, the pillow portions may be used with the pillow gasket portion 250-2 or pillow gasket portion 450-2). The specific variations associated with this embodiment are described below.

This embodiment is generally made up of the first general form of the pillow portion (described earlier). The specific variations associated with this embodiment are described below.

In this embodiment the walls of the inner cap 3750-1b and the outer cap 3750-1a taper in cross sectional thickness, as best seen in FIG. 37c. The wall of the inner cap 3750-1b is preferably thicker at the base 3705 of the inner cap 3750-1b than at the rim 3707 of the inner cap 3750-1b. The wall of the outer cap 3750-1a is preferably thicker at the base of the 3704 of the outer cap 3750-1a than at the rim 3706 of the outer cap 3750-1a. Alternatively the wall thickness of the inner cap 3750-1b and the outer cap 3750-1a may be uniform. As another alternative the wall thickness of the inner and outer caps may be equal to each other—meaning the wall of the inner cap 3750-1b is the same thickness as the wall of the outer cap 3750-1a. Further to this the wall cross section of the inner and outer cap may be identical to each other. As a further alternative the thickness of the wall of one of the caps may taper while the thickness of the other cap wall may be uniform—for example the thickness of the wall of the inner cap 3750-1b may taper while the thickness of the wall of the outer cap 3750-1a may be uniform.

There is a cavity 3710 or air gap formed between the outer cap 3750-1a and the inner cap 3750-1b (except at the point where they are connected at their bases to the stalk 3750-3 and to each other). The cavity or air gap 3710 is not in the direct air path of the stream of gases, as best seen in FIG. 37c.

The cap 3750-1 includes at least one "rib" feature within the cap. Preferably this rib feature is a solid fin 3701 that passes through the entire cap 3750-1. The fin 3701 joins the inner cap 3750-1b with the outer cap 3750-1a, as seen if FIGS. 37a and 37b. Preferably part of the fin 3701 lies within the path of the stream of gases delivered to the user or patient, as seen in FIG. 37a. The fin 3701 extends from the inside surface of the outer cap 3750-1a to the outside surface of the inner cap 3750-1b, as best seen in the left cap of FIG. 37b. The fin 3701 preferably extends from the top edge of the outer cap 3750-1a to the top edge of the inner cap 3750-1b. The fin 3701 extends from one side of the cap to the other side of the cap, spanning the diameter of the cap 3750-1, as seen in FIG. 37 b, and from the top to the bottom of the cap. Preferably the fin 3701 follows the contours of the overall cap shape. Preferably the fin 3701 extends vertically from the bottom of the outer surface of the inner cap 3750-1b to the top of the outer cap 3750-1a. The fin is shown as straight in plan view as it passes from one side of the cap to the other. Alternatively the fin 3701 could be curved in shape (not shown), instead of being straight as shown in FIGS. 37a and 37b, and form a gentle curve, preferably an inverted parabola as it passes through the entire cap 3750-1. As a further alternative the fin 3701 could be angled about the central vertical axis of the exit orifice 3720 of the cap 3750-1, or alternatively the fin 3701 may be offset about the vertex point. The vertex point preferably is situated in the middle of the exit orifice 3720 of the cap 3750-1. However, the vertex point may be at any point along the width of the cap 3750-1. As a further alternative the fin 3701 may completely extend through the cap 3750-1. In this alternative form the fin 3701 may only extend from the inner surface of the outer cap 3750-1a to the point where the cap 3750-1 extends from the stalk (this arrangement is not illustrated), similar to the sixth embodiment previously described.

The fin 3701 preferably tapers in thickness. The fin 3701 is thicker at its base than at the rim 3706 of the outer cap 3750-1a, meaning the fin 3701 is thicker where it attaches to the outer surface of the inner cap 3750-1b than at the point where it attaches to the inner surface of the outer cap 3750-1a. Alternatively the fin 3701 may be thicker at the rim 3706 of the outer cap 3750-1a than at the base of the caps. As a further alternative the fin 3701 may have uniform thickness along its profile. In the preferred form the cap 3750-1 only includes one fin 3701 per cap 3750-1, but the each cap may include multiple fins 3701 spaced at varying or constant distances from one another. The fin is preferably rigid and made from the same materials as the cap portion 3750-1.

Surprisingly it has been found that adding a fin 3701 to the cap 3750-1 may result in strengthening the entire cap 3750-1 structure. The addition of the fin 3701 adds stiffness to the cap 3750-1 and strengthens both the inner and outer caps. The fin may prevent the inner and outer caps from folding and permanently deforming. Since the cap 3750-1 is stiffer and can resist permanent deformation, this provides the advantage that the cap 3750-1 and hence the pillow portions 3700 can be correctly fitted into a patient's nostrils and the cap 3750-1.

While strengthening the cap 3750-1 structure the addition of the fin 3701 still allows the cap to maintain flexibility either side of the fin 3701. This flexibility may allow the cap 3750-1 to elastically deform as the cap conforms to the nostrils of the user and allows the cap to provide a better seal with the nostrils of the user.

It has also surprisingly been found that the addition of the fin 3701 may go some way to prevent the collapse of the outer cap 3750-1a from collapsing into the path of the stream of gases and close the orifice 3720 of the caps. The closing or partially closing of the orifice 3720 increases pressure drop of across of the cap 3750-1 and increases the effort needed by the user or patient to exhale through the nasal interface. The addition of the fin 3701 may aide in preventing the outer cap 3750-1a from collapsing into the orifice 3720 and into the path of the stream gases, thus improving comfort and safety for the user. The fin 3701 also provides the advantage of delivering more effective therapy since the addition of the fin 3701 provides a better seal and helps in preventing the outer cap 3750-1a from collapsing into the path of the stream of gases and from sealing up the orifice 3720.

In the preferred form the fin 3701 cross sectional thickness is tapered. The fin 3701 is thicker at the base of the inner 3750-1b and outer 3750-1a caps than at the rim 3706 of the outer cap 3750-1a, as described. This tapering thickness directs airflow from the stalks out of the orifice 3720 and out of the cap 3750-1. The addition of the fin and the tapered cross section of the fin helps in reducing the velocity of the delivered gases to a velocity that is comfortable for a user to accept the stream of gas. The possible reduction in velocity may also help prevent air jetting effects that can annoy or damage the nasal passages of a user. The fin 3701 helps to maintain a low level of pressure drop across the nasal interface when the interface is in use. This again increases comfort for the user.

Figure 38A:
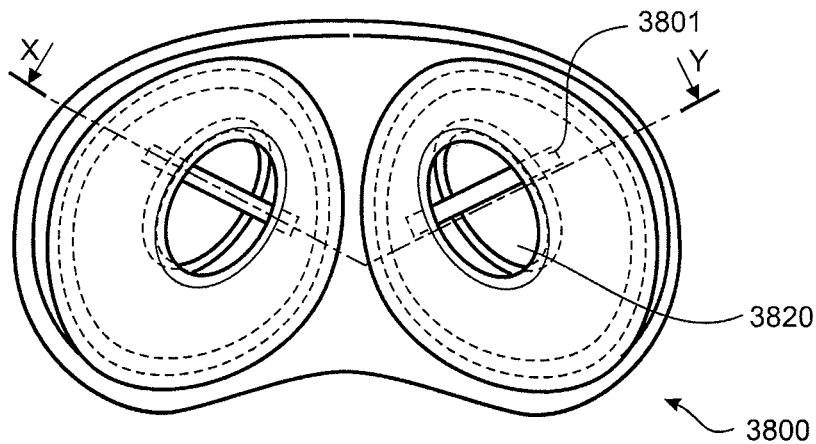
FIG. 38a shows a top view of a further embodiment of a nasal pillow section, the nasal pillow section comprising a pair of pillow portions connected to a pillow gasket portion with internal hidden detail including an internal solid fin within each of the pillow portion shown, and section lines X and Y which bisect each of the pillows also shown, section line X bisecting one of the pillow portions and the fin within the pillow portion, and section line Y bisecting the other pillow portion to one side of the fin.
Figure 38B:
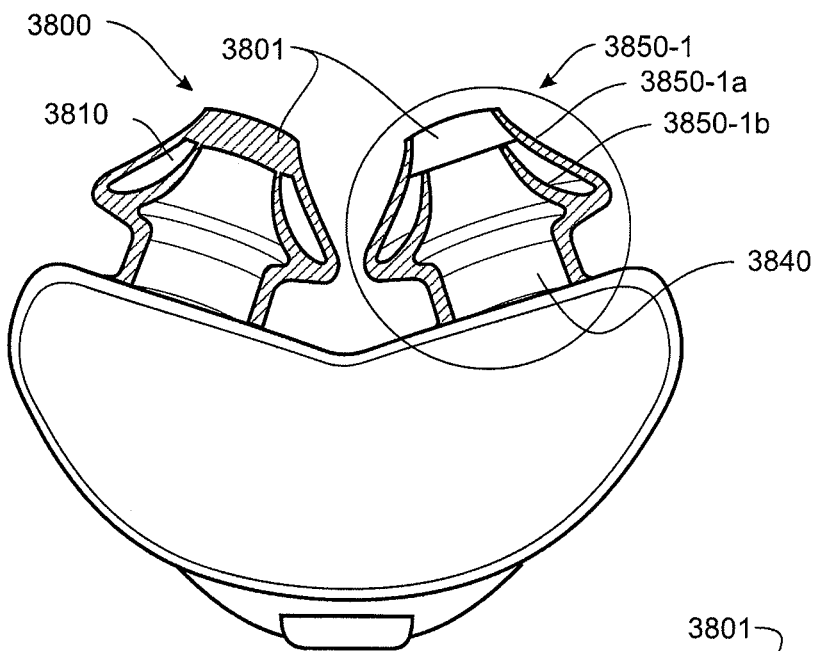
FIG. 38b shows a view of the nasal pillow section of FIG. 38a from the point of view of a user or patient, each of the nasal pillow portions shown in cross-section to show an inner cap and an outer cap, the cross-section for each pillow taken along the section line X and Y, the cross section showing the internal detail of the structure of each of the pillow portions, each pillow portion having a flat fin like structure extending upward and across the cap.
Figure 38C:
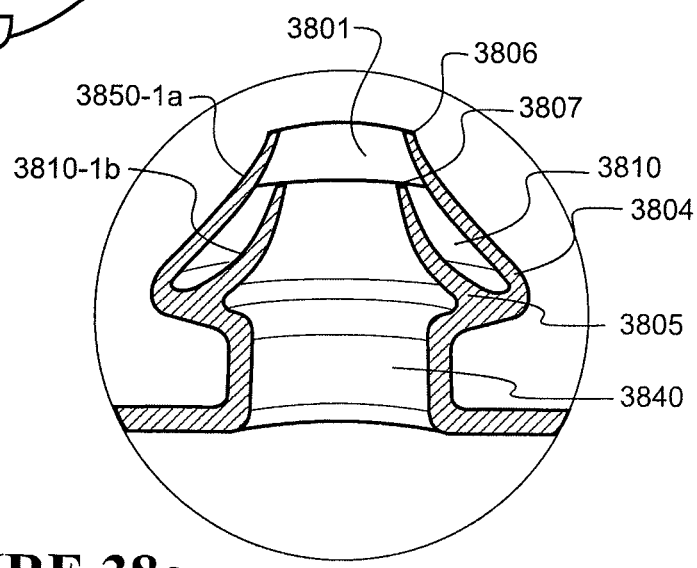
FIG. 38c a detail view of the right hand nasal pillow of FIG. 38b.

A further embodiment of the pillow portions is shown in FIGS. 38a, 38b, and 38c. In this variation, the pillow portions are shown as being used with the pillow gasket portion 350-2, (but as outlined above, the pillow portions may be used with the pillow gasket portion 250-2 or pillow gasket portion 450-2). The specific variations associated with this embodiment are described below.

This embodiment is made up of the first general form of the pillow portion (described earlier). Specific variations associated with this embodiment are described below.

In the preferred form of this embodiment the walls of the inner cap 3850-1b and the outer cap 3850-1a taper in cross sectional thickness, as best seen in FIG. 38c. The wall of the inner cap 3850-1b is preferably thicker at the base 3805 of the inner cap 3850-1b than at the rim 3807 of the inner cap 3850-1b. The wall of the outer cap 3850-1a is preferably thicker at the base of the 3804 of the outer cap 3850-1a than at the rim 3806 of the outer cap 3850-1a. Alternatively the wall thickness of the inner cap 3850-1b and the outer cap 3850-1a may be uniform. As another alternative the wall thickness of the inner and outer caps may be equal to each other—meaning the wall of the inner cap 3850-1b is the same thickness as the wall of the outer cap 3850-1a. Further to this the wall cross section of the inner and outer cap may be identical to each other. As a further alternative the thickness of the wall of one of the caps may taper while the thickness of the other cap wall may be uniform—for example the thickness of the wall of the inner cap 3850-1b may taper while the thickness of the wall of the outer cap 3850-1a may be uniform.

There is a cavity 3810 or air gap formed between the outer cap 3850-1a and the inner cap 3850-1b (except at the point where they are connected at their bases to the stalk 3850-3 and to each other). The cavity or air gap 3810 is not in the direct air path of the stream of gases, as best seen in FIG. 38c.

The cap 3850-1 includes at least one "rib" feature within the cap. Preferably this rib feature is a solid fin 3801 that passes through the entire cap 3850-1. The fin 3801 joins the inner cap 3850-1b with the outer cap 3850-1a, as seen if FIGS. 38b and 38c. Preferably part of the fin 3801 lies within the path of the stream of gases delivered to the user or patient, as seen in FIG. 38a. The fin 3801 extends from the inside surface of the outer cap 3850-1a to the outside surface of the inner cap 3850-1b, as best seen in the left cap of FIGS. 38b and 38c. The fin 3801 preferably extends across the width or diameter of the outer cap 3850-1a, with the lower edge of the fin 3801 passing across and contacting (or formed with) the rim 3807 of the inner cap 3850-1b. The fin 3801 only extends downwards as far as the rim 3807 of the inner cap 3850-1b. The fin 3801 extends from one side of the cap to the other side of the cap, spanning the diameter of the cap 3850-1, as seen in FIG. 38 b. Preferably the fin 3801 extends vertically from rim of the inner cap 3850-1b to the rim of outer cap 3850-1a. The fin 3801 follows the general shape of the top edges of the cap 3850-1. Alternatively the fin 3801 could be curved in shape (not shown), instead of being straight as shown in FIGS. 38a and 38b, and form a gentle curve along between the rim of the inner and outer caps. As a further alternative the fin 3801 could be even angled about the central vertical axis of the exit orifice 3820 of the cap 3850-1, as seen in FIG. 38a or alternatively the fin 3801 may be offset about the vertex point. The vertex point preferably is situated in the middle of the exit orifice 3820 of the cap 3850-1. However, the vertex point may be at any point along the width of the cap 3850-1. As a further alternative the fin 3801 may completely extend through the cap 3850-1. In this alternative form the fin 3801 may only extend from the inner surface of the outer cap 3850-1a to the point where the cap 3850-1 extends from the stalk (this arrangement is not illustrated), similar to the sixth embodiment previously described.

The fin 3801 preferably tapers in thickness. The fin 3801 is thicker at its base, along the rim of the inner cap 3850-1b, than at the rim 3806 of the outer cap 3850-1a. Alternatively the fin 3801 may be thicker at the rim 3806 of the outer cap 3850-1a than at the rim 3807 of the inner cap 3850-1b. As a further alternative the fin 3801 may have uniform thickness along its profile. In the preferred form the cap 3850-1 only includes one fin 3801 per cap 3850-1, but the each cap may include multiple fins 3801 spaced at varying or constant distances from one another. The fin is preferably made from the same materials as the cap portion 3850-1.

Surprisingly it has been found that adding a fin 3801 to the cap 3850-1 may result in strengthening the entire cap 3850-1 structure. The addition of the fin 3801 adds stiffness to the cap 3850-1 and strengthens both the inner and outer caps. The fin may prevent the inner and outer caps from folding and permanently deforming. Since the cap 3850-1 is stiffer and can resist permanent deformation, this provides the advantage that the cap 3850-1 and hence the pillow portions 3800 can be correctly fitted into a patient's nostrils and the cap 3850-1.

While strengthening the cap 3850-1 structure the addition of the fin 3801 still allows the cap to maintain flexibility either side of the fin 3801. This flexibility may allow the cap 3850-1 to elastically deform as the cap conforms to the nostrils of the user and allows the cap to provide a better seal with the nostrils of the user and make it easier to fit into a patient or user's nostrils.

It has also surprisingly been found that the addition of the fin 3801 may go some way to prevent the collapse of the outer cap 3850-1a from collapsing into the path of the stream of gases and close the orifice 3820 of the caps. The closing or partially closing of the orifice 3820 increases pressure drop of across of the cap 3850-1 and increases the effort needed by the user or patient to exhale through the nasal interface. The addition of the fin 3801 may aide in preventing the outer cap 3850-1a from collapsing into the orifice 3820 and into the path of the stream gases, thus improving comfort and safety for the user. The fin 3801 also provides the advantage of delivering more effective therapy since the addition of the fin 3801 provides a better seal and helps in preventing the outer cap 3850-1a from collapsing into the path of the stream of gases and from sealing up the orifice 3820.

In the preferred form the fin 3801 cross sectional thickness is tapered. The fin 3801 is thicker at the base of the inner 3850-1b and outer 3850-1a caps than at the rim 3806 of the outer cap 3850-1a, as described. This tapering thickness directs airflow from the stalks out of the orifice 3820 and out of the cap 3850-1. The addition of the fin and the tapered cross section of the fin helps in reducing the velocity of the delivered gases to a velocity that is comfortable for a user to accept the stream of gas. The possible reduction in velocity may also help prevent air jetting effects that can annoy or damage the nasal passages of a user. The fin 3801 helps to maintain a low level of pressure drop across the nasal interface when the interface is in use. This again increases comfort for the user.

Figure 39A:
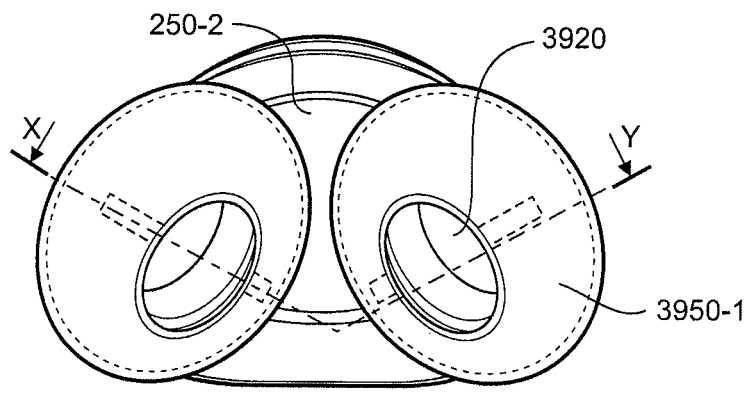
FIG. 39a shows a top view of a further embodiment of nasal pillow section, the nasal pillow section comprising a pair of pillow portions connected to a pillow gasket portion with internal detail of each of the pillow portions shown, each of the pillow portions including internal ribs, and section lines X and Y which bisect each of the pillow portions also shown, section line Y bisecting the right-hand pillow portion and the ribs within the pillow portion, and section line X bisecting the left-hand pillow portion to one side of the internal ribs.
Figure 39B:
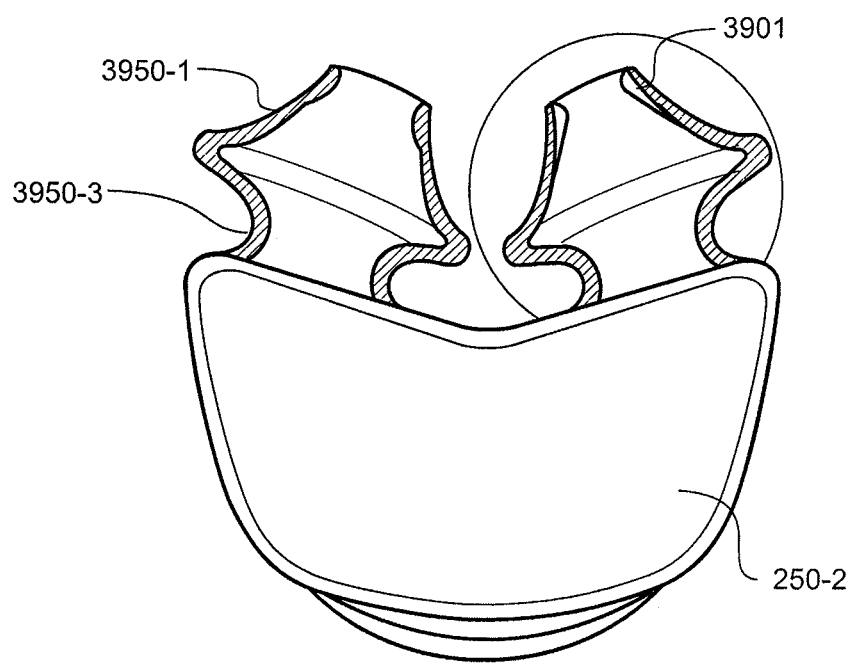
FIG. 39b shows a view of the nasal pillow section of FIG. 39a from the point of view of a user, each of the nasal pillow portions shown in cross-section, the cross-section for each pillow portion taken along the section lines X and Y, the cross-section showing internal detail of the structure of each of the nasal pillow portions.
Figure 39C:
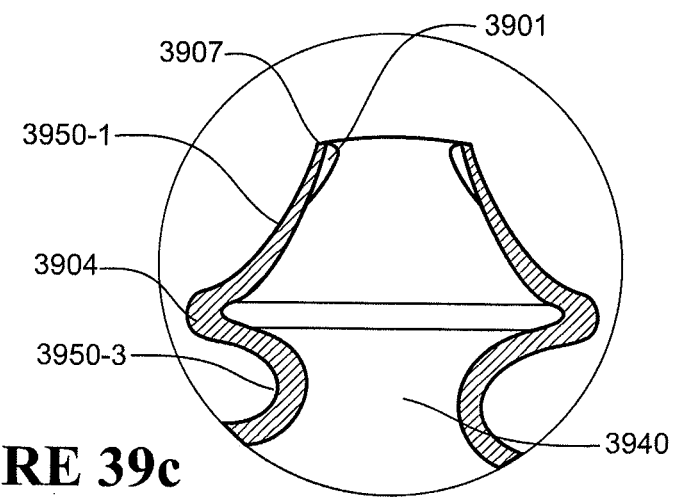
FIG. 39c shows a detail view of the right hand nasal pillow of FIG. 39b, bisected by line Y.

A further embodiment of the pillow portions is shown in FIGS. 39a, 39b, and 39c. In this variation, the pillow portions are shown as being used with the pillow gasket portion 250-2 (but as outlined above, the pillow portions may be used with the pillow gasket portion 350-2 or pillow gasket portion 450-2).

This embodiment is formed from the same elements as form the third general form of the pillows portion (described above), with specific differences as described below.

In the preferred form of this embodiment the wall of the cap 3950-1 tapers in thickness, being thicker at the base 3904 than at the rim 3907. It is preferred that the wall thickness tapers gradually. Most preferably the wall thickness at the base 3904 of the cap 3950-1 is twice the thickness at the rim 3907 of the cap 3950-1. In alternative forms the wall of the cap 3950-1 may be thicker at the rim 3907 and thinner at the base 3904. In further alternate forms the thickness of the wall of the cap 3950-1 may be uniform along the entire height of the cap 3950-1.

The inside surface of the cap 3950-1 includes at least one and preferably a series of ribs 3901 which extend inward from the inner surface of the cap 3950-1. The rib or ribs 3901 preferably extend toward the centre of the cap or inward toward each other. The ribs 3901 are preferably located within the top third of the cap 3950-1. That is, the ribs are situated between the top 3907 of the cap 3950-1 and approximately one third of the way down the inside surface of the rib when measured from the top 3907. In the most preferred form, the top of the rib or ribs 3901 is located at the rim 3907 of the cap 3950-1. The inner edge of the rib 3901 is attached to the inside surface of the cap 3950-1 wall, while the outer edge is a free edge. Preferably the free edge of the rib 3901 is substantially curved between the top and the bottom, as shown in FIG. 39c. Preferably the rib or ribs are thicker closer to the top of the rib. The rib tapers or curves and becomes thinner toward the bottom of the rib, merging with the pillow wall at the bottom of the rib. It can be seen that the rib has a 'teardrop' shape in cross-section.

In alternative forms the free edge the rib 3901 may have a cross-section in the shape of some other polygon, for example a triangle or rectangle. The rib 3901 is substantially elongate vertically. Preferably the edge attached to the inner wall of the cap 3950-1 extends downward along the inner wall of the cap 3950-1, toward the stalk 3950-3. Most preferably the rib extends down approximately one third of the total cap 3950-1 height, along the inner wall of the cap 3950-1, when measured from the rim 3907. Most preferably the rib extends downward from the rim 3907 of the cap 3950-1. Alternatively the rib 3901 may extend downward anywhere between one eighth and two thirds of the total height of the cap 3950-1 from the rim 3907. These rib/ribs 3901 can be called partial ribs since in the preferred form the rib or ribs 3901 do not extend all the way to the base of the cap 3950-1.

It is preferred that the rib 3901 has the same cross-sectional thickness as the cross-sectional thickness of the cap 3950-1, at the thickest point along the height of the cap 3950-1. More preferably the rib is thicker than the cap 3950-1 at the thickest point of the cap (that is, the rib extends inwards further than the thickness of the cap). In alternative, less preferred forms, the rib 3901 may be thinner than the cap 3950-1 wall thickness.

If a series of ribs 3901 are used, it is most preferred that they are all identical to each other. In the preferred form the ribs 3901 are positioned at regular, evenly spaced intervals around the perimeter of the cap 3950-1. Alternatively the ribs 3901 may be placed at irregular intervals around the perimeter of the cap 3950-1. Preferably all the ribs 3901 extend the same length downwards from the rim of the cap 3950-1. Alternatively the various ribs 3901 may extend varying distances along the height of the cap 3950-1. These varying intervals and varying extension along the height may be used to add strength (via the rib or ribs) along specific weak points on the cap 3950-1. Preferably all the ribs are placed along one axis around the perimeter of cap 3950-1, meaning all the ribs are at the same height around the perimeter of the cap 3950-1. Alternatively the ribs may be placed at various heights around the perimeter of the cap 3950-1. In the most preferred form the ribs 3901 all have the same cross-sectional thickness. However, it is conceivable that the ribs may vary in cross-sectional thickness from rib to rib. In the most preferred form, the cap 3950-1 has two ribs 3901 spaced at 180 degrees (radially opposite) from each other along the perimeter of the cap.

The addition of the rib(s) 3901, and more preferably a series of ribs helps to strengthen or stiffen the wall of the cap 3950-1. The added stiffness, in particular added flexural stiffness, helps to reduce the amount of deformation of the cap 3950-1, when the cap is fitted into a patient's nostrils.

The rib or ribs 3901 help to control the amount of deformation of those portions of the cap 3950-1 where the rib is present. The areas of the cap 3950-1 with the rib are stiffer and move less than the areas of the cap 3950-1 without the rib 3901. The additional stiffening of certain areas of the cap 3950-1 can help to form a more effective seal with the patient's nostril. This allows the cap 3950-1 to be used and fitted to a variety of different shaped nostrils. The addition of the rib or ribs 3901 makes the cap 3950-1 more comfortable for the user to use.

The addition of the rib 3901 around the perimeter of the cap 3950-1 helps to stiffen and strengthen the cap 3950-1 so that it does not collapse onto itself and block the airway 3940. If the cap 3950-1 blocks the airway 3940 partially or completely, the pressure drop across the pillow portion 3900 increases making it harder for a user to breathe through the pillow portion 3900. The ribs 3901 help to stiffen the cap and may act as load bearing members as the cap 3950-1 deforms when inserted into a patient's nostrils, thus reducing or stopping the cap 3950-1 from collapsing into the airway 3940. This makes it easier for the patient to breathe through the pillow portion 3900 and cap 3950-1 when in use and thus makes it more comfortable and safer for the patient to use the cap and pillow portion.

Figure 40A:
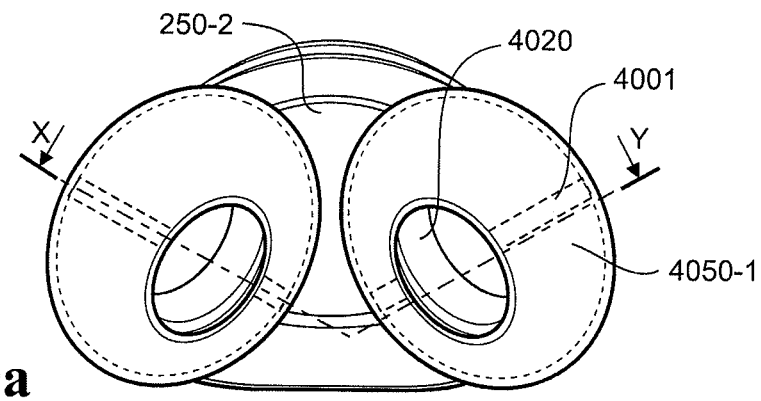
FIG. 40a shows a top view of a further embodiment of nasal pillow section, the nasal pillow section comprising a pair of pillow portions connected to a pillow gasket portion with internal detail of the pillow portions shown, each of the pillow portions having internal ribs, and section lines X and Y which bisect each of the pillows also shown, section line Y bisecting one of the pillows and the ribs within the pillow, and section line X bisecting the other of the pillows to one side of the ribs.
Figure 40B:
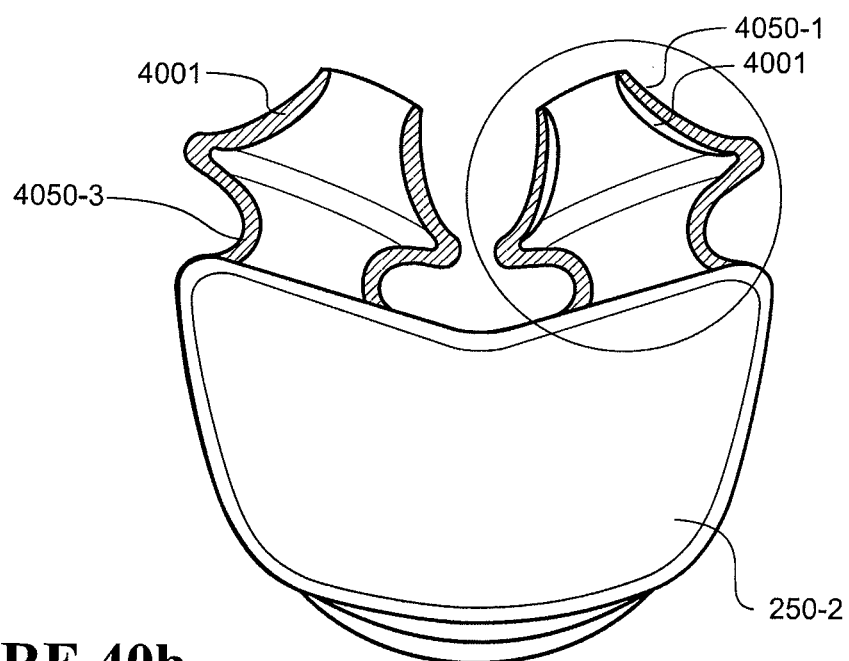
FIG. 40b shows a view of the nasal pillow section of FIG. 40a from the point of view of a user, each of the nasal pillow portions shown in cross-section, the cross-section for each pillow portion taken along the section lines X and Y, the cross-section showing internal detail of the structure of each of the nasal pillow portions.
Figure 40C:
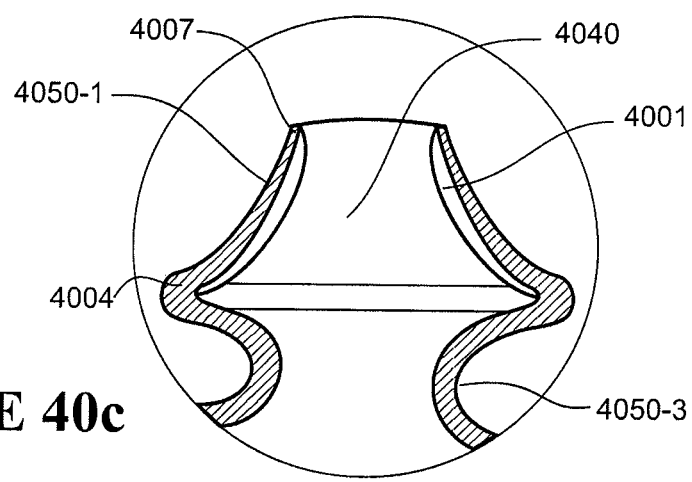
FIG. 40c shows a detail view of the right hand nasal pillow of FIG. 40b, through the section line Y.

A further embodiment of the pillows portion is shown in FIGS. 40a, 40b and 40c. In this variation, the pillows portion is shown as being used with the pillow gasket 250-2. However, the pillow portion may be used with the pillow gasket portion 350-2 or pillow gasket portion 450-2, as outlined above. The pillow section 4050 is formed from the pillow portion and pillow gasket in combination.

This embodiment is formed from the same elements as form the third general form of the pillows portion (described above), with specific differences as described below.

In the preferred embodiment the walls the cap 4050-1 taper in cross sectional thickness as best seen in FIG. 40c. The walls of the cap 4050-1 are thicker at the lower end than at the upper end. The wall of the cap 4050-1 is thicker at the base 4004 than at the rim 4006 of the cap 4050-1. Alternatively the cross-sectional thickness of the walls of the cap may be constant.

The inside wall of the cap 4050-1 comprises at least one, but more preferably a series of ribs 4001. Each of the rib or ribs 4001 is preferably located on the inside surface of the wall of the cap 4050-1 and extends from just above the base of the cap 4050-1 to the top rim of the cap 4050-1, as seen in FIG. 40c. In the preferred form the rib extends from the top edge of the cap 4050-1 (or just below the top edge of the cap 4050-1) to just above the base of the cap 4050-1. In alternative forms the rib 4001 could extend from just above the base to just below the rim, without reaching either the base or the rim. In the most preferred form the rib 4001 is shaped to follow the contour of the inside wall of the cap 4050-1, as seen in FIG. 40c. Alternatively the outer edge of the rib 4001 may follow a curved path different to that of the inside wall of the cap 4050-1. The rib 4001 is preferably thicker at its mid-point than at its extremes (top and bottom). The rib 4001 at its thickest point may be the same thickness of thicker than the cross sectional thickness of the wall of the cap 3950-1. In the most preferred form the rib 4001, at its thickest point, is the same thickness as the cap wall, at the cap wall's base. Alternatively the rib 4001 may taper in thickness, for example the rib 4001 may be thicker at its base than at its rim, or vice versa. In a further alternative form the rib 4001 may be of constant cross-sectional thickness along its entire height.

If a series of ribs 4001 are used, they are preferably all identical to each other. In the preferred form the ribs 4001 are positioned at regular intervals around the perimeter of the inside surface of the cap 4050-1. Alternatively the ribs 4001 may be placed at irregular intervals around the perimeter of the inside surface of the cap 4050-1. Preferably all the ribs 4001 extend the same length or height within the cap 4050-1. Alternatively the various ribs 4001 may extend varying distances along the height of the cap 4050-1. Having varying intervals and varying extensions along the height can help to add strength at specific weak points on the cap 4050-1. If multiple ribs are used, it is preferred that the tops are in the same plane and the bottoms are in the same plane. Alternatively the top and the bottom of the ribs may be out of plane. In the most preferred form the ribs 4001 are all of the same cross-sectional thickness as each other. However, it is conceivable that the ribs may vary in thickness from rib to rib. Further each rib 4001 may be thicker at differing points along its height when compared to the other ribs.

The addition of the rib 4001, and more preferably a series of ribs helps strengthen or stiffen the cap 4050-1 wall. The added stiffness, in particular added flexural stiffness, can help to reduce the amount of deformation of the cap 4050-1, as the cap is fitted into a patient's nostrils. The addition of the ribs 4001 adds stiffness while allowing the cap 4050-1 to maintain at least substantial flexibility. The cap 4050-1 being substantially flexible allows the cap 4050-1 to conform to a patient's nostrils in use and allows the cap 4050-1 to be fitted with a variety of users nostril shapes.

The addition of the rib 4001 around the perimeter of the cap 4050-1 helps to stiffen and strengthen the cap 4050-1 so that it does not collapse onto itself and block the airway 4040. If the cap 4050-1 blocks the airway 4040 partially or completely, the pressure drop across the pillow portion increases making it harder for a user to breathe through the pillow portion. The ribs 4001 can help to stiffen the cap and they can act as load bearing members as the cap 4050-1 deforms when inserted into a patient's nostrils, thus reducing or stopping the cap 4050-1 from collapsing into the airway 4040. This makes it easier for the patient to breathe through the pillow portion and cap 4050-1 when in use and thus makes it more comfortable and safer for the patient to use the cap and pillow portion.

Figure 41A:
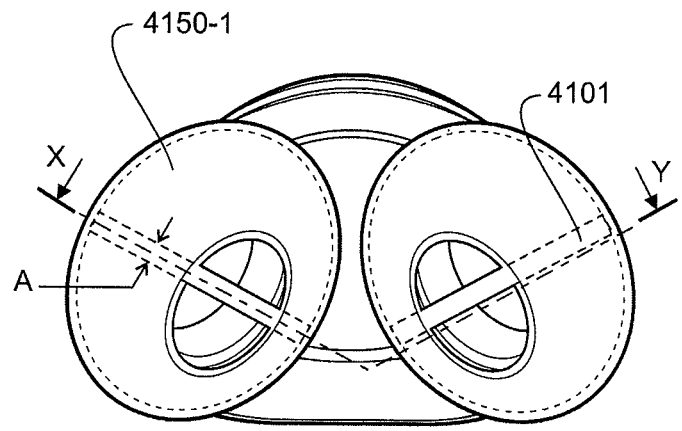
FIG. 41a shows a top view of a still further embodiment of nasal pillow section, the nasal pillow section comprising a pair of pillow portions connected to a pillow gasket portion with internal detail within the pillow portion shown, each of the pillow portions having an internal fin, and section lines X and Y which bisect each of the pillows also shown, section line X bisecting the left hand one of the pillows and the fin within the pillows, and section line Y bisecting the right hand pillow to one side of the fin.
Figure 41B:
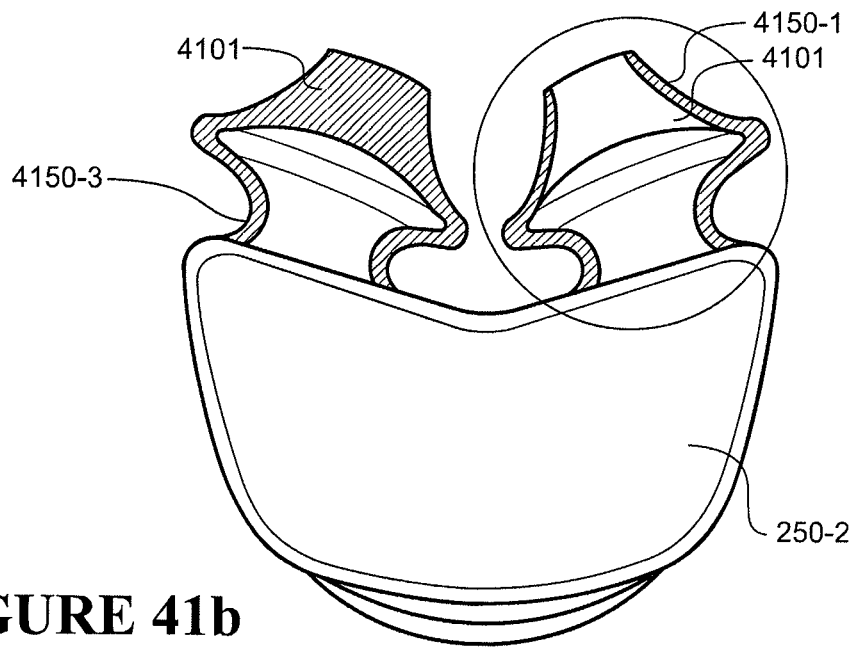
FIG. 41b shows a view of the nasal pillow section of FIG. 41a from the point of view of a user or patient, each of the nasal pillow portions shown in cross-section, the cross-section for each pillow taken along the section lines X and Y, the cross section showing the internal detail of the structure of each of the pillow portions.
Figure 41C:
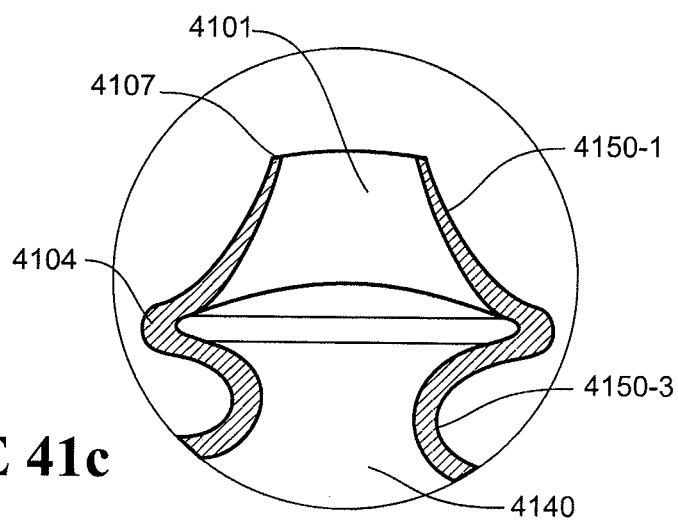
FIG. 41c shows a detail view of the right hand nasal pillow of FIG. 41b along section line Y.

A further embodiment of the pillows portion is shown in FIGS. 41*a*, 41*b* and 41*c*. In this variation, the pillows portion is shown as being used with the pillow gasket 250-2. However, the pillow portion may be used with the pillow gasket portion 350-2 or pillow gasket portion 450-2, as outlined above. The pillow section 4150 is formed from the combination of the pillow portion and the pillow gasket.

This embodiment is formed from the same elements as form the third general form of the pillows portion (described above), with specific differences as described below.

In the preferred form the walls of the cap 4150-1 taper in cross sectional thickness as best seen in FIG. 41*c*. The walls of the cap 4150-1 are thicker at the lower end than at the upper end. The wall of the cap 4150-1 is thicker at the base 4104 than at the rim 4106 of the cap 4150-1. Alternatively the thickness of the walls of the cap may be constant or the wall thickness of one of the walls may taper while the wall thickness of the other wall may remain constant.

The cap 4150-1 has at least one "rib" feature. The rib feature is preferably a solid fin 4101, as seen in FIGS. 41*a* and 41*b*. The fin 4101 is preferably substantially diametrically aligned across the pillow portion. The fin 4101 extends from a position at or close to the top edge or rim 4107 of the cap 4150-1 downwardly. In the most preferred form the fin extends approximately three quarters of the way down the height of the cap 4150-1. Alternatively the fin 4101 may extend from the rim 4107 of the cap to the base 4104 of the cap 4150-1. Preferably the fin is aligned substantially vertically or upright in use. Alternatively the fin may be curved in the vertical or horizontal plane. As outlined above, the fin 4101 is preferably substantially diametrically aligned across the pillow portion. However, the fin 4101 may be offset to one side of the cap 4150-1. In the most preferred form the fin is aligned and sized to bisect the upper opening of the cap 4150-1, with the fin having straight sides, as seen in FIG. 41*a*. In alternative forms, the fin may be curved or have curved side walls. Preferably the lower or bottom edge of the fin 4101 is curved upwards as best seen in FIG. 41*c*.

The fin 4101 is preferably thicker than the cap 4150-1 wall (greater cross-sectional thickness). In the most preferred form the fin 4101 is twice the thickness of the cap 4150-1 wall. Alternatively the fin 4101 may be thinner in cross-section than the wall of the cap. Preferably the thickness of the fin 4101 is constant over the entire height of the fin 4101. Alternatively the thickness of the fin 4101 may taper—the fin 4101 may be thicker at its base than at its top edge, or vice versa. The lateral thickness or width, the dimension labelled A on FIG. 41*a* is preferably uniform. That is, the lateral cross section (dimension A), is uniform from one side of the cap 4150-1 to the other side of the cap 4150-1, although the thickness may differ at different heights of the fin.

The addition of the fin 4101 helps to strengthen or stiffen the entire cap 4150-1 while still allowing the sides of the cap 4150-1 to be substantially flexible. The added stiffness helps to reduce the amount of deformation of the cap 4150-1, as the cap is fitted into a patient's nostrils. The sides of the cap 4150-1 not engaged to the fin 4101 are substantially flexible, and this allows the cap 4150-1 to conform to a patient's nostrils in use and allows the cap 4150-1 to be fitted with a variety of users nostril shapes.

The addition of the fin 4101 to the cap 4150-1 helps to stiffen and strengthen the cap 4150-1 so that it does not collapse onto itself and block the airway 4141. If the cap 4150-1 blocks the airway 4140 partially or completely, the pressure drop across the pillow portion increases, making it harder for a user to breathe through the pillow portion. The fin 4101 helps to stiffen the cap and acts as a load bearing member as the cap 4150-1 deforms when inserted into a patient's nostrils, thus reducing the amount the cap 4150-1 collapses into the airway 4140. This makes it easier for the patient to breathe through the pillow portion and cap 4150-1 when in use and thus makes it more comfortable and safer for the patient to use the cap and pillow portion.

If the fin 4101 has tapered thickness over the height of the cap 4150-1, this provides the advantage of directing airflow out of the opening of the pillow. The fin 4101 is preferably thicker at its base than at its rim. The tapering thickness assists in gently directing airflow or a stream of gases towards the opening in the cap 4150-1 and helps to maintain a low pressure drop across the pillow portion and the cap 4150-1 when the cap 4150-1 is inserted into a patient's nostril.

Figure 42A:
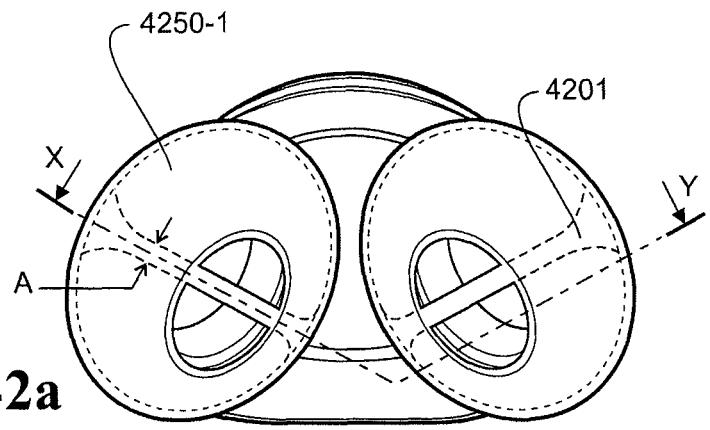
FIG. 42a shows a top view of a still further embodiment of nasal pillow section, the nasal pillow section comprising a pair of pillow portions connected to a pillow gasket portion with internal hidden detail within each of the pillow portions shown, each of the pillow portions having an internal fin, and section lines X and Y which bisect each of the pillows also shown, section line X bisecting the left-hand pillow and the fin within the pillows, and section line Y bisecting the right-hand pillow to one side of the fin, the figure further showing the fin being tapered in thickness, with the fin thicker at edges than in the centre.
Figure 42B:
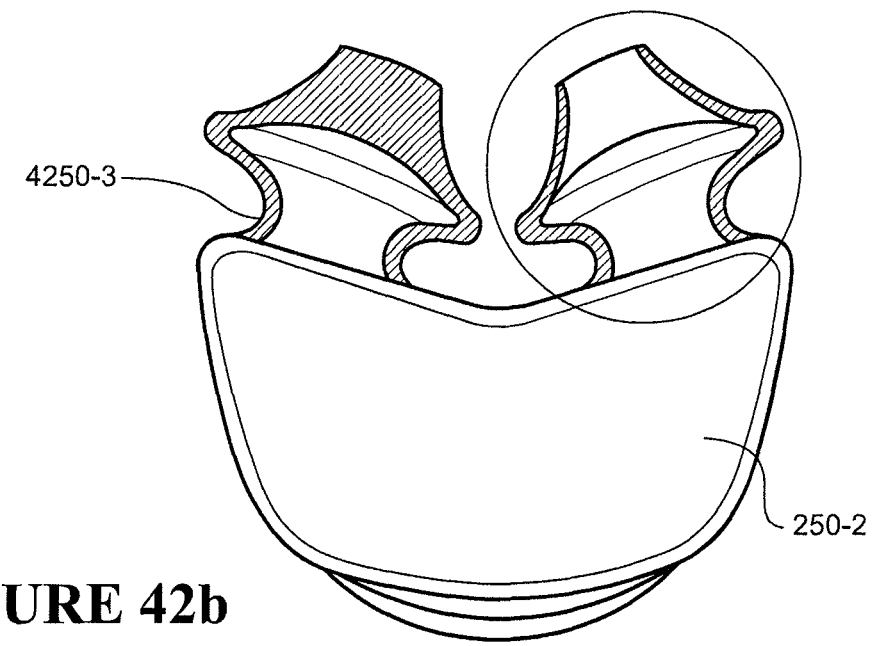
FIG. 42b shows a view of the nasal pillow section of FIG. 42a from the point of view of a user or patient, each of the nasal pillow portions shown in cross-section, the cross-section for each pillow taken along the section lines X and Y, the cross section showing the internal detail of the structure of each of the pillow portions.
Figure 42C:
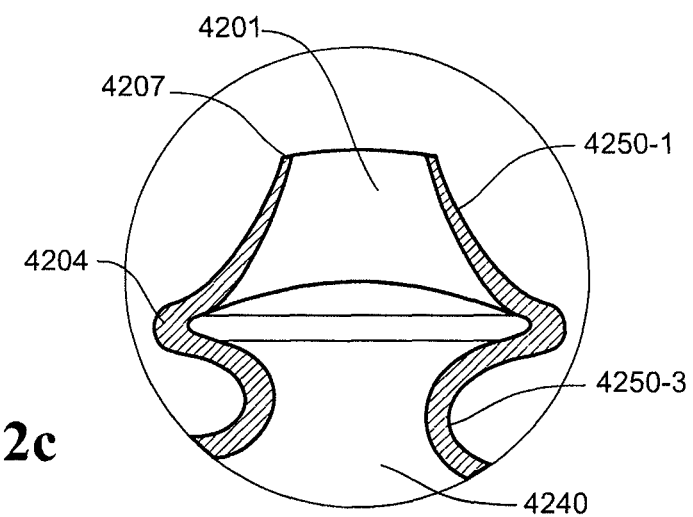
FIG. 42c shows a detail view of the right hand nasal pillow of FIG. 42b, taken along the section line Y.

A further embodiment of the nasal pillow portion is shown in FIGS. 42*a*, 42*b* and 42*c*. This embodiment is the same as that described above with reference to FIGS. 41*a*-*c*, with specific differences as follows:

In this embodiment, the cap 4250-1 is connected to the stalk 4250-3. The cap 4250-1 has at least one fin 4201. The fin 4201 is wider at the sides than in the centre. That is, towards the inner surface of the walls of the cap, the cross-sectional thickness of the fin 4201 increases. The fin 4201 is wider at the sides than in the centre.

Figure 43:
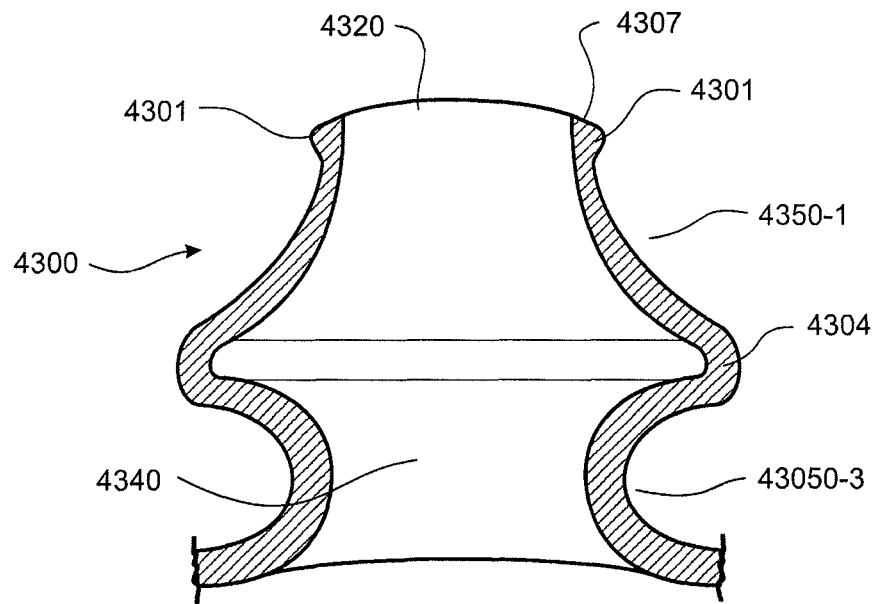
FIG. 43 shows a still further embodiment of a nasal pillow portion, the pillow portion comprising a stalk and a cap section, with a bead extending outwards from the rim of the cap section around the perimeter of the cap section.

A further embodiment of pillow portion is shown in FIG. 43. The figure only shows only one pillow portion 4300 of what would normally be a pair used together. A pair of pillow portions would normally be used with a pillow gasket 250-2 (not shown). The pillow portions could also be used with other pillow gaskets such as gaskets 350-2 and 450-2.

As can be seen in FIG. 43, the pillow portion is formed from a cap 4350-1 and a stalk 4350-1. The cap 4350-1 is wider than the stalk 4350-3. The walls of the cap 4350-1 taper in cross sectional thickness, as seen in FIG. 43. The wall of the cap 4350-1 is thicker at its base 4304 than at the rim 4307. Alternatively, the wall of the cap 4350-1 may be uniform in thickness. Preferably the thickness of the cap 4350-1 wall at its base 4304, is the same thickness or thicker than the wall thickness of the stalk 4350-3. Alternatively the wall of the stalk 4350-3 may be thicker than the wall of the cap 4350-1 along all points of the cap 4350-1.

The cap 4350-1 has a bead 4301, located on the cap 4350-1, as seen in FIG. 43. The bead 4301 extends outward from the outer surface of the cap 4350-1. Most preferably the bead 4301 is located at the rim 4307 of the cap 4350-1 and extends around the rim 4307. Alternatively the bead 4301 may be located anywhere in the upper third of the outer surface of the cap 4350-1.

Preferably the bead 4301 extends continuously around the perimeter of the cap 4350-1. Preferably the bead 4301 extends uniformly around the perimeter of the cap 4350-1—the bead 4301 forms a continuous ring with no breaks. Also, it is preferred that the cross-sectional thickness of the bead is constant. Preferably the bead follows a symmetrical path around the perimeter of the cap 4350-1. Alternatively the bead 4301 may follow any path along the outer surface of the cap 4350-1 perimeter—that is, not strictly following the upper rim 4307, but dipping below this if required. Furthermore, the bead 4301 may be formed discontinuously around the perimeter or the rim if required.

Preferably the bead 4301 is circular in cross section. Alternatively the bead 4301 may be any other suitable cross section, for example rectangular, triangular or elliptical. The bead 4301 is preferably thicker than the cross sectional thickness of the cap 4350-1 wall at the rim 4307. More preferably the bead 4301 is twice the cross sectional thickness of the cap wall at the rim 4307. Alternatively the bead 4301 may be the same thickness or thinner than the cross sectional thickness of the cap wall at its rim 4307. Preferably the thickness of the bead 4301 is uniform or constant along its perimeter. Alternatively the thickness of the bead 4301 may vary along its perimeter, the thickness of the bead being different from point to point along its perimeter. The cross section of the bead 4301 is preferably constant along the perimeter of the cap 4350-1. Alternatively the cross section of the bead 4301 may vary around the perimeter of the cap 4350-1. The variation in thickness or cross section or both can help to provide improved strength or flexibility where required around the perimeter of the cap 4350-1.

Surprisingly it has been found that the addition of the bead 4301 to the outer surface of the cap 4350-1 helps to strengthen or stiffen the top part or rim 4307 of the cap 4350-1. The added stiffness, in particular flexural stiffness, to the top part or rim 4307 helps prevent the rim 4307 or top part of the cap 4350-1 from collapsing and blocking the airway 4340 and restricting the flow of gases out of the airway 4340 and the cap 4350-1, while fitting the cap 4350-1 into a patient's nostrils. This provides the advantage of keeping the exit orifice 4320 as large as possible while the cap 4350-1 is being fitted into a patient's nostrils. Preventing the airway 4340 or exit orifice 4320 from being blocked reduces the amount of pressure drop across the pillow portion 4300, and reduces the effort required by a patient to exhale through the cap 4350-1. This provides the advantage of added comfort for the patient and ease of breathing for the patient while using and fitting the pillow portion 4300.

The bead 4301 is purposely placed on the outer surface of the cap 4350-1 so that the bead is out of the path of the gases travelling through the airway 4340. This helps reduce the amount of pressure drop across the pillow portion 4300 and cap 4350-1. Reduced pressure drop across the cap 4350-1 and pillow portion 4300 is advantageous as it makes it easier for a patient to breathe normally and makes using the pillow portion 4300 more comfortable.

It has surprisingly been found that while the bead 4301 may strengthen or stiffen the top part or rim 4307 of the outer cap 4350-1, the lower part of the outer cap 4350-1 remains substantially flexible and supple. This flexibility and suppleness allows the outer cap 4350-1 to distort to fit into a variety of nostril shapes and form an effective seal. This allows this particular type of pillows portion 4300 and caps 4350-1 to be used with a variety of users to create an effective seal, while delivering therapy gases.

Figure 44:
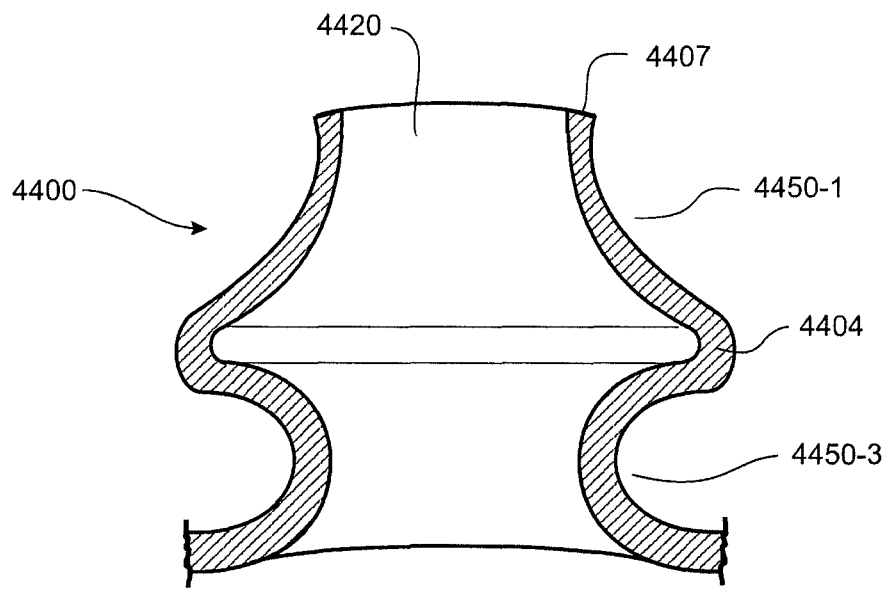
FIG. 44 shows a still further embodiment of a nasal pillow portion, the pillow portion comprising a stalk and a cap section, the top or rim of the cap section wall being thicker in cross-sectional thickness than cross-sectional thickness of the middle part of the cap wall.

A further embodiment of pillow portion is shown as pillow portion 4400 in FIG. 44.

As outlined above, a pair of pillow portions is normally used with a pillow gasket such as pillow gasket 250-2. The pillow portion 4400 is similar to pillow portion 4300 described above. The pillow portion 4400 can also be used as one of a pair with pillow gasket 350-2 or 450-2, these gaskets being described earlier in the specification.

In this embodiment, the wall of the cap 4450-1 tapers in thickness. Most preferably the wall of the cap 4450-1 is thicker at the rim 4407 than at the base 4404 of the cap 4450-1. The wall of the cap 4450-1 follows a uniform cross section from the base 4404 toward the rim, with the wall of the cap beginning to thicken in the upper one fifth of the cap, the cap wall being thickest at the rim 4407. Alternatively the base 4404 of the cap 4450-1 may be the same thickness as the rim 4407, while the middle or centre portion of the cap wall between the base and the rim is thinner than the rim and the base. In this alternative form the wall of the cap begins to thicken at the base 4404, becoming thinner as it approaches the middle and then becoming thicker again as it approaches the rim 4407, with the wall becoming thickest at the rim 4407.

A pillow portion with the features outlined above provides many of the same advantages as those outlined above in relation to the pillow portion described in relation to FIG. 43. However, the construction differs from that described for FIG. 43.

Figure 45:
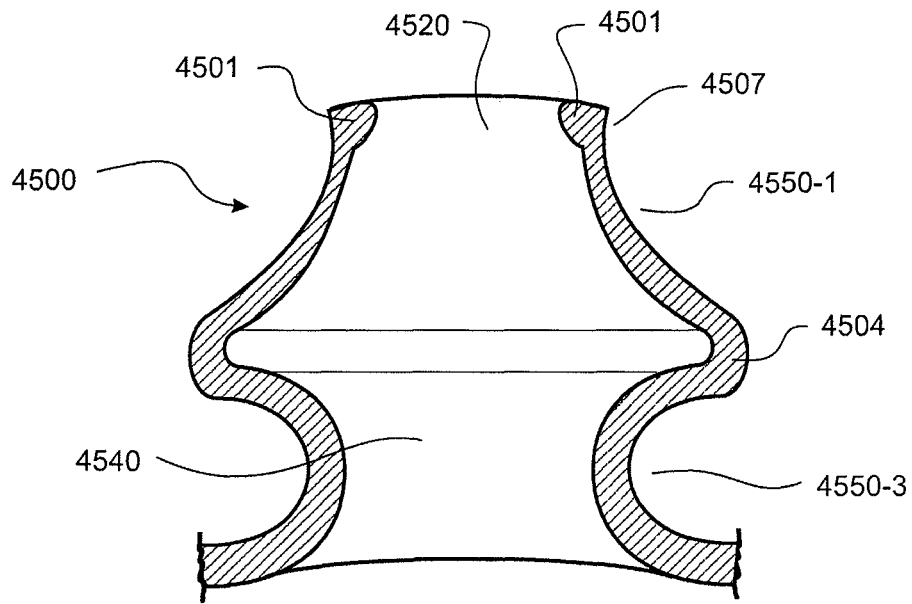
FIG. 45 shows a still further embodiment of a nasal pillow portion, the pillow portion comprising a stalk and a cap section, the wall of the cap section having a uniform cross section, and a bead applied to the inside surface of the cap section and extending inwards and running around the perimeter of the cap section.

A further embodiment of pillow portion is shown in FIG. 45.

The pillow portion 4500 is similar to the pillow portion 4300, with specific structural differences as outlined below. The pillow portion 4500 may be used with any one of the pillow gaskets described above (250-2, 350-2 or 450-2), or any other suitable device.

In this embodiment of the pillow portion, the cross sectional thickness of the wall of the cap 4550-1 is uniform along the height of the cap 4550-1, as seen in FIG. 45. In a less preferred form the thickness of the wall of the cap 4550-1 may taper. For example the wall thickness at the base 4504 may be greater than at the rim 4507 or vice versa.

The cap 4550-1 has a bead 4501 located on the inner wall of the cap 4550-1. The bead is preferably located at and extends around the rim 4507 of the cap 4550-1. Alternatively the bead 4501 may be located below the rim 4507 of the cap 4550-1. Preferably the bead 4501 is symmetrical at all points around the perimeter of the cap 4550-1, meaning the bead has a uniform cross-section around the entire perimeter of the pillow portion. In the most preferred form the bead 4501 is located at the same vertical position on the inner surface of the wall of the cap path at all points around the perimeter of the cap 4550-1. In alternative arrangements the bead may follow an asymmetrical path around the perimeter of the cap 4550-1—that is, at any one point it may be below or above another point at a different location. It should be noted that the word 'vertical' is used to indicate the position of the bead between the rim and the base of the cap. The cap may not be aligned with the central axis vertical (the cap may be at an angle) as has been outlined above.

FIG. 45 shows the preferred form of the bead 4501, in which the bead 4501 has a substantially semi-circular cross section. Alternatively the bead 4501 may have any other cross section shape, for example a rectangular or oval cross section. The cross section shapes identified are only examples and should not be construed as limiting, since many shapes for the bead 4501 would suggest themselves to a person skilled in the art once they have read the description above. Preferably the bead 4501 is thicker in cross sectional thickness than the cross sectional thickness of the wall of the cap 4550-1, as best seen in FIG. 45. Even more preferably the bead 4501 is twice as thick as the wall of the cap 4550-1. Alternatively the thickness of the bead may be thinner than the thickness of the wall of the cap 4550-1. Preferably the thickness of the bead 4501 is uniform along the entire perimeter of the outer cap 4550-1. Alternatively the bead thickness may vary from point to point along the perimeter of the cap 4550-1. As a further alternative the bead 4501 may be thicker at one end of the rim and thinner at the other end. The varying thickness of the bead 4501 may be due random errors caused during the manufacturing processes or maybe deliberate to strengthen certain parts of the rim 4507

It has surprisingly been found that the addition of the bead 4501 to the inside wall of the cap 4550-1 adds strength and increased stiffness to the upper section of the cap 4550-1, in particular the rim 4507 and the surrounding area of the rim. The additional stiffness due to the bead 4501 helps to stop or reduce the amount the cap 4550-1 collapses into the airway 4540, while fitting the cap 4550-1 into a patient's nostrils. The cap 4550-1 flexes during fitting into a patient's nostrils. The load on a cap from the patient's nostril can cause the cap to partially or completely collapse or bend and block the airway 4540 or exit orifice 4520, if it were not fitted with a bead. Blockage of the airway or orifice restricts the amount of gases being delivered to a patient, increases the pressure drop across a cap and increases the difficulty of breathing through the cap. The bead 4501 helps to reduce or stop the cap 4550-1 from collapsing into the airway 4540 and prevents the exit orifice 4520 from being blocked or closed. Hence sufficient amount of therapy gases are delivered to the patient, there is less of a pressure drop across the cap 4550-1 and this reduces the difficulty of breathing through the cap 4550-1 and pillows portion 4500. This leads to added comfort for the patient and effective therapy for the patient.

Figure 46:
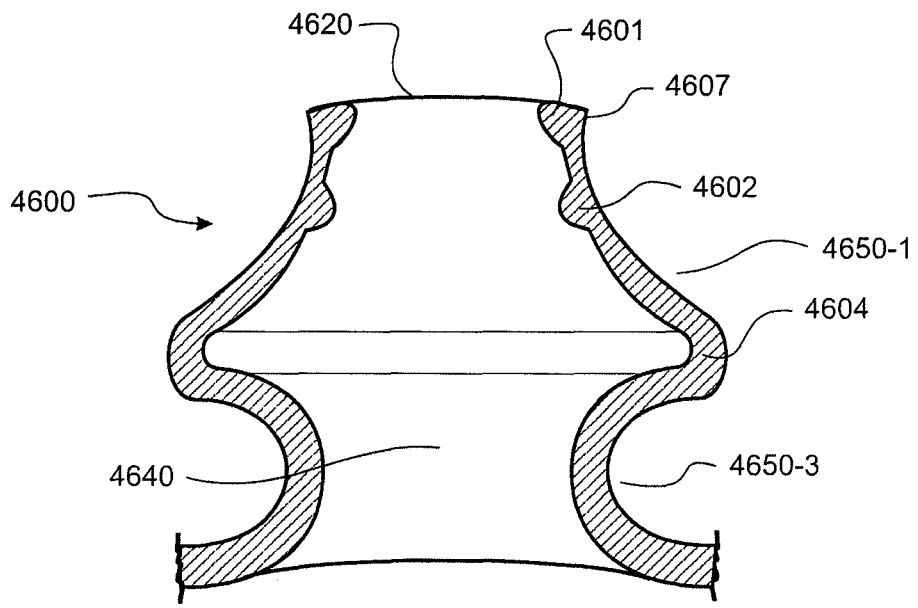
FIG. 46 shows a still further embodiment of a nasal pillow portion, the pillow portion comprising a stalk and a cap section, the cap wall having a uniform cross sectional thickness, the cap section having two beads applied to the inside surface of the cap, at least one of the beads extending inwards from the rim of the cap and the other of the beads extending inwards from the wall of the cap section below the first bead, the beads extending around the perimeter of the cap.

A further embodiment of the pillow portion is shown in FIG. 46.

This embodiment is substantially the same as that described above, except that the cap also has a second bead, below the first one. The cap 4650-1 therefore has a pair of beads 4601 and 4602 located on the inner wall of the cap 4650-1, with bead 4601 being the same as bead 4501 in the embodiment described above. Preferably both beads extend around the perimeter of the cap 4650-1 and both beads are located in the upper section of the cap 4650-1, as seen in FIG. 46. The second bead or lower bead 4602 extends from the cap wall around the perimeter of the cap 4650-1 and is located in the upper third of the height of the cap 4650-1. Preferably there is a space between the two beads. Preferably the space between the two beads is between 2 mm and 25 mm.

In the most preferred form the two beads 4601 and 4602 are identical to each other. Preferably both beads have a substantially semi-circular cross section. Alternatively both beads can have any other cross sectional shape, like a rectangular cross section, a triangular cross section, an elliptical cross section and so on. The beads 4601, 4602 are preferably twice the thickness of the wall of the cap 4650-1, and the beads are preferably the same thickness as each other. Alternatively the beads may both be the same thickness as the cap 4650-1 or both beads may thinner than the cap 4650-1 wall thickness. Preferably both beads are substantially parallel to each other along the perimeter of the cap 4650-1. Alternatively the beads 4601 and 4602 may not be identical to each other. Each bead may have a separate cross sectional shapes to each other—for example the first bead 4601 may be circular in cross section, while the second bead 4602 may be rectangular in cross section and so on. The beads may vary in thickness from each other—meaning one bead may be twice the thickness of the cap wall while the other bead may be thrice the thickness as the cap wall, or one bead may be thicker than the cap wall while the other bead may be thinner or the same thickness as the cap wall, and so on. In a further alternative the beads may not extend parallel to each other around the perimeter of the cap 4650-1, meaning at least one of the beads may vary in vertical position along the internal wall. Most preferably the first bead 4601 is generally circular around the perimeter of the cap 4650-1 and follows a straight circular path, while the second bead 4602 preferably follows a more elliptical path. The second bead 4602 may extend downward along the wall toward the stalk 4650-3 at some points along the perimeter of the cap and then return to its original path. A variety of combinations are available for design by combining the various features described above. The above descriptions are general descriptions of preferred features and any combinations of these will suggest themselves to persons skilled in the art.

Figure 47A:
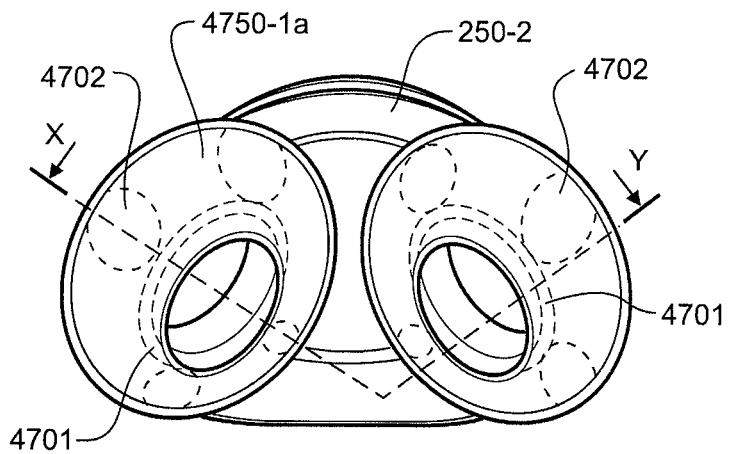
FIG. 47a shows a top view of a still further embodiment of nasal pillow section, the nasal pillow section comprising a pair of pillow portions connected to a pillow gasket portion with internal detail also shown, each of the pillow portions having a cap section that consists of an inner and an outer cap separated by an air gap, the inner cap having a bead around the rim extending outwards, and a series of holes passing through the wall of the inner cap, a pair of section lines X and Y for each of the pillow portions also shown.

A further embodiment of the pillow portion is shown in FIGS. 47a, b, and c.

Figure 47B:
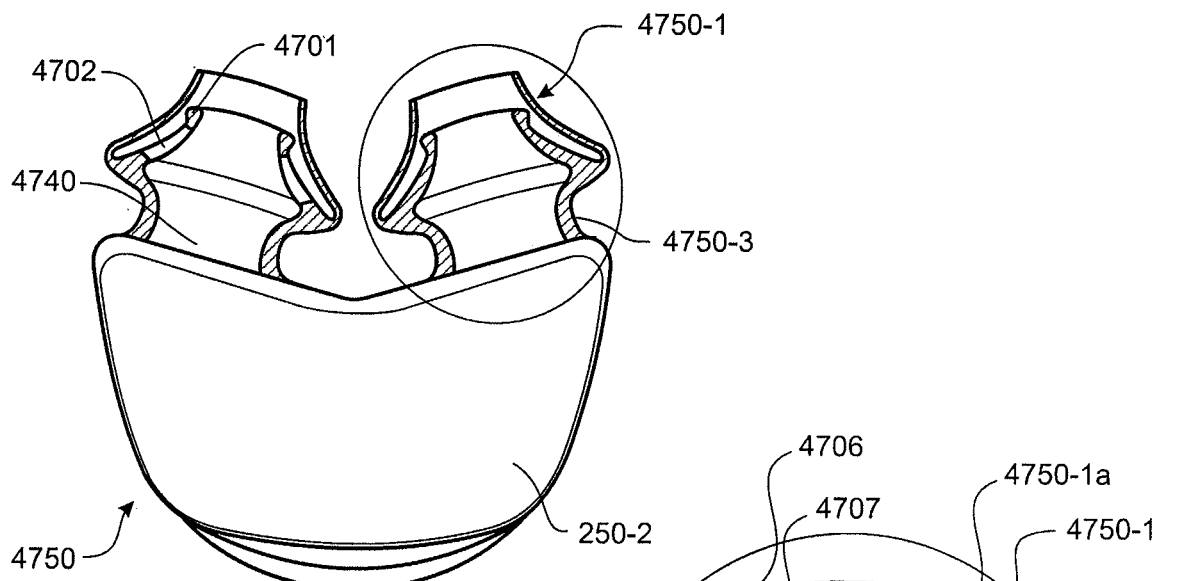
FIG. 47b shows a view of the nasal pillow section of FIG. 47a from the point of view of a user or patient, each of the nasal pillow portions shown in cross-section, the cross-section for each pillow taken along the section lines X and Y, the cross section showing the internal detail of the structure of each of the pillow portions.

In this embodiment, a pair of pillow portions is used in combination with pillow gasket 250-2, as shown in FIG. 47b. The pillow portions could alternatively be used with other pillow gaskets such as pillow gaskets 350-2 and 450-2 described above. The pillow portion and pillow gasket in combination form the pillow section 4700 of this embodiment.

The pillow portions consist of an inner cap 4750-1b and an outer cap 4750-1a, connected to a stalk 4750-3, with the base of the stalk fluidically or gaseously connected to the pillow gasket, and the inner and outer caps connected to the top of the stalk.

Figure 47C:
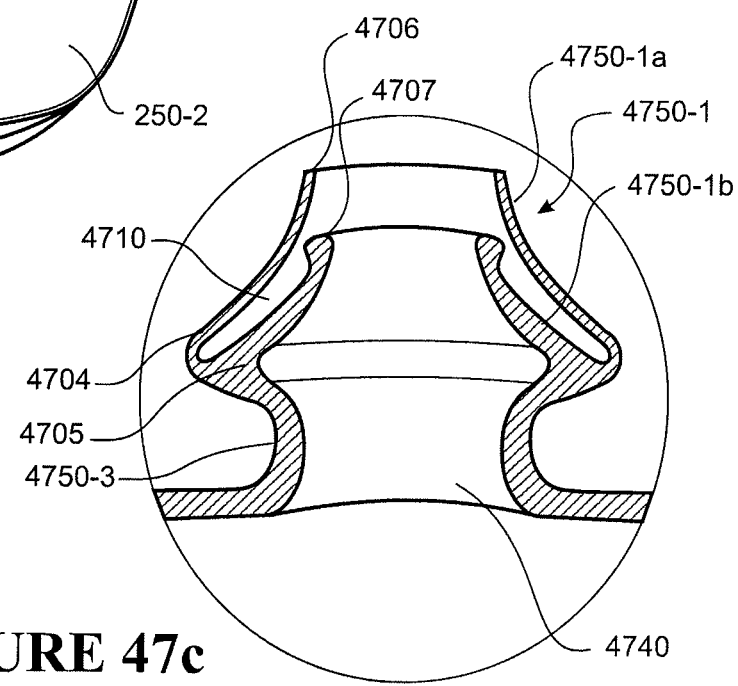
FIG. 47c shows a detail view of the right hand nasal pillow of FIG. 47b.

In the preferred form the wall of the inner cap 4750-1b is uniform in thickness. The wall of the outer cap 4750-1a is also uniform in thickness. Preferably the wall of the inner cap 4750-1b is much thicker than the wall of the outer cap 4750-1a, as seen in FIG. 47c. Alternatively the wall of the inner cap 4750-1b may taper in thickness, for example the wall of the inner cap 4750-1b may be thicker at its base 4705 and thinner at its rim 4707, or vice versa. Alternatively the wall of the outer cap 4750-1a may also be tapered in thickness, for example the wall of the outer cap 4750-1a may be thicker at its base 4704 and thinner at its rim 4706, or vice versa. In a further alternative form the outer cap 4750-1a may be thicker than the inner cap 4750-1b. Further alternatively the inner cap 4750-1b may taper in thickness while the outer cap 4750-1a may be uniform in thickness, or vice versa.

The outer surface of the inner cap 4750-1b preferably has a continuous bead 4701 that extends along the top edge or rim 4707 of the inner cap 4750-1b, as best seen in FIGS. 47a and 47c. Preferably the bead 4701 extends outward toward the outer cap 4750-1a from the outer surface of the inner cap 4750-1b as seen best in FIG. 47c. Preferably the bead 4701 extends around the perimeter of the inner cap 4750-1b. As a further alternative the bead 4701 may extend around the perimeter of the inner cap 4750-1b and may extend from any point between the base 4705 and the rim 4707 of the inner cap 4750-1b. The bead 4701 is preferably hemispherical or semi-circular in shape. Alternatively the bead may be any other shape for example, rectangle, triangle or oval. The bead is preferably of constant thickness along the entire length of the bead. Alternatively the bead may vary in thickness along the perimeter of the inner cap 4750-1b. In the alternative form the bead 4701 may be discontinuous along the perimeter of the inner cap 4750-1b. The bead 4701 may only be applied to areas of the inner cap 4750-1b that are weaker. In a further alternative form the bead 4701 may change shape at differing points along its perimeter, for example the bead 4701 may be circular along part of its length and then change to a triangular shape for another part of its length, and so on.

The outer surface of the inner cap 4750-1b also includes at least one, but preferably a plurality of openings 4702 around the outer surface of the inner cap 4750-1b, as seen in FIG. 47a. The openings 4702 are preferably circular. Alternatively the openings may be elliptical, oval, square or any other suitable shape. The openings 4702 are preferably positioned at regular intervals around the outer surface of the inner cap 4750-1b. Alternatively the openings 4702 may be positioned at irregular intervals around the inner cap 4750-1b. The openings are cut into the inner cap 4750-1b by any suitable process, for example milling or the like. Preferably the openings 4702 are all identical to each other. Alternatively the openings 4702 may be different from each other. The diameter or size of the hole in the opening 4702 may vary from opening to opening in an alternative form. The above descriptions are general descriptions of features and any combination of the described features is possible and falls within scope the invention.

Surprisingly it has been found that the addition of the bead 4701 to the inner cap 4750-1b strengthens or stiffens the upper section or rim area of the inner cap 4750-1b. The added strength or stiffness reduces the amount by which the inner cap 4750-1b collapses while the cap 4750-1 is being fitted to a patient's nose. Generally as the cap is being fitted into a patient's nose the cap deforms to conform to the shape of the patient or user's nostril shape. The deformation of the cap causes the outer cap 4750-1a and the inner cap 4750-1b to deform. Often the inner cap 4750-1b can deform and collapse into the airway 4740. The collapse of the inner cap 4750-1b into the airway 4740 can cause the airway 4740 to be completely or partially blocked. The blocked airway restricts the amount of gases flowing to the patient. This can lead to less gases being delivered to the patient and can lead to incorrect or ineffective therapy for the patient. The blocking or partial blocking of the airway 4740 can also increase the pressure drop across the entire pillow section, making it harder for a patient to breathe through the pillows portion. The added strength or stiffness to the upper part of the inner cap 4750-1b, due to the bead 4701, reduces the amount the inner cap 4750-1b collapses while fitting the pillows portion into the nostril of a patient. The reduced collapse of the inner cap 4750-1b, in particular the upper region of the inner cap 4750-1b, leads to the airway being open while fitting the pillows portion into a patient's or user's nostrils. This leads to a reduced pressure drop across the pillow section and makes it easier for a patient to breathe through the pillows portion or pillow section, leading to added comfort for the patient. Further the reduced blocking of the airway 4740 leads to more gases being delivered to a patient or user, leading to more effective therapy delivered to a patient.

Surprisingly it has also been found that the bead 4701 can act as a seat or support for the outer cap 4750-1a as the outer cap 4750-1a depresses or deforms as it is being fitted into the nostrils of a patient or user. The bead 4701 acts to support and reduce the amount the outer cap 4750-1a collapses into the inner cap 4750-1b. The bead 4701 acts as a load bearing support to support the weight of the outer cap 4750-1a as it collapses or deforms when being fitted.

Surprisingly it has also been found that by having the openings 4702 at least some of the air flowing through the airway 4740 can flow into the air gap 4710 or air space between the outer cap 4750-1a and inner cap 4750-1b. The bead 4701 acts to seal the air gap 4710 if the outer cap 4750-1a, in particular the upper part of the upper cap 4750-1a, deforms or collapses onto the bead 4701, while fitting the cap to into a patient's nostrils or in use. If the outer cap 4750-1a does deform on to the bead 4701 the air flowing into the air gap 4710 can partially inflate the lower part of the outer cap 4750-1a. The partial inflation of the outer cap 4750-1a allows the outer cap 4750-1a to contort and adapt to different shaped nostrils and provide a more effective seal with the users nostrils. In particular the partially inflated lower part of the outer cap 4750-1a, allows the upper part of the outer cap 4750-1a to contort and adapt to different shaped nostrils while letting the inflated lower part of the outer cap 4750-1a form a more effective seal with the nostrils of a user. This is advantageous as an effective seal leads to more effective therapy being delivered to a patient.

Figure 48A:
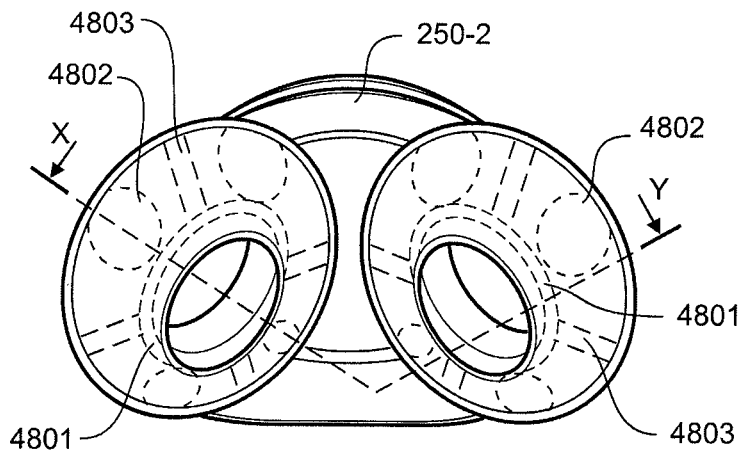
FIG. 48a shows a top view of a still further embodiment of nasal pillow section, the nasal pillow section comprising a pair of pillow portions connected to a pillow gasket portion with internal detail also shown, each of the pillow portions having a cap section that consists of an inner and an outer cap separated by an air gap, the inner cap having a bead around the rim extending outwards, and a series of holes passing through the wall of the inner cap, each of the pillow sections also having a number of ribs passing between the inner and outer caps within the air gap, a pair of section lines X and Y for each of the pillow portions also shown.

A further embodiment of the pillow portion is shown in FIGS. 48a, b, and c.

Figure 48B:
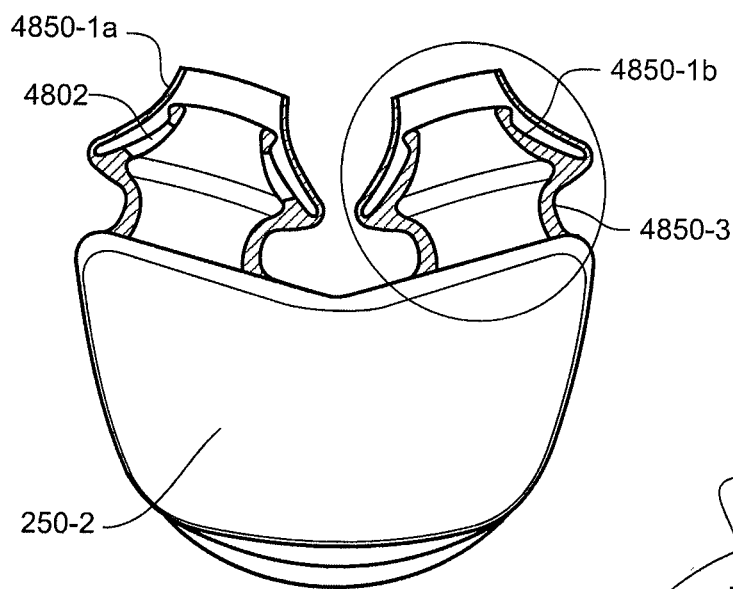
FIG. 48b shows the nasal pillow section of FIG. 48a from the point of view of a user or patient, each of the nasal pillow portions shown in cross-section, the cross-section for each pillow taken along the section lines X and Y, the cross section showing the internal detail of the structure of each of the pillow portions.
Figure 48C:
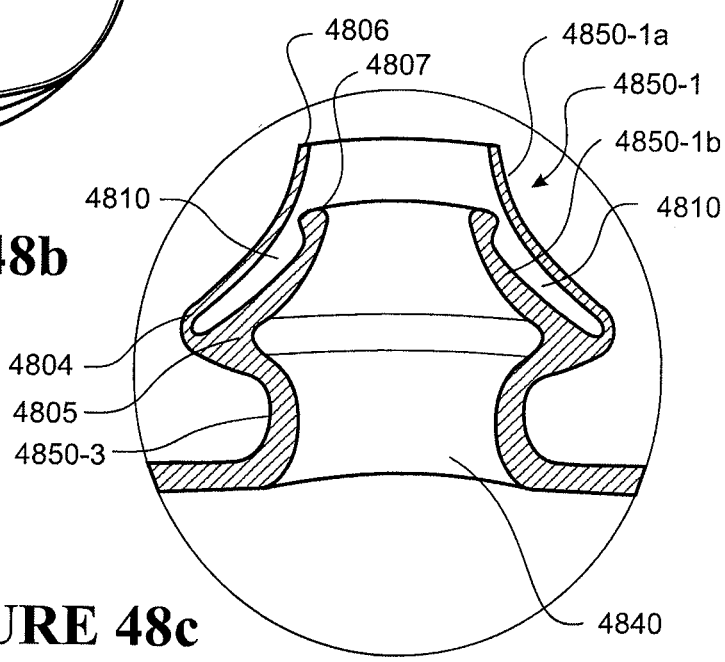
FIG. 48c shows a detail view of the right hand nasal pillow of FIG. 47b.

The embodiment shown in FIGS. 48a-c is identical to the embodiment (and variants thereof) described above in relation to FIGS. 47a-c, with structural differences as outlined below.

The outer surface of the inner cap 4850-1b also has at least one, and preferably a series of, ribs 4803 extending outward from the outer surface of the inner cap 4850-1b towards the inner surface of the outer cap. The ribs 4803 extend into the air gap 4810. Most preferably there are four ribs 4803 on the outer surface of the inner cap 4850-1b, interspersed between the openings 4802. Alternatively there may be any number between one and ten ribs 4803 placed on the outer surface of the inner cap 4850-1b. The ribs preferably extend from the bead 4801 to the base 4805 of the inner cap 4850-1b.

Alternatively the ribs 4803 may extend any distance along the outer surface of the inner cap 4850-1b. In a further alternative the ribs 4803 may extend from below the bead 4801 to just above the base 4805, or any point there between.

Preferably all the ribs are identical to each other. Preferably the ribs 4803 all extend the same distance along the outer surface of the inner cap 4850-1*b*. However alternatively the distance the ribs 4803 extend down the outer surface of the inner cap 4850-1*b* may vary from rib to rib. The ribs 4803 are preferably rectangular in cross-section. Alternatively the ribs may be any other suitable shape. The ribs are preferably placed at regular intervals around the outer surface of the inner cap 4850-1*b*. Even more preferably each rib 4803 is placed between two openings 4802, as seen in FIG. 48*a*. Alternatively the ribs 4803 may be placed at irregular intervals along the outer surface of the inner cap 4850-1*b*. As a further alternative the number of ribs 4803 between openings 4802 can vary. The ribs are preferably the same thickness as each other. Most preferably the ribs are twice the thickness of the outer cap 4850-1*a* wall thickness. Alternatively the ribs 4803 may be thinner than the outer cap wall or may be any other suitable thickness that fits between the inner cap 4850-1*b* and outer cap 4850-1*a*. As a further alternative arrangement the ribs may be added at specific points along the outer surface of the inner cap 4850-1*b*, in order to strengthen certain areas of the inner cap 4850-1*b*.

It has also been found that the addition of the ribs 4803 to the outer surface of the inner cap 4850-1*b* helps to strengthen or stiffen the inner cap 4850-1*b*. This added strength or stiffness further reduces the amount the inner cap 4850-1*b* collapses or deforms while fitting the cap into a patient's nostrils. The ribs 4803 also act as a further support for the outer cap 4850-1*a* and support the outer cap as it deforms or collapses. The ribs 4803 support the outer cap 4850-1*a* and stop it from collapsing into the inner cap 4850-1*b*. The ribs support the cap in a manner that still allows the outer cap 4850-1*a* to be partially inflated by air entering the air gap 4810, and retaining the advantages described earlier in relation to the embodiment described with reference to FIGS. 47*a-c*.

A further embodiment of the pillow portion is shown in FIGS. 49*a*, *b*, and *c*.

The embodiment shown in FIGS. 49*a-c* is identical to the embodiments described above in relation to FIGS. 47*a-c*, and FIGS. 48*a-c*, with specific structural differences as outlined below.

The embodiment shown in FIGS. 49*a-c* also includes at least one and preferably a series of ribs. In this variation or embodiment, the ribs 4903 are curved in profile, as seen in FIG. 49*a*. The ribs 4903 curve in a generally C shape when viewed in plan, as seen in FIG. 49*a*. The ribs 4903 curve outward from the top of the rib and curve inward toward the base of the rib, such that the top and base of rib 4903 are co-axial. Alternatively the ribs 4903 may be substantially S shaped.

A further embodiment of pillow portion is shown in FIGS. 50*a*, *b* and *c*.

In the embodiment of FIGS. 50*a-c*, a pair of pillow portions is used with pillow gasket 250-2, as shown in FIG. 50*a*. Alternatively, the pillow portions could be used with pillow gaskets 350-2 or 450-2. The pillow portion and pillow gasket in combination form a pillow section 5000.

This embodiment is formed from the same elements as form the third general form of the pillows portion (described above), with specific differences as described below.

The pillow portion shown in FIGS. 50*a-c* comprises a stalk 5050-3 and a cap portion 5050-1. Preferably each stalk 5050-3 also has at least one, but more preferably a plurality of ribs 5001 extending outward substantially perpendicularly to the body of the stalk(s), from the outer surface of the stalks 5050-3, as seen best in FIG. 50*c*. The ribs are preferably elongate extensions with rounded (hemispherical) ends. The ribs 5001 are preferably positioned at substantially the midpoint of each of the stalks 5050-3. Alternatively the ribs 5001 may be positioned at the base of the stalks 5050-3 or at the top of the stalk 5050-3. The ribs 5001 in the preferred form extend from the centre of the stalk 5050-3 outward and do not contact any other surface except the centre of the stalk 5050-3, when the apparatus is not in use.

Preferably there are two ribs 5001. Each of the ribs 5001 are preferably identical to each other in height, width and thickness. Alternatively the ribs 5001 may vary in height, thickness and width from each other. The ribs 5001 are preferably placed at regular intervals around the perimeter of the stalk 5050-3—i.e. if two only are used they are placed at diametrically opposed positions. Alternatively the ribs 5001 may be placed at varying or irregular intervals around the perimeter of the stalk 5050-3.

The purpose of the ribs is to strengthen the stalk 5050-3 while maintaining the flexibility of the stalks 5050-3. The stalks 5050-3 flex and contort as the cap 5050-1 is being fitted into the nostrils of the patient. The flexing of the stalk 5050-3 helps the cap to conform to the shape of a user's nostrils and form an effective seal. The stiffness added by the ribs 5001 allows the stalk 5050-3 to hold its shape once the cap 5050-1 is fitted into a user's nostril, thus allowing for a more effective seal. The strength and stiffness provided by the ribs 5001 to the stalk 5050-3 allows the stalk 5050-3 to exert a greater force against the face of a users leading to a more effective seal being formed with a user's face. The combination of flexibility of the stalk 5050-3 and stiffness from the ribs 5001 allows the stalks, and hence the cap to form a more effective seal with the user's nostrils. A more effective seal with a users nostrils results in more effective therapy being delivered to the patient or user.

The ribs 5001 are out of the pathway of the gases and hence they do not act to cause resistance to the flow of gases as the gases pass through the stalk 5050-3 and out of the cap 5050-1. Surprisingly it has been found that the ribs act to provide a suitable stiffness to the pillow portion, but do not adversely affect the ability of a user to breathe through the pillow portions. Further the added stiffness of the stalk 5050-3, reduces or prevents the stalk 5050-3 from collapsing and deforming. The reduced deformation means the airway 5040 remains open and unrestricted. The open airway 5040 reduces the pressure drop across the pillow portions and makes it easier for a patient to breathe through the pillow portion.

Surprisingly it has been found that the rib 5001 also acts to support the cap 5050-1 as it deforms or contorts while in use. The cap 5050-1 can deform or contort until the base of the cap 5050-1 rests on the ribs 5001. The support provided by the ribs 5001 limits the amount the cap 5050-1 deforms while in use leading to a more effective seal being formed between the cap 5050-1 and the nostrils of a user.

Figure 51C:
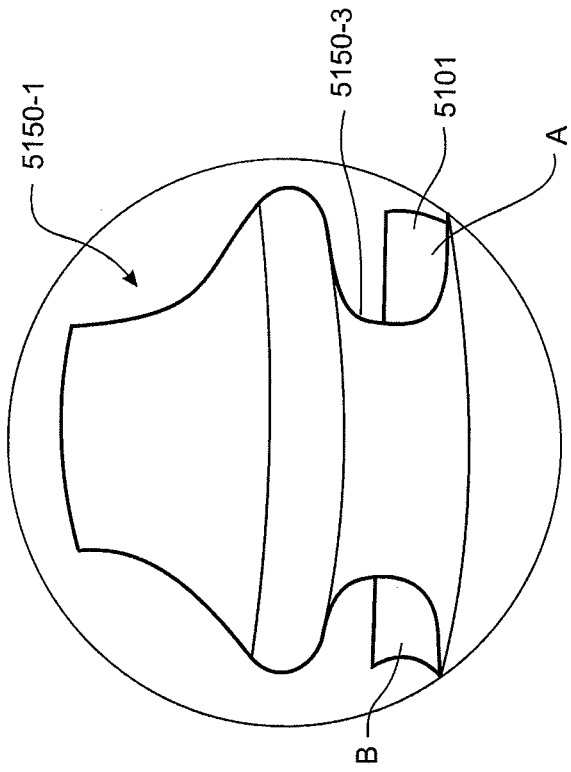
Figure 51A:
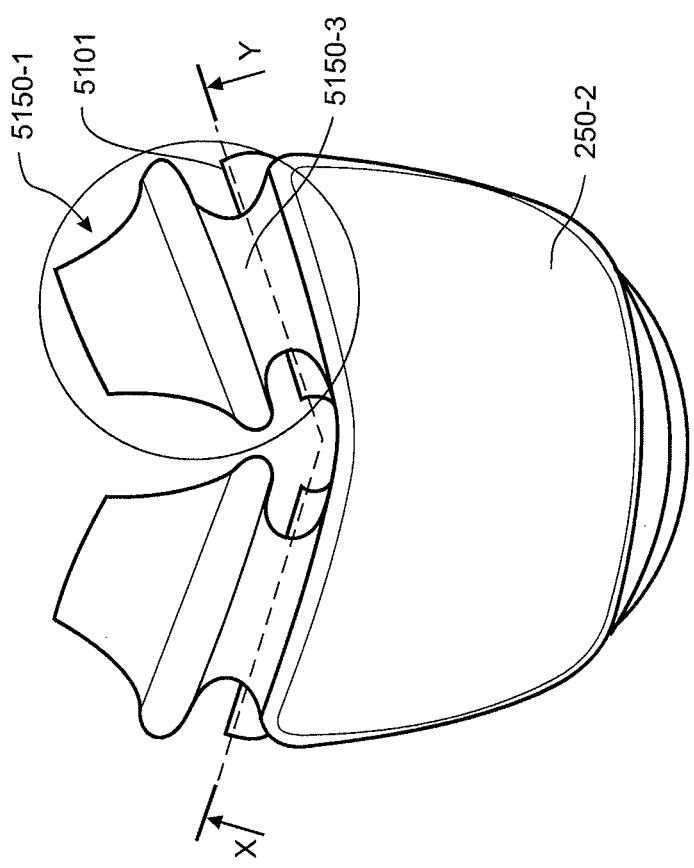
FIG. 51a shows a user or rear view of a still further embodiment of nasal pillow section, the nasal pillow section comprising a pair of pillow portions connected to a pillow gasket portion, each of the pillow portions comprising a stalk and a cap, the stalk having a series of ribs extending outwards from the outer surface of the stalk at or close to the base of the stalk, the ribs located at regular intervals around the perimeter of the stalk, a pair of section lines X and Y which bisect each of the stalks perpendicular to the main axis of the stalk also shown, section line X bisecting the left hand one of the stalks, section line Y bisecting the right-hand one of the stalks, the ribs generally extending upwards from the base of each of the stalk to approximately midway up each of the stalks.

A further embodiment of the pillows portion is shown in FIGS. 51*a*, *b* and *c*.

Figure 51B:
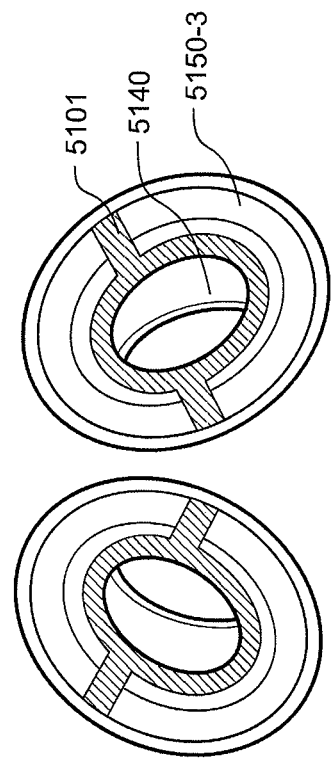
FIG. 51b shows a view of the stalks of FIG. 51a through the section lines X and Y looking upwards towards the top of the pillow portions.

The pair of pillow portions shown in FIGS. 51*a-c* is used with pillow gasket 250-2, as shown in FIG. 50*a*. However, the pillow portions can be used with pillow gaskets 350-2 or 450-2, as described earlier. The pillow portion and pillow gasket in combination form the pillow section 5100.

The embodiment as shown in FIGS. 51*a-c* is substantially the same as the embodiment described above in relation to FIGS. 50*a-c*. The pillow portion comprises a stalk 5150-3 and a cap portion 5150-1. Preferably each pillow portion also has at least one, but more preferably a plurality of ribs

5101. The ribs 5101 preferably extend outward in a substantially perpendicular manner from the outer surface of the stalks 5150-3. The ribs preferably extend outwards from the base of the stalk, where the stalk is connected to the gasket. Although in the preferred form the ribs are connected to or are formed integrally with the stalk, it can be seen that they could also be formed integrally with or be connected to the gasket, extending upwards from the gasket in the same direction as the axis of the stalk. Preferably the ribs 5101 extend upward for around one-third of the height of the stalk. If a pair of ribs are used, it is preferred that the outer edge of one of the ribs 5101 curves away from the centre of the stalk 5150-3 (see feature A in FIG. 51*c*), and the outer edge of the other rib curves toward the centre of the stalk 5150-3 (see feature B, FIG. 51*c*). It is preferred that a pair of ribs are used, and that they are located so as to be diametrically opposed around the stalk. The ribs 5101 are preferably identical to each other in height, width and thickness. Alternatively the ribs 5101 may vary in height, thickness and width from each other.

As the cap is placed into the nostril of a user, the stalk will compress and the base of the stalk will contact the upper surface of the rib or ribs. The ribs will act to support the cap, and to assist in stopping the cap and the stalk from collapsing. This provides advantages similar to those outlined above for the embodiment described in relation to FIGS. 51*a-c*.

A further embodiment of pillows portion is shown in FIGS. 52*a-c*.

In this embodiment, a pair of pillow portions is used with pillow gasket 250-2, as shown in FIG. 50*a*, although the pillow portion could also be used with pillow gaskets 350-2 or 450-2. The pillow portion and pillow gasket in combination form the pillow section 5200.

The embodiment as shown in FIGS. 52*a-c* comprises a stalk 5250-3 and a cap portion 5250-1 connected to a gasket (e.g. gasket 250-2) so that gases can flow between the two.

The embodiment shown in FIGS. 52*a-c* is substantially the same as that described above in relation to FIGS. 50*a-c*, except that the rib or ribs are located directly under the base of the cap rather than at the point where the stalk is connected to the gasket. The rib or ribs 5201 preferably extend outward from the outer surface of the stalks 5250-3, as seen best in FIG. 52*c*. The ribs are preferably elongate extensions. In the preferred form the ribs are integrally formed with both the stalk and the underside of the base of the cap. In the preferred form the height of the ribs 5201 is substantially half the height of the stalk 5250-3.

Preferably the ribs 5201 are positioned around the perimeter of the stalk 5250-3. It is preferred that a pair of ribs is used, and that the ribs 5201 are identical to each other in height, width and thickness. Alternatively the ribs 5201 may vary in height, thickness and width from each other. The ribs 5201 are preferably placed at regular intervals around the perimeter of the stalk 5250-3. Alternatively the ribs 5201 may be placed at varying or irregular intervals around the perimeter of the stalk 5250-3. If a pair of ribs is used, it is most preferred that these are placed at diametrically opposed positions around the stalk.

Having the ribs directly underneath the cap at the top of the stalk, rather than directly over the gasket and at the bottom of the stalk, provides the same advantages as have already been outlined in relation to the embodiment described with reference to FIGS. 51*a-c*. As the stalk is compressed in use, the rib or ribs act to support the stalk and to a certain extent the cap, and help to prevent the collapse of the stalk or the cap or both.

Figure 53C:
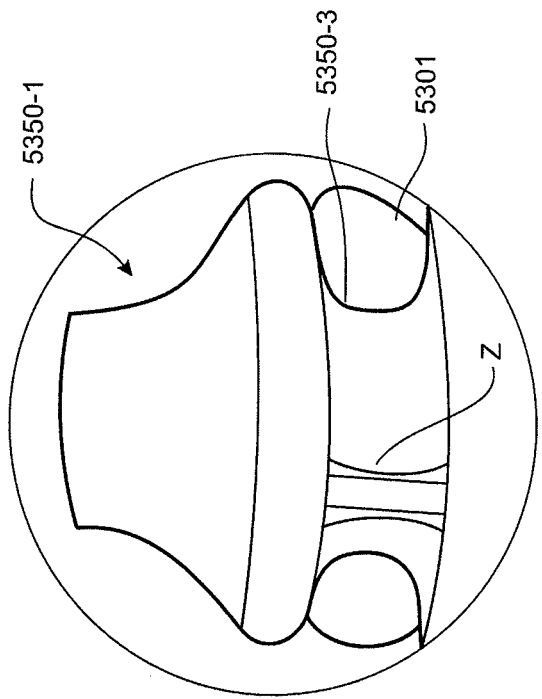
Figure 53B:
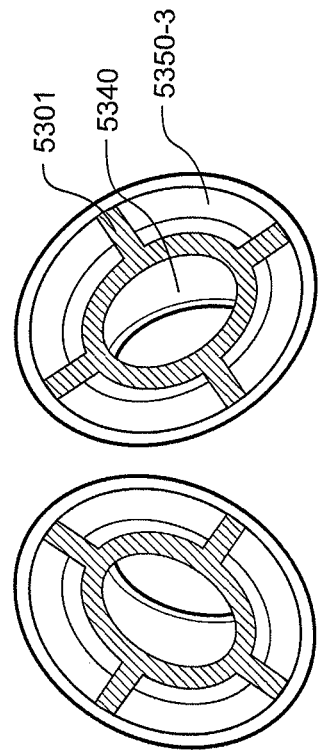
FIG. 53b shows a view of the nasal pillow section of FIG. 53a along the lines X and Y looking upwards towards the top of the pillow portions.
Figure 53A:
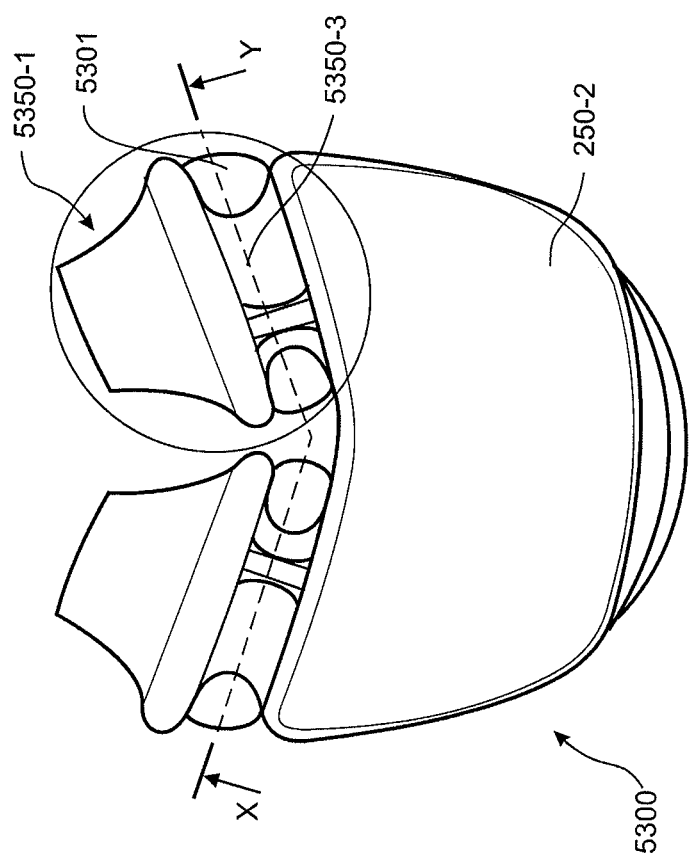
FIG. 53a shows a user or rear view of a still further embodiment of nasal pillow section, the nasal pillow section comprising a pair of pillow portions connected to a pillow gasket portion, each of the pillow portions comprising a stalk and a cap, the stalks generally curving and the ribs extending outward from the stalk and generally substantially identical to each of the other ribs in thickness and shape, the ribs all located at regular intervals around the perimeter of the stalk, the ribs extending from the lower edge of the cap to the base of the stalk the ribs curved in the horizontal plane, section lines X and Y which bisect each of the stalks also shown, section line X bisecting the left-hand stalk and ribs, and section line Y bisecting the right hand stalk and ribs.

A further embodiment of the pillow portion is shown in FIGS. 53*a*, *b* and *c*.

A pair of pillow portions is used with pillow gasket 250-2, as shown in FIG. 53*a*. The pillow portions can also be used with pillow gaskets 350-2 or 450-2.

The pillow portion and pillow gasket in combination form a pillow section 5300.

The embodiment of pillow portion as shown in FIGS. 53*a-c* comprises a stalk 5350-3 and a cap portion 5350-1, the lower end of the stalk connecting to the pillow gasket in such a manner that gases can flow from the gasket to the stalk, and the cap portion connected to the upper end of the stalk. In this embodiment, each stalk 5350-3 has at least one, and preferably a plurality of ribs 5301 which are located on the outside of the stalk. The ribs 5301 preferably extend outward from the outer surface of each of the stalks 5350-3, as seen best in FIG. 53*c*. The ribs are curved in shape with a flat outer surface or edge (furthest from the stalk). More preferably the ribs 5301 are crescent shaped when viewed in a side view. Preferably the body of the rib 5301 is at least partially concave, as seen in FIG. 53*c* (feature Z). The ribs 5301 extend between the underside or base of the cap 5350-1 and the base of the stalks 5350-3 (the upper surface of the gasket). Preferably the ribs 5301 are the same thickness as the wall of the cap 5350-1. Alternatively the ribs may be half the thickness of the cap wall. As a further alternative the rib or ribs 5301 may be thinner than the cap wall or less than half the thickness of the cap wall.

Preferably the ribs 5301 are positioned around the perimeter of the stalk 5350-3, at generally equidistant intervals. The ribs 5301 are preferably identical to each other in height, width and thickness. Alternatively the ribs 5301 may vary in height, thickness and width from each other. The ribs 5301 are preferably placed at regular intervals around the perimeter of the stalk 5350-3. Alternatively the ribs 5301 may be placed at varying or irregular intervals around the perimeter of the stalk 5350-3.

The purpose of the rib or ribs 5301 is to strengthen the stalk 5350-3 while maintaining the flexibility. The stalks 5350-3 flex and contort as the cap 5350-1 is being fitted into the nostrils of the patient. The flexing of the stalk 5350-3 helps the cap to conform to the shape of a user's nostrils and form an effective seal. The stiffness added by the ribs 5301 allows the stalk 5350-3 to hold its shape once the cap 5350-1 is fitted into a user's nostril, thus allowing for a more effective seal. The strength and stiffness provided by the ribs 5301 to the stalk 5350-3 allows the stalk 5350-3 to exert a greater force against the face of a user leading to a more effective seal being formed with a user's face. The combination of flexibility of the stalk 5350-3 and stiffness from the ribs 5301 allows the stalks, and hence the cap to form a more effective seal with the user's nostrils. A more effective seal with a users nostrils results in more effective therapy being delivered to the patient or user.

It has been found that having the ribs on the outside of the stalk is beneficial. The pressure drop across the pillow portion remains more consistent in use due to the ribs 5301 being on the outer surface of the stalk 5350-3. The ribs 5301 are out of the pathway of the gases and hence do not add to the flow resistance experienced by the gases as they pass through the stalk 5350-3 and out of the cap 5350-1. This can help to make it easier for a user to breathe through the pillow portions. Further, the support added to the stalk helps to reduce or prevents the stalk 5350-3 from collapsing and deforming.

A further embodiment of the pillow portion is shown in FIGS. 54*a-c*.

A pair of pillow portions according to this embodiment can be used with pillow gasket 250-2, as shown in FIG. 54*a*. The pillow portions could also be used with pillow gaskets 350-2 or 450-2.

The pillow portion and pillow gasket in combination form a pillow section 5300.

The embodiment of pillow portion as shown in FIGS. 54*a-c* comprises a stalk 5450-3 and a cap 5450-1. Preferably each stalk 5450-3 also has at least one, but more preferably a plurality of ribs 5401. The ribs 5401 preferably extend outward from the outer surface of the stalks 5450-3, as seen best in FIG. 54*c*. The ribs 5401 extend between the underside of the cap 5450-1 and the base of the stalk 5450-3. The ribs 5401 spiral around the stalk 5450-3 as the ribs extend down along the stalk 5450-3, as seen in FIGS. 54*a* and 54*c*. The ribs 5401 are preferably extend along the outer surface of the stalk in a spiral or helical shape. Preferably the ribs 5401 on one stalk 5450-3 spiral in opposite directions to the ribs 5401 on the opposite stalk 5450-3, as seen in FIG. 54*a* (clockwise and anticlockwise). The ribs are arranged so that the helical angles of one set of ribs on one stalk 5450-3 are opposite to the helical angle of the ribs on the other stalk 5450-3. The rib angles between two sets of ribs 5401 on two opposite stalks are effectively mirror images of each other.

Preferably the ribs 5401 are positioned around the perimeter of the stalk 5450-3. Each of the separate ribs 5401 are preferably identical to each other in height, width and thickness. Alternatively the ribs 5401 may vary in height, thickness and width from each other. The ribs 5401 are preferably placed at regular intervals around the perimeter of the stalk 5450-3. Alternatively the ribs 5401 may be placed at varying or irregular intervals around the perimeter of the stalk 5450-3. Preferably the helical angle, meaning the amount the rib curves around the stalk, is the same from rib to rib. Alternatively the helical angle may vary from rib to rib. In the most preferred form there are three ribs that extend between the underside of the cap 5450-1 and the base of the cap 5450-3 on each of the pillow portions.

The purpose of the rib or ribs 5401 is to strengthen the stalk 5450-3 while maintaining the flexibility of the stalks 5450-3. The stalks 5450-3 flex and contort as the cap 5450-1 is being fitted into the nostrils of the patient. The flexing of the stalk 5450-3 helps the cap to conform to the shape of a user's nostrils and form an effective seal. The stiffness added by the ribs 5401 allows the stalk 5450-3 to hold its shape once the cap 5450-1 is fitted into a user's nostril, thus allowing for a more effective seal. The strength and stiffness provided by the ribs 5401 to the stalk 5450-3 allows the stalk 5450-3 to exert a greater force against the face of a users leading to a more effective seal being formed with a user's face. The combination of flexibility of the stalk 5450-3 and stiffness from the ribs 5401 allows the stalks, and hence the cap to form a more effective seal with the user's nostrils. A more effective seal with a users nostrils results in more effective therapy being delivered to the patient or user.

This is substantially similar to the advantages described above in relation to the embodiment shown in FIGS. 53*a-c*. The spiral ribs 5401 to the outer surface of the stalks 5450-3 cause the stalk and cap to rotate as the cap is depressed while fitting the cap 5450-1 into a patient's nostrils. The cap 5450-1 and stalk 5450-3 rotate due to the ribs 5401 transmitting the force applied to the cap in a rotational direction due to the spiral shape of the ribs 5401. By varying the helical angle of the ribs 5401 the force transmission can be varied and the ribs can be angled so that the cap 5450-1 or stalk 5450-3 or both rotate in only one direction. This is advantageous because rotational movement in a single direction allows for a better seal with a patient's nostrils since the deformation of the cap 5450-1 or stalk 5450-3 or both is controlled. The rotational movement limits the lateral and axial deformation of the cap 5450-1 or stalk 5450-3, thus allowing the cap and stalk to remain in the correct alignment, leading to a more effective seal being formed and more effective therapy being delivered to the patient. The limited axial and lateral deformation of the cap 5450-1 or stalk 5450-3 or both also ensures that the airway 5440 remains unblocked since the cap 5450-1 or stalk 5450-3 will rotate under load rather than collapsing. The airway 5440 being unblocked leads to a reduced pressure drop across the cap and stalk resulting in more comfort for the patient and easier breathing for the patient through the pillow section 5400 or pillow portion or both.

A further embodiment of the pillow portion is shown in FIGS. 55*a-c*. The elements are substantially identical to those described above for the embodiment shown in FIGS. 54*a-c*. However, the ribs terminate at the middle of the stalk 5550-3. That is, the ribs extend downwards from the top of the stalk for approximately half the length of the stalk, rather than all the way to the base as described above for the embodiment of the FIGS. 54*a-c*.

Figure 56A:
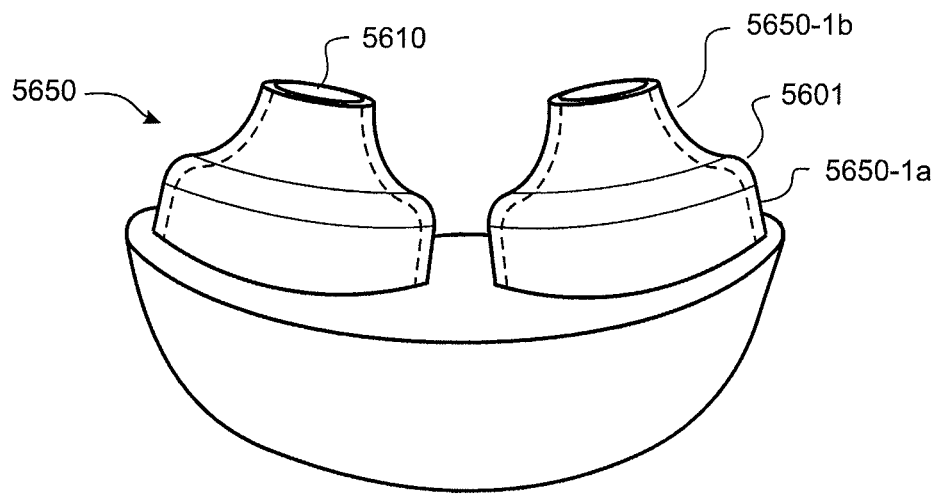
FIG. 56a shows a user or rear view of a still further embodiment of nasal pillow section, the nasal pillow section comprising a pair of nasal pillow portions connected to a nasal gasket portion, the pillow portions having a wide base section with parallel sides and a narrow cap section so that each of the pillow portions generally has a bottle neck shape, the pillow portions in this figure shown in an undepressed position.
Figure 56B:
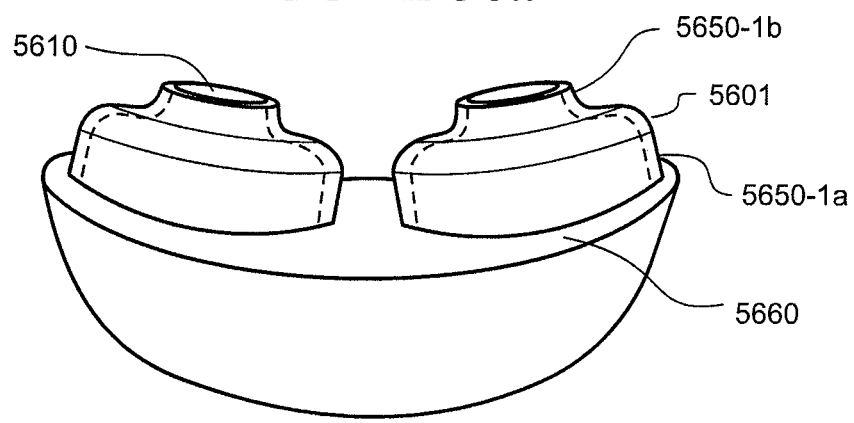
FIG. 56b shows a view of the nasal pillow section of FIG. 56a with the pillow portions depressed or pressed inwards along their main axis towards the gasket portion, the upper bottleneck section deforming downward due to the width of the base section.
Figure 56C:
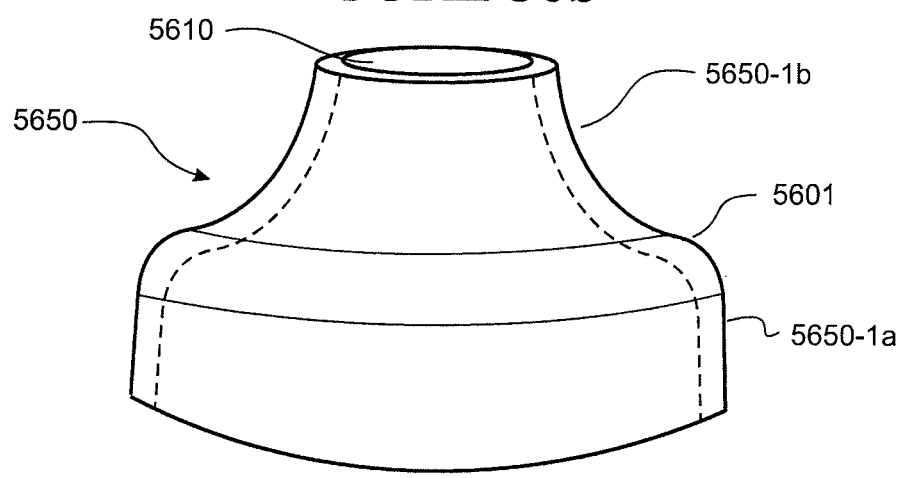
FIG. 56c shows a detail view of one of the pillow sections of FIG. 56a, in an undepressed state.

A further embodiment of the nasal pillow portions is shown in FIGS. 56*a*, 56*b* and 56*c*.

In this variation the pillows portion is shown as being used with a gasket portion 550-2. However the pillow portion can be used with other pillow gasket portions such as 250-2, 350-2 and 450-2 described in detail above.

In a similar manner to pillow gasket portions 250-2, 350-2 and 450-2 described in detail above, the pillow gasket portion 550-2 forms part of a patient interface for receiving gases from a gases supply. The pillow gasket portion 550-2 has an open lower portion that receives gases from a conduit. The main portion of the gasket portion 550-2 comprises a manifold section. The manifold section of the gasket portion 550-2 has a substantially flat top platform 5660, to which a pair of cap sections are attached. The cap sections will be described in detail below. Preferably the pillow portions 5650 are formed integral to the platform 5660.

Preferably the pillow portions 5650 extend directly from the top platform 5660. Each of the pillow portions 5650 has a base section 5650-1*a* that extends a short distance from the platform 5660, with a cap 5650-1*b* extending from the base section 5650-1*a*. The base section 5650-1*a* and cap 5650-1*b* together form the pillow portion 5650. The base section 5650-1*a* can preferably maintain its shape when loaded in a vertical direction. The base section 5650-1*a* acts as the support structure for the cap 5650-1*b*. The base section is shaped such that it resists compression, thus ensuring the entire pillow portion 5650-1 does not collapse and block the gases from reaching the user. The base section 5650-1*a* extends upwards (that is, substantially perpendicular to the surface of the top platform 5660) with parallel sides. The cap 5650-1*b* connects to the base section 5650-1*a* at the round 5601, at the upper extreme of the base section 5650-1*a*. The base section 5650-1*a* is preferably at least as wide or wider than the bottom of the cap 5650-1*b*.

The cap 5650-1*b* is capable of deforming and flexing to fit the nostrils of a user and create a seal. The cap 5650-1*b* is shaped to guide gases into a patient's nostrils. The cap 5650-1*b* has curved or sloping walls that narrow to an exit orifice 5610. Most preferably the cap 5650-1*b* is shaped substantially like a bottle neck as seen in FIG. 56*c*—that is, funnel shaped. The base section 5650-1*a* and cap 5650-1*b* define an airway. The airway is a hollow pathway that passes through the base section 5650-1*a* and the funnel 5650-1*b* and connects the orifice 5610 to the platform. The airway allows gases flowing from the gasket 550-2 to exit through the orifice 5610 by travelling through the airway. The pillow portion 5650-1 preferably has a uniform wall thickness along the entire pillow portion 5650-1. Alternatively the thickness of the pillow portion wall may vary. The pillow portion wall may be thicker at the base of the base section 5650-1a and thinner at the rim of the cap 5650-1b.

The sides of the pillow portion extend outwards (funnel-shaped) to the edges of the upper part of the base section.

By extending the pillows support structure (the base section) so that the upper part merges or connects to the outer edge of the pillow portion, rather than having a stalk or stem which is narrower than the pillow and the pillow connecting to the stem, the opening or air path through the base section or pillow support structure to the cap is held as open as possible and can be as wide as possible, which assists with minimising the pressure drop as gases pass through the pillows portion. As shown in FIG. 57b, the air path through the base and cap only begins to narrow once it enters the cap—it does not widen as it enters the cap as it does in the embodiments described above which use a stalk and a cap. That is, the gases path through said base section and said cap is as wide as possible through said base section and at the point of entry to said cap. This assists in maintaining an unblocked airway and helps to keep the orifice open in use and while the pillow portions are being fitted into a patient's nostrils. Also, by having a base section 5650-1a extending directly from the platform (that is, no stalk) and having the base section wider and more rigid than the cap 5650-1b, this can also help to support the cap 5650-1b as the cap contorts or deforms while being fitted into a user's nostrils. The cap contorting or deforming can cause the cap 5650-1b to deform in such a way that the airway becomes blocked. A blocked airway causes an increased pressure drop across the pillows portion 5650, resulting in increased breathing effort by the user or patient. The increased breathing effort makes the pillows portion difficult and uncomfortable to use and results in ineffective therapy. The increased breathing effort can also lead to respiratory problems and possible damage to the respiratory system of a user. The ability of the base section 5650-1a to move laterally also helps to keep the orifice 5610 open and airway unblocked.

The base section 5650-1a supports vertical loading and allows the cap to contract (as explained above) and the base section 5650-1a is flexible enough to move laterally in response of any forces with a horizontal component. The lateral movement of the base section 5650-1a causes the cap 5650-1b to contract and move laterally to take the shape of a user's nostril and maintain the orifice 5610 in an open position. The lateral movement allows the pillows portion 5650 as a whole to remain in the correct position as the user sleeps and moves. The lateral movement of the base section 5650-1a helps maintain the cap 5650-1b in the correct position to provide effective therapy. The lateral movement of the base section 5650-1a allows the caps 5650-1b to be fitted into nostrils with varying spacing between the nostrils. This allows the pillows portion 5650 to be more adaptive and allows the pillows portions to be used with a variety of different shaped noses.

Figure 57A:
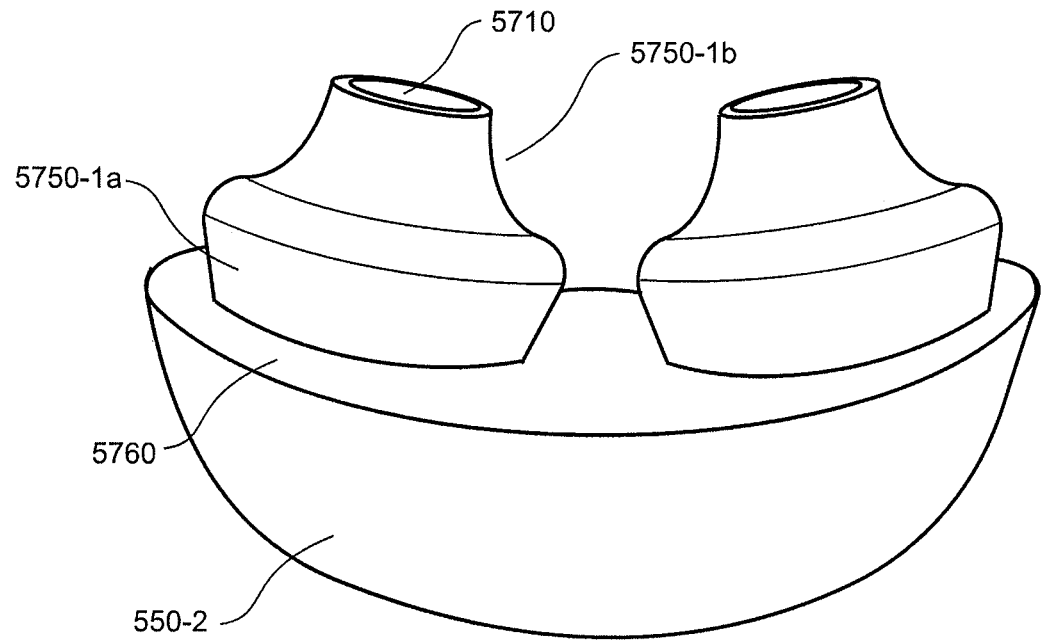
FIG. 57a shows a user or rear view of a still further embodiment of nasal pillow section, similar to that shown in FIGS. 56a-56c, except that in this variation the base section is slightly tapered inwards towards the point of connection with the gasket portion.
Figure 57B:
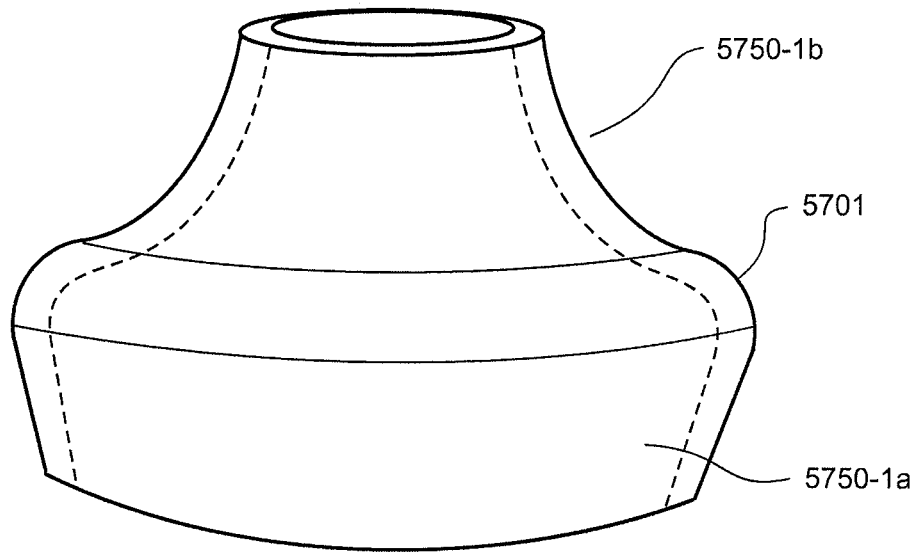

A further embodiment of the nasal pillow portions is shown in FIGS. 57a and 57b.

The general form of the nasal pillows portion is the same as the embodiment described above with reference to FIGS. 56a and 56b, with a structural difference as follows: The base section 5750-1a is shaped with tapering sides that taper inward towards each other from the top of the base section (or outwards from the bottom of the base section), as seen in FIG. 57a. The bottom of the base section is therefore narrower than the top of the base section 5750-1a. The gases path from the bottom of the base section to the bottom of the attached cap will therefore widen from the bottom of the base section to the top.

This construction offers similar advantages to those described above for the embodiment described with reference to FIGS. 56a and 56b. That is, it assists with minimising the pressure drop as gases pass through the pillows portion. The other advantages as outlined above also apply. However, the variation in the design also has the advantage that the strength and flexibility is improved.

Figure 58A:
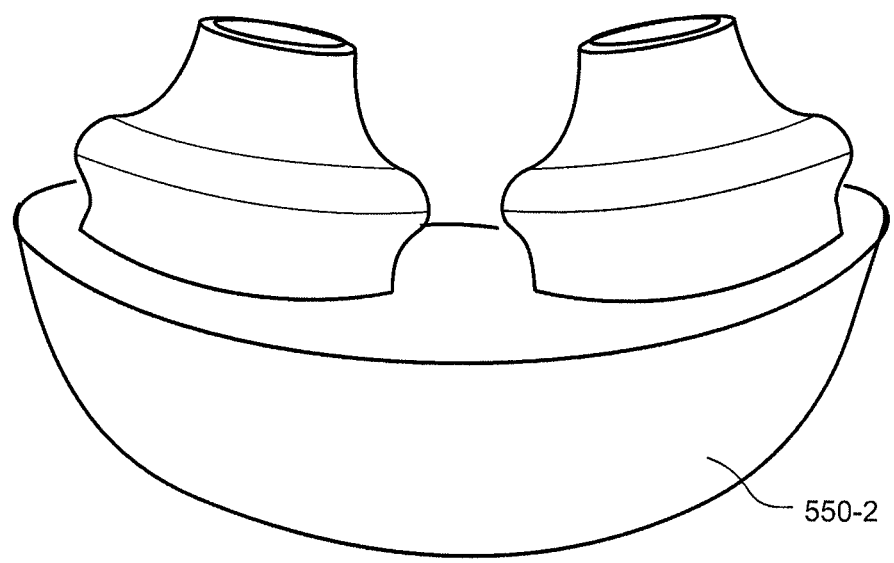
FIG. 58a shows a user or rear view of a still further embodiment of nasal pillow section, similar to that shown in FIGS. 56a-56c, except that in this variation the base section is tapered or angled inwards at the top, the tapered portion changing to a parallel sided portion approximately halfway along the base section.
Figure 58B:
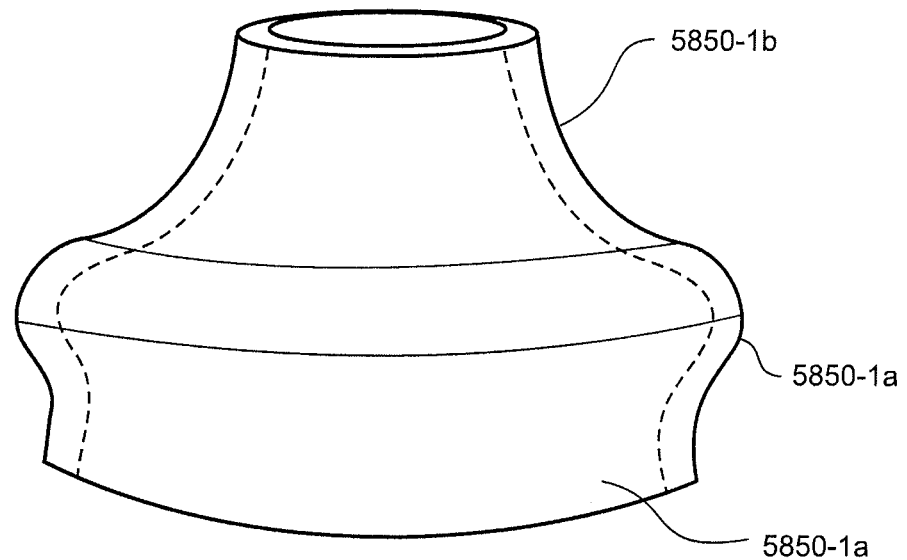

A further embodiment of the nasal pillow portions is shown in FIGS. 58a and 58b.

The embodiment shown in FIGS. 58a and 58b is substantially similar to that shown in FIGS. 56a-b, and 57a-b, with the following structural difference: The base section 5850-1a has tapering sides that extend upwards from the gasket portion substantially parallel to each other, and then curve outwards before connecting to the cap, as seen in FIGS. 58b and 58a. In appearance, there is a central bulge or wider section where the base section and the cap connect.

This construction offers similar advantages to those described above for the embodiment described with reference to FIGS. 56a-b and 57a-b. That is, it assists with minimising the pressure drop as gases pass through the pillows portion. The other advantages as outlined above also apply. However, the variation in the design also has the advantage that the strength and flexibility is improved.

A further embodiment of the nasal pillow portions is shown in FIGS. 59a and 59b.

The embodiment shown in FIGS. 58a and 58b is substantially similar to that shown in FIGS. 56a-b, 57a-b, and 58a-b, with the following structural difference: The base section 5950-1a has tapering sides that taper or angle inwards towards each other, so that the base section has a wider bottom than top (where it is connected to the cap). This is best seen in FIGS. 59a and 59b. The sides of the base section 5950-1a are angled outward (from the top) such that the lower portion of the base section 5950-1a is wider than the upper portion of the base section 5950-1a.

This construction offers similar advantages to those described above for the embodiment described with reference to FIGS. 56a-b and 57a-b. That is, it assists with minimising the pressure drop as gases pass through the pillows portion. The other advantages as outlined above also apply. However, the variation in the design also has the advantage that the strength and flexibility is improved.

A further embodiment of the nasal pillow portions is shown in FIGS. 60a and 60b. The embodiment shown in FIGS. 58a and 58b is substantially similar to that shown in FIGS. 56a-b, 57a-b, and 58a-b, with the following structural difference: The base section 6050-1a wall is rounded outwards at the centre so that the base section is wider at the central portion of the base section than at the upper and lower ends. That is, the base section 6050-1a is wider at the middle of the base section than at the upper and lower ends—the base section bulges outwards in the centre before narrowing inwards at each end.

This construction offers similar advantages to those described above for the embodiment described with reference to FIGS. 56a-b, 57a-b 58a-b, and 59a-b. That is, it assists with minimising the pressure drop as gases pass through the pillows portion. The other advantages as outlined above also apply. However, the variation in the design also has the advantage that the strength and flexibility is improved.

For the embodiments described above with reference to FIGS. 56-60, it is preferred that the wall thickness of the base section is substantially constant over the height of said base section air path through the base section is substantially defined by the contours of the walls of said base section.

A variation of the embodiments described above in relation to FIGS. 56-60 of the nasal pillow portions is shown in FIGS. 61a and 61b.

The nasal pillow portion of FIGS. 56a to 56c is shown in cross-section in FIG. 61b. The cross-section lines X and Y are shown in FIG. 61b. In this variation, four ribs are equally spaced around the perimeter of the pillow portion, extending inwards from the wall of the pillow portion towards the centre of the pillow portion generally radially.

In the preferred embodiment shown in FIGS. 61a and b, the ribs extend from the bottom of the base section, upwards to a point just above the bottom of the cap. The inner edge or surface of the rib or ribs curves inwards—that is, it curves towards the central axis of the pillow portion. As can be seen in FIG. 61b, the nozzle or opening at the top of the cap has a certain width, and it is preferred that the ribs do not extend inwards from the walls far enough to overlap with the edges of this. That is, the maximum size of the ribs would be on or before this interference point. The edge or perimeter of this interference point would be the perimeter of a circle defined by looking straight down the axis of the pillow portion from the top opening of the cap from above. That is, the maximum inwards extent of the rib or ribs is the perimeter of a circle defined by looking straight down the axis of the pillow portion from the top opening of the cap from above.

The ribs 6101 are preferably thicker than the wall of the pillow portion. More preferably the ribs 6101 are twice the thickness of the pillow portion wall. As an alternative the ribs 6101 may be thinner than the pillow portion wall. The ribs 6101 are preferably all substantially identical to each other in terms of dimensions and shape. However the ribs 6101 may vary from each other in thickness, width, length and height. The ribs 6101 are preferably arranged at equal intervals around the perimeter of the pillow portion. Alternatively the ribs 6101 may be arranged at irregular intervals.

The addition of the ribs 6101 offers the same advantages as described previously for fifty second to fifty sixth embodiments. The addition of the ribs 6101 strengthens and stiffens the base section and cap of the pillow portion. The ribs 6101 help to prevent the base section from deforming or folding when the pillow portions are being fitted or while in use, by acting as a strengthening member to stiffen or strengthen the base section. The ribs also act to support and strengthen the cap from deforming and collapsing into the airway or blocking the orifice. This ensures the airway is unblocked and reduces the pressure drop across the pillow portions, making it easier for a user to breathe through the pillow portions.

A variation of this arrangement is shown in FIGS. 62a and 62b. In this variation, instead of the inner surface or edge of the ribs being rounded inwards towards the centre axis of the pillow section, the inner surface or edge follows a straighter line between the bottom of the base section and a point just above the bottom of the cap. The inner surface or edge of the rib or ribs can be substantially straight or even slightly curved outwards towards the inner wall of the pillow portion.

A further embodiment of the nasal pillow portions is shown in FIGS. 63a, 63b and 63c.

In this variation a pair of pillows portions 6350-1, similar to those described above with reference to FIGS. 56a-c is shown being used with a gasket portion 550-2.

The base portions 6350-1a are substantially the same as the base portions 5650-1a described with reference to FIGS. 56a-c. The caps connected at each upper end of the base portions are different as described below.

The cap 6350-1b is substantially flexible and supple and capable of deforming and flexing to fit the nostrils of a user to create a seal. The cap 6350-1b is shaped to guide gases into a patient's nostrils with curved or sloping walls that narrow to an exit orifice 6310. Most preferably the cap 6350-1b is shaped substantially like a bottle neck as seen in FIG. 63c. The base portion 6350-1a and cap 6350-1b define an airway or hollow pathway that passes through the pillow portion to allow gases flowing from the gasket 550-2 to exit through the orifice 6310. It can be seen from FIG. 63a that there is an intermediate portion 6301 which extends upwards from the base portion 6350-1a, with the perimeter of the bottom of the intermediate portion 6301 generally congruent with the perimeter of the upper part of the base portion. The bottom of the cap, which is the widest part of the cap, fits inside the intermediate portion so that the intermediate portion generally forms a rampart, parapet or boundary wall around the top of the base portion, with the bottom of the cap inside this boundary wall.

The boundary wall formed by the intermediate portion 6301 acts to form a secondary seal with the users nostrils once the caps 6350-1b are fitted into the nostrils of the user. The intermediate portion 6301 abuts against the outside of the nose to form a seal. The border of this secondary seal is shown in FIGS. 65a and 65b as the dotted line B.

It should be noted that the three separate parts forming the pillow portion (the base portion, the intermediate portion and the cap) are in the preferred embodiment formed as one single piece—they are not formed separately and then connected together.

A variation to the nasal pillow portions shown in FIGS. 63a, 63b and 63c is shown in FIGS. 64a, 64b and 64c, and the specific structural difference are described in detail below.

The rampart, parapet or boundary wall formed by the intermediate portion 6401 of the base portion 6401 of FIGS. 64a and 64b is constructed differently to the intermediate portion 6301 as shown in FIGS. 63a and 63b and described above. The intermediate portion 6401 and the base portion and cap are generally similar, but in the embodiment shown in FIGS. 64a and 64b, the intermediate portion is substantially flexible and soft and deforms when it abuts against the nostrils of a user. The deformation assists with allowing the intermediate portion 6401 to conform to the shape of a user's nose and form a secondary seal. The deformation increases the effective area of the edge, as shown by dotted line C in FIG. 65b. This increase in the effective area assists in the creation of a larger secondary seal.

A further embodiment of a nasal pillow portion is shown in FIGS. 66a and 66b.

The nasal pillow portion shown in FIGS. 66a and 66b can be used with pillow gasket 250-2 (not shown), or alternatively with a different pillow gasket such as for example pillow gasket 350-2 or 450-2, as described above.

The nasal pillow portion 6600 of this embodiment consists of two main parts—a stalk 6650-3 and a cap 6650-1. The pillow portion is connected to the pillow gasket at the base or lower end of the stalk.

The cap 6650-1 of this embodiment is connected to the top of the stalk 6650-3. The stalk forms a gases path so that gases can pass from the pillow gasket through the stalk into the cap, the gases exiting the cap through an aperture 6610 at the top of the cap. Internally, the cap 6650-1 has an enlarged cavity 6603, which has a width slightly wider than the width or diameter of the inside of the stalk—the diameter or width of the air passage.

The cap 6650-1 also has a flange portion 6601, which in the preferred embodiment is formed integrally with the cap, around the lower part of the cap, sloping downward and outward so that the upper part of the stalk is surrounded by the flange portion 6601, which forms an overhanging 'eve', mantle or ledge. The flange portion 6601 is substantially flexible. The pillow portion 6600 also has at least one, but more preferably a plurality of ribs 6602. Most preferably the pillow portion 6600 includes four ribs 6601. The ribs 6601 are located underneath the flange portion and extend between the underside of the flange portion and the outer surface of the stalk. The ribs extend from the stalk 6650-3 to the edge of the flange portion 6601, as seen in FIG. 66*b*. It is preferred that the lower edge or surface of said rib or ribs does not extend downwards further than the lower edge of said flange. Preferably the width of the ribs 6602 is greater than or equal to the thickness of the wall of the cap 6650-1. More preferably the width of the ribs 6602 is equal to the thickness of the cap 6650-1 wall. Preferably the ribs 6602 are identical to each other in shape and dimensions. Preferably the ribs 6602 are spaced apart at equal intervals to each other around the stalk, extending radially outward. In the preferred embodiment, as shown in FIG. 66*a*, two ribs are located towards one side of the cap 6650-1 and the other two ribs are located at the opposite end, as shown in FIG. 66*a*.

The purpose of the ribs 6602 is to hold the flange away from the stalk in use. The ribs 6602 act to support the flange against loads exerted upon the flange portion 6601. The flange portion 6601 generally deforms or folds while the cap 6650-1 is being fitted into a user's nostrils. If there is too much folding or deforming, the seal can become ineffective. The flange portion 6601 folding can also cause the flange portion 6601 to bear on the stalk 6650-3 and may lead to the stalk 6650-3 pinching inward and constricting the airway 6640. Surprisingly it has been found that the addition of the ribs to the flange portion 6601 localises movement of the cap 6650-1 to the upper areas of the cap 6650-1. The upper part of the cap 6650-1 flexes and deforms in order to conform to the shape of a user's nostrils. This leads to reduced movement of the flange portion 6601 and stalk 6650-3 resulting in a minimising of the leak of gases around the opening of the nostrils. The flange portions 6601 help to create a more effective seal with the user's nostrils.

A further embodiment of the nasal pillow portion is shown in FIGS. 67*a* and 67*b*. The embodiment shown in FIGS. 67*a* and 67*b* is substantially the same as that described above in relation to FIGS. 66*a* and 66*b* above, with specific structural differences as outlined below.

For the embodiment described in relation to FIGS. 66*a* and 66*b*, the internal cavity 6603 or enlarged cavity 6603 is described as being slightly wider than the internal width or diameter of the stalk. In the embodiment shown in FIGS. 67*a* and 67*b*, the internal walls of the pillow portion which form the gases path between the base of the stalk and the aperture 6710 are straight-sided or parallel, or possibly slightly tapered towards on another from the bottom to the top. The aim of this straight-sided or tapered arrangement is to reduce the pressure drop across the interface.

3.16 Lexicon

'Supple' or 'flexible' as these words are used in this specification with reference to the nasal pillows or pillow portions should be taken to mean that the item can be substantially and repeatedly deformed, for example, by a user pinching, squashing or crushing it in their hand, with the item returning to its original shape with little to no plastic deformation occurring. An item having a rectangular or square cross-section, with a thickness of 1-2 mm, a width of e.g. 1 cm, and a length of 5 cm or more, formed from a 'supple' or 'flexible' material as it should be understood in this specification, will, if held at one end, bend to an extent easily appreciable to the naked eye—i.e. it will bend at least 2-3 mm. The most preferred materials having 'supple' or 'flexible' properties as they should be understood within the context of this specification will, if formed in the manner referred to above, bend completely—that is, bending enough so that the unsupported end points substantially directly downwards. If the material does not bend to an appreciable extent, then it is a rigid or semi-rigid material for the purposes of this specification—see below. It should also be understood that 'flexible' is intended to mean a material that is soft, supple and flexible enough that an item formed with the dimensions outlined above (1-2 mm×10 mm×50 mm) could be rolled into a solid tube (i.e. with no central 'hollow' portion), and when the tube is unrolled there would be little to no plastic deformation of the material.

'Rigid' or 'semi-rigid' as it is used in this specification should be understood to mean that an item described in this manner can be elastically deformed, but that it would require application of an external force apart from gravity (i.e. more than its own weight) to do so—a 'rigid' or 'semi-rigid' item will not collapse or bend under its own weight, in any orientation. It is noted that all items usually described as rigid do have a certain degree of elasticity, but the elastic limit will normally be reached before the elastic deformation of the rigid material is appreciable to the naked eye. Glass, for example, will shatter before the average person is able to appreciate that it has elastically deformed at all. An item having rectangular or square cross-section, with a thickness of 1-2 mm and a length of up to 10 cm, formed from a 'rigid' or 'semi-rigid' material as it should be understood in this specification, will not bend to an extent easily appreciable to the naked eye. As an example, the arms of the Fisher & Paykel Opus™ interface or the ResMed Mirage Swift™ II interface are around 10-11 cm long and have a thickness of less than 1 mm. The arms of these devices are formed from a plastic having a rigidity so that they will not bend under their own weight if held at one end, and for the purposes of this specification can be considered to be 'rigid' or semi-rigid'.

'Substantially vertically downwards' as it is written in this specification should be interpreted as not necessarily meaning absolutely vertical—an angle of 10-20 degrees or more off-vertical lies within the meaning of 'substantially vertical' as it is used in this specification.

It should also be noted that 'downwards', 'outwards', 'inner', 'outer', 'rear', 'front', and similar terms as they are used in this specification refer to the mask being worn by a user who is standing up. For example, 'inner' and 'rear' refer to that side of the interface nearest a users face in use. However, in use the interface is intended to be used by a user who is asleep and will be lying on a bed, either on their back, front or side. The convention referred to above (a user standing) has been adopted for ease of reference.

It should also be noted that the term 'interface' or 'interface assembly' as it is used in this specification refers to any combination of the interface core section 11, 311 or 411, the interface conduit 19, and the headgear assembly 12—that is, for the preferred embodiment, the term 'interface' could refer to the interface core section 11 with or without the headgear 14, and with or without the supply conduit 19.

The terms 'swivel' and 'rotate' have their normal dictionary definitions. However, it should specifically be noted that as used in this specification, 'rotate' means that the item turns around an axis or centre point and movement is in a single plane. In contrast, 'swivel' as used in this specification should be taken to mean that the item is capable of movement in more than one plane.

The thickness of the wall of either the inner cap or outer cap is the cross sectional thickness, meaning the thickness of the wall when viewed in cross section.

The thickness of the bead or any other feature refers to the cross sectional thickness, meaning the thickness of the bead when viewed in cross section, unless otherwise stated.

The term tri-type shape describes a generally triangular type shape. It is the shape formed from the lines joining each vertex point of a triangle to the centre.

The term user and patient can be interchangeably used in this specification. They both have the same meaning in terms of the specification.

4. Ribbed Nasal Pillows

Nasal interfaces with reference to FIGS. 68 to 75 will now be described.

4.1 Headgear

FIG. 68 and FIG. 69 show a preferred embodiment of a nasal interface 6850, comprising a headgear 6821 and nasal cannula assembly 6802. The headgear 6821 is worn by the user in use, and holds the nasal cannula assembly 6802 in the required position. The headgear 6821 in the preferred form is comprised of headgear straps 6835, 6836, 6837, 6838, and two arms 6833, 6834 which are connected on each side of the nasal cannula assembly 6802. The two arms and manifold are substantially rigid, or at least more rigid than the headgear straps.

It should be noted that many equivalent forms of headgear known in the art may be suitable for use with the nasal cannula assembly 6802 of the present invention. What has been described above is the preferred form for use with the nasal cannula assembly 6802 of FIGS. 68 to 75.

4.2 Nasal Cannula Assembly

The nasal cannula assembly 6802 of the preferred embodiment of the invention shall now be described in detail with reference to FIG. 68, and FIGS. 70a and 70b. The nasal cannula assembly 6802 is comprised of a manifold 6822 and a pair of nasal pillows 6840.

The manifold 6822 is preferably made from a substantially hard (rigid) plastics material, such as polypropylene, polycarbonate or acetyl, or other similar rigid materials. Alternatively, the manifold may be made from a semi-rigid material such as a thermoplastic elastomer, silicone rubber or urethane, or other similar semi-rigid material.

In use, the manifold 6822 is located adjacent the patient's nose, below the nose and in front of the patient's philtrum.

The two arms 6833, 6834 of the headgear are attached to the manifold 6822 in use. In the preferred form they are integrally moulded with the manifold 6822, one arm being moulded to a first end of the manifold, and the second arm being moulded to a second end of the manifold.

Alternatively, the two arms may be connected to form a continuous elongate member, the elongate member being attached to the manifold. The elongate member may be attached to a front surface of the manifold, passing across the front of the manifold. Alternatively the elongate member may be attached to any other surface of the manifold, for example passing underneath the manifold.

When a user is wearing the nasal interface 6850, the load of the nasal cannula assembly is transferred away from the user's nose and onto the cheek regions of the user.

The manifold 6822 has an inlet 6828 which in use receives a flow of respiratory gases from the gases conduit 6803. In the preferred embodiment, the inlet 6828 comprises a semi-tubular projection from the main body of the manifold 6822, which in the preferred form is adapted to receive joint end 6861 of a connector 6860 in use. In the preferred embodiment, the connector 6860 is an L-shaped tube, with end 6861 shaped as a ball joint. The projection 6828 forms a socket for the end 6861 of the connector 6860 and in use the connector 6860 can swivel within the socket. The other end of the connector 61 is attached to gases conduit 6803 to allow for gases to be passed into the manifold 6822.

In alternative embodiments, the manifold 6822 may not include projection 6828 and the inner surface of the manifold 6822 may be curved and form a socket for receiving the connector joint end 6861. In other alternative forms, other types of connection may be utilised between the manifold 6822 and the connector 6860, such as a flexible piece of silicone, or other appropriate connection mechanism.

The flexible joints described above allow the conduit 6803 to swivel and move relative to the manifold 6822. In this manner, small movements of the connected conduit 6803 and the headgear 6821 can be absorbed without movement of the nasal pillows 6840 in the nostrils or nares of the patient 6801. In the preferred form, the body of the conduit 6803 slightly upstream of the nasal cannula assembly 6802 may be attached to any of the headgear straps in order to hold it out of the way.

It should be noted that the connection between the manifold 6822 and the conduit 6803 as described above allows the conduit to be flexed or rotated to allow for minor 'in use' movements of the conduit without causing the dislodgement of the nasal pillows 6840 of the nasal cannula assembly 6802 from the user's nares. However, this is not an essential part of the invention, it is a preferred variant.

4.3 Nasal Pillows

The nasal cannula assembly 6802 of the present invention includes two nasal pillows 40, which are shown connected to the manifold 6822 in FIG. 74, and which are shown in exploded view in FIGS. 70a and 70b. A single nasal pillow 6840 is shown in FIG. 71. Each of the nasal pillows 6840 is frustoconical in shape and in use rests against the patient's nostrils, to substantially seal against the patient's nostrils.

Each nasal pillow 6840 is composed of two main parts: a stem or tubular base 6841 and a nasal puff 6849. The nasal puff 6849 is supported on the integral tubular base 6841. The tubular base 6841 and nasal pillow 6840 are preferably integrally moulded as a one piece item from a substantially flexible plastics material. In the preferred form this material is silicone, but other appropriate materials, such as rubber or a thermoset elastomer or thermoplastic elastomer such as Kraton™ may be used.

The preferred form of manifold 6822 includes two holes 6823 side by side in the top of the manifold 6822. In use, the bottom end of each tubular base 6841 fits into each of the holes 6823. It is preferred that the tubular base 6841 has a circumferential groove 6842 running around the base 6841 near the bottom end. The circumferential groove 6842 provides a channel. An edge portion 6824 of the manifold hole 6823 fits within the groove 6842 to hold the nasal pillow 6840 in position on the manifold 6822 in use. The diameter of the circumferential groove may be slightly larger than the diameter of the hole, so that when installed, the flexible material of the tubular base is slightly compressed. When installed in the hole, the tubular base 6841 is firmly retained due to friction between the edge of the manifold hole 6823 and the base of the groove 6842.

Alternatively, the diameter of the circumferential groove may be slightly larger than the diameter of the manifold hole. In this case the circumferential grove width may be slightly thinner than the thickness of the manifold edge portion 6824. When installed into the manifold hole, the pillow tubular base 6841 is firmly retained by friction between the edge portion of the hole 6823 and the sides of the groove 6842.

Alternatively, the diameter of the circumferential grove and the width of the circumferential groove may be sized to provide a relatively loose fit between the tubular base and the manifold hole.

The manifold holes 6823 and the tubular base 6841 of each of the nasal pillows 40 may be round, or alternatively they may be substantially elliptical in shape. Preferably the holes 6823 and tubular bases 6841 are substantially elliptical. This allows only two orientations of fit between the tubular base 6841 and the manifold hole 6823. Due to the shape of the nasal pillows 6840 and with only two orientations of fit possible, when fitting the tubular base 6841 to the manifold 6822, the correct orientation between the tubular base 6841 and hole 6823 will be obvious to a user.

Alternatively, the bottom end of the tubular base 6841 and corresponding manifold hole 6823 could be mutually shaped to provide a single possible orientation for fitting, so that the user cannot fit the nasal pillow 6840 to the manifold 6822 incorrectly.

Alternatively, to ensure correct orientation between the hole 6823 and tubular base 6841, the tubular base may incorporate a key or keyway, with the manifold hole 6823 incorporating a corresponding keyway or key. For example, the groove 6842 may not pass around the entire circumference of the tubular base so that a tab 6843 is formed between each end of the groove 6842. A corresponding notch 6825 in the edge of the manifold hole 6823 ensures correct alignment. Any such key and keyway arrangement known to a person skilled in the art may be used to ensure correct alignment between the nasal pillow 6840 and the manifold 6822.

Additionally, each tubular base 6841 may be shaped or keyed, or both, so that it may be fitted to only one manifold hole 6823. This arrangement ensures the left hand nasal pillow can only be fitted to the left hand manifold hole, and the right hand pillow to the right hand manifold hole.

Alternatively, the tubular bases 6841 of the nasal pillows 6840 may be over moulded onto a substantially rigid tubular material, shaped and sized to conform to the shape and size of the manifold 6822. In this alternative embodiment, the interface between each of the tubular bases 6841 and the manifold 6822 is between the rigid material of the nasal pillow base and the rigid material of the manifold. For this arrangement, a snap or bump type fitting, or a clip type fitting may be incorporated to cause fitting between the nasal pillows 6840 and the manifold 6822.

Alternatively, the manifold 6822 may incorporate two tubular projections 6826 (shown in FIG. 70b) that extend from an upper surface of the manifold 6822. When assembling each of the nasal pillows 6840 to the manifold 6822, the tubular base 41 of each pillow 6840 may fit over a corresponding tubular projection 6826 extending from the manifold 6822. Each pillow 6840 is maintained on a corresponding tube 6826 by friction fit. Other types of fitting may be provided for, such as a snap or bump fitted part, or the tubular pillow base 6841 may be over moulded to a clip that is fitted to the manifold 6822. To assist with a friction fit, the internal diameter of the tubular base 6841 may be slightly smaller that the outer diameter of the tubular projection 6826, so that the pillow base 6841 must be slightly stretched over the tubular projection in order to hold it in place. Alternatively, the tubular projections 6826 and the tubular bases 6841 can be sized so that the ends of the bases 6841 fit inside the projections 6826.

The interface between the tubular projection 6826 and the tubular base 6841 may incorporate a key and keyway to ensure correct orientation of the nasal pillow to the manifold 6822. A projection 6827 on the manifold tubular projection 6826 allows for correct fitting or keying of the nasal pillow 6840 to the manifold 6822, such that when the tubular pillow base is fitted onto the manifold tube, the projection 6827 enters a corresponding recess 6844 formed in the nasal pillow tubular base 6841. Alternatively, a recess may be provided in the outer surface of the manifold tube, and a corresponding projection provided on the internal surface of the pillow tubular base 6841.

For the embodiments described above, the nasal cannula assembly 6802 of the present invention incorporates two nasal pillows 6840, each having a separate base 6841, each base 6841 fitted individually to the manifold 6822.

In an alternative embodiment, the two nasal pillows 6840 may be integrated into a common base. In this alternative embodiment, the common base interfaces with the manifold in a similar way to that of each individual tubular base 41 of the embodiments described previously.

The nasal puff 6849 of the nasal pillow 6840 of the present invention preferably has the general overall form of an elliptical cone and as such each nasal puff 6849 is tubular and allows gases to flow from the conduit 3, through the manifold 22 through the nasal pillows 6840 and to the user 6801. The nasal puffs 6849 of the pillows 6840 include an outlet 6845, which in the preferred embodiment is at the top of the elliptical cone, with the outlet 6845 preferably being elliptical as well. When mounted on the manifold 6822, it is preferred that the pillows 6840 are angled toward one another and also that each of the puff portions 6849 (or at least the outlets 6845) are slightly offset from the centre of each pillow 6840 as shown in FIG. 5.

FIGS. 72 and 73a show the offset outlet 6845 of the preferred form of nasal pillow in more detail. Viewed from above, the pillow 6840 has an outer profile 7300 and the outlet 6845 has an inner profile 7301 with respective centre points 7302, 7303. The inner profile 7301 (formed by the outlet 6845 of the nasal pillow 6840) is offset inward, by a horizontal spacing 7304 and vertical spacing 7305. This means that the outlet 6845 of the nasal pillow 6840 is offset horizontally by the distance shown as horizontal spacing 7304 towards the middle of the nose, and vertically by the distance shown as vertical spacing 7305 towards the user's upper lip. Offsetting the outlet profile 7301 in this manner allows the nasal puff 6849 and the outlet 6845 to be inserted into a user's nostril without the outer profile 7300 pushing or impacting on the user's upper lip. Offsetting the inner profile 7301 inwards allows the nasal puff 6849 of the pillow 6840 to better seal on the septum of the user's nose in use.

The outlet profile 7301 of outlet 6845 may also be angled compared to the outer profile 7300 of the pillow 6840. For example in FIG. 72, there is a horizontal angle difference between the outer profile 7300 and inner profile 7301. This difference is shown as horizontal angle difference 7306. A similar vertical angle difference between the outer profile 7300 and inner profile 7301 is shown as vertical angle difference 7307.

As outlined above, the outer profile 7300 and inner profile 7301 have different sections or offsets. This allows the gradient of the connecting surface between the profiles to be changeable. This is shown in the graphs of FIGS. 73*b*, 73*c* and 73*d*. The connecting surface between the inner profile 7301 and outer profile 7300 can have a different surface profile as shown by gradients 7308, 7309, 7310. The different surface profiles 7308, 7309, 7310 of the connecting surface are possible due to the offset difference 7311, 7312 (horizontal, vertical or angled) between the inner profile 7301 and outer profile 7300.

There may also be a difference in the rate of change of the gradient (as illustrated in the difference between 7308 and 7310). This allows easier insertion of the nasal puff 6849 into a user's nostrils due to the increased amount of 'lead in'. This also allows improved sealing due to more ergonomic contouring of the connecting surface which is in contact with the user's nostril.

4.4 Parallel Tubular Bases

Some prior art nasal cannula interfaces have their tubular bases angled in towards the centre of the user's nose, with the nasal puffs mounted substantially perpendicularly to each corresponding tubular base. The puffs of the prior art cannulae are spaced closer together compared to the manifold end of the tubular bases. It is normal for a user to tighten the head gear of their particular interface to fit it correctly and also to help create a pressure seal between the user's nostrils and the nasal pillows. In prior art assemblies, as the headgear is tightened, the pressure between each pillow and the nare of a user increases. The puff is compressed downwards onto the tubular base, which is also compressed downwards, substantially along the axis of the puff and tubular base. As the headgear is tightened in place on a user's head, it can be seen that the distance between the pillows increases, as each pillow is compressed downwards and substantially along the angled axis of its respective tubular base. The distance between the nasal pillows increases because the pillow tubular bases are spaced further apart at the manifold end, compared to the distance between the tubular bases at the puff end. This configuration can result in a poor fit and therefore poor seal between the user's nostrils and the nasal puffs.

The nasal interface of the present invention helps to overcome this problem by arranging the tubular bases of the two pillows substantially in parallel. This is shown in FIG. 74. Each tubular base 6841 extends substantially parallel from the manifold 7322, relative to a centre line of the user's nose. To accommodate the typically angled nostrils and base of a user's nose and create a good seal, each puff 6849 is connected to the upper end of the tubular base 6841 at an angle.

As the nasal puffs 6849 and tubular bases 6841 of the present invention are compressed during fitting of the assembly 6802 to the user's nose, the puffs and tubular bases are compressed downwards and substantially along parallel axes and therefore do not separate. It has been found that this configuration, with tubular bases 6841 arranged in parallel, with puffs 6849 integrated to the tubular bases 6841 at an angle, results in an improved seal between the puffs and the user's nostrils. The seal is less likely to be broken by a user over-tightening the headgear straps, and is therefore more consistent.

In the preferred embodiment of the present invention, the puffs 6849 are integrated to the top of the tubular bases 6841 at an angle of between 10 and 30 degrees. Preferably, the puffs 6849 are integrated to the top of the tubular base at an angle of between 15 and 25 degrees. It has been found that for the majority of users, the best seal is achieved with a puff angle of substantially 20 degrees to the top of the tubular base 6841.

4.5 Ribbed Tubular Bases

A further improvement has been achieved by adding a ribbed section 6848 to each tubular base 6841. In the preferred form, the ribbed section extends around the circumferential perimeter of the tubular base 6841, between the nasal puff 6849 and close to the bottom end of the tubular base 6841. Alternatively, the ribbed section may extend part way around the circumferential perimeter of the tubular base. In the most preferred form, the ribbed section 6848 extends from the top of the tubular base 6841, where the puff 6849 connects to the top of the tubular base 6841, to part way down the tubular base. The bottom of the ribbed section may be at an angle to the axis of the tubular base, the angle being substantially the same as the angle of the puff to the tubular base. Alternatively, the bottom of the ribbed section may be perpendicular to the axis of the tubular base 6841. The ribbed section may also extend the full length of the tubular base.

The ribbed section is formed from a plurality of adjacent parallel ribs 6846, with the ribs 6846 in the most preferred form being parallel to the longitudinal axis of the tubular base 6841. Each of the ribs 6846 is formed in the tubular base 6841 by having thick walled portions 6850 parallel to the longitudinal axis of the tubular base, the thick walled portions being spaced apart at intervals around the circumference of the tubular base 6841. The thick walled portions 6850 are separated from adjacent thick walled portions 6850 by intervening thin walled portions 6847, the thin walled portions being parallel to the longitudinal axis of the tubular base (that is, around the perimeter or circumference of the base 6841, the thick-walled portions 6850 alternate with the thin-walled portions 6847. Each rib 6846 is made up of one thick wall portion 6850 with a thin wall portion 6847 on either side). In the preferred form, the wall thickness (between the inside and the outside of the tubular base) of the thick-walled portions 6850 is approximately 1.5 mm, slightly thicker than the wall thickness of a nasal pillow known in the art. The thin-walled sections 6847 are slightly thinner than the wall thickness of a nasal pillow known in the art, approximately 0.5 mm.

The thick walled portions 6850 and the thin walled portions 6847 may be formed substantially rectangular in cross section. As shown in FIG. 75*a*, the ribbed section 6848 of the tubular base 6841 may be formed with the outer surface of the ribbed section 6848 of the tubular base 6841 substantially smooth, with a resulting square-wave type ribbed profile in the inner surface of the ribbed section 6848 of the tubular base 6841. Alternatively, as shown in FIG. 75*b*, the ribbed section 6848 of the tubular base 6841 may be formed with the inner surface of the ribbed section 6848 of the tubular base 6841 substantially smooth, with a resulting square-wave type ribbed profile in the outer surface of the ribbed section 6848 of the tubular base 6841. Or, alternatively a centre line of the thick wall portions 6850 and a centre line of the thin wall portions 6847 may be aligned or offset so that a square-wave type ribbed profile results in both the inner and outer surfaces of the ribbed section 6848 of the tubular base 6841, as shown in FIG. 75*c*.

Furthermore, the thick-walled portions 6850 may have a rounded form, or the thin walled portions 6847 may have a rounded form, or both the thick walled portions 6850 and thin walled portions 6847 may have rounded forms. A wave type ribbed profile may result in the inner surface of the ribbed section 6848 of the tubular base 6841, with a smooth outer surface of the ribbed section 6848 of the tubular base 6841, as shown in FIG. 75*d*. Or, a wave type ribbed profile may result in the outer surface of the ribbed section 6848 of the tubular base 6841, with a smooth inner surface of the ribbed section 6848 of the tubular base 6841, as shown in FIG. 75*e*. Alternatively, the thick walled portions 6850 and thin walled portions 6847 may be arranged so that a wave type ribbed profile results in both the inner and outer surfaces of the ribbed section 6848 of the tubular base 6841, as shown in FIG. 75*f*.

Alternatively, the ribs could for example be formed by adjoining cylindrical sections, as shown in FIG. 75*g*. The thick wall section would be the largest distance (usually the diameter) from the inner surface to the outer surface of the ribbed section 6848 of the base 6841, with the thin wall section being the point at which adjacent ones of the cylindrical sections are touching or connected, the shortest distance from the inside to the outside of the ribbed section 6848 of the base 6841.

The cross-section of the tubular base of the present invention with thin portions 6847 and thick portions 6850 is substantially similar to the cross-section of the tubular base of prior art nasal pillows without ribs. This means that the tubular bases 6841 of the present invention are able to resist similar compressive loads to a prior art pillow base, in a similar manner. To create a good seal between the puffs 6849 and the user's nostrils, it is important for the nasal puffs 6849 and the tubular bases 6841 to provide some compressive resistance to push the puffs 6849 against the user's nostrils as the headgear is tightened onto the user's head. The thick portions 6850 substantially parallel to the longitudinal axis of the tubular base 6841 provide the longitudinal support in the pillows necessary for achieving a good seal with the user's nostrils.

The longitudinal thin portions 6847 allow the tubular bases to twist axially more easily compared to prior art (unribbed) nasal pillows. The thin sections 6847 create a 'laminated' type construction for the tubular bases 6841, allowing the thick walled portions 6850 to move relative to each other more easily compared to a tube with uniform cross-section, so that axial twisting occurs more easily. It has been found that twisting of the pillows 6840 onto the user's nostrils occurs as the cannula assembly 6802 is fitted to the user. Allowing this twisting action to occur more easily helps to seat the puffs 6849 onto the user's nostrils and create a good seal.

Also, the ribs and thin intervening portions allow the pillow bases to be more easily deflected sideways, perpendicular to the tubular bases axis, compared to the prior art nasal pillows. This side ways deflection allows for varying nose shapes while still providing a seal between the nasal puff and the user's nostril.

It should be noted that although ribs parallel to the longitudinal axis of the tubular base have been described above, the rib sections may also be angled or spiralled around the base 6841.

It has been found that an improved seal is achieved with the nasal pillows 6840 of the present invention. The parallel tubular bases 6841 help to maintain a constant distance between each pair of nasal pillows 6840 as the nasal assembly 6802 is fitted to the user's head. The ribbed section 6848 in each tubular base 6841 allows each pillow to twist into place on each nostril to create a good seal.

In the preferred form, a range of nasal pillows 6840 of various different sizes is available, such that a user may remove a pair of existing nasal pillows 6840 from the manifold 6822, and simply attach a different sized pair of pillows 6840 to the manifold 6822.

5. Nasal Interface with Silicone Side Arms (Nano)

FIG. 76 shows a perspective view from the front and to the side of the preferred embodiment of an interface assembly 7601, showing an interface core portion 7602 or interface core section 7602, with a headgear assembly 7603 and a supply conduit 7604 connected to the interface core portion 7602. A lanyard 7605 is connected to the supply conduit 7604, with the interface 7601 ready for use by a patient or user. The interface core section 7602, headgear assembly 7603, supply conduit 7604 and lanyard 7605 which make up the preferred form of interface 1, and their inter-relationship, will now be described.

5.1 Interface Core Section

The interface core section 7602 includes a main body section that forms a manifold 7608. The manifold 7608 includes an inlet or gases supply aperture 7609 which is adapted for releasable connection to the gases supply conduit 7604. That is, the gases supply aperture 7609 and the gases supply conduit 7604 are mutually adapted to releasably connect together in use. How this connection is formed for the preferred embodiment will be described in further detail below. In the most preferred embodiment, the gases inlet or supply aperture 7609 is located at the front of the manifold 7608, and in use (i.e. with a user wearing the interface and standing up) the supply aperture 7609 is aligned substantially vertically downwards. In variations of this most preferred form, the gases inlet 7609 may be angled forwards as well as substantially downwards. 'Substantially vertically downwards' as it is written in this specification should be interpreted as not meaning absolutely vertical—an angle of 10-20 degrees or more off-vertical lies within the meaning of 'substantially vertical' as it is used in this specification. In use, gases from the supply conduit 7604 enter the manifold 7608 via the gases supply aperture 7609. In the most preferred from, the aperture 7609 is located at the outer end of a short length of tube which forms part of the manifold 7608, the aperture 7609 being oval in cross-section (viewed along the longitudinal axis of the short length of tube). In the preferred form, the manifold 7608 (including the gases supply aperture 7609) is formed from a rigid or semi-rigid plastic. Examples of a suitable rigid or semi-rigid material would be a polycarbonate plastic, a polypropylene plastic or similar. The manifold 7608 can be formed from e.g. a plastic that is similar to that used in the frame or side arms of the Fisher & Paykel Opus™ interface or the ResMed Mirage Swift™ II interface. Examples of what is meant in this specification by the terms 'rigid' or 'semi-rigid' are included in the 'Lexicon' section below.

The most preferred form of manifold 7608 includes a limited flow outlet 7610 for providing gas washout from the interface 7601. The preferred form of outlet 7610 is a collection or group of small apertures in the manifold 7608, in the preferred form located on the manifold 7608 so that they are close to the connection with the supply conduit 7604, that is close to the gases supply aperture 7609, and on the top of the manifold 7608 in use.

A pair of nasal pillows 7611 are connected to the manifold 7608 by way of a gasket 7636. The nasal pillows 7611 and the gasket 7636 are fluidically connected to the manifold 7608 in such a manner that a stream of gases entering the manifold 7608 through the gases supply aperture 7609 passes through the manifold 7608 and enters the nasal pillows 7611. The gases stream enters at the bases of the pillows where they are fluidically connected to the manifold 7608, passes through the nasal pillows 7611, and exits at the open ends 7612 which in use are located in the nostrils of a user. Each of the nasal pillows 7611 is generally mushroom-shaped, having a stem 7613 and a cap 7614, the lower end of the stem 7613 fluidically connected to the gasket 7636, which is fluidically connected to the manifold 7608. The open end 7612 is located at the top of the cap 7614. The outer surface of the cap 7614 substantially seals against a users nares in use. 'Substantially seals' as it is used in this specification should be taken to mean that perfectly sealing against the nares with no leaks is the most desirable outcome. However, a small degree of leakage around the sides of the cap 7614 in use is almost certainly inevitable, and a person skilled in the art will understand that the phrase 'substantially sealing' is intended to indicate that a very small amount of leakage may sometimes, but not always, occur. As the nasal pillows 7611 are substantially sealed against the nares of a user, all or substantially all of the stream of gases which passes through the manifold 768 and the nasal pillows 7611 will be delivered to a user.

In order to aid in sealing the nasal pillows 7611 against the nares of a wide variety of users, each of whom will have differently shaped and sized nostrils, the pillows 7611 are in the preferred form formed from a soft and supple material with a high degree of flexibility, such as silicone or similar.

5.2 Connecting or Supporting Arms

The interface also includes a pair of connecting arms 7615a, 7616a, extending one from each of the sides of the core section 7602. The connecting arms 7615a, 7616a connect the headgear assembly 7603 to the core section 7602 in use. In the preferred embodiment, the connecting arms are attached to the core section 7602 so that they are angled slightly backwards, towards the face of a user in use, and slightly upwards. Each of the arms has a generally rectangular cross-section, is between 1 and 2 mm thick, around 10 and 11 cm in length and has a width of around 15 mm. In plan, the arms are generally rectangular, but taper towards their outer ends.

In the preferred embodiment, each of the arms 7615a, 7616a is formed from a supple and flexible material which has the same or very similar properties to the nasal pillows 7611, that is, the arms 7615a, 7616a can be crushed into a ball in the hand of a user, flexed so that their ends meet, etc, and once this external deforming force is removed, they will return to their original shape with little to no plastic deformation occurring. The material is soft, supple and flexible enough that each of the arms could be rolled into a tube, starting at e.g. the outer end, with little or no central hollow portion in the tube, and when unrolled there would be little to no plastic deformation of the material.

In the most preferred form, the supple and flexible material from which the nasal pillows 7611 and the connecting arms 7615a, 7616a is a material which has a hardness of between 10 and 60 on the shore A scale. In the most preferred form, the material used is a silicone material.

The ends of each of the connecting arms 7615a, 7616a are adapted to allow the attachment of the ends of corresponding arms on the ends of the headgear assembly 7603. In the preferred embodiment, each of the outer ends 7622, 7623 of the arms 7615a, 7616a includes a detachable element 7630, 7631. In the preferred embodiment, the inner end of each of the detachable elements 7630, 7631 is barbed or notched on each side, and the outer ends 7622, 7623 of the arms 7615a, 7616a include a loop on the outer surface of the arm. The inner end of each of the detachable elements 7630, 7631 is slipped through the loop in use so that the barb engages with the edge of the loop to hold the detachable element in place on the arm. The outer ends of each of the detachable elements 7630, 7631 include slots 7632, 7633 which are generally vertically aligned in use.

In the most preferred form, the arms are formed so that in profile they have a bent or 'L' shape, shaped so that the bend generally follows the rear corner of the manifold 7608. One face of the 'L'-shape extends generally outwards, from the rear of the interface core portion 7602 towards the front, and is generally aligned with the top portion or face of the gasket 76036 where the arm connects to or with the gasket 7636. The other face of the 'L' extends generally downwards along the rear portion of the interface core portion 7602. One face (the inner face) of the L-shape of each arm rests against the face of a user in use.

5.3 Headgear

The headgear assembly 7603 of the preferred form comprises at least one strap 7620 which passes around the back of a users head in use, with the ends 7624, 7625 of the strap 7620 connecting to the connecting arms 7615a, 7616. In the preferred form, the headgear assembly 7603 includes a main strap 7620 and a secondary upper strap 7621. In the preferred form, the ends 7624, 7625 of the main strap 7620 include two patches of Velcro™ on the outer surface at each end—one 'hook' patch and one 'loop' patch. When each of the ends 7624, 7625 is doubled back on itself to form a loop, the Velcro™ patches engage to hold this loop together. In use, the ends 7624, 7625 are passed one each through the slots 7632, 7633 and then doubled back on themselves to engage the headgear assembly 3 with the core section 7602.

The secondary upper strap 7621 is arranged so that it passes across the top of a users head, with each end of the secondary strap 7621 connecting to the main strap 7620 just behind the ears of a user.

One, or both, of the straps 7620, 7621 can include an adjuster such as buckle 7640 shown in FIG. 77 for lengthening or shortening the strap 7620 or strap 7621 if required. More than one buckle can be included on each strap if required. These could be Velcro™ adjusters or buckles as preferred. The headgear secondary upper strap 7621 could also be independently formed and connected to the main strap 7620. The adjustments could be at any location on the strap that is convenient, sides, front or rear. The straps could be of different widths or thicknesses as required for user comfort. For example, in the most preferred form, the main strap 7620 is wider than the secondary strap 7621, and the main strap 7620 is wider at the front than it is around the back of the users head.

Suitable strap materials may include a woven elastic strip or a narrow strip of foam and fabric, such as Breathoprene™. Alternatively, the headgear could be formed from silicone, or coated with silicone. The headgear arms could be padded or cushioned on their inside surfaces if they are formed from silicone, in order to increase user comfort. Padding could also be added to the preferred form of arms—those made from Breathoprene™ or similar.

5.4 Supply Conduit

In the preferred embodiment, the supply conduit 7604 is a flexible tube formed from a plastic type material. The most preferred form of supply conduit 7604 is approximately 30 cm or 1 foot in length, with an external diameter of between 1 and 2 cm and a thin ribbed wall, the ribs being approximately 2 to 3 mm thick and the wall between the ribs being significantly less that 1 mm thick. However, it should be noted that variations from these dimensions are possible without departing from the scope of the invention, and also a non-ribbed conduit could be used if required. It should further be noted that 'flexible tube' as it is used in this specification should be taken to mean that the tube or conduit is flexible enough so that it is capable of being bent or deformed repeatedly (for example, by bringing the two ends of the conduit together, or by tying a loose knot in the conduit if it is long enough, e.g. approximately 30 cm or more in length), with the tube or conduit returning to its original undeformed shape with little to no plastic deformation occurring, every single time the tube or conduit is bent or deformed in this manner.

In the most preferred form, the supply conduit 7604 will not support its own weight when held at one end in such a manner that the main body of the conduit extends outwards from the held end generally horizontally. Over a 20 to 30 cm length of supply conduit (which has a diameter of 1 to 2 cm and a wall thickness at the ribs of 1 to 3 mm and a wall thickness between the ribs of less than 1 mm), the unsupported end of the supply conduit will bend and 'droop' so that the unsupported end points substantially or directly downwards. Therefore, the supply conduit bends through at least 70 degrees over this length. This is in contrast to the supply conduit used on for example the Opus™ nasal mask, where a supply conduit having substantially the same dimensions will only bend by around 10 to 20 degrees over its length, and 'droop' by around 2 to 3 cm.

The supply conduit 7604 has a first or distal end 7606 and a second, or proximal end 7607. In the preferred form, the second, or proximal end 7607 is in use connected to the interface core portion 7602 by a friction push fit, a bayonet connection or similar, or by any other suitable connection as might be known in the art. The gases supply aperture 7609 and the proximal end 7607 are for example mutually formed as a male/female couple or similar. However, it should be noted that this connection could be made by way of a ball joint socket or similar to allow the flexible conduit and more specifically the proximal end 7607 to be rotated through different angles and orientations relative to the interface core portion 7602. This connection could also be made in such a manner that the supply conduit 7604 and the manifold 7608 can swivel relative to one another.

The first or distal end 7606 is connected to a main CPAP delivery tube or similar (not shown) so that when the preferred form of interface 7601 is being used in the most preferred manner, the supply conduit 7604 receives a stream of heated, humidified gases from a humidifier chamber or similar connected in line with a CPAP blower or similar, via the main supply conduit. This connection can be made in the same or a similar manner to the connection described above for the gases supply aperture 7609 and the proximal end 7607, or by any other suitable connection as might be known in the art.

As outlined above, the most preferred form of manifold 7608 includes a limited flow outlet 7610 for providing gas washout from the interface 7601, this being a collection or group of small apertures in the manifold 7608. However, in alternate forms, the gas washout or bias flow could be by way of bias flow holes in the gases supply conduit 7604, at or close to the proximal end 7607. These could be a group or groups of perforations in the gases supply conduit 7604.

5.5 Lanyard

In the most preferred form, a lanyard 7635 is connected at or close to the distal end 7606 of the supply conduit 7604. In the most preferred form, the lanyard 7635 is a loop intended to be connected to the body of the user of the interface. For example, the lanyard 7635 may be worn around the neck of the user, or it may be clipped to the users clothing or similar. The lanyard 7635 carries the weight of the main delivery tube allowing less pressure to be used to hold the interface in place. In the preferred form, the lanyard 7635 is configured so that it will pass around the back of a users neck so the weight is supported by the users neck, with one point of the loop of the lanyard 7635 connected at or close to the distal end 7606 of the supply conduit 7604. In alternate forms, the lanyard could be formed as two separate lengths, with the inner or user ends of the lanyard 35 connected directly to the headgear as shown in FIG. 84*c*. In all the embodiments, that end of the lanyard 7635 which is connected to the conduit 7604 could be connected in any one of several ways which are known in the art. For example, by using a c-shaped clip which clips around either the conduit or a connector attached to the end of the conduit, the c-clip being push-fitted into place. Alternatively, the end of the lanyard could be fitted with a hook and the conduit 7604 fitted with a corresponding loop or aperture on the surface to engage with the hook. Alternatively, a drawcord could be used. Alternative forms of connection of the lanyard 7635 to the supply conduit, and the lanyard to the headgear, are shown in FIGS. 84*a* to 84*c*.

The advantage of the flexible tube and lanyard is that the need for rigid headgear to support the load is removed, as the load from the CPAP tubing is not transferred to the mask body. This is due to a combination of support from the lanyard 7635 and the fact that the supply conduit 764 is significantly more flexible than a supply conduit of the type that is used with the Fisher & Paykel Opus™ or the ResMed Mirage Swift™ II nasal masks.

5.6 Combined Connecting Arms and Nasal Pillows

The most form of interface 7601 will now be described with reference to FIGS. 78*a* and 78*b*.

In the most preferred form, as described above, the interface 7601 includes a rigid or semi-rigid manifold 7608. The centrally located gases supply aperture 7609 feeds into the central aperture or cavity of the manifold 7608. That part of the manifold 7608 which is furthest away from the aperture 7609 and in use closest to a user is substantially open or a substantially fully open face as best shown in FIG. 78*b*, the upper part or face of the manifold 7608 is open. It should be noted that 'upper' in this specification refers to the 'in use' position with a user standing up.

The pair of nasal pillows 7611 are integrally formed with the base gasket 7636, the pillows and base gasket 7636 being formed from a supple and flexible material as outlined above. The base gasket 7636 includes an open lower face or open lower portion 7637 which corresponds in use to the open upper face of the manifold 7608. In use, the perimeter of the open portion 7637 of the base gasket 7636 is stretched and pressed or passed over the outside of the open upper face of the manifold 7608 so that it covers and closes the open face of the manifold 7608, with the gasket 7636 sealing against the outer surface of the manifold 7608. It can be seen that all of the gases passing through the manifold 7608 will pass into the gasket 7636 and the nasal pillows 7611. As can be seen in FIGS. 78*a* and 78*b*, the manifold 7608 in this form is tapered, flaring or expanding in a direction away from the inlet aperture 769, and towards the user. When the base gasket 7636 is stretched and placed into position, it contracts back to an un-stretched state when it is over the manifold 7608, and the flaring of the manifold 768 helps to keep the base gasket 7636 and pillows 7611 in position. The base gasket 7636 will naturally be forced further on to the manifold 7608 as it contracts. It should be noted that the gasket 7636 and connected pillows 7611 and arms 7615*a*, 7616a can be attached and removed repeatedly from the rigid manifold 7608 as required by a user.

In this preferred embodiment, the support arms or connecting arms 7615a, 7616a are formed integrally with the gasket 7636 and the nasal pillows 7611. The arms 7615a, 7616a, the base gasket 7636, and the nasal pillows 7611 are all formed as a one-piece item.

Surprisingly, the combination of a rigid manifold 7608 and soft or flexible gasket 7636 with soft and flexible arms 7615a, 7616a has been found to provide an interface which will remain in position, is comfortable for a user, and which will allow the delivery of gases for therapeutic purposes over sustained periods (e.g. an 8 hour sleep cycle) without coming loose, moving out of position, or becoming uncomfortable for a user. No marks are left on the patients face after use due to soft flexible nature of arms, and there is no need for the addition of padding to the inner surface of the arms to achieve this. Also, the interface fits a wider range of patients face shapes due to soft flexible nature of arms.

Even more surprisingly, it has been found that this can be achieved in the most preferred form by moulding the gasket 7636, pillows 7611 and the supporting arms 7615a, 7616a as a one-piece item, and then connecting this to a rigid manifold such as manifold 7608 which receives gases. This also offers a manufacturing advantage as the core section 7602 can be formed from two elements only, each of which are relatively simple in shape (compared to those used to form the core section of either the Fisher & Paykel Opus™ or the ResMed Mirage Swift™ II nasal masks. The surprising advantage is that there is less complexity for a patient when assembling or disassembling the interface as there are fewer parts. This also offers an advantage to the manufacturer as there are fewer parts to manufacture. There is also a surprising efficiency advantage as there is a lower probability of leaks due to there being fewer connecting joints in the system.

Even more surprisingly, it has been found that by using a rigid or semi-rigid manifold and a supple or flexible gasket, pillows and supporting arms, with the gases supply aperture arranged facing substantially vertically downwards when a user is wearing the manifold and standing upright, the front-rear profile or dimensions can be decreased to the point where the front-most features or portions of the interface can in use be kept further back than the front tip or front-most part of a typical or average users nose. This is shown in FIG. 81. This has proved to be surprisingly advantageous and beneficial for users, as it allows a user greater freedom in choosing a preferred sleeping or 'use' position. Unlike prior art interfaces such as the Fisher & Paykel Opus™ or the ResMed Mirage Swift™ II nasal masks, a user can more easily sleep prone on their face or at least their front without portions of the interface or associated elements such as headgear being pressed into their face or head. The oval entry can also be used to achieve this surprising advantage either independently of, or in combination with, the downwards-facing aperture, as it helps facilitate this slim-line design, helping to ensure the interface does not protrude further out than end of nose and allowing more freedom of sleeping position without dislodging the interface. As outlined above, this can help to facilitate a prone or stomach sleeping position.

It has also been found that the use of a core portion and supporting arms configured in the manner outlined above allows a user to more comfortably sleep on their side. As the gases supply conduit 7604 extends vertically downwards from the interface core portion 7602 (when a user is standing), they will not, if lying in bed, crush or squeeze a supply tube that feeds in or is connected to the side of the interface.

5.7 First Alternative Form

The first alternative form will now be described with reference to FIG. 79.

The first alternative form is almost identical to the preferred embodiment described above when assembled. However, in this alternative form, the soft, supple and flexible arms 7615b, 7616b are moulded or connected directly on to the sides of the rigid manifold 7608. The gasket 7636b and the pillows 7611 are a one-piece item, and are attached to the manifold 7608 in a similar fashion to that outlined above in use, except that the gasket 7636b includes slits or slots 7650 at each side to allow the arms 7615b, 7616b to pass through so that the gasket 7636b can seal against the outer surface of the manifold 7608.

5.8 Second Alternative Form

The second alternative form shall now be described with reference to FIG. 80.

In the second alternative form, the gasket 7636c and pillows 7611 are permanently or integrally connected to the rigid manifold 7608, but the gasket 7636c and pillows 7611 are still soft and flexible. The arms 7615c and 7616c are formed as a unitary or one-piece item, merging at their inner ends into a hollow aperture 7660 which is shaped and sized with the outer sides or surfaces of the gasket 7636. The gasket 7636c is flared from the outer part towards the inner part (closest to a user), and the hollow aperture 7660 corresponds to this flaring, so that when the manifold is passed into the hollow aperture 7660, that part of the manifold 7608 which forms the gases supply aperture 7609 and the outer part of the manifold 7608, including the limited flow outlet 7610, passes through the aperture 7660 and the inner part then wedges into the hollow aperture 7660. Any pulling force exerted on the inner ends of the arms 7615c, 7616c will cause the gasket 7636c to become wedged in tighter in the hollow aperture 7660. In this second alternative form, it is preferred that the thickness of the walls of the gasket 7636c or the thickness of the walls of the hollow aperture 7660 are thick enough that the maximum anticipated force exerted on the inner ends of the arms 7615c, 7616c in use will not cause either the aperture 7660 or the gasket 7636c to deform sufficiently to allow the gasket 7636c to pass through the hollow aperture 7660.

Further Alternative Forms

In the most preferred form and the two alternative forms described above, the interface core section 7602 has a gases supply aperture 7609 which is a male or female connector (male in the most preferred form) which connects by push-fit or similar to the gases supply conduit 7604, with the gases supply aperture extending downwards from the bottom of the interface core portion 7602.

In other alternative forms, this connection could be made e.g. by way of a ball joint and socket, or any other suitable connection such as are known in the art. It should also be noted that in alternative but less preferred forms, the gases supply aperture could be arranged so that it extends to one side of the interface. This would not provide the advantages of the most preferred form or the two alternative forms as described above, but would still allow a user to take advantage of the soft, flexible and supple support arms. If the interface is configured so that a gases supply conduit extends to the side or over the top of a users head, the headgear can be fitted with a connector to clip or connect the supply hose to the headgear.

5.10 Gasket

The preferred form of gasket 7636 shall now be described with particular reference to FIGS. 78a, 81 and 82a.

In the most preferred form of gasket 7636, the gasket is shaped so that the two side portions are slightly angled towards one another. That is, the top surface which covers the open rear face of the manifold 7608 appears to have a V-shape when viewed from the front, with the pillows 7611 one on each of the two sub-surfaces or inner faces of the 'V'. The angle of the 'V' is not acute. Each edge or plane of the 'V' of the gasket 7636 is raised by a few degrees only (e.g. 5 to 10 degrees). The pillows 7611 are mounted one on each of the two planes, and are in this manner included inwards towards one another slightly in the most preferred form. Although there are of course many other ways in which this could be achieved without creating a 'V' shape.

In the preferred form, as described above, the nasal pillows and the gasket 7636 are formed as a one-piece item. However, the pillows 7611 could be removably connected to the gasket 7636, either individually or as a pair. For example, the gasket could include a pair of stub bases to which the pillows are press-fitted in use, the stub base and the base of the stem 7613 being mutually adapted to connect together by way of a press-fit, a keyed connection, or similar. This would potentially allow pillows which are of different shapes or sizes to be fitted to the gasket 7636. This would be advantageous if a user required pillows moulded specifically to the shape of their nares, or pillows of different sizes. This would also allow a range of standard pillows to be manufactured, the range having different sizes or different shapes, or both. This would provide a range of off-the-shelf adjustment.

The rear of the gasket 7636 includes a lip cushion 7638, which is a rounded elongate surface on the rear of the gasket 7636, the lip cushion resting on the upper lip of a user in use. In the most preferred form the lip cushion 7638 is hollow and formed from the same supple and flexible material as is used to form the gasket and pillows. The lip cushion 7638 rests against the top lip of a user in use. Detail of the preferred form of lip cushion 7638 is particularly shown in FIG. 83.

The lip cushion could, in alternative forms, be formed from foam or similar.

5.11 Gasket and Manifold Connection

In the most preferred form, as outlined above, the gasket 7636 is stretched over the top of the rear opening or open face of the manifold 7608. The gasket 7636 (and pillows 7611 in the most preferred form) could be overmoulded over the top of the manifold 7608, or bump-fitted or push-fitted into place. In the most preferred form shown in FIG. 82a, the lower rear edge 7640a of the gasket 7636 (which also forms the lower rear part of the lip cushion 7638) slots into a corresponding slot 7641 in the rear wall of the manifold 7608. In an alternative form, as shown in FIG. 82b, the gasket 7636 could be connected at the rear of the manifold 7608 in the following manner: the inner surface of the gasket 7636 includes a protrusion or bump 7650, which 'hooks' over the top edge 7651 of the rear wall 7652 of the manifold 7608 to hold the gasket 7636 in place. In this first alternative form, the lower rear edge 7640b of the gasket 7636 is free hanging, unattached or unconstrained, and rests freely against the rear face of the manifold 7608 when pushed against the rear wall 7652, e.g. by the pressure of a user's lip.

In the preferred embodiment described above, and as shown in FIG. 82a, a slot for receiving the lower rear edge 7640a is described and shown. However, either a top and a bottom slot and tongue could be used, or one or the other (upper or lower). The tongues and slots would not necessarily run the entire width of the manifold and gasket, but would run part of the width, or several corresponding tongue/grooves could be used across the width.

As shown in FIG. 83, the lip cushion 7638 is formed as part of the gasket 7636, extending from the top rear edge of the gasket 7636 in use, and looping outwards and downwards to touch or connect against the rear wall of the manifold 7608. The lip cushion 7638 and the manifold 7608 in the most preferred form as shown do not include a gas path between the interior of the manifold 7608 and the interior of lip cushion 7638. The lip cushion is sealed from the flow of gases which passes through the interface to a user as shown in FIG. 82a. However in alternative forms, as shown in FIG. 82c, there could be a gases path 7660 between the two so that the lip cushion receives part of said flow of gases in use. This could be advantageous in some forms as it would allow the use of the thin walled lip cushion 7638 which would inflate or partially inflate as gases from the manifold 7608 pass into the interior of the lip cushion 7638 and provide an inflation pressure.

5.12 Lexicon

'Supple' and 'flexible' as they are used in this specification with reference to the nasal pillows 7611 should be taken to mean that, for example the pillows 7611 or the side support arms 7615, 7616 can be substantially and repeatedly deformed. For example, by a user pinching, squashing or crushing these in their hand. The pillows and side support arms return to their original shape with little to no plastic deformation occurring.

An item having rectangular or square cross-section, with a thickness of 1 to 2 mm and a length of 5 cm or more, formed from a 'supple' or 'flexible' material as it should be understood in this specification, will, if held at one end, bend to an extent easily appreciable to the naked eye, i.e. at least 2 to 3 mm. If it does not bend to an appreciable extent, then it is a rigid or semi-rigid material for the purposes of this specification, see below.

It should also be understood that 'flexible' is intended to mean a material that is soft, supple and flexible enough that each of the arms could be rolled into a tube, starting at for example the outer end, with sufficient bending that the end fold completely back on itself so that there is little or no central 'hollow' portion in the tube formed by the rolling. When the tube is unrolled there would be little to no plastic deformation of the material.

'Rigid' as it is used in this specification should be understood to mean that an item described as rigid can be elastically deformed, but that it would require application of an external force apart from gravity (i.e. its own weight). To do so a 'rigid' item will not collapse or bend under its own weight, in any orientation. It is noted that all items usually described as rigid have a certain degree of elasticity, but the elastic limit will normally be reached before the elastic deformation of the rigid material is appreciable to a user. Glass, for example, will shatter before the average person is able to appreciate that it has elastically deformed at all. An item having rectangular or square cross-section, with a thickness of 1 to 2 mm and a length of up to 10 cm, formed from a 'rigid' or 'semi-rigid' material as it should be understood in this specification, will not bend to an extent easily appreciable to the naked eye. For example, the arms of the Fisher & Paykel Opus™ interface or the ResMed Mirage Swift™ II interface are around 10 to 11 cm long and have a thickness of 1 to 2 mm. The arms of these devices are formed from a plastic having a rigidity so that they will not bend under their own weight if held at one end, and for the purposes of this specification can be considered to be 'rigid' or semi-rigid'.

'Substantially vertically downwards' as it is written in this specification should be interpreted as not meaning absolutely vertical. An angle of 10 to 20 degrees or more off-vertical lies within the meaning of 'substantially vertical' as it is used in this specification.

It should also be noted that 'downwards', 'outwards', 'inner' and 'outer', and similar terms as they are used in this specification refer to the mask being worn by a user who is standing up. However, in use the interface is intended to be used by a user who is asleep and will be lying on a bed, either on their back, front or side. The convention referred to above (a user standing) has been adopted for ease of reference.

It should also be noted that the term 'interface' as it is used in this specification refers either to the interface assembly inclusive of the supply conduit 7604 and the headgear 7603. That is, for the preferred embodiment, the term 'interface' could refer to the manifold 7608, the gasket 7636, support arms 7615, 7616 and pillows 7611 in combination with the headgear 7603. Alternatively the term 'interface' as used in relation to, for example, the preferred embodiment could refer to the manifold 7608 and the connected gasket 7636 and pillows 7611 and support arms 7615, 7616 only. That is without the headgear 7603 and the supply conduit 7604.

6. Nasal Interface with Nasal Plugs

In a general form, a nasal patient interface includes a connector piece that connects the nasal patient interface to the breathing circuit, transportation passageway or conduit, which is then connected to the source of pressurised gas.

A nasal plug type nasal interface has nasal members that usually have a type of tapered end that terminates in an aperture (cannula). In use, when a patient inserts each of the nasal plugs into their nasal cavities and positive pressure ventilation therapy, oxygen therapy or the like is commenced, gases pass through a conduit, into a connector, through each of the nasal members exiting into the patient's nostrils through each nasal cannula. Thereby administering positive pressure ventilation therapy, oxygen therapy or the like to the patient.

In general, nasal plugs made from a foam material are known. For example, foam nasal plugs are disclosed in U.S. Pat. No. 4,782,832 and WO2003/041780. In use, a foam nasal plug provides a seal between a nasal cavity and the cannula, effectively eliminating gases leakage yet is comfortable for the patient. The expanding foam provides an outward force upon the inner surface of each of the patient's nasal cavities, which also prevents each plug from falling from the nasal cavity.

The nasal plugs of the present invention are adapted to fit a mask and headgear arrangement. One such example is that mask 8051 shown in FIG. 85. The nasal plugs 8050 can be of any of the embodiments described herein. The mask and headgear arrangement will usually include a mask 8051 including nasal plugs for insertion in the patient's nares, headgear 8052, holding the mask 8051 in place, an elbowed connector 8054 and conduit 8053 supplying gases to the mask 8051.

FIGS. 86 to 88 show three forms of a nasal plugs 8100. The nasal plug 8100 of the type that in use is fitted inside a patient's nasal cavities (nares). The nasal plug 8100 is of a generally cylindrical shape. However, other appropriate shapes, such as ellipsoidal, conical or spherical are envisaged.

The nasal plug 8100 has a body 8101 that is made of a foam type material, such as an open cell polyurethane foam. However other foam materials can be used, for example a silicone foam. In the case of a silicone foam, a skin would be formed automatically, thus the plug would be self-skinning.

The plug 8100 is tubular with a curved tip 8105 resembling a dome. A tubular bore 8102 extending centrally through the plug. When in use, the bore allows gases to flow through the plug 8100 to the patient.

The plug 8100 is comprised of an inner body 8101 and an outer coating layer cover or skin 8103 formed about the inner body 8101. The skin 8103 may be made from a plastics material such as a thermo plastic elastomer, for example, Kraton or Santoprene, or from a polyurethane or a thermoset plastics, such as silicone.

The skin 8103 can be applied by spraying or dipping after the foam body has been formed. Alternatively, a skin can first be applied to a plug mould, then after some drying time, a foam inner injected, resulting in a coated foam plug 8100.

The skin is preferably a thin coating relative to the size of the nasal plug.

The skin provides a barrier between the foam and the patient's nose. The skin may provide comfort advantages and will prevent nasal fluid or humidified air from penetrating the foam, preventing deterioration. Therefore, a coated nasal plug will be more durable.

In FIG. 3, the nasal plug 8100 is shown having a skin 8103 around its outer surface but not on the bottom surface 8104 of the plug 8100. An open bottom surface 8104 allows air to flow in and out of the foam body so that its shape can be compressed or expanded to a greater degree.

A second form of a nasal plug is shown in FIG. 87. This nasal plug 8110 is tubular with a curved tip resembling a dome. It has an inner body 8111 and a central tubular bore 8112 through it. The nasal plug 8110 has a coated surface, cover or skin 8113. The whole external surface of the foam nasal plug including its bottom surface 8109 is covered in the skin 8113.

The skin has perforations 8114 to allow air to flow into the foam inner to assist in expansion and compression of the nasal plug. The perforations can be set out equidistantly along the coated surface as is shown in FIG. 88, but can be randomly placed or formed in a non-uniform manner in the skin.

A third form of a nasal plug is shown in FIG. 88. The nasal plug 8115 has an inner body 8116 made of foam. This nasal plug 8115 is tubular with a curved tip resembling a dome. It has a central tubular bore 8117 and a coated surface, cover or skin 8118. The skin has perforations 8119. The bottom surface 8120 of the nasal plug 8115 is not coated. Therefore, this embodiment provides the advantage of allowing more air to enter and exit from the bottom of the foam plug. The perforations 8119 in the coating may be placed randomly or in the uniform manner as shown in FIG. 88.

FIGS. 89 to 101 show different shaped nasal plugs. These nasal plugs are of a similar construction as those described above. That is, they have a foam inner core or body with a tubular bore for the passage of air. These nasal plugs also have an outer coating, cover or skin preferably made of a plastics or silicone material. In some forms these nasal plugs may also have perforations in the skin. The skin covers the bottom surface of the nasal plugs in some configurations. In others the coating does not cover the bottom surface. The perforations may be placed uniformly or randomly in the skin.

FIG. 89 shows a nasal plug 8120 that has a head or sealing part 8121 that is substantially spherical in shape. The diameter of the plug 8120 reduces along its length creating a trough 8122 at the centre of the plug. The diameter then increases toward its end or bottom surface 8123. Insertion of this plug into a patient's nares is made easier by reducing the surface of contact between the plug and the nares.

In FIG. 90 the nasal plug 8125 has a more extreme contour than the nasal plug 8120. The plug 8125 has a spherical head 8126 and trough 8127. The head or sealing part 8126 is substantially spherical in shape. The end or bottom of the nasal plug 8125 has a rectangular cross-sectional flange such that the edges 8128, 8129 of the flange abut the outer surface of a patient's nares in use. This embodiment offers a more aggressive seal against a patient's nare walls than the nasal plug of FIG. 89. The radiuses used to design the curves L1 and L2 can vary from zero to infinity.

FIG. 91 shows a further embodiment of a nasal plug 8130. The nasal plug 8130 has a narrow bottom section 8131 and quickly expands along its length to a larger diameter and dome like tip 8132. The length L3 is a sealing length, the length that in use seals in the patient's nares. The increased sealing length of this configuration maximises its sealing capability. An optimisation of this length keeps the plug easily within the patient's nares. Also, optimisation of the sealing length may keep allergy or irritation levels marginal or non existent.

FIG. 92 shows yet a further form of a nasal plug 8140 where the plug seals along the nares wall and about the outer circumference of the nares. The nasal plug 8140 has a flange or lip 8141 at its end that in use will protrude from a patient's nares. The lip 8141 transfers part of the pressure applied on the nares wall to the outer circumference of nares. It is believed this provides less irritation to the patient's nares. In the embodiment of FIG. 92 the tip has a square cross-section 8142.

FIG. 93 shows an alternative nasal plug to that plug of FIG. 92. The nasal plug 8145 has a flange or lip 8146 that is more curved in shape to that of FIG. 92. The length of the nasal plug 8145 reduces in diameter to its tip 8147 thus giving the nasal plug a conical shape. The conical shape of the length to the tip allows easy insertion of the nasal plug into the patient's nares.

FIG. 94 is yet another nasal plug that is of similar configuration to that of FIG. 9. The nasal plug 150 has a flange or lip 151, but its tip 152 is curved in cross-section so the tip 152 is spherical in shape.

FIG. 95 shows a further embodiment of a nasal plug 8200. The nasal plug 8200 is conical in shape with a curved tip 8201. It has a tubular bore running through it in order to supply gases to a patient. The nasal plug 8200 has a flange or lip 8202 at its bottom end. The nasal plug 8200 has an inner body 8203 made of a foam type material, such as an open cell polyurethane foam, but other foam type material may be used. This region immediately surrounds the tubular bore 8205. A coating, cover or skin 8204 encases the inner body 8203. The skin is made from a plastics material or silicone. The skin 8204 forms the flange or lip 8202 of the nasal plug.

The nasal plug 8210 of FIG. 96 is of the same shape as that of FIG. 95. However, the inner foam region or body extends out at the nasal plugs bottom into a lip 8211. The nasal plug 8210 has a cover 8204 that follows the contours of the inner foam region 8211.

The embodiments of nasal plugs of FIGS. 95 and 96 can include perforations in the skin so as to allow air to flow into the foam inner region to assist in expansion and compression of the nasal plug. The perforations may be formed uniformly or randomly in the skin.

Yet another form of a nasal plug is shown in FIGS. 97 to 101. In all these figures the nasal plug 8160 has the same shape. The nasal plug 8160 has a tip or head 8166 that has a curved profile that approximately matches the shape of a nasal cavity. In use, the tip or head 8166 is fitted in the patient's nares. Additionally, the nasal patient interface 8160 has a flange 8161 that seals at the inlet to the nare about the external surface of the nare. The sealing capability of this embodiment is such that it helps to maximise the seal and the patient's comfort.

The nasal plug 8160 has a tubular bore 8167 through it to allow for gases to flow through the plug.

This embodiment of the nasal plug 8160 has a coating, cover or skin 8163, preferably of plastic or silicone, but other materials may be used. The skin substantially covers the external surface of the nasal plug 8160.

In FIG. 97 the nasal plug has a foam body 8162 and an outer skin 8163. The skin 8163 extends completely about the foam inner 8162.

In FIG. 98 the skin 8163 on the nasal plug 8160 does not extend over the bottom surface 8164 of the nasal plugs.

In FIG. 99 the skin 8163 on the nasal plug 8160 does not extend over the inner surface of the tubular bore 8165.

In FIG. 100 the skin 8163 on the nasal plug 8160 does not extend over the surface of the inner bore 8165, nor on the bottom surface 8164 of the nasal plug 8160.

FIGS. 106 and 107 show additions to the nasal plugs of FIGS. 97 to 101. In the embodiments of FIGS. 106 and 107 the nasal plugs 8190, 8195 each have an external circumferential flap 8191, 8196. The flap may be one of two configurations, a tip-jointed flap 8191 of FIG. 106 or a flange-jointed flap 8196 of FIG. 107.

FIG. 106 shows a nasal plug 8190 of the same configuration as FIG. 98, but including a tip jointed flap 8191. The flap 8191 extends from the tip 8192 of the nasal plug 8190 out toward the flange 8193.

FIG. 107 shows a nasal plug 8195 of the same configuration as FIG. 98, but including a flange-jointed flap 8196. The flap 8196 extends from the flange 8197 up towards the tip 8198. This configuration provides a particularly good seal when the patient is exhaling in use.

The flaps 8191, 8196 are constructed from a flexible plastics material, such as silicone, although other suitable materials may be used. The flaps are hinged to the tip 8192 or flange 8197 and so can be moved away or toward the corresponding flange 8193 or tip 8198.

Each of the nasal plugs can be covered to give it additional durability. The nasal plugs have an inner body 8194, 8199. The inner body is constructed from a foam type material, such as an open cell polyurethane foam or silicone foam. The plugs each have a cover, coating or skin 8200, 8201 made from a plastics or silicone material. In the case of a silicone foam, a skin would be formed automatically, thus the plug would be self-skinning.

The skin 8200, 8201 about the inner body can include perforations to allow for air to flow into and out of the inner body. The perforations can be formed in a uniform or non-uniform manner in the skin.

The flap, of either embodiment of FIG. 106 or 107, is formed integrally with the skin of the nasal plug 8190, 8195. For forming or moulding of the nasal plug, a mould includes one region for the flaps and another for the body of the nasal plug. A plastics or silicone for the skin is injected into the mould, lining the mould and creating the flaps. Then a foaming type material, such as open cell polyurethane foam, is injected into the mould. The result is a foam nasal plug covered in a skin with a circumferential flap. To allow for injection moulding of the nasal plugs in this embodiment the bottom surfaces of each of the embodiments described must be open.

Once a nasal plug is in place in the patient's nares, the flap will rest against the body of the plug in a closed position, providing a second layer or wall that increases both the comfort of the patient and seal of the plug in the patient's nares. Also, the flap allows for adaptation of the nasal plug to a wider range of nare diameter.

FIGS. 86 to 101, 106 and 107 are single nasal plugs. In use, it is preferred that two are used. However one may be all that is required for a particular application. In the preferred form two nasal plugs are attached to a body or manifold of a patient interface, such as that manifold 8055 as shown in FIG. 85.

In a further form a nasal plug 8170 is shown in FIG. 102. The nasal plug has a body 8183 made from a foam type material, such as an open cell polyurethane foam, or a silicone foam. In the case of a silicone foam, a skin would be formed automatically, s thus the plug would be self-skinning.

The nasal plug 8170 has a gases inlet 8175 capable of receiving gases from a conduit or tubing. The nasal plug has two nasal members 8171, 8172 separated by a cavity 8173. The inlet 8175 is a tubular bore 8176 that is bifurcated. Each of the branches 8177, 8178 of the bifurcated bore 8176 extend one each into one of the nasal members 8171, 8172. Each branch 8177, 8178 of the tubular bore terminates in a gases outlet 8179, 8180.

Below each of the nasal members 8171, 8172 is a flange or lip 8174. Therefore, the nasal interface 8170 has an overall y-shaped configuration. This configuration is such that it's curved profile approximately matches the bottom of the nose and nasal cavities of a human.

In use, the nasal members 8171, 8172 extend into both of a patient's nares and the cavity 8173 receives the patient's nasal septum. The lip 8174 rests against the outer surface of the nares to seal on the naris of the nose.

As the nasal plug 8170 is predominantly made from a foam type material the foam can to be deformed during insertion of the plugs in the nasal passages and the foam will expand and mould to the shape of the nasal passages.

The nasal plug 8170 can be provided with a coating, cover or skin 8181 extending completely about the exterior surface of the interface. The coating 8181 is made from a material such as a thermo plastic elastomer, for example, Kraton or Santoprene, or from a polyurethane or a thermoset plastics, such as silicone, making the nasal plug more durable. FIGS. 104 and 105 show two different coatings. In FIG. 104 the coating 8181 extends completely about the external surfaces. In FIG. 105 the coating does not extend along the bottom surface (or inlet 8175 surface) 8182. The absence of coating along the bottom surface will serve to allow more air movement into and out of the foam body, allowing for better deformation and expansion.

The coating can have perforations to allow for air to flow into and out of the foam body.

The nasal plugs of FIGS. 102 to 105 are formed by injection moulding. The foam is injected into a mould to make the body of the nasal interface. In the embodiments with an outer coating, the plastics or silicone for the coating is injected first into the mould, then the foam, resulting in a coating foam nasal plug.

For any of the nasal plugs as described herein (FIGS. 85 to 107), to use, a patient need only apply pressure to the sides of a nasal plug, depressing the foam and deforming the shape of each of the nasal plugs so that each is easily insertable into each nasal cavity. Once each plug is within each cavity the foam will expand to its original form where the external surface of the foam abuts the internal surface of the patient's nasal cavity, filling the area within each nostril. These nasal plugs substantially seal in the patient's nasal cavity, but in some forms may not form a complete seal, or seal at all.

In other forms the nasal plugs of the present invention as described herein, may not extend into the nares of the patient, but rest against the patient external surfaces and abut against the patient nares.

What is claimed is:

1. A patient interface for supplying a flow of respiratory gases to a user comprising:
 a gasket portion arranged to receive the flow of respiratory gases;
 a pair of pillow portions connected to and extending from the gasket portion, the pair of pillow portions arranged to receive the flow of respiratory gases from the gasket portion and provide the flow of respiratory gases to the user, each of the pair of pillow portions being defined between a lower end at which each of the pair of pillow portions connects to the gasket portion and an upper end comprising an upper opening of each of the pair of pillow portions; and
 at least one rib disposed in one of the pair of pillow portions, the at least one rib configured to provide rigidity to the pillow portion and to limit collapse of the pillow portion, in use, the at least one rib having a first end and a second end, and an upper surface and a lower surface extending between the first end and the second end, wherein the at least one rib extends across the upper opening of the pillow portion from the first end at a first location to the second end at a second location, the first location and the second location being located on an inner side of the pillow portion, the first location being located diametrically across the upper opening of the pillow portion from the second location,
 wherein the at least one rib lies within the flow of respiratory gases delivered to the user with each of the upper surface and the lower surface located between the upper end and the lower end of the pillow portion, and
 wherein the at least one rib is curved between the first location and the second location.

2. The patient interface of claim 1, wherein a height of the at least one rib varies along its length from the first end to the second end.

3. The patient interface of claim 2, wherein the height of the at least one rib increases towards the inner side of the pillow portion.

4. The patient interface of claim 1, wherein the at least one rib has a cross-sectional thickness that varies along its length.

5. The patient interface of claim 4, wherein the cross-sectional thickness of the at least one rib increases towards the inner side of the pillow portion.

6. The patient interface of claim 4, wherein the cross-sectional thickness of the at least one rib is wider at the first end and the second end than at a center of the at least one rib.

7. The patient interface of claim 1, wherein the at least one rib is rounded and the first end and the second end blend with the inner side of the pillow portion.

8. The patient interface of claim 1, wherein the at least one rib extends downwardly from a position below the upper opening of the pillow portion.

9. The patient interface of claim 1, wherein the upper surface of the at least one rib is curved between the first end and the second end.

10. The patient interface of claim 1, wherein the lower surface of the at least one rib is curved between the first end and the second end.

11. The patient interface of claim 10, wherein the lower surface of the at least one rib is curved upwardly.

12. The patient interface of claim 1, wherein the at least one rib extends across an entire diameter of the pillow portion.

13. The patient interface of claim 1, wherein the at least one rib is offset from a notional diametrically aligned center line of the pillow portion.

14. The patient interface of claim 1, wherein the at least one rib has a cross-sectional thickness that is greater than a cross-sectional thickness of the pillow portion.

15. The patient interface of claim 1, wherein the at least one rib has a larger cross-sectional thickness at a base than at a top edge.

16. The patient interface of claim 1, wherein a cross-sectional thickness of the pillow portion tapers from the lower end towards the upper end.

17. The patient interface of claim 16, wherein the cross-sectional thickness of the pillow portion is thicker at the lower end than at the upper end.

18. The patient interface of claim 1, wherein a cross-sectional thickness of the at least one rib differs at different heights of the at least one rib.

* * * * *